(12) United States Patent
Tabata et al.

(10) Patent No.: US 8,647,839 B2
(45) Date of Patent: Feb. 11, 2014

(54) METHOD FOR PRODUCTION OF GLUTATHIONE OR GAMMA-GLUTAMYLCYSTEINE

(75) Inventors: Kazuhiko Tabata, Ibaraki (JP); Yoshiyuki Yonetani, Tokyo (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 596 days.

(21) Appl. No.: 12/594,928

(22) PCT Filed: Apr. 4, 2008

(86) PCT No.: PCT/JP2008/056759
§ 371 (c)(1),
(2), (4) Date: Oct. 6, 2009

(87) PCT Pub. No.: WO2008/126784
PCT Pub. Date: Oct. 23, 2008

(65) Prior Publication Data
US 2010/0203592 A1 Aug. 12, 2010

(30) Foreign Application Priority Data
Apr. 6, 2007 (JP) .................................. 2007-099957

(51) Int. Cl.
*C12P 21/06* (2006.01)
(52) U.S. Cl.
USPC ........................................ 435/69.1; 435/71.1
(58) Field of Classification Search
None
See application file for complete search history.

(56) References Cited

U.S. PATENT DOCUMENTS

| | | | |
|---|---|---|---|
| 6,610,836 B1 * | 8/2003 | Breton et al. | 536/23.1 |
| 7,041,874 B2 * | 5/2006 | Johal et al. | 800/290 |
| 7,476,526 B2 * | 1/2009 | Phadtare et al. | 435/193 |

FOREIGN PATENT DOCUMENTS

| | | |
|---|---|---|
| JP | 60-027396 A | 2/1985 |
| JP | 60-027397 A | 2/1985 |
| JP | 01-228473 A | 9/1989 |
| WO | WO0148209 * | 7/2001 |
| WO | WO0277183 * | 10/2002 |
| WO | WO 2004/113373 A1 | 12/2004 |

OTHER PUBLICATIONS

Gushima et al., *Journal of Applied Biochemistry*, 5: 43-52 (1983).
Li et al., *Appl. Microbiol. Biotechnol.*, 67(1): 83-90 (2005).
Ohtake et al., *Journal of Fermentation and Bioengineering*, 68(6): 390-394 (1989).
Bentley et al., *Gene*, 127: 117-120 (1993).
Cohen et al., *Journal of Bacteriology*, 175(5): 1484-1492 (Mar. 1993).
Eguchi et al., *Microbiology*, 149: 2819-2828 (2003).
Grant et al., *Molecular Biology of the Cell*, 8: 1699-1707 (Sep. 1997).
Harvat et al., *Journal of Biological Chemistry*, 280(12): 12028-12034 (2005).
Inoue et al., *Biochimica et Biophysica Acta*, 1395: 315-320 (1998).
Li et al., *Appl. Microbiol. Biotechnol.*, 66: 233-242 (2004).
Murata et al., *Applied and Environmental Microbiology*, 44(6): 1444-1448 (Dec. 1982).
Murata et al., *Agric. Biol. Chem.*, 47(6): 1381-1383 (1983).
Nakayama et al., *Applied and Environmental Microbiology*, 47(4): 653-657 (Apr. 1984).
Nielsen et al., *Journal of Bacteriology*, 178(11): 3188-3193 (Jun. 1996).
Nishino et al., *Journal of Bacteriology*, 183(20): 5803-5812 (Oct. 2001).
Ohtake et al., *Agric. Biol. Chem.*, 52(11): 2753-2762 (1988).
Ohtake et al., *Agric. Biol. Chem.*, 54(12): 3145-3150 (1990).
Owens et al., *Journal of Bacteriology*, 168(1): 109-114 (Oct. 1986).
Parry et al., *FEMS Microbiology Letters*, 209: 81-85 (2002).
Pittman et at., *Journal of Biological Chemistry*, 280(37): 32254-32261 (Sep. 16, 2005).
Suzuki et al., *Seigaku, Shoroku CD*, p. A11376 (2006).
Suzuki et al., *Japan Society for Bioscience, Biotechnology, and Agrochemistry 2006* Nendo Heisei 18 Nendo), Taikai Koen Yoshishu (2006), p. 108.
Suzuki et al., *Journal of Bacteriology*, 169(9): 3926-3931 (Sep. 1987).
Suzuki et al., *Journal of Bacteriology*, 187(17): 5861-5867 (Sep. 2005).
Watanabe et al., *Appl. Microbiol. Biotechnol.*, 24: 375-378 (1986).

* cited by examiner

*Primary Examiner* — Jennifer Graser
(74) *Attorney, Agent, or Firm* — Leydig, Voit & Mayer, Ltd.

(57) ABSTRACT

The invention provides a process for producing glutathione or γ-glutamylcysteine by culturing in a medium a microorganism with a higher activity of a protein having an activity to transport intracellular glutathione to the outside of cells, and a higher activity of a protein involved in glutathione or γ-glutamylcysteine biosynthesis, compared with that of the parent strain, forming and accumulating glutathione or γ-glutamylcysteine in the medium, and recovering the glutathione or γ-glutamylcysteine from the culture.

7 Claims, No Drawings

```
                        SEQUENCE LISTING

<160> NUMBER OF SEQ ID NOS: 108

<210> SEQ ID NO 1
<211> LENGTH: 588
<212> TYPE: PRT
<213> ORGANISM: Escherichia coli

<400> SEQUENCE: 1

Met Asn Lys Ser Arg Gln Lys Glu Leu Thr Arg Trp Leu Lys Gln Gln
  1               5                  10                  15

Ser Val Ile Ser Gln Arg Trp Leu Asn Ile Ser Arg Leu Leu Gly Phe
             20                  25                  30

Val Ser Gly Ile Leu Ile Ile Ala Gln Ala Trp Phe Met Ala Arg Ile
```

```
                    35                  40                  45
Leu Gln His Met Ile Met Glu Asn Ile Pro Arg Glu Ala Leu Leu Leu
         50                  55                  60
Pro Phe Thr Leu Leu Val Leu Thr Phe Val Leu Arg Ala Trp Val Val
 65                  70                  75                  80
Trp Leu Arg Glu Arg Val Gly Tyr His Ala Gly Gln His Ile Arg Phe
                 85                  90                  95
Ala Ile Arg Arg Gln Val Leu Asp Arg Leu Gln Ala Gly Pro Ala
            100                 105                 110
Trp Ile Gln Gly Lys Pro Ala Gly Ser Trp Ala Thr Leu Val Leu Glu
            115                 120                 125
Gln Ile Asp Asp Met His Asp Tyr Tyr Ala Arg Tyr Leu Pro Gln Met
        130                 135                 140
Ala Leu Ala Val Ser Val Pro Leu Leu Ile Val Val Ala Ile Phe Pro
145                 150                 155                 160
Ser Asn Trp Ala Ala Leu Ile Leu Leu Gly Thr Ala Pro Leu Ile
            165                 170                 175
Pro Leu Phe Met Ala Leu Val Gly Met Gly Ala Ala Asp Ala Asn Arg
        180                 185                 190
Arg Asn Phe Leu Ala Leu Ala Arg Leu Ser Gly His Phe Leu Asp Arg
        195                 200                 205
Leu Arg Gly Met Glu Thr Leu Arg Ile Phe Gly Arg Gly Glu Ala Glu
        210                 215                 220
Ile Glu Ser Ile Arg Ser Ala Ser Glu Asp Phe Arg Gln Arg Thr Met
225                 230                 235                 240
Glu Val Leu Arg Leu Ala Phe Leu Ser Ser Gly Ile Leu Glu Phe Phe
            245                 250                 255
Thr Ser Leu Ser Ile Ala Leu Val Ala Val Tyr Phe Gly Phe Ser Tyr
        260                 265                 270
Leu Gly Glu Leu Asp Phe Gly His Tyr Asp Thr Gly Val Thr Leu Ala
        275                 280                 285
Ala Gly Phe Leu Ala Leu Ile Leu Ala Pro Glu Phe Phe Gln Pro Leu
        290                 295                 300
Arg Asp Leu Gly Thr Phe Tyr His Ala Lys Ala Gln Ala Val Gly Ala
305                 310                 315                 320
Ala Asp Ser Leu Lys Thr Phe Met Glu Thr Pro Leu Ala His Pro Gln
            325                 330                 335
Arg Gly Glu Ala Glu Leu Ala Ser Thr Asp Pro Val Thr Ile Glu Ala
            340                 345                 350
Glu Glu Leu Phe Ile Thr Ser Pro Glu Gly Lys Thr Leu Ala Gly Pro
        355                 360                 365
Leu Asn Phe Thr Leu Pro Ala Gly Gln Arg Ala Val Leu Val Gly Arg
        370                 375                 380
Ser Gly Ser Gly Lys Ser Leu Leu Asn Ala Leu Ser Gly Phe Leu
385                 390                 395                 400
Ser Tyr Gln Gly Ser Leu Arg Ile Asn Gly Ile Glu Leu Arg Asp Leu
            405                 410                 415
Ser Pro Glu Ser Trp Arg Lys His Leu Ser Trp Val Gly Gln Asn Pro
            420                 425                 430
Gln Leu Pro Ala Ala Thr Leu Arg Asp Asn Val Leu Leu Ala Arg Pro
        435                 440                 445
Asp Ala Ser Glu Gln Glu Leu Gln Ala Ala Leu Asp Asn Ala Trp Val
450                 455                 460
```

-continued

Ser Glu Phe Leu Pro Leu Leu Pro Gln Gly Val Asp Thr Pro Val Gly
465                 470                 475                 480

Asp Gln Ala Ala Arg Leu Ser Val Gly Gln Ala Gln Arg Val Ala Val
            485                 490                 495

Ala Arg Ala Leu Leu Asn Pro Cys Ser Leu Leu Leu Asp Glu Pro
        500                 505                 510

Ala Ala Ser Leu Asp Ala His Ser Glu Gln Arg Val Met Glu Ala Leu
        515                 520                 525

Asn Ala Ala Ser Leu Arg Gln Thr Thr Leu Met Val Thr His Gln Leu
530                 535                 540

Glu Asp Leu Ala Asp Trp Asp Val Ile Trp Val Met Gln Asp Gly Arg
545                 550                 555                 560

Ile Ile Glu Gln Gly Arg Tyr Ala Glu Leu Ser Val Ala Gly Gly Pro
            565                 570                 575

Phe Ala Thr Leu Leu Ala His Arg Gln Glu Ile
        580                 585

<210> SEQ ID NO 2
<211> LENGTH: 573
<212> TYPE: PRT
<213> ORGANISM: Escherichia coli

<400> SEQUENCE: 2

Met Arg Ala Leu Leu Pro Tyr Leu Ala Leu Tyr Lys Arg His Lys Trp
1               5                   10                  15

Met Leu Ser Leu Gly Ile Val Leu Ala Ile Val Thr Leu Leu Ala Ser
            20                  25                  30

Ile Gly Leu Leu Thr Leu Ser Gly Trp Phe Leu Ser Ala Ser Ala Val
        35                  40                  45

Ala Gly Val Ala Gly Leu Tyr Ser Phe Asn Tyr Met Leu Pro Ala Ala
    50                  55                  60

Gly Val Arg Gly Ala Ala Ile Thr Arg Thr Ala Gly Arg Tyr Phe Glu
65                  70                  75                  80

Arg Leu Val Ser His Asp Ala Thr Phe Arg Val Leu Gln His Leu Arg
                85                  90                  95

Ile Tyr Thr Phe Ser Lys Leu Leu Pro Leu Ser Pro Ala Gly Leu Ala
            100                 105                 110

Arg Tyr Arg Gln Gly Glu Leu Leu Asn Arg Val Val Ala Asp Val Asp
        115                 120                 125

Thr Leu Asp His Leu Tyr Leu Arg Val Ile Ser Pro Leu Val Gly Ala
130                 135                 140

Phe Val Val Ile Met Val Val Thr Ile Gly Leu Ser Phe Leu Asp Phe
145                 150                 155                 160

Thr Leu Ala Phe Thr Leu Gly Gly Ile Met Leu Leu Thr Leu Phe Leu
                165                 170                 175

Met Pro Pro Leu Phe Tyr Arg Ala Gly Lys Ser Thr Gly Gln Asn Leu
            180                 185                 190

Thr His Leu Arg Gly Gln Tyr Arg Gln Leu Thr Ala Trp Leu Gln
        195                 200                 205

Gly Gln Ala Glu Leu Thr Ile Phe Gly Ala Ser Asp Arg Tyr Arg Thr
    210                 215                 220

Gln Leu Glu Asn Thr Glu Ile Gln Trp Leu Glu Ala Gln Arg Arg Gln
225                 230                 235                 240

Ser Glu Leu Thr Ala Leu Ser Gln Ala Ile Met Leu Leu Ile Gly Ala
                245                 250                 255

```
Leu Ala Val Ile Leu Met Leu Trp Met Ala Ser Gly Val Gly Gly
            260                 265                 270

Asn Ala Gln Pro Gly Ala Leu Ile Ala Leu Phe Val Phe Cys Ala Leu
            275                 280                 285

Ala Ala Phe Glu Ala Leu Ala Pro Val Thr Gly Ala Phe Gln His Leu
            290                 295                 300

Gly Gln Val Ile Ala Ser Ala Val Arg Ile Ser Asp Leu Thr Asp Gln
305                 310                 315                 320

Lys Pro Glu Val Thr Phe Pro Asp Thr Gln Thr Arg Val Ala Asp Arg
                325                 330                 335

Val Ser Leu Thr Leu Arg Asp Val Gln Phe Thr Tyr Pro Glu Gln Ser
            340                 345                 350

Gln Gln Ala Leu Lys Gly Ile Ser Leu Gln Val Asn Ala Gly Glu His
            355                 360                 365

Ile Ala Ile Leu Gly Arg Thr Gly Cys Gly Lys Ser Thr Leu Leu Gln
            370                 375                 380

Gln Leu Thr Arg Ala Trp Asp Pro Gln Gln Gly Glu Ile Leu Leu Asn
385                 390                 395                 400

Asp Ser Pro Ile Ala Ser Leu Asn Glu Ala Ala Leu Arg Gln Thr Ile
                405                 410                 415

Ser Val Val Pro Gln Arg Val His Leu Phe Ser Ala Thr Leu Arg Asp
            420                 425                 430

Asn Leu Leu Leu Ala Ser Pro Gly Ser Ser Asp Glu Ala Leu Ser Glu
            435                 440                 445

Ile Leu Arg Arg Val Gly Leu Glu Lys Leu Leu Glu Asp Ala Gly Leu
            450                 455                 460

Asn Ser Trp Leu Gly Glu Gly Gly Arg Gln Leu Ser Gly Gly Glu Leu
465                 470                 475                 480

Arg Arg Leu Ala Ile Ala Arg Ala Leu Leu His Asp Ala Pro Leu Val
                485                 490                 495

Leu Leu Asp Glu Pro Thr Glu Gly Leu Asp Ala Thr Thr Glu Ser Gln
            500                 505                 510

Ile Leu Glu Leu Ala Glu Met Met Arg Glu Lys Thr Val Leu Met
            515                 520                 525

Val Thr His Arg Leu Arg Gly Leu Ser Arg Phe Gln Gln Ile Ile Val
            530                 535                 540

Met Asp Asn Gly Gln Ile Ile Glu Gln Gly Thr His Ala Glu Leu Leu
545                 550                 555                 560

Ala Arg Gln Gly Arg Tyr Tyr Gln Phe Lys Gln Gly Leu
                565                 570

<210> SEQ ID NO 3
<211> LENGTH: 396
<212> TYPE: PRT
<213> ORGANISM: Escherichia coli

<400> SEQUENCE: 3

Met Thr Thr Arg Gln His Ser Ser Phe Ala Ile Val Phe Ile Leu Gly
1               5                   10                  15

Leu Leu Ala Met Leu Met Pro Leu Ser Ile Asp Met Tyr Leu Pro Ala
            20                  25                  30

Leu Pro Val Ile Ser Ala Gln Phe Gly Val Pro Ala Gly Ser Thr Gln
            35                  40                  45

Met Thr Leu Ser Thr Tyr Ile Leu Gly Phe Ala Leu Gly Gln Leu Ile
        50                  55                  60
```

```
Tyr Gly Pro Met Ala Asp Ser Phe Gly Arg Lys Pro Val Val Leu Gly
 65                  70                  75                  80

Gly Thr Leu Val Phe Ala Ala Ala Val Ala Cys Ala Leu Ala Asn
                 85                  90                  95

Thr Ile Asp Gln Leu Ile Val Met Arg Phe Phe His Gly Leu Ala Ala
                100                 105                 110

Ala Ala Ala Ser Val Val Ile Asn Ala Leu Met Arg Asp Ile Tyr Pro
            115                 120                 125

Lys Glu Glu Phe Ser Arg Met Met Ser Phe Val Met Leu Val Thr Thr
130                 135                 140

Ile Ala Pro Leu Met Ala Pro Ile Val Gly Gly Trp Val Leu Val Trp
145                 150                 155                 160

Leu Ser Trp His Tyr Ile Phe Trp Ile Leu Ala Leu Ala Ala Ile Leu
                165                 170                 175

Ala Ser Ala Met Ile Phe Phe Leu Ile Lys Glu Thr Leu Pro Pro Glu
            180                 185                 190

Arg Arg Gln Pro Phe His Ile Arg Thr Thr Ile Gly Asn Phe Ala Ala
            195                 200                 205

Leu Phe Arg His Lys Arg Val Leu Ser Tyr Met Leu Ala Ser Gly Phe
210                 215                 220

Ser Phe Ala Gly Met Phe Ser Phe Leu Ser Ala Gly Pro Phe Val Tyr
225                 230                 235                 240

Ile Glu Ile Asn His Val Ala Pro Glu Asn Phe Gly Tyr Tyr Phe Ala
                245                 250                 255

Leu Asn Ile Val Phe Leu Phe Val Met Thr Ile Phe Asn Ser Arg Phe
            260                 265                 270

Val Arg Arg Ile Gly Ala Leu Asn Met Phe Arg Ser Gly Leu Trp Ile
275                 280                 285

Gln Phe Ile Met Ala Ala Trp Met Val Ile Ser Ala Leu Leu Gly Leu
            290                 295                 300

Gly Phe Trp Ser Leu Val Val Gly Val Ala Ala Phe Val Gly Cys Val
305                 310                 315                 320

Ser Met Val Ser Ser Asn Ala Met Ala Val Ile Leu Asp Glu Phe Pro
                325                 330                 335

His Met Ala Gly Thr Ala Ser Ser Leu Ala Gly Thr Phe Arg Phe Gly
            340                 345                 350

Ile Gly Ala Ile Val Gly Ala Leu Leu Ser Leu Ala Thr Phe Asn Ser
            355                 360                 365

Ala Trp Pro Met Ile Trp Ser Ile Ala Phe Cys Ala Thr Ser Ser Ile
            370                 375                 380

Leu Phe Cys Leu Tyr Ala Ser Arg Pro Lys Lys Arg
385                 390                 395

<210> SEQ ID NO 4
<211> LENGTH: 397
<212> TYPE: PRT
<213> ORGANISM: Escherichia coli

<400> SEQUENCE: 4

Met Ser Glu Ser Val His Thr Asn Thr Ser Leu Trp Ser Lys Gly Met
  1               5                  10                  15

Lys Ala Val Ile Val Ala Gln Phe Leu Ser Ala Phe Gly Asp Asn Ala
                 20                  25                  30

Leu Leu Phe Ala Thr Leu Ala Leu Leu Lys Ala Gln Phe Tyr Pro Glu
             35                  40                  45
```

```
Trp Ser Gln Pro Ile Leu Gln Met Val Phe Val Gly Ala Tyr Ile Leu
    50                  55                  60

Phe Ala Pro Phe Val Gly Gln Val Ala Asp Ser Phe Ala Lys Gly Arg
65                  70                  75                  80

Val Met Met Phe Ala Asn Gly Leu Lys Leu Leu Gly Ala Ala Ser Ile
                    85                  90                  95

Cys Phe Gly Ile Asn Pro Phe Leu Gly Tyr Thr Leu Val Gly Val Gly
                100                 105                 110

Ala Ala Ala Tyr Ser Pro Ala Lys Tyr Gly Ile Leu Gly Glu Leu Thr
            115                 120                 125

Thr Gly Ser Lys Leu Val Lys Ala Asn Gly Leu Met Glu Ala Ser Thr
130                 135                 140

Ile Ala Ala Ile Leu Leu Gly Ser Val Ala Gly Gly Val Leu Ala Asp
145                 150                 155                 160

Trp His Val Leu Val Ala Leu Ala Ala Cys Ala Leu Ala Tyr Gly Gly
                165                 170                 175

Ala Val Val Ala Asn Ile Tyr Ile Pro Lys Leu Ala Ala Arg Pro
                180                 185                 190

Gly Gln Ser Trp Asn Leu Ile Asn Met Thr Arg Ser Phe Leu Asn Ala
            195                 200                 205

Cys Thr Ser Leu Trp Arg Asn Gly Glu Thr Arg Phe Ser Leu Val Gly
    210                 215                 220

Thr Ser Leu Phe Trp Gly Ala Gly Val Thr Leu Arg Phe Leu Leu Val
225                 230                 235                 240

Leu Trp Val Pro Val Ala Leu Gly Ile Thr Asp Asn Ala Thr Pro Thr
                245                 250                 255

Tyr Leu Asn Ala Met Val Ala Ile Gly Ile Val Val Gly Ala Gly Ala
            260                 265                 270

Ala Ala Lys Leu Val Thr Leu Glu Thr Val Ser Arg Cys Met Pro Ala
            275                 280                 285

Gly Ile Leu Ile Gly Val Val Val Leu Ile Phe Ser Leu Gln His Glu
            290                 295                 300

Leu Leu Pro Ala Tyr Ala Leu Leu Met Leu Ile Gly Val Met Gly Gly
305                 310                 315                 320

Phe Phe Val Val Pro Leu Asn Ala Leu Leu Gln Glu Arg Gly Lys Lys
                325                 330                 335

Ser Val Gly Ala Gly Asn Ala Ile Ala Val Gln Asn Leu Gly Glu Asn
            340                 345                 350

Ser Ala Met Leu Leu Met Leu Gly Ile Tyr Ser Leu Ala Val Met Ile
            355                 360                 365

Gly Ile Pro Val Val Pro Ile Gly Ile Gly Phe Gly Ala Leu Phe Ala
            370                 375                 380

Leu Ala Ile Thr Ala Leu Trp Ile Trp Gln Arg Arg His
385                 390                 395

<210> SEQ ID NO 5
<211> LENGTH: 408
<212> TYPE: PRT
<213> ORGANISM: Escherichia coli

<400> SEQUENCE: 5

Met Ser Pro Cys Glu Asn Asp Thr Pro Ile Asn Trp Lys Arg Asn Leu
1               5                   10                  15

Ile Val Ala Trp Leu Gly Cys Phe Leu Thr Gly Ala Ala Phe Ser Leu
            20                  25                  30
```

Val Met Pro Phe Leu Pro Leu Tyr Val Glu Gln Leu Gly Val Thr Gly
         35                  40                  45

His Ser Ala Leu Asn Met Trp Ser Gly Ile Val Phe Ser Ile Thr Phe
 50                  55                  60

Leu Phe Ser Ala Ile Ala Ser Pro Phe Trp Gly Gly Leu Ala Asp Arg
 65                  70                  75                  80

Lys Gly Arg Lys Leu Met Leu Leu Arg Ser Ala Leu Gly Met Gly Ile
                 85                  90                  95

Val Met Val Leu Met Gly Leu Ala Gln Asn Ile Trp Gln Phe Leu Ile
                100                 105                 110

Leu Arg Ala Leu Leu Gly Leu Leu Gly Gly Phe Val Pro Asn Ala Asn
            115                 120                 125

Ala Leu Ile Ala Thr Gln Val Pro Arg Asn Lys Ser Gly Trp Ala Leu
130                 135                 140

Gly Thr Leu Ser Thr Gly Gly Val Ser Gly Ala Leu Leu Gly Pro Met
145                 150                 155                 160

Ala Gly Gly Leu Leu Ala Asp Ser Tyr Gly Leu Arg Pro Val Phe Phe
                165                 170                 175

Ile Thr Ala Ser Val Leu Ile Leu Cys Phe Phe Val Thr Leu Phe Cys
                180                 185                 190

Ile Arg Glu Lys Phe Gln Pro Val Ser Lys Lys Glu Met Leu His Met
                195                 200                 205

Arg Glu Val Val Thr Ser Leu Lys Asn Pro Lys Leu Val Leu Ser Leu
    210                 215                 220

Phe Val Thr Thr Leu Ile Ile Gln Val Ala Thr Gly Ser Ile Ala Pro
225                 230                 235                 240

Ile Leu Thr Leu Tyr Val Arg Glu Leu Ala Gly Asn Val Ser Asn Val
                245                 250                 255

Ala Phe Ile Ser Gly Met Ile Ala Ser Val Pro Gly Val Ala Ala Leu
                260                 265                 270

Leu Ser Ala Pro Arg Leu Gly Lys Leu Gly Asp Arg Ile Gly Pro Glu
            275                 280                 285

Lys Ile Leu Ile Thr Ala Leu Ile Phe Ser Val Leu Leu Leu Ile Pro
290                 295                 300

Met Ser Tyr Val Gln Thr Pro Leu Gln Leu Gly Ile Leu Arg Phe Leu
305                 310                 315                 320

Leu Gly Ala Ala Asp Gly Ala Leu Leu Pro Ala Val Gln Thr Leu Leu
                325                 330                 335

Val Tyr Asn Ser Ser Asn Gln Ile Ala Gly Arg Ile Phe Ser Tyr Asn
                340                 345                 350

Gln Ser Phe Arg Asp Ile Gly Asn Val Thr Gly Pro Leu Met Gly Ala
            355                 360                 365

Ala Ile Ser Ala Asn Tyr Gly Phe Arg Ala Val Phe Leu Val Thr Ala
370                 375                 380

Gly Val Val Leu Phe Asn Ala Val Tyr Ser Trp Asn Ser Leu Arg Arg
385                 390                 395                 400

Arg Arg Ile Pro Gln Val Ser Asn
                405

<210> SEQ ID NO 6
<211> LENGTH: 410
<212> TYPE: PRT
<213> ORGANISM: Escherichia coli

<400> SEQUENCE: 6

```
Met Gln Asn Lys Leu Ala Ser Gly Ala Arg Leu Gly Arg Gln Ala Leu
1               5                   10                  15

Leu Phe Pro Leu Cys Leu Val Leu Tyr Glu Phe Ser Thr Tyr Ile Gly
            20                  25                  30

Asn Asp Met Ile Gln Pro Gly Met Leu Ala Val Val Glu Gln Tyr Gln
            35                  40                  45

Ala Gly Ile Asp Trp Val Pro Thr Ser Met Thr Ala Tyr Leu Ala Gly
50                  55                  60

Gly Met Phe Leu Gln Trp Leu Leu Gly Pro Leu Ser Asp Arg Ile Gly
65                  70                  75                  80

Arg Arg Pro Val Met Leu Ala Gly Val Val Trp Phe Ile Val Thr Cys
                85                  90                  95

Leu Ala Ile Leu Leu Ala Gln Asn Ile Glu Gln Phe Thr Leu Leu Arg
            100                 105                 110

Phe Leu Gln Gly Ile Ser Leu Cys Phe Ile Gly Ala Val Gly Tyr Ala
            115                 120                 125

Ala Ile Gln Glu Ser Phe Glu Glu Ala Val Cys Ile Lys Ile Thr Ala
            130                 135                 140

Leu Met Ala Asn Val Ala Leu Ile Ala Pro Leu Leu Gly Pro Leu Val
145                 150                 155                 160

Gly Ala Ala Trp Ile His Val Leu Pro Trp Glu Gly Met Phe Val Leu
                165                 170                 175

Phe Ala Ala Leu Ala Ala Ile Ser Phe Phe Gly Leu Gln Arg Ala Met
            180                 185                 190

Pro Glu Thr Ala Thr Arg Ile Gly Glu Lys Leu Ser Leu Lys Glu Leu
            195                 200                 205

Gly Arg Asp Tyr Lys Leu Val Leu Lys Asn Gly Arg Phe Val Ala Gly
210                 215                 220

Ala Leu Ala Leu Gly Phe Val Ser Leu Pro Leu Leu Ala Trp Ile Ala
225                 230                 235                 240

Gln Ser Pro Ile Ile Ile Thr Gly Glu Gln Leu Ser Ser Tyr Glu
            245                 250                 255

Tyr Gly Leu Leu Gln Val Pro Ile Phe Gly Ala Leu Ile Ala Gly Asn
            260                 265                 270

Leu Leu Leu Ala Arg Leu Thr Ser Arg Arg Thr Val Arg Ser Leu Ile
            275                 280                 285

Ile Met Gly Gly Trp Pro Ile Met Ile Gly Leu Leu Val Ala Ala Ala
            290                 295                 300

Ala Thr Val Ile Ser Ser His Ala Tyr Leu Met Thr Ala Gly Leu
305                 310                 315                 320

Ser Ile Tyr Ala Phe Gly Ile Gly Leu Ala Asn Ala Gly Leu Val Arg
            325                 330                 335

Leu Thr Leu Phe Ala Ser Asp Met Ser Lys Gly Thr Val Ser Ala Ala
            340                 345                 350

Met Gly Met Leu Gln Met Leu Ile Phe Thr Val Gly Ile Glu Ile Ser
            355                 360                 365

Lys His Ala Trp Leu Asn Gly Asn Gly Leu Phe Asn Leu Phe Asn
            370                 375                 380

Leu Val Asn Gly Ile Leu Trp Leu Ser Leu Met Val Ile Phe Leu Lys
385                 390                 395                 400

Asp Lys Gln Met Gly Asn Ser His Glu Gly
            405                 410
```

<210> SEQ ID NO 7

```
<211> LENGTH: 125
<212> TYPE: PRT
<213> ORGANISM: Escherichia coli

<400> SEQUENCE: 7

Met Val Asn Gln Lys Lys Asp Arg Leu Leu Asn Glu Tyr Leu Ser Pro
 1               5                  10                  15

Leu Asp Ile Thr Ala Ala Gln Phe Lys Val Leu Cys Ser Ile Arg Cys
                20                  25                  30

Ala Ala Cys Ile Thr Pro Val Glu Leu Lys Lys Val Leu Ser Val Asp
            35                  40                  45

Leu Gly Ala Leu Thr Arg Met Leu Asp Arg Leu Val Cys Lys Gly Trp
        50                  55                  60

Val Glu Arg Leu Pro Asn Pro Asn Asp Lys Arg Gly Val Leu Val Lys
 65                  70                  75                  80

Leu Thr Thr Gly Gly Ala Ala Ile Cys Glu Gln Cys His Gln Leu Val
                85                  90                  95

Gly Gln Asp Leu His Gln Glu Leu Thr Lys Asn Leu Thr Ala Asp Glu
            100                 105                 110

Val Ala Thr Leu Glu Tyr Leu Leu Lys Lys Val Leu Pro
        115                 120                 125

<210> SEQ ID NO 8
<211> LENGTH: 129
<212> TYPE: PRT
<213> ORGANISM: Escherichia coli

<400> SEQUENCE: 8

Met Thr Met Ser Arg Arg Asn Thr Asp Ala Ile Thr Ile His Ser Ile
 1               5                  10                  15

Leu Asp Trp Ile Glu Asp Asn Leu Glu Ser Pro Leu Ser Leu Glu Lys
                20                  25                  30

Val Ser Glu Arg Ser Gly Tyr Ser Lys Trp His Leu Gln Arg Met Phe
            35                  40                  45

Lys Lys Glu Thr Gly His Ser Leu Gly Gln Tyr Ile Arg Ser Arg Lys
        50                  55                  60

Met Thr Glu Ile Ala Gln Lys Leu Lys Glu Ser Asn Glu Pro Ile Leu
 65                  70                  75                  80

Tyr Leu Ala Glu Arg Tyr Gly Phe Glu Ser Gln Gln Thr Leu Thr Arg
                85                  90                  95

Thr Phe Lys Asn Tyr Phe Asp Val Pro Pro His Lys Tyr Arg Met Thr
            100                 105                 110

Asn Met Gln Gly Glu Ser Arg Phe Leu His Pro Leu Asn His Tyr Asn
        115                 120                 125

Ser

<210> SEQ ID NO 9
<211> LENGTH: 72
<212> TYPE: PRT
<213> ORGANISM: Escherichia coli

<400> SEQUENCE: 9

Met Lys Pro Leu Ser Ser Ala Ile Ala Ala Leu Ile Leu Phe Ser
 1               5                  10                  15

Ala Gln Gly Val Ala Glu Gln Thr Thr Gln Pro Val Val Thr Ser Cys
                20                  25                  30

Ala Asn Val Val Val Val Pro Ser Gln Glu His Pro Pro Phe Asp
            35                  40                  45
```

Leu Asn His Met Gly Thr Gly Ser Asp Lys Ser Asp Ala Leu Gly Val
        50                  55                  60

Pro Tyr Tyr Asn Gln His Ala Met
 65                  70

<210> SEQ ID NO 10
<211> LENGTH: 397
<212> TYPE: PRT
<213> ORGANISM: Escherichia coli

<400> SEQUENCE: 10

Met Asn Lys Asn Arg Gly Phe Thr Pro Leu Ala Val Val Leu Met Leu
 1               5                  10                  15

Ser Gly Ser Leu Ala Leu Thr Gly Cys Asp Asp Lys Gln Ala Gln Gln
                20                  25                  30

Gly Gly Gln Gln Met Pro Ala Val Gly Val Val Thr Val Lys Thr Glu
            35                  40                  45

Pro Leu Gln Ile Thr Thr Glu Leu Pro Gly Arg Thr Ser Ala Tyr Arg
    50                  55                  60

Ile Ala Glu Val Arg Pro Gln Val Ser Gly Ile Ile Leu Lys Arg Asn
 65                  70                  75                  80

Phe Lys Glu Gly Ser Asp Ile Glu Ala Gly Val Ser Leu Tyr Gln Ile
                85                  90                  95

Asp Pro Ala Thr Tyr Gln Ala Thr Tyr Asp Ser Ala Lys Gly Asp Leu
            100                 105                 110

Ala Lys Ala Gln Ala Ala Ala Asn Ile Ala Gln Leu Thr Val Asn Arg
        115                 120                 125

Tyr Gln Lys Leu Leu Gly Thr Gln Tyr Ile Ser Lys Gln Glu Tyr Asp
    130                 135                 140

Gln Ala Leu Ala Asp Ala Gln Gln Ala Asn Ala Ala Val Thr Ala Ala
145                 150                 155                 160

Lys Ala Ala Val Glu Thr Ala Arg Ile Asn Leu Ala Tyr Thr Lys Val
                165                 170                 175

Thr Ser Pro Ile Ser Gly Arg Ile Gly Lys Ser Asn Val Thr Glu Gly
            180                 185                 190

Ala Leu Val Gln Asn Gly Gln Ala Thr Ala Leu Ala Thr Val Gln Gln
        195                 200                 205

Leu Asp Pro Ile Tyr Val Asp Val Thr Gln Ser Ser Asn Asp Phe Leu
    210                 215                 220

Arg Leu Lys Gln Glu Leu Ala Asn Gly Thr Leu Lys Gln Glu Asn Gly
225                 230                 235                 240

Lys Ala Lys Val Ser Leu Ile Thr Ser Asp Gly Ile Lys Phe Pro Gln
                245                 250                 255

Asp Gly Thr Leu Glu Phe Ser Asp Val Thr Val Asp Gln Thr Thr Gly
            260                 265                 270

Ser Ile Thr Leu Arg Ala Ile Phe Pro Asn Pro Asp His Thr Leu Leu
        275                 280                 285

Pro Gly Met Phe Val Arg Ala Arg Leu Glu Glu Gly Leu Asn Pro Asn
    290                 295                 300

Ala Ile Leu Val Pro Gln Gln Gly Val Thr Arg Thr Pro Arg Gly Asp
305                 310                 315                 320

Ala Thr Val Leu Val Val Gly Ala Asp Asp Lys Val Glu Thr Arg Pro
                325                 330                 335

Ile Val Ala Ser Gln Ala Ile Gly Asp Lys Trp Leu Val Thr Glu Gly
            340                 345                 350

Leu Lys Ala Gly Asp Arg Val Val Ile Ser Gly Leu Gln Lys Val Arg
            355                 360                 365

Pro Gly Val Gln Val Lys Ala Gln Glu Val Thr Ala Asp Asn Asn Gln
        370                 375                 380

Gln Ala Ala Ser Gly Ala Gln Pro Glu Gln Ser Lys Ser
385                 390                 395

<210> SEQ ID NO 11
<211> LENGTH: 1049
<212> TYPE: PRT
<213> ORGANISM: Escherichia coli

<400> SEQUENCE: 11

Met Pro Asn Phe Phe Ile Asp Arg Pro Ile Phe Ala Trp Val Ile Ala
  1               5                  10                  15

Ile Ile Ile Met Leu Ala Gly Gly Leu Ala Ile Leu Lys Leu Pro Val
             20                  25                  30

Ala Gln Tyr Pro Thr Ile Ala Pro Pro Ala Val Thr Ile Ser Ala Ser
         35                  40                  45

Tyr Pro Gly Ala Asp Ala Lys Thr Val Gln Asp Thr Val Thr Gln Val
     50                  55                  60

Ile Glu Gln Asn Met Asn Gly Ile Asp Asn Leu Met Tyr Met Ser Ser
 65                  70                  75                  80

Asn Ser Asp Ser Thr Gly Thr Val Gln Ile Thr Leu Thr Phe Glu Ser
                 85                  90                  95

Gly Thr Asp Ala Asp Ile Ala Gln Val Gln Val Gln Asn Lys Leu Gln
            100                 105                 110

Leu Ala Met Pro Leu Leu Pro Gln Glu Val Gln Gln Gln Gly Val Ser
        115                 120                 125

Val Glu Lys Ser Ser Ser Ser Phe Leu Met Val Val Gly Val Ile Asn
    130                 135                 140

Thr Asp Gly Thr Met Thr Gln Glu Asp Ile Ser Asp Tyr Val Ala Ala
145                 150                 155                 160

Asn Met Lys Asp Ala Ile Ser Arg Thr Ser Gly Val Gly Asp Val Gln
                165                 170                 175

Leu Phe Gly Ser Gln Tyr Ala Met Arg Ile Trp Met Asn Pro Asn Glu
            180                 185                 190

Leu Asn Lys Phe Gln Leu Thr Pro Val Asp Val Ile Thr Ala Ile Lys
        195                 200                 205

Ala Gln Asn Ala Gln Val Ala Ala Gly Gln Leu Gly Gly Thr Pro Pro
    210                 215                 220

Val Lys Gly Gln Gln Leu Asn Ala Ser Ile Ile Ala Gln Thr Arg Leu
225                 230                 235                 240

Thr Ser Thr Glu Glu Phe Gly Lys Ile Leu Leu Lys Val Asn Gln Asp
                245                 250                 255

Gly Ser Arg Val Leu Leu Arg Asp Val Ala Lys Ile Glu Leu Gly Gly
            260                 265                 270

Glu Asn Tyr Asp Ile Ile Ala Glu Phe Asn Gly Gln Pro Ala Ser Gly
        275                 280                 285

Leu Gly Ile Lys Leu Ala Thr Gly Ala Asn Ala Leu Asp Thr Ala Ala
    290                 295                 300

Ala Ile Arg Ala Glu Leu Ala Lys Met Glu Pro Phe Phe Pro Ser Gly
305                 310                 315                 320

Leu Lys Ile Val Tyr Pro Tyr Asp Thr Thr Pro Phe Val Lys Ile Ser
                325                 330                 335

```
Ile His Glu Val Val Lys Thr Leu Val Glu Ala Ile Ile Leu Val Phe
            340                 345                 350
Leu Val Met Tyr Leu Phe Leu Gln Asn Phe Arg Ala Thr Leu Ile Pro
            355                 360                 365
Thr Ile Ala Val Pro Val Leu Leu Gly Thr Phe Ala Val Leu Ala
            370                 375                 380
Ala Phe Gly Phe Ser Ile Asn Thr Leu Thr Met Phe Gly Met Val Leu
385                 390                 395                 400
Ala Ile Gly Leu Leu Val Asp Asp Ala Ile Val Val Glu Asn Val
                405                 410                 415
Glu Arg Val Met Ala Glu Gly Leu Pro Pro Lys Glu Ala Thr Arg
                420                 425                 430
Lys Ser Met Gly Gln Ile Gln Gly Ala Leu Val Gly Ile Ala Met Val
                435                 440                 445
Leu Ser Ala Val Phe Val Pro Met Ala Phe Phe Gly Gly Ser Thr Gly
            450                 455                 460
Ala Ile Tyr Arg Gln Phe Ser Ile Thr Ile Val Ser Ala Met Ala Leu
465                 470                 475                 480
Ser Val Leu Val Ala Leu Ile Leu Thr Pro Ala Leu Cys Ala Thr Met
                485                 490                 495
Leu Lys Pro Ile Ala Lys Gly Asp His Gly Glu Gly Lys Lys Gly Phe
            500                 505                 510
Phe Gly Trp Phe Asn Arg Met Phe Glu Lys Ser Thr His His Tyr Thr
            515                 520                 525
Asp Ser Val Gly Gly Ile Leu Arg Ser Thr Gly Arg Tyr Leu Val Leu
            530                 535                 540
Tyr Leu Ile Ile Val Val Gly Met Ala Tyr Leu Phe Val Arg Leu Pro
545                 550                 555                 560
Ser Ser Phe Leu Pro Asp Glu Asp Gln Gly Val Phe Met Thr Met Val
                565                 570                 575
Gln Leu Pro Ala Gly Ala Thr Gln Glu Arg Thr Gln Lys Val Leu Asn
            580                 585                 590
Glu Val Thr His Tyr Tyr Leu Thr Lys Glu Lys Asn Asn Val Glu Ser
                595                 600                 605
Val Phe Ala Val Asn Gly Phe Gly Phe Ala Gly Arg Gly Gln Asn Thr
            610                 615                 620
Gly Ile Ala Phe Val Ser Leu Lys Asp Trp Ala Asp Arg Pro Gly Glu
625                 630                 635                 640
Glu Asn Lys Val Glu Ala Ile Thr Met Arg Ala Thr Arg Ala Phe Ser
                645                 650                 655
Gln Ile Lys Asp Ala Met Val Phe Ala Phe Asn Leu Pro Ala Ile Val
            660                 665                 670
Glu Leu Gly Thr Ala Thr Gly Phe Asp Phe Glu Leu Ile Asp Gln Ala
            675                 680                 685
Gly Leu Gly His Glu Lys Leu Thr Gln Ala Arg Asn Gln Leu Leu Ala
            690                 695                 700
Glu Ala Ala Lys His Pro Asp Met Leu Thr Ser Val Arg Pro Asn Gly
705                 710                 715                 720
Leu Glu Asp Thr Pro Gln Phe Lys Ile Asp Ile Asp Gln Glu Lys Ala
                725                 730                 735
Gln Ala Leu Gly Val Ser Ile Asn Asp Ile Asn Thr Thr Leu Gly Ala
            740                 745                 750
Ala Trp Gly Gly Ser Tyr Val Asn Asp Phe Ile Asp Arg Gly Arg Val
```

```
                    755                 760                 765
Lys Lys Val Tyr Val Met Ser Glu Ala Lys Tyr Arg Met Leu Pro Asp
    770                 775                 780

Asp Ile Gly Asp Trp Tyr Val Arg Ala Ala Asp Gly Gln Met Val Pro
785                 790                 795                 800

Phe Ser Ala Phe Ser Ser Arg Trp Glu Tyr Gly Ser Pro Arg Leu
                805                 810                 815

Glu Arg Tyr Asn Gly Leu Pro Ser Met Glu Ile Leu Gly Gln Ala Ala
            820                 825                 830

Pro Gly Lys Ser Thr Gly Glu Ala Met Glu Leu Met Glu Gln Leu Ala
        835                 840                 845

Ser Lys Leu Pro Thr Gly Val Gly Tyr Asp Trp Thr Gly Met Ser Tyr
850                 855                 860

Gln Glu Arg Leu Ser Gly Asn Gln Ala Pro Ser Leu Tyr Ala Ile Ser
865                 870                 875                 880

Leu Ile Val Val Phe Leu Cys Leu Ala Ala Leu Tyr Glu Ser Trp Ser
                885                 890                 895

Ile Pro Phe Ser Val Met Leu Val Val Pro Leu Gly Val Ile Gly Ala
            900                 905                 910

Leu Leu Ala Ala Thr Phe Arg Gly Leu Thr Asn Asp Val Tyr Phe Gln
        915                 920                 925

Val Gly Leu Leu Thr Thr Ile Gly Leu Ser Ala Lys Asn Ala Ile Leu
    930                 935                 940

Ile Val Glu Phe Ala Lys Asp Leu Met Asp Lys Glu Gly Lys Gly Leu
945                 950                 955                 960

Ile Glu Ala Thr Leu Asp Ala Val Arg Met Arg Leu Arg Pro Ile Leu
                965                 970                 975

Met Thr Ser Leu Ala Phe Ile Leu Gly Val Met Pro Leu Val Ile Ser
            980                 985                 990

Thr Gly Ala Gly Ser Gly Ala Gln Asn Ala Val Gly Thr Gly Val Met
        995                 1000                1005

Gly Gly Met Val Thr Ala Thr Val Leu Ala Ile Phe Phe Val Pro Val
    1010                1015                1020

Phe Phe Val Val Arg Arg Arg Phe Ser Arg Lys Asn Glu Asp Ile
1025                1030                1035                1040

Glu His Ser His Thr Val Asp His His
            1045

<210> SEQ ID NO 12
<211> LENGTH: 390
<212> TYPE: PRT
<213> ORGANISM: Escherichia coli

<400> SEQUENCE: 12

Met Ser Ala Asn Ala Glu Thr Gln Thr Pro Gln Gln Pro Val Lys Lys
1               5                   10                  15

Ser Gly Lys Arg Lys Arg Leu Leu Leu Leu Thr Leu Leu Phe Ile
            20                  25                  30

Ile Ile Ala Val Ala Ile Gly Ile Tyr Trp Phe Leu Val Leu Arg His
        35                  40                  45

Phe Glu Glu Thr Asp Asp Ala Tyr Val Ala Gly Asn Gln Ile Gln Ile
    50                  55                  60

Met Ser Gln Val Ser Gly Ser Val Thr Lys Val Trp Ala Asp Asn Thr
65                  70                  75                  80

Asp Phe Val Lys Glu Gly Asp Val Leu Val Thr Leu Asp Pro Thr Asp
```

85                  90                  95
Ala Arg Gln Ala Phe Glu Lys Ala Lys Thr Ala Leu Ala Ser Ser Val
            100                 105                 110

Arg Gln Thr His Gln Leu Met Ile Asn Ser Lys Gln Leu Gln Ala Asn
        115                 120                 125

Ile Glu Val Gln Lys Ile Ala Leu Ala Lys Ala Gln Ser Asp Tyr Asn
    130                 135                 140

Arg Arg Val Pro Leu Gly Asn Ala Asn Leu Ile Gly Arg Glu Glu Leu
145                 150                 155                 160

Gln His Ala Arg Asp Ala Val Thr Ser Ala Gln Ala Gln Leu Asp Val
                165                 170                 175

Ala Ile Gln Gln Tyr Asn Ala Asn Gln Ala Met Ile Leu Gly Thr Lys
            180                 185                 190

Leu Glu Asp Gln Pro Ala Val Gln Gln Ala Thr Glu Val Arg Asn
        195                 200                 205

Ala Trp Leu Ala Leu Glu Arg Thr Arg Ile Ile Ser Pro Met Thr Gly
    210                 215                 220

Tyr Val Ser Arg Arg Ala Val Gln Pro Gly Ala Gln Ile Ser Pro Thr
225                 230                 235                 240

Thr Pro Leu Met Ala Val Val Pro Ala Thr Asn Met Trp Val Asp Ala
                245                 250                 255

Asn Phe Lys Glu Thr Gln Ile Ala Asn Met Arg Ile Gly Gln Pro Val
            260                 265                 270

Thr Ile Thr Thr Asp Ile Tyr Gly Asp Asp Val Lys Tyr Thr Gly Lys
        275                 280                 285

Val Val Gly Leu Asp Met Gly Thr Gly Ser Ala Phe Ser Leu Leu Pro
    290                 295                 300

Ala Gln Asn Ala Thr Gly Asn Trp Ile Lys Val Val Gln Arg Leu Pro
305                 310                 315                 320

Val Arg Ile Glu Leu Asp Gln Lys Gln Leu Glu Gln Tyr Pro Leu Arg
                325                 330                 335

Ile Gly Leu Ser Thr Leu Val Ser Val Asn Thr Thr Asn Arg Asp Gly
            340                 345                 350

Gln Val Leu Ala Asn Lys Val Arg Ser Thr Pro Val Ala Val Ser Thr
        355                 360                 365

Ala Arg Glu Ile Ser Leu Ala Pro Val Asn Lys Leu Ile Asp Asp Ile
    370                 375                 380

Val Lys Ala Asn Ala Gly
385                 390

<210> SEQ ID NO 13
<211> LENGTH: 512
<212> TYPE: PRT
<213> ORGANISM: Escherichia coli

<400> SEQUENCE: 13

Met Gln Gln Gln Lys Pro Leu Glu Gly Ala Gln Leu Val Ile Met Thr
1               5                   10                  15

Ile Ala Leu Ser Leu Ala Thr Phe Met Gln Val Leu Asp Ser Thr Ile
            20                  25                  30

Ala Asn Val Ala Ile Pro Thr Ile Ala Gly Asn Leu Gly Ser Ser Leu
        35                  40                  45

Ser Gln Gly Thr Trp Val Ile Thr Ser Phe Gly Val Ala Asn Ala Ile
    50                  55                  60

Ser Ile Pro Leu Thr Gly Trp Leu Ala Lys Arg Val Gly Glu Val Lys

```
            65                  70                  75                  80
Leu Phe Leu Trp Ser Thr Ile Ala Phe Ala Ile Ala Ser Trp Ala Cys
                        85                  90                  95
Gly Val Ser Ser Ser Leu Asn Met Leu Ile Phe Phe Arg Val Ile Gln
                    100                 105                 110
Gly Ile Val Ala Gly Pro Leu Ile Pro Leu Ser Gln Ser Leu Leu Leu
                115                 120                 125
Asn Asn Tyr Pro Pro Ala Lys Arg Ser Ile Ala Leu Ala Leu Trp Ser
            130                 135                 140
Met Thr Val Ile Val Ala Pro Ile Cys Gly Pro Ile Leu Gly Gly Tyr
145                 150                 155                 160
Ile Ser Asp Asn Tyr His Trp Gly Trp Ile Phe Phe Ile Asn Val Pro
                        165                 170                 175
Ile Gly Val Ala Val Val Leu Met Thr Leu Gln Thr Leu Arg Gly Arg
                    180                 185                 190
Glu Thr Arg Thr Glu Arg Arg Ile Asp Ala Val Gly Leu Ala Leu
                195                 200                 205
Leu Val Ile Gly Ile Gly Ser Leu Gln Ile Met Leu Asp Arg Gly Lys
            210                 215                 220
Glu Leu Asp Trp Phe Ser Ser Gln Glu Ile Ile Ile Leu Thr Val Val
225                 230                 235                 240
Ala Val Val Ala Ile Cys Phe Leu Ile Val Trp Glu Leu Thr Asp Asp
                        245                 250                 255
Asn Pro Ile Val Asp Leu Ser Leu Phe Lys Ser Arg Asn Phe Thr Ile
                    260                 265                 270
Gly Cys Leu Cys Ile Ser Leu Ala Tyr Met Leu Tyr Phe Gly Ala Ile
                275                 280                 285
Val Leu Leu Pro Gln Leu Leu Gln Glu Val Tyr Gly Tyr Thr Ala Thr
            290                 295                 300
Trp Ala Gly Leu Ala Ser Ala Pro Val Gly Ile Pro Val Ile Leu
305                 310                 315                 320
Ser Pro Ile Ile Gly Arg Phe Ala His Lys Leu Asp Met Arg Arg Leu
                        325                 330                 335
Val Thr Phe Ser Phe Ile Met Tyr Ala Val Cys Phe Tyr Trp Arg Ala
                    340                 345                 350
Tyr Thr Phe Glu Pro Gly Met Asp Phe Gly Ala Ser Ala Trp Pro Gln
                355                 360                 365
Phe Ile Gln Gly Phe Ala Val Ala Cys Phe Phe Met Pro Leu Thr Thr
            370                 375                 380
Ile Thr Leu Ser Gly Leu Pro Pro Glu Arg Leu Ala Ala Ala Ser Ser
385                 390                 395                 400
Leu Ser Asn Phe Thr Arg Thr Leu Ala Gly Ser Ile Gly Thr Ser Ile
                        405                 410                 415
Thr Thr Thr Met Trp Thr Asn Arg Glu Ser Met His His Ala Gln Leu
                    420                 425                 430
Thr Glu Ser Val Asn Pro Phe Asn Pro Asn Ala Gln Ala Met Tyr Ser
                435                 440                 445
Gln Leu Glu Gly Leu Gly Met Thr Gln Gln Ala Ser Gly Trp Ile
            450                 455                 460
Ala Gln Gln Ile Thr Asn Gln Gly Leu Ile Ile Ser Ala Asn Glu Ile
465                 470                 475                 480
Phe Trp Met Ser Ala Gly Ile Phe Leu Val Leu Leu Gly Leu Val Trp
                        485                 490                 495
```

```
Phe Ala Lys Pro Pro Phe Gly Ala Gly Gly Gly Gly Gly Ala His
                500                 505                 510
```

```
<210> SEQ ID NO 14
<211> LENGTH: 110
<212> TYPE: PRT
<213> ORGANISM: Escherichia coli

<400> SEQUENCE: 14

Met Asn Pro Tyr Ile Tyr Leu Gly Gly Ala Ile Leu Ala Glu Val Ile
  1               5                  10                  15

Gly Thr Thr Leu Met Lys Phe Ser Glu Gly Phe Thr Arg Leu Trp Pro
                 20                  25                  30

Ser Val Gly Thr Ile Ile Cys Tyr Cys Ala Ser Phe Trp Leu Leu Ala
             35                  40                  45

Gln Thr Leu Ala Tyr Ile Pro Thr Gly Ile Ala Tyr Ala Ile Trp Ser
         50                  55                  60

Gly Val Gly Ile Val Leu Ile Ser Leu Leu Ser Trp Gly Phe Phe Gly
 65                  70                  75                  80

Gln Arg Leu Asp Leu Pro Ala Ile Ile Gly Met Met Leu Ile Cys Ala
                 85                  90                  95

Gly Val Leu Ile Ile Asn Leu Leu Ser Arg Ser Thr Pro His
                100                 105                 110
```

```
<210> SEQ ID NO 15
<211> LENGTH: 403
<212> TYPE: PRT
<213> ORGANISM: Escherichia coli

<400> SEQUENCE: 15

Met Gln Pro Gly Lys Arg Phe Leu Val Trp Leu Ala Gly Leu Ser Val
  1               5                  10                  15

Leu Gly Phe Leu Ala Thr Asp Met Tyr Leu Pro Ala Phe Ala Ala Ile
                 20                  25                  30

Gln Ala Asp Leu Gln Thr Pro Ala Ser Ala Val Ser Ala Ser Leu Ser
             35                  40                  45

Leu Phe Leu Ala Gly Phe Ala Ala Gln Leu Leu Trp Gly Pro Leu
         50                  55                  60

Ser Asp Arg Tyr Gly Arg Lys Pro Val Leu Ile Gly Leu Thr Ile
 65                  70                  75                  80

Phe Ala Leu Gly Ser Leu Gly Met Leu Trp Val Glu Asn Ala Ala Thr
                 85                  90                  95

Leu Leu Val Leu Arg Phe Val Gln Ala Val Gly Val Cys Ala Ala Ala
                100                 105                 110

Val Ile Trp Gln Ala Leu Val Thr Asp Tyr Tyr Pro Ser Gln Lys Val
                115                 120                 125

Asn Arg Ile Phe Ala Ala Ile Met Pro Leu Val Gly Leu Ser Pro Ala
            130                 135                 140

Leu Ala Pro Leu Leu Gly Ser Trp Leu Leu Val His Phe Ser Trp Gln
145                 150                 155                 160

Ala Ile Phe Ala Thr Leu Phe Ala Ile Thr Val Val Leu Ile Leu Pro
                165                 170                 175

Ile Phe Trp Leu Lys Pro Thr Thr Lys Ala Arg Asn Asn Ser Gln Asp
                180                 185                 190

Gly Leu Thr Phe Thr Asp Leu Leu Arg Ser Lys Thr Tyr Arg Gly Asn
            195                 200                 205

Val Leu Ile Tyr Ala Ala Cys Ser Ala Ser Phe Phe Ala Trp Leu Thr
```

-continued

```
                210                 215                 220
Gly Ser Pro Phe Ile Leu Ser Glu Met Gly Tyr Ser Pro Ala Val Ile
225                 230                 235                 240

Gly Leu Ser Tyr Val Pro Gln Thr Ile Ala Phe Leu Ile Gly Gly Tyr
            245                 250                 255

Gly Cys Arg Ala Ala Leu Gln Lys Trp Gln Gly Lys Gln Leu Leu Pro
        260                 265                 270

Trp Leu Leu Val Leu Phe Ala Val Ser Val Ile Ala Thr Trp Ala Ala
    275                 280                 285

Gly Phe Ile Ser His Val Ser Leu Val Glu Ile Leu Ile Pro Phe Cys
290                 295                 300

Val Met Ala Ile Ala Asn Gly Ala Ile Tyr Pro Ile Val Val Ala Gln
305                 310                 315                 320

Ala Leu Arg Pro Phe Pro His Ala Thr Gly Arg Ala Ala Ala Leu Gln
            325                 330                 335

Asn Thr Leu Gln Leu Gly Leu Cys Phe Leu Ala Ser Leu Val Val Ser
        340                 345                 350

Trp Leu Ile Ser Ile Ser Thr Pro Leu Leu Thr Thr Thr Ser Val Met
    355                 360                 365

Leu Ser Thr Val Met Leu Val Ala Leu Gly Tyr Met Met Gln Arg Cys
370                 375                 380

Glu Glu Val Gly Cys Gln Asn His Gly Asn Ala Glu Val Ala His Ser
385                 390                 395                 400

Glu Ser His

<210> SEQ ID NO 16
<211> LENGTH: 395
<212> TYPE: PRT
<213> ORGANISM: Escherichia coli

<400> SEQUENCE: 16

Met Asn Leu Ser Leu Arg Arg Ser Thr Ser Ala Leu Leu Ala Ser Ser
1               5                   10                  15

Leu Leu Leu Thr Ile Gly Arg Gly Ala Thr Leu Pro Phe Met Thr Ile
            20                  25                  30

Tyr Leu Ser Arg Gln Tyr Ser Leu Ser Val Asp Leu Ile Gly Tyr Ala
        35                  40                  45

Met Thr Ile Ala Leu Thr Ile Gly Val Val Phe Ser Leu Gly Phe Gly
    50                  55                  60

Ile Leu Ala Asp Lys Phe Asp Lys Lys Arg Tyr Met Leu Leu Ala Ile
65                  70                  75                  80

Thr Ala Phe Ala Ser Gly Phe Ile Ala Ile Thr Leu Val Asn Asn Val
                85                  90                  95

Thr Leu Val Val Leu Phe Phe Ala Leu Ile Asn Cys Ala Tyr Ser Val
            100                 105                 110

Phe Ala Thr Val Leu Lys Ala Trp Phe Ala Asp Asn Leu Ser Ser Thr
        115                 120                 125

Ser Lys Thr Lys Ile Phe Ser Ile Asn Tyr Thr Met Leu Asn Ile Gly
    130                 135                 140

Trp Thr Ile Gly Pro Pro Leu Gly Thr Leu Leu Val Met Gln Ser Ile
145                 150                 155                 160

Asn Leu Pro Phe Trp Leu Ala Ala Ile Cys Ser Ala Phe Pro Met Leu
                165                 170                 175

Phe Ile Gln Ile Trp Val Lys Arg Ser Glu Lys Ile Ile Ala Thr Glu
            180                 185                 190
```

Thr Gly Ser Val Trp Ser Pro Lys Val Leu Gln Asp Lys Ala Leu
                195                 200                 205

Leu Trp Phe Thr Cys Ser Gly Phe Leu Ala Ser Phe Val Ser Gly Ala
210                 215                 220

Phe Ala Ser Cys Ile Ser Gln Tyr Val Met Val Ile Ala Asp Gly Asp
225                 230                 235                 240

Phe Ala Glu Lys Val Val Ala Val Val Leu Pro Val Asn Ala Ala Met
                245                 250                 255

Val Val Thr Leu Gln Tyr Ser Val Gly Arg Arg Leu Asn Pro Ala Asn
                260                 265                 270

Ile Arg Ala Leu Met Thr Ala Gly Thr Leu Cys Phe Val Ile Gly Leu
                275                 280                 285

Val Gly Phe Ile Phe Ser Gly Asn Ser Leu Leu Leu Trp Gly Met Ser
                290                 295                 300

Ala Ala Val Phe Thr Val Gly Glu Ile Ile Tyr Ala Pro Gly Glu Tyr
305                 310                 315                 320

Met Leu Ile Asp His Ile Ala Pro Pro Glu Met Lys Ala Ser Tyr Phe
                325                 330                 335

Ser Ala Gln Ser Leu Gly Trp Leu Gly Ala Ala Ile Asn Pro Leu Val
                340                 345                 350

Ser Gly Val Val Leu Thr Ser Leu Pro Pro Ser Ser Leu Phe Val Ile
                355                 360                 365

Leu Ala Leu Val Ile Ile Ala Ala Trp Val Leu Met Leu Lys Gly Ile
                370                 375                 380

Arg Ala Arg Pro Trp Gly Gln Pro Ala Leu Cys
385                 390                 395

<210> SEQ ID NO 17
<211> LENGTH: 396
<212> TYPE: PRT
<213> ORGANISM: Escherichia coli

<400> SEQUENCE: 17

Met Thr Thr Asn Thr Val Ser Arg Lys Val Ala Trp Leu Arg Val Val
1               5                   10                  15

Thr Leu Ala Val Ala Ala Phe Ile Phe Asn Thr Thr Glu Phe Val Pro
                20                  25                  30

Val Gly Leu Leu Ser Asp Ile Ala Gln Ser Phe His Met Gln Thr Ala
                35                  40                  45

Gln Val Gly Ile Met Leu Thr Ile Tyr Ala Trp Val Val Ala Leu Met
            50                  55                  60

Ser Leu Pro Phe Met Leu Met Thr Ser Gln Val Glu Arg Arg Lys Leu
65                  70                  75                  80

Leu Ile Cys Leu Phe Val Val Phe Ile Ala Ser His Val Leu Ser Phe
                85                  90                  95

Leu Ser Trp Ser Phe Thr Val Leu Val Ile Ser Arg Ile Gly Val Ala
                100                 105                 110

Phe Ala His Ala Ile Phe Trp Ser Ile Thr Ala Ser Leu Ala Ile Arg
                115                 120                 125

Met Ala Pro Ala Gly Lys Arg Ala Gln Ala Leu Ser Leu Ile Ala Thr
                130                 135                 140

Gly Thr Ala Leu Ala Met Val Leu Gly Leu Pro Leu Gly Arg Ile Val
145                 150                 155                 160

Gly Gln Tyr Phe Gly Trp Arg Met Thr Phe Phe Ala Ile Gly Ile Gly
                165                 170                 175

```
Ala Leu Ile Thr Leu Leu Cys Leu Ile Lys Leu Leu Pro Leu Leu Pro
            180                 185                 190

Ser Glu His Ser Gly Ser Leu Lys Ser Leu Pro Leu Leu Phe Arg Arg
        195                 200                 205

Pro Ala Leu Met Ser Ile Tyr Leu Leu Thr Val Val Val Thr Ala
210                 215                 220

His Tyr Thr Ala Tyr Ser Tyr Ile Glu Pro Phe Val Gln Asn Ile Ala
225                 230                 235                 240

Gly Phe Ser Ala Asn Phe Ala Thr Ala Leu Leu Leu Leu Gly Gly
                245                 250                 255

Ala Gly Ile Ile Gly Ser Val Ile Phe Gly Lys Leu Gly Asn Gln Tyr
            260                 265                 270

Ala Ser Ala Leu Val Ser Thr Ala Ile Ala Leu Leu Val Cys Leu
        275                 280                 285

Ala Leu Leu Leu Pro Ala Ala Asn Ser Glu Ile His Leu Gly Val Leu
    290                 295                 300

Ser Ile Phe Trp Gly Ile Ala Met Met Ile Ile Gly Leu Gly Met Gln
305                 310                 315                 320

Val Lys Val Leu Ala Leu Ala Pro Asp Ala Thr Asp Val Ala Met Ala
                325                 330                 335

Leu Phe Ser Gly Ile Phe Asn Ile Gly Ile Gly Ala Gly Ala Leu Val
            340                 345                 350

Gly Asn Gln Val Ser Leu His Trp Ser Met Ser Met Ile Gly Tyr Val
        355                 360                 365

Gly Ala Val Pro Ala Phe Ala Ala Leu Ile Trp Ser Ile Ile Ile Phe
    370                 375                 380

Arg Arg Trp Pro Val Thr Leu Glu Glu Gln Thr Gln
385                 390                 395

<210> SEQ ID NO 18
<211> LENGTH: 204
<212> TYPE: PRT
<213> ORGANISM: Escherichia coli

<400> SEQUENCE: 18

Met Asn Ala Ile Ile Ile Asp Asp His Pro Leu Ala Ile Ala Ala Ile
1               5                   10                  15

Arg Asn Leu Leu Ile Lys Asn Asp Ile Glu Ile Leu Ala Glu Leu Thr
            20                  25                  30

Glu Gly Gly Ser Ala Val Gln Arg Val Glu Thr Leu Lys Pro Asp Ile
        35                  40                  45

Val Ile Ile Asp Val Asp Ile Pro Gly Val Asn Gly Ile Gln Val Leu
    50                  55                  60

Glu Thr Leu Arg Lys Arg Gln Tyr Ser Gly Ile Ile Ile Val Ser
65                  70                  75                  80

Ala Lys Asn Asp His Phe Tyr Gly Lys His Cys Ala Asp Ala Gly Ala
                85                  90                  95

Asn Gly Phe Val Ser Lys Lys Glu Gly Met Asn Asn Ile Ile Ala Ala
            100                 105                 110

Ile Glu Ala Ala Lys Asn Gly Tyr Cys Tyr Phe Pro Phe Ser Leu Asn
        115                 120                 125

Arg Phe Val Gly Ser Leu Thr Ser Asp Gln Gln Lys Leu Asp Ser Leu
    130                 135                 140

Ser Lys Gln Glu Ile Ser Val Met Arg Tyr Ile Leu Asp Gly Lys Asp
145                 150                 155                 160
```

```
Asn Asn Asp Ile Ala Glu Lys Met Phe Ile Ser Asn Lys Thr Val Ser
            165                 170                 175

Thr Tyr Lys Ser Arg Leu Met Glu Lys Leu Glu Cys Lys Ser Leu Met
            180                 185                 190

Asp Leu Tyr Thr Phe Ala Gln Arg Asn Lys Ile Gly
            195                 200

<210> SEQ ID NO 19
<211> LENGTH: 387
<212> TYPE: PRT
<213> ORGANISM: Escherichia coli

<400> SEQUENCE: 19

Met Glu Gln Ile Asn Ser Asn Lys Lys His Ser Asn Arg Arg Lys Tyr
 1               5                  10                  15

Phe Ser Leu Leu Ala Val Val Leu Phe Ile Ala Phe Ser Gly Ala Tyr
            20                  25                  30

Ala Tyr Trp Ser Met Glu Leu Glu Asp Met Ile Ser Thr Asp Asp Ala
         35                  40                  45

Tyr Val Thr Gly Asn Ala Asp Pro Ile Ser Ala Gln Val Ser Gly Ser
     50                  55                  60

Val Thr Val Val Asn His Lys Asp Thr Asn Tyr Val Arg Gln Gly Asp
 65                  70                  75                  80

Ile Leu Val Ser Leu Asp Lys Thr Asp Ala Thr Ile Ala Leu Asn Lys
                 85                  90                  95

Ala Lys Asn Asn Leu Ala Asn Ile Val Arg Gln Thr Asn Lys Leu Tyr
            100                 105                 110

Leu Gln Asp Lys Gln Tyr Ser Ala Glu Val Ala Ser Ala Arg Ile Gln
            115                 120                 125

Tyr Gln Gln Ser Leu Glu Asp Tyr Asn Arg Arg Val Pro Leu Ala Lys
        130                 135                 140

Gln Gly Val Ile Ser Lys Glu Thr Leu Glu His Thr Lys Asp Thr Leu
145                 150                 155                 160

Ile Ser Ser Lys Ala Ala Leu Asn Ala Ala Ile Gln Ala Tyr Lys Ala
                165                 170                 175

Asn Lys Ala Leu Val Met Asn Thr Pro Leu Asn Arg Gln Pro Gln Val
            180                 185                 190

Val Glu Ala Ala Asp Ala Thr Lys Glu Ala Trp Leu Ala Leu Lys Arg
        195                 200                 205

Thr Asp Ile Lys Ser Pro Val Thr Gly Tyr Ile Ala Gln Arg Ser Val
    210                 215                 220

Gln Val Gly Glu Thr Val Ser Pro Gly Gln Ser Leu Met Ala Val Val
225                 230                 235                 240

Pro Ala Arg Gln Met Trp Val Asn Ala Asn Phe Lys Glu Thr Gln Leu
                245                 250                 255

Thr Asp Val Arg Ile Gly Gln Ser Val Asn Ile Ile Ser Asp Leu Tyr
            260                 265                 270

Gly Glu Asn Val Val Phe His Gly Arg Val Thr Gly Ile Asn Met Gly
        275                 280                 285

Thr Gly Asn Ala Phe Ser Leu Leu Pro Ala Gln Asn Ala Thr Gly Asn
    290                 295                 300

Trp Ile Lys Ile Val Gln Arg Val Pro Val Glu Val Ser Leu Asp Pro
305                 310                 315                 320

Lys Glu Leu Met Glu His Pro Leu Arg Ile Gly Leu Ser Met Thr Ala
                325                 330                 335
```

Thr Ile Asp Thr Lys Asn Glu Asp Ile Ala Glu Met Pro Glu Leu Ala
            340                 345                 350

Ser Thr Val Thr Ser Met Pro Ala Tyr Thr Ser Lys Ala Leu Val Ile
            355                 360                 365

Asp Thr Ser Pro Ile Glu Lys Glu Ile Ser Asn Ile Ile Ser His Asn
370                 375                 380

Gly Gln Leu
385

<210> SEQ ID NO 20
<211> LENGTH: 512
<212> TYPE: PRT
<213> ORGANISM: Escherichia coli

<400> SEQUENCE: 20

Met Ala Ile Thr Lys Ser Thr Pro Ala Pro Leu Thr Gly Gly Thr Leu
1               5                   10                  15

Trp Cys Val Thr Ile Ala Leu Ser Leu Ala Thr Phe Met Gln Met Leu
            20                  25                  30

Asp Ser Thr Ile Ser Asn Val Ala Ile Pro Thr Ile Ser Gly Phe Leu
        35                  40                  45

Gly Ala Ser Thr Asp Glu Gly Thr Trp Val Ile Thr Ser Phe Gly Val
    50                  55                  60

Ala Asn Ala Ile Ala Ile Pro Val Thr Gly Arg Leu Ala Gln Arg Ile
65                  70                  75                  80

Gly Glu Leu Arg Leu Phe Leu Leu Ser Val Thr Phe Phe Ser Leu Ser
                85                  90                  95

Ser Leu Met Cys Ser Leu Ser Thr Asn Leu Asp Val Leu Ile Phe Phe
            100                 105                 110

Arg Val Val Gln Gly Leu Met Ala Gly Pro Leu Ile Pro Leu Ser Gln
        115                 120                 125

Ser Leu Leu Leu Arg Asn Tyr Pro Pro Glu Lys Arg Thr Phe Ala Leu
    130                 135                 140

Ala Leu Trp Ser Met Thr Val Ile Ile Ala Pro Ile Cys Gly Pro Ile
145                 150                 155                 160

Leu Gly Gly Tyr Ile Cys Asp Asn Phe Ser Trp Gly Trp Ile Phe Leu
                165                 170                 175

Ile Asn Val Pro Met Gly Ile Ile Val Leu Thr Leu Cys Leu Thr Leu
            180                 185                 190

Leu Lys Gly Arg Glu Thr Glu Thr Ser Pro Val Lys Met Asn Leu Pro
        195                 200                 205

Gly Leu Thr Leu Leu Val Leu Gly Val Gly Leu Gln Ile Met Leu
    210                 215                 220

Asp Lys Gly Arg Asp Leu Asp Trp Phe Asn Ser Ser Thr Ile Ile Ile
225                 230                 235                 240

Leu Thr Val Val Ser Val Ile Ser Leu Ile Ser Leu Val Ile Trp Glu
                245                 250                 255

Ser Thr Ser Glu Asn Pro Ile Leu Asp Leu Ser Leu Phe Lys Ser Arg
            260                 265                 270

Asn Phe Thr Ile Gly Ile Val Ser Ile Thr Cys Ala Tyr Leu Phe Tyr
        275                 280                 285

Ser Gly Ala Ile Val Leu Met Pro Gln Leu Leu Gln Glu Thr Met Gly
    290                 295                 300

Tyr Asn Ala Ile Trp Ala Gly Leu Ala Tyr Ala Pro Ile Gly Ile Met
305                 310                 315                 320

```
Pro Leu Leu Ile Ser Pro Leu Ile Gly Arg Tyr Gly Asn Lys Ile Asp
            325                 330                 335

Met Arg Leu Leu Val Thr Phe Ser Phe Leu Met Tyr Ala Val Cys Tyr
            340                 345                 350

Tyr Trp Arg Ser Val Thr Phe Met Pro Thr Ile Asp Phe Thr Gly Ile
            355                 360                 365

Ile Leu Pro Gln Phe Phe Gln Gly Phe Ala Val Ala Cys Phe Phe Leu
            370                 375                 380

Pro Leu Thr Thr Ile Ser Phe Ser Gly Leu Pro Asp Asn Lys Phe Ala
385                 390                 395                 400

Asn Ala Ser Ser Met Ser Asn Phe Phe Arg Thr Leu Ser Gly Ser Val
            405                 410                 415

Gly Thr Ser Leu Thr Met Thr Leu Trp Gly Arg Arg Glu Ser Leu His
            420                 425                 430

His Ser Gln Leu Thr Ala Thr Ile Asp Gln Phe Asn Pro Val Phe Asn
            435                 440                 445

Ser Ser Ser Gln Ile Met Asp Lys Tyr Tyr Gly Ser Leu Ser Gly Val
            450                 455                 460

Leu Asn Glu Ile Asn Asn Glu Ile Thr Gln Gln Ser Leu Ser Ile Ser
465                 470                 475                 480

Ala Asn Glu Ile Phe Arg Met Ala Ala Ile Ala Phe Ile Leu Leu Thr
            485                 490                 495

Val Leu Val Trp Phe Ala Lys Pro Pro Phe Thr Ala Lys Gly Val Gly
            500                 505                 510

<210> SEQ ID NO 21
<211> LENGTH: 394
<212> TYPE: PRT
<213> ORGANISM: Escherichia coli

<400> SEQUENCE: 21

Met Lys Arg Gln Arg Asn Val Asn Leu Leu Met Leu Val Leu Leu
  1               5                  10                  15

Val Ala Val Gly Gln Met Ala Gln Thr Ile Tyr Ile Pro Ala Ile Ala
            20                  25                  30

Asp Met Ala Arg Asp Leu Asn Val Arg Glu Gly Ala Val Gln Ser Val
            35                  40                  45

Met Gly Ala Tyr Leu Leu Thr Tyr Gly Val Ser Gln Leu Phe Tyr Gly
        50                  55                  60

Pro Ile Ser Asp Arg Val Gly Arg Pro Val Ile Leu Val Gly Met
 65                  70                  75                  80

Ser Ile Phe Met Leu Ala Thr Leu Val Ala Val Thr Thr Ser Ser Leu
            85                  90                  95

Thr Val Leu Ile Ala Ala Ser Ala Met Gln Gly Met Gly Thr Gly Val
            100                 105                 110

Gly Gly Val Met Ala Arg Thr Leu Pro Arg Asp Leu Tyr Glu Arg Thr
            115                 120                 125

Gln Leu Arg His Ala Asn Ser Leu Leu Asn Met Gly Ile Leu Val Ser
            130                 135                 140

Pro Leu Leu Ala Pro Leu Ile Gly Gly Leu Leu Asp Thr Met Trp Asn
145                 150                 155                 160

Trp Arg Ala Cys Tyr Leu Phe Leu Leu Val Leu Cys Ala Gly Val Thr
            165                 170                 175

Phe Ser Met Ala Arg Trp Met Pro Glu Thr Arg Pro Val Asp Ala Pro
            180                 185                 190
```

Arg Thr Arg Leu Leu Thr Ser Tyr Lys Thr Leu Phe Gly Asn Ser Gly
            195                 200                 205

Phe Asn Cys Tyr Leu Leu Met Leu Ile Gly Gly Leu Ala Gly Ile Ala
        210                 215                 220

Ala Phe Glu Ala Cys Ser Gly Val Leu Met Gly Ala Val Leu Gly Leu
225                 230                 235                 240

Ser Ser Met Thr Val Ser Ile Leu Phe Ile Leu Pro Ile Pro Ala Ala
                245                 250                 255

Phe Phe Gly Ala Trp Phe Ala Gly Arg Pro Asn Lys Arg Phe Ser Thr
            260                 265                 270

Leu Met Trp Gln Ser Val Ile Cys Cys Leu Leu Ala Gly Leu Leu Met
        275                 280                 285

Trp Ile Pro Asp Trp Phe Gly Val Met Asn Val Trp Thr Leu Leu Val
        290                 295                 300

Pro Ala Ala Leu Phe Phe Phe Gly Ala Gly Met Leu Phe Pro Leu Ala
305                 310                 315                 320

Thr Ser Gly Ala Met Glu Pro Phe Pro Phe Leu Ala Gly Thr Ala Gly
                325                 330                 335

Ala Leu Val Gly Gly Leu Gln Asn Ile Gly Ser Gly Val Leu Ala Ser
            340                 345                 350

Leu Ser Ala Met Leu Pro Gln Thr Gly Gln Gly Ser Leu Gly Leu Leu
        355                 360                 365

Met Thr Leu Met Gly Leu Leu Ile Val Leu Cys Trp Leu Pro Leu Ala
        370                 375                 380

Thr Arg Met Ser His Gln Gly Gln Pro Val
385                 390

<210> SEQ ID NO 22
<211> LENGTH: 456
<212> TYPE: PRT
<213> ORGANISM: Escherichia coli

<400> SEQUENCE: 22

Met Val Met Asn Asp Tyr Lys Met Thr Pro Gly Glu Arg Arg Ala Thr
1               5                   10                  15

Trp Gly Leu Gly Thr Val Phe Ser Leu Arg Met Leu Gly Met Phe Met
            20                  25                  30

Val Leu Pro Val Leu Thr Thr Tyr Gly Met Ala Leu Gln Gly Ala Ser
        35                  40                  45

Glu Ala Leu Ile Gly Ile Ala Ile Gly Ile Tyr Gly Leu Thr Gln Ala
    50                  55                  60

Val Phe Gln Ile Pro Phe Gly Leu Leu Ser Asp Arg Ile Gly Arg Lys
65                  70                  75                  80

Pro Leu Ile Val Gly Gly Leu Ala Val Phe Ala Ala Gly Ser Val Ile
                85                  90                  95

Ala Ala Leu Ser Asp Ser Ile Trp Gly Ile Ile Leu Gly Arg Ala Leu
            100                 105                 110

Gln Gly Ser Gly Ala Ile Ala Ala Ala Val Met Ala Leu Leu Ser Asp
        115                 120                 125

Leu Thr Arg Glu Gln Asn Arg Thr Lys Ala Met Ala Phe Ile Gly Val
    130                 135                 140

Ser Phe Gly Ile Thr Phe Ala Ile Ala Met Val Leu Gly Pro Ile Ile
145                 150                 155                 160

Thr His Lys Leu Gly Leu His Ala Leu Phe Trp Met Ile Ala Ile Leu
                165                 170                 175

Ala Thr Thr Gly Ile Ala Leu Thr Ile Trp Val Val Pro Asn Ser Ser
            180                 185                 190

Thr His Val Leu Asn Arg Glu Ser Gly Met Val Lys Gly Ser Phe Ser
            195                 200                 205

Lys Val Leu Ala Glu Pro Arg Leu Leu Lys Leu Asn Phe Gly Ile Met
210                 215                 220

Cys Leu His Ile Leu Leu Met Ser Thr Phe Val Ala Leu Pro Gly Gln
225                 230                 235                 240

Leu Ala Asp Ala Gly Phe Pro Ala Ala Glu His Trp Lys Val Tyr Leu
            245                 250                 255

Ala Thr Met Leu Ile Ala Phe Gly Ser Val Val Pro Phe Ile Ile Tyr
            260                 265                 270

Ala Glu Val Lys Arg Lys Met Lys Gln Val Phe Val Phe Cys Val Gly
            275                 280                 285

Leu Ile Val Val Ala Glu Ile Val Leu Trp Asn Ala Gln Thr Gln Phe
            290                 295                 300

Trp Gln Leu Val Val Gly Val Gln Leu Phe Phe Val Ala Phe Asn Leu
305                 310                 315                 320

Met Glu Ala Leu Leu Pro Ser Leu Ile Ser Lys Glu Ser Pro Ala Gly
            325                 330                 335

Tyr Lys Gly Thr Ala Met Gly Val Tyr Ser Thr Ser Gln Phe Leu Gly
            340                 345                 350

Val Ala Ile Gly Gly Ser Leu Gly Gly Trp Ile Asn Gly Met Phe Asp
            355                 360                 365

Gly Gln Gly Val Phe Leu Ala Gly Ala Met Leu Ala Ala Val Trp Leu
            370                 375                 380

Thr Val Ala Ser Thr Met Lys Glu Pro Pro Tyr Val Ser Ser Leu Arg
385                 390                 395                 400

Ile Glu Ile Pro Ala Asn Ile Ala Ala Asn Glu Ala Leu Lys Val Arg
            405                 410                 415

Leu Leu Glu Thr Glu Gly Ile Lys Glu Val Leu Ile Ala Glu Glu Glu
            420                 425                 430

His Ser Ala Tyr Val Lys Ile Asp Ser Lys Val Thr Asn Arg Phe Glu
            435                 440                 445

Ile Glu Gln Ala Ile Arg Gln Ala
450                 455

<210> SEQ ID NO 23
<211> LENGTH: 471
<212> TYPE: PRT
<213> ORGANISM: Escherichia coli

<400> SEQUENCE: 23

Met Thr Asp Leu Pro Asp Ser Thr Arg Trp Gln Leu Trp Ile Val Ala
1               5                   10                  15

Phe Gly Phe Phe Met Gln Ser Leu Asp Thr Thr Ile Val Asn Thr Ala
            20                  25                  30

Leu Pro Ser Met Ala Gln Ser Leu Gly Glu Ser Pro Leu His Met His
            35                  40                  45

Met Val Ile Val Ser Tyr Val Leu Thr Val Ala Val Met Leu Pro Ala
            50                  55                  60

Ser Gly Trp Leu Ala Asp Lys Val Gly Val Arg Asn Ile Phe Phe Thr
65                  70                  75                  80

Ala Ile Val Leu Phe Thr Leu Gly Ser Leu Phe Cys Ala Leu Ser Gly
            85                  90                  95

```
Thr Leu Asn Glu Leu Leu Leu Ala Arg Ala Leu Gln Gly Val Gly Gly
            100                 105                 110
Ala Met Met Val Pro Val Gly Arg Leu Thr Val Met Lys Ile Val Pro
        115                 120                 125
Arg Glu Gln Tyr Met Ala Ala Met Thr Phe Val Thr Leu Pro Gly Gln
    130                 135                 140
Val Gly Pro Leu Leu Gly Pro Ala Leu Gly Gly Leu Leu Val Glu Tyr
145                 150                 155                 160
Ala Ser Trp His Trp Ile Phe Leu Ile Asn Ile Pro Val Gly Ile Ile
                165                 170                 175
Gly Ala Ile Ala Thr Leu Leu Leu Met Pro Asn Tyr Thr Met Gln Thr
            180                 185                 190
Arg Arg Phe Asp Leu Ser Gly Phe Leu Leu Ala Val Gly Met Ala
        195                 200                 205
Val Leu Thr Leu Ala Leu Asp Gly Ser Lys Gly Thr Gly Leu Ser Pro
    210                 215                 220
Leu Thr Ile Ala Gly Leu Val Ala Val Gly Val Val Ala Leu Val Leu
225                 230                 235                 240
Tyr Leu Leu His Ala Arg Asn Asn Asn Arg Ala Leu Phe Ser Leu Lys
                245                 250                 255
Leu Phe Arg Thr Arg Thr Phe Ser Leu Gly Leu Ala Gly Ser Phe Ala
            260                 265                 270
Gly Arg Ile Gly Ser Gly Met Leu Pro Phe Met Thr Pro Val Phe Leu
        275                 280                 285
Gln Ile Gly Leu Gly Phe Ser Pro Phe His Ala Gly Leu Met Met Ile
    290                 295                 300
Pro Met Val Leu Gly Ser Met Gly Met Lys Arg Ile Val Val Gln Val
305                 310                 315                 320
Val Asn Arg Phe Gly Tyr Arg Arg Val Leu Val Ala Thr Thr Leu Gly
                325                 330                 335
Leu Ser Leu Val Thr Leu Leu Phe Met Thr Thr Ala Leu Leu Gly Trp
            340                 345                 350
Tyr Tyr Val Leu Pro Phe Val Leu Phe Leu Gln Gly Met Val Asn Ser
        355                 360                 365
Thr Arg Phe Ser Ser Met Asn Thr Leu Thr Leu Lys Asp Leu Pro Asp
    370                 375                 380
Asn Leu Ala Ser Ser Gly Asn Ser Leu Leu Ser Met Ile Met Gln Leu
385                 390                 395                 400
Ser Met Ser Ile Gly Val Thr Ile Ala Gly Leu Leu Leu Gly Leu Phe
                405                 410                 415
Gly Ser Gln His Val Ser Val Asp Ser Gly Thr Thr Gln Thr Val Phe
            420                 425                 430
Met Tyr Thr Trp Leu Ser Met Ala Leu Ile Ile Ala Leu Pro Ala Phe
        435                 440                 445
Ile Phe Ala Arg Val Pro Asn Asp Thr His Gln Asn Val Ala Ile Ser
    450                 455                 460
Arg Arg Lys Arg Ser Ala Gln
465                 470

<210> SEQ ID NO 24
<211> LENGTH: 391
<212> TYPE: PRT
<213> ORGANISM: Escherichia coli

<400> SEQUENCE: 24
```

Met Ser Arg Phe Leu Ile Cys Ser Phe Ala Leu Val Leu Leu Tyr Pro
1               5                   10                  15

Ala Gly Ile Asp Met Tyr Leu Val Gly Leu Pro Arg Ile Ala Ala Asp
            20                  25                  30

Leu Asn Ala Ser Glu Ala Gln Leu His Ile Ala Phe Ser Val Tyr Leu
        35                  40                  45

Ala Gly Met Ala Ala Ala Met Leu Phe Ala Gly Lys Val Ala Asp Arg
    50                  55                  60

Ser Gly Arg Lys Pro Val Ala Ile Pro Gly Ala Ala Leu Phe Ile Ile
65              70                  75                  80

Ala Ser Val Phe Cys Ser Leu Ala Glu Thr Ser Thr Leu Phe Leu Ala
                85                  90                  95

Gly Arg Phe Leu Gln Gly Leu Gly Ala Gly Cys Cys Tyr Val Val Ala
                100                 105                 110

Phe Ala Ile Leu Arg Asp Thr Leu Asp Asp Arg Arg Ala Lys Val
                115                 120                 125

Leu Ser Leu Leu Asn Gly Ile Thr Cys Ile Ile Pro Val Leu Ala Pro
    130                 135                 140

Val Leu Gly His Leu Ile Met Leu Lys Phe Pro Trp Gln Ser Leu Phe
145                 150                 155                 160

Trp Ala Met Ala Met Met Gly Ile Ala Val Leu Met Leu Ser Leu Phe
                165                 170                 175

Ile Leu Lys Glu Thr Arg Pro Ala Ala Pro Ala Ala Ser Asp Lys Pro
                180                 185                 190

Arg Glu Asn Ser Glu Ser Leu Leu Asn Arg Phe Phe Leu Ser Arg Val
        195                 200                 205

Val Ile Thr Thr Leu Ser Val Ser Val Ile Leu Thr Phe Val Asn Thr
    210                 215                 220

Ser Pro Val Leu Leu Met Glu Ile Met Gly Phe Glu Arg Gly Glu Tyr
225                 230                 235                 240

Ala Thr Ile Met Ala Leu Thr Ala Gly Val Ser Met Thr Val Ser Phe
                245                 250                 255

Ser Thr Pro Phe Ala Leu Gly Ile Phe Lys Pro Arg Thr Leu Met Ile
                260                 265                 270

Thr Ser Gln Val Leu Phe Leu Ala Ala Gly Ile Thr Leu Ala Val Ser
        275                 280                 285

Pro Ser His Ala Val Ser Leu Phe Gly Ile Thr Leu Ile Cys Ala Gly
    290                 295                 300

Phe Ser Val Gly Phe Gly Val Ala Met Ser Gln Ala Leu Gly Pro Phe
305                 310                 315                 320

Ser Leu Arg Ala Gly Val Ala Ser Ser Thr Leu Gly Ile Ala Gln Val
                325                 330                 335

Cys Gly Ser Ser Leu Trp Ile Trp Leu Ala Ala Val Gly Ile Gly
                340                 345                 350

Ala Trp Asn Met Leu Ile Gly Ile Leu Ile Ala Cys Ser Ile Val Ser
        355                 360                 365

Leu Leu Leu Ile Met Phe Val Ala Pro Gly Arg Pro Val Ala Ala His
    370                 375                 380

Glu Glu Ile His His His Ala
385                 390

<210> SEQ ID NO 25
<211> LENGTH: 475
<212> TYPE: PRT

<213> ORGANISM: Escherichia coli

<400> SEQUENCE: 25

```
Met Ser Asp Lys Lys Arg Ser Met Ala Gly Leu Pro Trp Ile Ala
  1               5                  10                  15
Ala Met Ala Phe Phe Met Gln Ala Leu Asp Ala Thr Ile Leu Asn Thr
             20                  25                  30
Ala Leu Pro Ala Ile Ala His Ser Leu Asn Arg Ser Pro Leu Ala Met
         35                  40                  45
Gln Ser Ala Ile Ile Ser Tyr Thr Leu Thr Val Ala Met Leu Ile Pro
     50                  55                  60
Val Ser Gly Trp Leu Ala Asp Arg Phe Gly Thr Arg Arg Ile Phe Thr
 65                  70                  75                  80
Leu Ala Val Ser Leu Phe Thr Leu Gly Ser Leu Ala Cys Ala Leu Ser
                 85                  90                  95
Asn Ser Leu Pro Gln Leu Val Val Phe Arg Val Ile Gln Gly Ile Gly
                100                 105                 110
Gly Ala Met Met Met Pro Val Ala Arg Leu Ala Leu Leu Arg Ala Tyr
            115                 120                 125
Pro Arg Asn Glu Leu Leu Pro Val Leu Asn Phe Val Ala Met Pro Gly
        130                 135                 140
Leu Val Gly Pro Ile Leu Gly Pro Val Leu Gly Gly Val Leu Val Thr
145                 150                 155                 160
Trp Ala Thr Trp His Trp Ile Phe Leu Ile Asn Ile Pro Ile Gly Ile
                165                 170                 175
Ala Gly Leu Leu Tyr Ala Arg Lys His Met Pro Asn Phe Thr Thr Ala
            180                 185                 190
Arg Arg Arg Phe Asp Ile Thr Gly Phe Leu Leu Phe Gly Leu Ser Leu
        195                 200                 205
Val Leu Phe Ser Ser Gly Ile Glu Leu Phe Gly Glu Lys Ile Val Ala
    210                 215                 220
Ser Trp Ile Ala Leu Thr Val Ile Val Thr Ser Ile Gly Leu Leu Leu
225                 230                 235                 240
Leu Tyr Ile Leu His Ala Arg Arg Thr Pro Asn Pro Leu Ile Ser Leu
                245                 250                 255
Asp Leu Phe Lys Thr Arg Thr Phe Ser Ile Gly Ile Val Gly Asn Ile
            260                 265                 270
Ala Thr Arg Leu Gly Thr Gly Cys Val Pro Phe Leu Met Pro Leu Met
        275                 280                 285
Leu Gln Val Gly Phe Gly Tyr Gln Ala Phe Ile Ala Gly Cys Met Met
    290                 295                 300
Ala Pro Thr Ala Leu Gly Ser Ile Ile Ala Lys Ser Met Val Thr Gln
305                 310                 315                 320
Val Leu Arg Arg Leu Gly Tyr Arg His Thr Leu Val Gly Ile Thr Val
                325                 330                 335
Ile Ile Gly Leu Met Ile Ala Gln Phe Ser Leu Gln Ser Pro Ala Met
            340                 345                 350
Ala Ile Trp Met Leu Ile Leu Pro Leu Phe Ile Leu Gly Met Ala Met
        355                 360                 365
Ser Thr Gln Phe Thr Ala Met Asn Thr Ile Thr Leu Ala Asp Leu Thr
    370                 375                 380
Asp Asp Asn Ala Ser Ser Gly Asn Ser Val Leu Ala Val Thr Gln Gln
385                 390                 395                 400
Leu Ser Ile Ser Leu Gly Val Ala Val Ser Ala Ala Val Leu Arg Val
```

```
                    405                 410                 415
Tyr Glu Gly Met Glu Gly Thr Thr Thr Val Glu Gln Phe His Tyr Thr
                420                 425                 430

Phe Ile Thr Met Gly Ile Ile Thr Val Ala Ser Ala Ala Met Phe Met
            435                 440                 445

Leu Leu Lys Thr Thr Asp Gly Asn Asn Leu Ile Lys Arg Gln Arg Lys
        450                 455                 460

Ser Lys Pro Asn Arg Val Pro Ser Glu Ser Glu
465                 470                 475

<210> SEQ ID NO 26
<211> LENGTH: 410
<212> TYPE: PRT
<213> ORGANISM: Escherichia coli

<400> SEQUENCE: 26

Met Pro Arg Phe Phe Thr Arg His Ala Ala Thr Leu Phe Phe Pro Met
  1               5                  10                  15

Ala Leu Ile Leu Tyr Asp Phe Ala Ala Tyr Leu Ser Thr Asp Leu Ile
                 20                  25                  30

Gln Pro Gly Ile Ile Asn Val Val Arg Asp Phe Asn Ala Asp Val Ser
             35                  40                  45

Leu Ala Pro Ala Val Ser Leu Tyr Leu Ala Gly Gly Met Ala Leu
         50                  55                  60

Gln Trp Leu Leu Gly Pro Leu Ser Asp Arg Ile Gly Arg Arg Pro Val
 65                  70                  75                  80

Leu Ile Thr Gly Ala Leu Ile Phe Thr Leu Ala Cys Ala Ala Thr Met
                 85                  90                  95

Phe Thr Thr Ser Met Thr Gln Phe Leu Ile Ala Arg Ala Ile Gln Gly
                100                 105                 110

Thr Ser Ile Cys Phe Ile Ala Thr Val Gly Tyr Val Thr Val Gln Glu
            115                 120                 125

Ala Phe Gly Gln Thr Lys Gly Ile Lys Leu Met Ala Ile Ile Thr Ser
        130                 135                 140

Ile Val Leu Ile Ala Pro Ile Ile Gly Pro Leu Ser Gly Ala Ala Leu
145                 150                 155                 160

Met His Phe Met His Trp Lys Val Leu Phe Ala Ile Ile Ala Val Met
                165                 170                 175

Gly Phe Ile Ser Phe Val Gly Leu Leu Leu Ala Met Pro Glu Thr Val
                180                 185                 190

Lys Arg Gly Ala Val Pro Phe Ser Ala Lys Ser Val Leu Arg Asp Phe
            195                 200                 205

Arg Asn Val Phe Cys Asn Arg Leu Phe Leu Phe Gly Ala Ala Thr Ile
        210                 215                 220

Ser Leu Ser Tyr Ile Pro Met Met Ser Trp Val Ala Val Ser Pro Val
225                 230                 235                 240

Ile Leu Ile Asp Ala Gly Ser Leu Thr Thr Ser Gln Phe Ala Trp Thr
                245                 250                 255

Gln Val Pro Val Phe Gly Ala Val Ile Val Ala Asn Ala Ile Val Ala
            260                 265                 270

Arg Phe Val Lys Asp Pro Thr Glu Pro Arg Phe Ile Trp Arg Ala Val
        275                 280                 285

Pro Ile Gln Leu Val Gly Leu Ser Leu Leu Ile Val Gly Asn Leu Leu
    290                 295                 300

Ser Pro His Val Trp Leu Trp Ser Val Leu Gly Thr Ser Leu Tyr Ala
```

```
                305                 310                 315                 320
Phe Gly Ile Gly Leu Ile Phe Pro Thr Leu Phe Arg Phe Thr Leu Phe
                    325                 330                 335

Ser Asn Lys Leu Pro Lys Gly Thr Val Ser Ala Ser Leu Asn Met Val
                340                 345                 350

Ile Leu Met Val Met Ser Val Ser Val Glu Ile Gly Arg Trp Leu Trp
                355                 360                 365

Phe Asn Gly Gly Arg Leu Pro Phe His Leu Leu Ala Val Val Ala Gly
            370                 375                 380

Val Ile Val Val Phe Thr Leu Ala Gly Leu Leu Asn Arg Val Arg Gln
385                 390                 395                 400

His Gln Ala Ala Glu Leu Val Glu Glu Gln
                405                 410

<210> SEQ ID NO 27
<211> LENGTH: 3889
<212> TYPE: DNA
<213> ORGANISM: Escherichia coli
<220> FEATURE:
<221> NAME/KEY: CDS
<222> LOCATION: (201)..(1967)
<220> FEATURE:
<221> NAME/KEY: CDS
<222> LOCATION: (1968)..(3689)

<400> SEQUENCE: 27
attacttcgg ccggtacagg ctgcatggca gcacttgatg cggaacgcta cctcgatggt      60
ttagctgacg caaataatt ttacaaatca gtaacaaaag taaagaaggc gacaccatgc     120
gactatgggt cgcctttatt ttttccccgt tgtaacattg ctctgcaaat aattctgata    180
actcacctgc taagcgtgca atg aat aaa tct cgt caa aaa gag tta acc cgc   233
                        Met Asn Lys Ser Arg Gln Lys Glu Leu Thr Arg
                          1               5                  10 tgg tta aaa cag caa agc gtc atc tcc caa cgt tgg ctg aat att tct    281
Trp Leu Lys Gln Gln Ser Val Ile Ser Gln Arg Trp Leu Asn Ile Ser
                15                  20                  25 cgt ctg ctg ggc ttt gtg agc ggc ata ttg atc att gcc cag gcc tgg    329
Arg Leu Leu Gly Phe Val Ser Gly Ile Leu Ile Ile Ala Gln Ala Trp
        30                  35                  40 ttc atg gcg cga att ctg caa cat atg att atg gag aat att ccc cgt    377
Phe Met Ala Arg Ile Leu Gln His Met Ile Met Glu Asn Ile Pro Arg
    45                  50                  55 gaa gcc ctg ctg ctt ccc ttt acg tta ctg gtt ctg acc ttt gta ctg    425
Glu Ala Leu Leu Leu Pro Phe Thr Leu Leu Val Leu Thr Phe Val Leu
60                  65                  70                  75 cgc gca tgg gtg gtc tgg tta cgc gaa cgg gtg ggt tat cac gcc ggg    473
Arg Ala Trp Val Val Trp Leu Arg Glu Arg Val Gly Tyr His Ala Gly
                80                  85                  90 cag cat atc cgc ttt gcc atc cgc cgt cag gtt ctc gac cgt ctg caa    521
Gln His Ile Arg Phe Ala Ile Arg Arg Gln Val Leu Asp Arg Leu Gln
            95                  100                 105 caa gca ggg cca gcg tgg att cag ggt aaa cct gcg ggg agc tgg gcg    569
Gln Ala Gly Pro Ala Trp Ile Gln Gly Lys Pro Ala Gly Ser Trp Ala
        110                 115                 120 acg ctg gta ctc gag caa att gac gat atg cat gat tac tat gca cgc    617
Thr Leu Val Leu Glu Gln Ile Asp Asp Met His Asp Tyr Tyr Ala Arg
    125                 130                 135 tat ctg ccg caa atg gcg ctg gca gtg tcg gtg ccg ttg ctg att gtg    665
Tyr Leu Pro Gln Met Ala Leu Ala Val Ser Val Pro Leu Leu Ile Val
140                 145                 150                 155
```

```
                                            -continued gtg gca atc ttc ccc tct aac tgg gct gcg gcg ctc att ctg ctg ggc      713
Val Ala Ile Phe Pro Ser Asn Trp Ala Ala Ala Leu Ile Leu Leu Gly
                160                 165                 170 act gca ccg tta att ccg ttg ttt atg gcg ctg gtt gga atg ggg gct      761
Thr Ala Pro Leu Ile Pro Leu Phe Met Ala Leu Val Gly Met Gly Ala
            175                 180                 185 gcc gat gct aac cga cgt aac ttt ctc gct ctt gct cgc tta agt ggg      809
Ala Asp Ala Asn Arg Arg Asn Phe Leu Ala Leu Ala Arg Leu Ser Gly
        190                 195                 200 cat ttc ctc gat cgc ctg cgc ggc atg gaa aca ttg cgt att ttt ggt      857
His Phe Leu Asp Arg Leu Arg Gly Met Glu Thr Leu Arg Ile Phe Gly
    205                 210                 215 cgt ggt gaa gct gaa att gaa agt att cgt tct gct tcg gaa gat ttc      905
Arg Gly Glu Ala Glu Ile Glu Ser Ile Arg Ser Ala Ser Glu Asp Phe
220                 225                 230                 235 cgc caa cgg aca atg gaa gtg cta cgg ctg gcg ttt tta tcc tcc ggc      953
Arg Gln Arg Thr Met Glu Val Leu Arg Leu Ala Phe Leu Ser Ser Gly
                240                 245                 250 att ctc gaa ttt ttt acc tcg ctg tca att gct ctg gtg gcg gtc tac     1001
Ile Leu Glu Phe Phe Thr Ser Leu Ser Ile Ala Leu Val Ala Val Tyr
            255                 260                 265 ttt ggt ttt tcc tat ctc ggc gag ctg gat ttt ggt cac tac gat acc     1049
Phe Gly Phe Ser Tyr Leu Gly Glu Leu Asp Phe Gly His Tyr Asp Thr
        270                 275                 280 ggt gtg acg ctg gct gcg ggt ttt ctg gcc ctg atc ctt gcg cca gag     1097
Gly Val Thr Leu Ala Ala Gly Phe Leu Ala Leu Ile Leu Ala Pro Glu
    285                 290                 295 ttt ttc cag cca tta cgc gat ctc ggt acg ttt tat cat gct aaa gcc     1145
Phe Phe Gln Pro Leu Arg Asp Leu Gly Thr Phe Tyr His Ala Lys Ala
300                 305                 310                 315 cag gct gtt ggc gca gct gac agt ctg aaa acg ttt atg gaa acc ccg     1193
Gln Ala Val Gly Ala Ala Asp Ser Leu Lys Thr Phe Met Glu Thr Pro
                320                 325                 330 ctc gcc cat ccg caa cgt ggt gag gcg gaa tta gca tcg acc gat ccg     1241
Leu Ala His Pro Gln Arg Gly Glu Ala Glu Leu Ala Ser Thr Asp Pro
            335                 340                 345 gtg acc att gag gcc gag gag ctg ttt atc acg tcg ccg gaa ggt aaa     1289
Val Thr Ile Glu Ala Glu Glu Leu Phe Ile Thr Ser Pro Glu Gly Lys
        350                 355                 360 acg ctg gcc gga ccg ctg aac ttt act ttg cca gca ggc caa cgt gcg     1337
Thr Leu Ala Gly Pro Leu Asn Phe Thr Leu Pro Ala Gly Gln Arg Ala
    365                 370                 375 gtg ttg gtt ggt cgc agc ggt tca ggt aaa agc tca ctg ctg aac gcg     1385
Val Leu Val Gly Arg Ser Gly Ser Gly Lys Ser Ser Leu Leu Asn Ala
380                 385                 390                 395 ctt tct ggt ttt ctc tca tat cag gga tcg cta cga atc aac ggg ata     1433
Leu Ser Gly Phe Leu Ser Tyr Gln Gly Ser Leu Arg Ile Asn Gly Ile
                400                 405                 410 gaa tta cgc gat tta tca cca gaa tca tgg cgt aaa cat ctc tcc tgg     1481
Glu Leu Arg Asp Leu Ser Pro Glu Ser Trp Arg Lys His Leu Ser Trp
            415                 420                 425 gtt ggg caa aac cca caa tta ccg gca gca aca ttg cgg gat aac gta     1529
Val Gly Gln Asn Pro Gln Leu Pro Ala Ala Thr Leu Arg Asp Asn Val
        430                 435                 440 cta ctg gcg cga cct gat gcc agc gaa caa gaa tta caa gca gcg ctg     1577
Leu Leu Ala Arg Pro Asp Ala Ser Glu Gln Glu Leu Gln Ala Ala Leu
    445                 450                 455 gat aac gcc tgg gtc agc gag ttt cta ccg ctc ctc cca caa ggc gtt     1625
Asp Asn Ala Trp Val Ser Glu Phe Leu Pro Leu Leu Pro Gln Gly Val
460                 465                 470                 475
```

```
gat acg cct gtt ggc gac cag gct gcc cgc ctt tcc gtg ggg cag gcg    1673
Asp Thr Pro Val Gly Asp Gln Ala Ala Arg Leu Ser Val Gly Gln Ala
            480                 485                 490 cag cgc gtg gcg gtg gcc cgt gcg tta cta aat ccc tgt tcg cta tta    1721
Gln Arg Val Ala Val Ala Arg Ala Leu Leu Asn Pro Cys Ser Leu Leu
        495                 500                 505 ctg ttg gat gaa ccc gct gcc agc ctt gat gct cac agt gaa cag cgc    1769
Leu Leu Asp Glu Pro Ala Ala Ser Leu Asp Ala His Ser Glu Gln Arg
    510                 515                 520 gta atg gag gcg ctg aat gcc gcc tct ctg cgc cag aca acg tta atg    1817
Val Met Glu Ala Leu Asn Ala Ala Ser Leu Arg Gln Thr Thr Leu Met
525                 530                 535 gtc acc cac cag tta gaa gat ctt gct gac tgg gat gtc att tgg gtt    1865
Val Thr His Gln Leu Glu Asp Leu Ala Asp Trp Asp Val Ile Trp Val
540                 545                 550                 555 atg cag gat ggc cgg att att gag caa gga cgt tac gcg gaa tta agt    1913
Met Gln Asp Gly Arg Ile Ile Glu Gln Gly Arg Tyr Ala Glu Leu Ser
            560                 565                 570 gtg gct ggt ggc cca ttc gcc aca tta ctg gcc cat cgt cag gag gag    1961
Val Ala Gly Gly Pro Phe Ala Thr Leu Leu Ala His Arg Gln Glu Glu
        575                 580                 585 att taa atg cgc gct ttg cta ccc tat ctg gca ctg tat aaa cgt cat    2009
Ile     Met Arg Ala Leu Leu Pro Tyr Leu Ala Leu Tyr Lys Arg His
    590                 595                 600 aaa tgg atg tta agt ctt ggt att gtg ctg gca att gtg acg ctg ctc    2057
Lys Trp Met Leu Ser Leu Gly Ile Val Leu Ala Ile Val Thr Leu Leu
            605                 610                 615 gcc agt atc ggt ctg ttg aca ctt tcc ggc tgg ttc ctc tcg gcc tca    2105
Ala Ser Ile Gly Leu Leu Thr Leu Ser Gly Trp Phe Leu Ser Ala Ser
620                 625                 630 gcg gtt gcg ggg gtt gcc gga ctg tac agc ttc aac tat atg cta ccc    2153
Ala Val Ala Gly Val Ala Gly Leu Tyr Ser Phe Asn Tyr Met Leu Pro
635                 640                 645                 650 gct gcg ggc gtg cgt ggc gca gca atc acc cgt act gcc ggg cgc tat    2201
Ala Ala Gly Val Arg Gly Ala Ala Ile Thr Arg Thr Ala Gly Arg Tyr
            655                 660                 665 ttt gaa cgt ctg gta agt cac gac gcg act ttc cgc gtg ttg cag cat    2249
Phe Glu Arg Leu Val Ser His Asp Ala Thr Phe Arg Val Leu Gln His
        670                 675                 680 ctg cgc att tac acc ttc agc aaa ttg ctg ccc ctc tcc cct gcc gga    2297
Leu Arg Ile Tyr Thr Phe Ser Lys Leu Leu Pro Leu Ser Pro Ala Gly
    685                 690                 695 ctg gcg cgc tat cgt cag ggc gaa ttg ctc aat cgc gtg gtg gcg gat    2345
Leu Ala Arg Tyr Arg Gln Gly Glu Leu Leu Asn Arg Val Val Ala Asp
700                 705                 710 gtt gat acg ctc gat cat ctt tac ctg cgc gtt atc tcg ccg ctg gtg    2393
Val Asp Thr Leu Asp His Leu Tyr Leu Arg Val Ile Ser Pro Leu Val
715                 720                 725                 730 ggc gct ttt gtg gtg att atg gtg gtg aca atc ggg tta agt ttc ctt    2441
Gly Ala Phe Val Val Ile Met Val Val Thr Ile Gly Leu Ser Phe Leu
            735                 740                 745 gat ttc acc ctc gcc ttt acg ctg ggc ggc att atg tta ctg acg ctt    2489
Asp Phe Thr Leu Ala Phe Thr Leu Gly Gly Ile Met Leu Leu Thr Leu
        750                 755                 760 ttc ctg atg cca ccg ctg ttt tat cgt gcg gga aaa agc acc ggg caa    2537
Phe Leu Met Pro Pro Leu Phe Tyr Arg Ala Gly Lys Ser Thr Gly Gln
    765                 770                 775 aat ctg act cat ctt cgc gga cag tat cgc caa caa ctg acg gcc tgg    2585
Asn Leu Thr His Leu Arg Gly Gln Tyr Arg Gln Gln Leu Thr Ala Trp
780                 785                 790
```

```
ctg caa ggg caa gct gag ctg acc att ttt ggt gcc agc gat cgt tat    2633
Leu Gln Gly Gln Ala Glu Leu Thr Ile Phe Gly Ala Ser Asp Arg Tyr
795                 800                 805                 810 cgc acg caa cta gag aat aca gaa att caa tgg ctg gaa gcg caa cgc    2681
Arg Thr Gln Leu Glu Asn Thr Glu Ile Gln Trp Leu Glu Ala Gln Arg
            815                 820                 825 cgt caa tct gaa ctg acc gca ttg tcg caa gcg ata atg ctg ctc att    2729
Arg Gln Ser Glu Leu Thr Ala Leu Ser Gln Ala Ile Met Leu Leu Ile
830                 835                 840 ggc gcg tta gcg gtg atc ctg atg ctg tgg atg gcg tct ggc ggc gtt    2777
Gly Ala Leu Ala Val Ile Leu Met Leu Trp Met Ala Ser Gly Gly Val
            845                 850                 855 ggc ggc aat gct caa ccc ggc gcg tta att gcc ctg ttt gtc ttc tgc    2825
Gly Gly Asn Ala Gln Pro Gly Ala Leu Ile Ala Leu Phe Val Phe Cys
860                 865                 870 gcg tta gcc gcg ttt gaa gca ctg gca cca gta acg ggt gca ttt cag    2873
Ala Leu Ala Ala Phe Glu Ala Leu Ala Pro Val Thr Gly Ala Phe Gln
875                 880                 885                 890 cat ctg ggg caa gtc att gcc tct gcc gta cgt atc tct gac tta acg    2921
His Leu Gly Gln Val Ile Ala Ser Ala Val Arg Ile Ser Asp Leu Thr
            895                 900                 905 gat caa aaa ccg gag gtc acc ttt cct gat acc caa act cgt gtt gcc    2969
Asp Gln Lys Pro Glu Val Thr Phe Pro Asp Thr Gln Thr Arg Val Ala
910                 915                 920 gat cgc gtt tcg ctg acg tta cgg gat gtt cag ttc act tat ccg gag    3017
Asp Arg Val Ser Leu Thr Leu Arg Asp Val Gln Phe Thr Tyr Pro Glu
            925                 930                 935 caa tct caa cag gca ctt aaa ggg att tct ctt cag gta aac gcc ggg    3065
Gln Ser Gln Gln Ala Leu Lys Gly Ile Ser Leu Gln Val Asn Ala Gly
940                 945                 950 gaa cat ata gcg att ctc ggg cga acc gga tgc ggc aaa tca aca ctg    3113
Glu His Ile Ala Ile Leu Gly Arg Thr Gly Cys Gly Lys Ser Thr Leu
955                 960                 965                 970 tta caa cag ctg acc cgc gca tgg gac ccg caa cag ggc gag att ttg    3161
Leu Gln Gln Leu Thr Arg Ala Trp Asp Pro Gln Gln Gly Glu Ile Leu
            975                 980                 985 ctt aac gat agc ccc ata gcc agc ctg aat gaa gcg gct cta cga cag    3209
Leu Asn Asp Ser Pro Ile Ala Ser Leu Asn Glu Ala Ala Leu Arg Gln
990                 995                 1000 acc atc agc gtt gtt cct cag cga gtg cat ctg ttt agc gcc acg        3254
Thr Ile Ser Val Val Pro Gln Arg Val His Leu Phe Ser Ala Thr
            1005                1010                1015 ctg cgt gat aat ctt tta ctc gcc tcg cct ggc agt agt gat gag        3299
Leu Arg Asp Asn Leu Leu Leu Ala Ser Pro Gly Ser Ser Asp Glu
1020                1025                1030 gct ctg tcg gag atc ttg cgt cgc gtt ggc ctg gaa aag ctg ctc        3344
Ala Leu Ser Glu Ile Leu Arg Arg Val Gly Leu Glu Lys Leu Leu
            1035                1040                1045 gag gat gca ggt ctc aac agt tgg tta ggt gaa ggc gga cgc cag        3389
Glu Asp Ala Gly Leu Asn Ser Trp Leu Gly Glu Gly Gly Arg Gln
1050                1055                1060 ctc tcc ggt ggt gaa ctg cgc cgt ctg gct atc gcc cgt gcg ctg        3434
Leu Ser Gly Gly Glu Leu Arg Arg Leu Ala Ile Ala Arg Ala Leu
            1065                1070                1075 tta cat gat gcg cca ctg gtg ttg ctg gat gaa cct acc gaa ggc        3479
Leu His Asp Ala Pro Leu Val Leu Leu Asp Glu Pro Thr Glu Gly
1080                1085                1090 tta gat gcc aca acc gaa agc cag atc ctt gaa ttg ctt gca gaa        3524
Leu Asp Ala Thr Thr Glu Ser Gln Ile Leu Glu Leu Leu Ala Glu
            1095                1100                1105
```

```
atg atg cgt gag aaa acg gtg tta atg gtc acc cat cga ctt cgc    3569
Met Met Arg Glu Lys Thr Val Leu Met Val Thr His Arg Leu Arg
        1110                1115                1120 gga ctc tct cgt ttc caa caa ata ata gtg atg gac aac ggg caa    3614
Gly Leu Ser Arg Phe Gln Gln Ile Ile Val Met Asp Asn Gly Gln
    1125                1130                1135 att att gag caa ggt act cac gca gaa ctg ctt gcc aga cag ggg    3659
Ile Ile Glu Gln Gly Thr His Ala Glu Leu Leu Ala Arg Gln Gly
1140                1145                1150 cgt tat tac cag ttc aag cag ggt ttg taa gctattattg aacgatccga  3709
Arg Tyr Tyr Gln Phe Lys Gln Gly Leu
        1155                1160 cttgcgtgga gttttgcggt catgcgcctg gttcagcttt ctcgccattc aatagccttc  3769
ccttccccgg aaggcgcatt acgtgagcct aacggcctgc tggcacttgg gggcgatctt    3829
agccctgcgc gcctgttaat ggcttaccag cgtggtattt ttccgtggtt ttctccaggc    3889

<210> SEQ ID NO 28
<211> LENGTH: 1591
<212> TYPE: DNA
<213> ORGANISM: Escherichia coli
<220> FEATURE:
<221> NAME/KEY: CDS
<222> LOCATION: (201)..(1388)

<400> SEQUENCE: 28
gtctgaccat cagcgaaggg cgttatcatc aggtgaaacg catgttcgcc gccgtgggta     60
accacgtggt tgagctgcat cgtgaacgta ttggcggtat tacgcggat gctgatttag    120 ccccggtga atatcgtccg ttaactgaag aagaaattgc cagcgtcgtc taacttttca    180
atgactttca ggagcccgtt gtg acc acc cga cag cat tcg tcg ttt gct        230
                       Met Thr Thr Arg Gln His Ser Ser Phe Ala
                        1               5                  10 att gtt ttt atc ctt ggc ctg ctg gcc atg ttg atg ccg ctg tcg att    278
Ile Val Phe Ile Leu Gly Leu Leu Ala Met Leu Met Pro Leu Ser Ile
                15                  20                  25 gat atg tat ctg ccc gcg cta ccg gta att tca gcg cag ttt ggc gta    326
Asp Met Tyr Leu Pro Ala Leu Pro Val Ile Ser Ala Gln Phe Gly Val
        30                  35                  40 ccg gcg ggc agt acg cag atg acc ctc agt act tat att ctg ggc ttt    374
Pro Ala Gly Ser Thr Gln Met Thr Leu Ser Thr Tyr Ile Leu Gly Phe
    45                  50                  55 gcg ttg ggg cag tta atc tac ggg ccg atg gca gac agc ttc ggg cgt    422
Ala Leu Gly Gln Leu Ile Tyr Gly Pro Met Ala Asp Ser Phe Gly Arg
60                  65                  70 aag ccg gtg gtg ctc ggc ggt acg ctg gtg ttt gcc gcc gcc gcg gtg    470
Lys Pro Val Val Leu Gly Gly Thr Leu Val Phe Ala Ala Ala Ala Val
75                  80                  85                  90 gcg tgt gcg ttg gca aac acc atc gat cag ctg att gtg atg cgt ttc    518
Ala Cys Ala Leu Ala Asn Thr Ile Asp Gln Leu Ile Val Met Arg Phe
                95                  100                 105 ttc cac ggg ctg gct gcg gct gcg gcc agc gtg gtc att aac gcc ctg    566
Phe His Gly Leu Ala Ala Ala Ala Ala Ser Val Val Ile Asn Ala Leu
        110                 115                 120 atg cgc gat att tac ccg aaa gaa gag ttc tcg cgg atg atg tcg ttt    614
Met Arg Asp Ile Tyr Pro Lys Glu Glu Phe Ser Arg Met Met Ser Phe
    125                 130                 135 gtc atg ctg gtg aca acc att gca ccg ctg atg gca ccg ata gtt ggc    662
Val Met Leu Val Thr Thr Ile Ala Pro Leu Met Ala Pro Ile Val Gly
140                 145                 150 ggc tgg gtg ctg gtg tgg ctg agc tgg cat tac atc ttc tgg atc ctg    710
```

```
Gly Trp Val Leu Val Trp Leu Ser Trp His Tyr Ile Phe Trp Ile Leu
155                 160                 165                 170 gca tta gcg gcg att ctg gct tcg gca atg att ttc ttc ctg att aaa      758
Ala Leu Ala Ala Ile Leu Ala Ser Ala Met Ile Phe Phe Leu Ile Lys
                175                 180                 185 gaa acc tta cca ccg gag cgt cgt cag cca ttt cac att cgt acc act      806
Glu Thr Leu Pro Pro Glu Arg Arg Gln Pro Phe His Ile Arg Thr Thr
                190                 195                 200 att ggt aac ttt gcg gcg ctg ttc cgc cat aaa cgt gtc ctg agc tac      854
Ile Gly Asn Phe Ala Ala Leu Phe Arg His Lys Arg Val Leu Ser Tyr
                205                 210                 215 atg ctt gcc agt ggt ttc agc ttt gcc ggg atg ttc tca ttc tta agc      902
Met Leu Ala Ser Gly Phe Ser Phe Ala Gly Met Phe Ser Phe Leu Ser
                220                 225                 230 gcc gga ccg ttt gtt tat att gaa att aac cac gtc gcg ccg gaa aac      950
Ala Gly Pro Phe Val Tyr Ile Glu Ile Asn His Val Ala Pro Glu Asn
235                 240                 245                 250 ttt ggt tat tac ttt gcg cta aac att gtt ttt ctg ttc gtg atg acc      998
Phe Gly Tyr Tyr Phe Ala Leu Asn Ile Val Phe Leu Phe Val Met Thr
                255                 260                 265 atc ttt aac agc cgc ttc gtc cgc cgc att ggc gcg tta aat atg ttc     1046
Ile Phe Asn Ser Arg Phe Val Arg Arg Ile Gly Ala Leu Asn Met Phe
                270                 275                 280 cgc tcg ggg ttg tgg ata caa ttt att atg gca gcg tgg atg gtc atc     1094
Arg Ser Gly Leu Trp Ile Gln Phe Ile Met Ala Ala Trp Met Val Ile
                285                 290                 295 agt gcg ctg ctg ggg ctg gga ttt tgg tcg ctg gtg gtt ggc gtt gcg     1142
Ser Ala Leu Leu Gly Leu Gly Phe Trp Ser Leu Val Val Gly Val Ala
300                 305                 310 gcg ttt gtg ggc tgc gtg tcg atg gtg tca tcc aat gcg atg gcg gtc     1190
Ala Phe Val Gly Cys Val Ser Met Val Ser Ser Asn Ala Met Ala Val
315                 320                 325                 330 att ctt gat gag ttt ccc cat atg gcg gga acg gca tct tcg ctg gca     1238
Ile Leu Asp Glu Phe Pro His Met Ala Gly Thr Ala Ser Ser Leu Ala
                335                 340                 345 gga acc ttc cgt ttt ggc ata ggg gca att gtt ggc gca ttg ctt tct     1286
Gly Thr Phe Arg Phe Gly Ile Gly Ala Ile Val Gly Ala Leu Leu Ser
                350                 355                 360 ctt gcg acc ttt aac tct gca tgg ccg atg att tgg tca att gca ttc     1334
Leu Ala Thr Phe Asn Ser Ala Trp Pro Met Ile Trp Ser Ile Ala Phe
                365                 370                 375 tgc gca acc agc tcc att ctc ttc tgt ctg tac gcc agt cgg ccg aaa     1382
Cys Ala Thr Ser Ser Ile Leu Phe Cys Leu Tyr Ala Ser Arg Pro Lys
380                 385                 390 aaa cgg tgatctattg cacaacgagg aagctaaaag gcttcctttg ttgatgcatg     1438
Lys Arg
395 tcaaccacaa atctatcatt cccccgatat atgtttattt tatgtaaaat caatttatgt    1498 aaaaagtcac atcattgtag ttaaaaaggt tgagttagat cgcagaaacg ggtacatata    1558 gccccgcaaa cgtgaccacg cccgcagata tta                                 1591

<210> SEQ ID NO 29
<211> LENGTH: 1594
<212> TYPE: DNA
<213> ORGANISM: Escherichia coli
<220> FEATURE:
<221> NAME/KEY: CDS
<222> LOCATION: (201)..(1391)

<400> SEQUENCE: 29
```

-continued

```
caaaggcgag gcactggtgc ttttcaccac agataacgaa ctgacgcgcg ataagttgca      60
acagtatgcc cgcgagcacg gcgtgccgga gcttgctgta ccgcgcgata ttcgctatct     120
gaaacagatg ccattacttg gcagcggcaa acctgacttt gtcacgttga aaagctgggt     180
agacgaagcg aacaacacg atg agt gag tca gtg cac act aac act tcg          230
                     Met Ser Glu Ser Val His Thr Asn Thr Ser
                      1               5                  10 ttg tgg tcg aag ggg atg aaa gcg gtt atc gtg gcg cag ttt ctc tct       278
Leu Trp Ser Lys Gly Met Lys Ala Val Ile Val Ala Gln Phe Leu Ser
             15                  20                  25 gcg ttt ggc gat aat gcc cta ctg ttt gcc act ctg gcg tta ctg aaa       326
Ala Phe Gly Asp Asn Ala Leu Leu Phe Ala Thr Leu Ala Leu Leu Lys
         30                  35                  40 gcg cag ttc tat ccg gag tgg agc cag ccc atc ctg caa atg gtg ttt       374
Ala Gln Phe Tyr Pro Glu Trp Ser Gln Pro Ile Leu Gln Met Val Phe
     45                  50                  55 gta ggt gct tac att ctt ttt gcg ccg ttt gtc ggg cag gtg gcg gat       422
Val Gly Ala Tyr Ile Leu Phe Ala Pro Phe Val Gly Gln Val Ala Asp
 60                  65                  70 agc ttc gcc aaa ggc cgg gtg atg atg ttt gcc aac ggc ctg aag ctg       470
Ser Phe Ala Lys Gly Arg Val Met Met Phe Ala Asn Gly Leu Lys Leu
75                  80                  85                  90 ctg ggc gca gcc agt atc tgc ttt ggt atc aat ccg ttt ctc ggc tat       518
Leu Gly Ala Ala Ser Ile Cys Phe Gly Ile Asn Pro Phe Leu Gly Tyr
                 95                 100                 105 acg ctg gtg ggt gtt ggt gct gca gcc tat tca ccg gcg aaa tac ggt       566
Thr Leu Val Gly Val Gly Ala Ala Ala Tyr Ser Pro Ala Lys Tyr Gly
             110                 115                 120 att ctc ggc gaa tta acc acg ggt agt aag tta gtg aaa gct aac ggt       614
Ile Leu Gly Glu Leu Thr Thr Gly Ser Lys Leu Val Lys Ala Asn Gly
         125                 130                 135 tta atg gaa gct tct acc ata gcg gcg att ttg ctc ggt tcc gta gcc       662
Leu Met Glu Ala Ser Thr Ile Ala Ala Ile Leu Leu Gly Ser Val Ala
     140                 145                 150 ggt ggt gtg ctg gct gac tgg cat gtc ctc gtc gcc ctg gcc gca tgc       710
Gly Gly Val Leu Ala Asp Trp His Val Leu Val Ala Leu Ala Ala Cys
155                 160                 165                 170 gca ctg gcc tac ggt ggt gcg gtc gtt gcc aat atc tac att ccc aaa       758
Ala Leu Ala Tyr Gly Gly Ala Val Val Ala Asn Ile Tyr Ile Pro Lys
                 175                 180                 185 ctg gcg gcg gcg cgt ccg ggg cag tcc tgg aat ctc atc aac atg acc       806
Leu Ala Ala Ala Arg Pro Gly Gln Ser Trp Asn Leu Ile Asn Met Thr
             190                 195                 200 cgc agt ttc ctg aat gcc tgc acc tcg cta tgg cgc aat ggt gaa acg       854
Arg Ser Phe Leu Asn Ala Cys Thr Ser Leu Trp Arg Asn Gly Glu Thr
         205                 210                 215 cgt ttt tcg ctg gtg ggc acc agt tta ttc tgg gga gcg ggt gtc acg       902
Arg Phe Ser Leu Val Gly Thr Ser Leu Phe Trp Gly Ala Gly Val Thr
     220                 225                 230 ctg cgt ttc ctg ttg gtg ctg tgg gta ccg gtg gcg ctg ggc att acc       950
Leu Arg Phe Leu Leu Val Leu Trp Val Pro Val Ala Leu Gly Ile Thr
235                 240                 245                 250 gat aac gct acg ccc acc tat ctc aac gcg atg gta gcg att ggt atc       998
Asp Asn Ala Thr Pro Thr Tyr Leu Asn Ala Met Val Ala Ile Gly Ile
                 255                 260                 265 gtg gtt ggc gca ggt gcg gca gcg aag tta gtt acg ctg gaa acc gtg      1046
Val Val Gly Ala Gly Ala Ala Lys Leu Val Thr Leu Glu Thr Val
             270                 275                 280 tca cgc tgt atg cca gcc ggg att ttg att ggc gtg gtg gta ctg att      1094
Ser Arg Cys Met Pro Ala Gly Ile Leu Ile Gly Val Val Val Leu Ile
```

-continued

```
               285                 290                 295
ttt tcc ctg caa cac gag ctg ctg cca gcc tat gcc ttg ttg atg ctg     1142
Phe Ser Leu Gln His Glu Leu Leu Pro Ala Tyr Ala Leu Leu Met Leu
300                 305                 310 att ggc gtg atg ggg ggc ttt ttt gtc gtt ccg ctc aat gcg ttg cta     1190
Ile Gly Val Met Gly Gly Phe Phe Val Val Pro Leu Asn Ala Leu Leu
315                 320                 325                 330 cag gag cgg ggt aaa aaa agc gtc ggg gcg ggg aat gcg att gca gta     1238
Gln Glu Arg Gly Lys Lys Ser Val Gly Ala Gly Asn Ala Ile Ala Val
                335                 340                 345 caa aac ctt ggc gaa aac agc gcc atg ttg ttg atg ctg ggc att tac     1286
Gln Asn Leu Gly Glu Asn Ser Ala Met Leu Leu Met Leu Gly Ile Tyr
            350                 355                 360 tcg ctg gcg gta atg ata ggc atc ccg gtc gtg ccc att ggc att ggc     1334
Ser Leu Ala Val Met Ile Gly Ile Pro Val Val Pro Ile Gly Ile Gly
            365                 370                 375 ttc ggt gcg ctg ttt gcg ctg gca ata acg gcg ctg tgg atc tgg cag     1382
Phe Gly Ala Leu Phe Ala Leu Ala Ile Thr Ala Leu Trp Ile Trp Gln
        380                 385                 390 cgc cgt cat taatatttaa cgccggtttt aaccggcgtt aatcttatgg             1431
Arg Arg His
395 tgccggataa gtataaacct gatgcaccgc ttcaatttca gctaatacgt cttcgcttaa   1491 ctccagatgc aaactttcga tgttagtttt cagctgatcc atcgtggttg cgcccagcag   1551 agtgctggca caaacggtt gacggcgtac aaacgcgagc gcc                      1594

<210> SEQ ID NO 30
<211> LENGTH: 1627
<212> TYPE: DNA
<213> ORGANISM: Escherichia coli
<220> FEATURE:
<221> NAME/KEY: CDS
<222> LOCATION: (201)..(1424)

<400> SEQUENCE: 30
gcccggaagg cgttccttca cgctattaaa tctcccatgc cggatgcttc agaatggcat     60
ccggcattac cacagcaaat cccctgatt tagcgataaa agctctctgg attgcgcccc    120
ctggaagtcg ggcgcataat tagtgtgctt atcttttctt cttatgttca ccgcgcctgg   180
cgcaccaaca gcggattgct atg tca ccc tgt gaa aat gac acc cct ata       230
                        Met Ser Pro Cys Glu Asn Asp Thr Pro Ile
                         1               5                  10 aac tgg aaa cga aac ctg atc gtc gcc tgg cta ggc tgt ttt ctt acc     278
Asn Trp Lys Arg Asn Leu Ile Val Ala Trp Leu Gly Cys Phe Leu Thr
                15                  20                  25 ggt gcc gcc ttc agt ctg gta atg ccc ttc tta ccc ctc tac gtt gag    326
Gly Ala Ala Phe Ser Leu Val Met Pro Phe Leu Pro Leu Tyr Val Glu
            30                  35                  40 cag ctt ggc gtt acc ggt cac tcc gcc ctg aat atg tgg tcc ggt att    374
Gln Leu Gly Val Thr Gly His Ser Ala Leu Asn Met Trp Ser Gly Ile
        45                  50                  55 gtc ttc agc att aca ttt tta ttt tcg gcc atc gcc tca ccg ttt tgg    422
Val Phe Ser Ile Thr Phe Leu Phe Ser Ala Ile Ala Ser Pro Phe Trp
    60                  65                  70 ggt gga ctc gcc gac cgt aaa ggc cga aaa ctc atg cta tta cgc tct    470
Gly Gly Leu Ala Asp Arg Lys Gly Arg Lys Leu Met Leu Leu Arg Ser
75                  80                  85                  90 gcc ctc ggc atg ggc atc gtg atg gtg ttg atg ggg ctg gca caa aat    518
Ala Leu Gly Met Gly Ile Val Met Val Leu Met Gly Leu Ala Gln Asn
                95                 100                 105
```

| | | |
|---|---|---|
| atc tgg cag ttt ttg atc ctg cgg gcg ctt ctt ggg tta ctt ggc gga<br>Ile Trp Gln Phe Leu Ile Leu Arg Ala Leu Leu Gly Leu Leu Gly Gly<br>110                              115                            120 | | 566 |
| ttt gtc ccc aac gct aat gct ctt atc gcc aca caa gta ccg cgt aat<br>Phe Val Pro Asn Ala Asn Ala Leu Ile Ala Thr Gln Val Pro Arg Asn<br>        125                            130                            135 | | 614 |
| aaa agc ggc tgg gcg ctg ggt acg ctc tcc aca ggc ggc gtt agt ggt<br>Lys Ser Gly Trp Ala Leu Gly Thr Leu Ser Thr Gly Gly Val Ser Gly<br>140                              145                            150 | | 662 |
| gcg ttg ctc ggc cca atg gct ggc ggc ctg ctc gcc gat agc tac ggc<br>Ala Leu Leu Gly Pro Met Ala Gly Gly Leu Leu Ala Asp Ser Tyr Gly<br>155                              160                            165                        170 | | 710 |
| tta cgt ccg gta ttc ttt att acc gcc agt gtg ctc ata ctc tgc ttt<br>Leu Arg Pro Val Phe Phe Ile Thr Ala Ser Val Leu Ile Leu Cys Phe<br>                175                            180                            185 | | 758 |
| ttc gtc acc ctg ttt tgc atc aga gaa aaa ttc cag ccg gtc agc aaa<br>Phe Val Thr Leu Phe Cys Ile Arg Glu Lys Phe Gln Pro Val Ser Lys<br>                190                            195                            200 | | 806 |
| aaa gag atg ctg cac atg cgg gaa gtg gtg aca tca ctt aaa aac ccg<br>Lys Glu Met Leu His Met Arg Glu Val Val Thr Ser Leu Lys Asn Pro<br>        205                            210                            215 | | 854 |
| aaa ctg gta ctc agc ctg ttt gtc act acg tta atc atc cag gtg gcg<br>Lys Leu Val Leu Ser Leu Phe Val Thr Thr Leu Ile Ile Gln Val Ala<br>220                              225                            230 | | 902 |
| acg ggc tca att gcc ccc att ctg acg ctg tat gtc cgc gaa ctg gcg<br>Thr Gly Ser Ile Ala Pro Ile Leu Thr Leu Tyr Val Arg Glu Leu Ala<br>235                              240                            245                        250 | | 950 |
| ggt aac gtc agt aac gtc gcc ttt atc agt ggc atg atc gcc tcg gtg<br>Gly Asn Val Ser Asn Val Ala Phe Ile Ser Gly Met Ile Ala Ser Val<br>                        255                            260                            265 | | 998 |
| cca ggc gtg gcg gct ctg cta agt gca cca cga ctc ggc aaa ctt ggc<br>Pro Gly Val Ala Ala Leu Leu Ser Ala Pro Arg Leu Gly Lys Leu Gly<br>                270                            275                            280 | | 1046 |
| gat cga atc gga ccc gaa aag atc ctg att aca gcg ctg atc ttt tct<br>Asp Arg Ile Gly Pro Glu Lys Ile Leu Ile Thr Ala Leu Ile Phe Ser<br>        285                            290                            295 | | 1094 |
| gta ctg ctg ttg atc cca atg tct tac gtt cag acg cca ttg caa ctt<br>Val Leu Leu Leu Ile Pro Met Ser Tyr Val Gln Thr Pro Leu Gln Leu<br>300                              305                            310 | | 1142 |
| ggg att tta cgt ttt ttg ctc ggt gcc gcc gat ggt gca cta ctc ccc<br>Gly Ile Leu Arg Phe Leu Leu Gly Ala Ala Asp Gly Ala Leu Leu Pro<br>315                              320                            325                        330 | | 1190 |
| gcc gta cag aca ctg ttg gtt tac aac tcg agc aac cag atc gcc ggg<br>Ala Val Gln Thr Leu Leu Val Tyr Asn Ser Ser Asn Gln Ile Ala Gly<br>                335                            340                            345 | | 1238 |
| cgt atc ttc agc tat aac caa tcg ttt cgt gat att ggc aac gtt acc<br>Arg Ile Phe Ser Tyr Asn Gln Ser Phe Arg Asp Ile Gly Asn Val Thr<br>                      350                            355                            360 | | 1286 |
| gga cca ttg atg gga gca gcg att tca gcg aac tac ggt ttc aga gcg<br>Gly Pro Leu Met Gly Ala Ala Ile Ser Ala Asn Tyr Gly Phe Arg Ala<br>        365                            370                            375 | | 1334 |
| gta ttt ctc gtc acc gct ggc gta gtg tta ttc aac gca gtc tat tca<br>Val Phe Leu Val Thr Ala Gly Val Val Leu Phe Asn Ala Val Tyr Ser<br>380                              385                            390 | | 1382 |
| tgg aac agt cta cgt cgt cgt cga ata ccc cag gta tcg aac tgattttcg<br>Trp Asn Ser Leu Arg Arg Arg Arg Ile Pro Gln Val Ser Asn<br>395                              400                            405 | | 1434 |
| cctttcatac ttgcaaaagc ggagaatcag ctatccttt ccctgaaacc tcatcaactc | | 1494 |
| aaagggagaa tcgtgatgac catgtacgca acgcttgaag aagccattga cgctgcacgc | | 1554 |

```
gaagaatttc ttgcagacaa ccccggcatc gacgccgaag atgcgaatgt gcaacagttc    1614
aatgcccaaa aat                                                       1627

<210> SEQ ID NO 31
<211> LENGTH: 1633
<212> TYPE: DNA
<213> ORGANISM: Escherichia coli
<220> FEATURE:
<221> NAME/KEY: CDS
<222> LOCATION: (201)..(1430)

<400> SEQUENCE: 31
catcgtctta tttccctcaa gcggcctgtt tacggtgggt gattgtaacg ggcataggtt    60
aaataaaact taagaaagc gtagctatac tcgtaataat gtaagaatgt gcttaaccgt    120
ggtttcagct acaaaattcg ctttctcgtt agctgcgctt ttattaaact ctgcgcgatt    180
attattggcg aagaaattgc atg caa aat aaa tta gct tcc ggt gcc agg      230
                         Met Gln Asn Lys Leu Ala Ser Gly Ala Arg
                          1               5                  10 ctt gga cgt cag gcg tta ctt ttc cct ctc tgt ctg gtg ctt tac gaa   278
Leu Gly Arg Gln Ala Leu Leu Phe Pro Leu Cys Leu Val Leu Tyr Glu
             15                  20                  25 ttt tca acc tat atc ggc aac gat atg att caa ccc ggt atg ttg gcc   326
Phe Ser Thr Tyr Ile Gly Asn Asp Met Ile Gln Pro Gly Met Leu Ala
         30                  35                  40 gtg gtg gaa caa tat cag gcg ggc att gat tgg gtt cct act tcg atg   374
Val Val Glu Gln Tyr Gln Ala Gly Ile Asp Trp Val Pro Thr Ser Met
     45                  50                  55 acc gcg tat ctg gcg ggc ggg atg ttt tta caa tgg ctg ctg ggg ccg   422
Thr Ala Tyr Leu Ala Gly Gly Met Phe Leu Gln Trp Leu Leu Gly Pro
 60                  65                  70 ctg tcg gat cgt att ggt cgc cgt ccg gtg atg ctg gcg gga gtg gtg   470
Leu Ser Asp Arg Ile Gly Arg Arg Pro Val Met Leu Ala Gly Val Val
 75                  80                  85                  90 tgg ttt atc gtc acc tgt ctg gca ata ttg ctg gcg caa aac att gaa   518
Trp Phe Ile Val Thr Cys Leu Ala Ile Leu Leu Ala Gln Asn Ile Glu
                 95                 100                 105 caa ttc acc ctg ttg cgc ttc ttg cag ggc ata agc ctc tgt ttc att   566
Gln Phe Thr Leu Leu Arg Phe Leu Gln Gly Ile Ser Leu Cys Phe Ile
            110                 115                 120 ggc gct gtg gga tac gcc gca att cag gaa tcc ttc gaa gag gcg gtt   614
Gly Ala Val Gly Tyr Ala Ala Ile Gln Glu Ser Phe Glu Glu Ala Val
        125                 130                 135 tgt atc aag atc acc gcg ctg atg gcg aac gtg gcg ctg att gct ccg   662
Cys Ile Lys Ile Thr Ala Leu Met Ala Asn Val Ala Leu Ile Ala Pro
    140                 145                 150 cta ctt ggt ccg ctg gtg ggc gcg gcg tgg atc cat gtg ctg ccc tgg   710
Leu Leu Gly Pro Leu Val Gly Ala Ala Trp Ile His Val Leu Pro Trp
155                 160                 165                 170 gag ggg atg ttt gtt ttg ttt gcc gca ttg gca gcg atc tcc ttt ttc   758
Glu Gly Met Phe Val Leu Phe Ala Ala Leu Ala Ala Ile Ser Phe Phe
                175                 180                 185 ggt ctg caa cga gcc atg cct gaa acc gcc acg cgt ata ggc gag aaa   806
Gly Leu Gln Arg Ala Met Pro Glu Thr Ala Thr Arg Ile Gly Glu Lys
            190                 195                 200 ctg tca ctg aaa gaa ctc ggt cgt gac tat aag ctg gtg ctg aag aac   854
Leu Ser Leu Lys Glu Leu Gly Arg Asp Tyr Lys Leu Val Leu Lys Asn
        205                 210                 215 ggc cgc ttt gtg gcg ggg gcg ctg gcg ctg gga ttc gtt agt ctg ccg   902
Gly Arg Phe Val Ala Gly Ala Leu Ala Leu Gly Phe Val Ser Leu Pro
    220                 225                 230
```

```
                                                                      950
ttg ctg gcg tgg atc gcc cag tcg ccg att atc atc att acc ggc gag
Leu Leu Ala Trp Ile Ala Gln Ser Pro Ile Ile Ile Ile Thr Gly Glu
235                 240                 245                 250

998
cag ttg agc agc tat gaa tat ggc ttg ctg caa gtg cct att ttc ggg
Gln Leu Ser Ser Tyr Glu Tyr Gly Leu Leu Gln Val Pro Ile Phe Gly
                    255                 260                 265

1046
gcg tta att gcg ggt aac ttg ctg tta gcg cgt ctg acc tcg cgc cgc
Ala Leu Ile Ala Gly Asn Leu Leu Leu Ala Arg Leu Thr Ser Arg Arg
                270                 275                 280

1094
acc gta cgt tcg ctg att att atg ggc ggc tgg ccg att atg att ggt
Thr Val Arg Ser Leu Ile Ile Met Gly Gly Trp Pro Ile Met Ile Gly
            285                 290                 295

1142
cta ttg gtc gct gct gcg gca acg gtt atc tca tcg cac gcg tat tta
Leu Leu Val Ala Ala Ala Thr Val Ile Ser Ser His Ala Tyr Leu
300                 305                 310

1190
tgg atg act gcc ggg tta agt att tat gct ttc ggt att ggt ctg gcg
Trp Met Thr Ala Gly Leu Ser Ile Tyr Ala Phe Gly Ile Gly Leu Ala
315                 320                 325                 330

1238
aat gcg gga ctg gtg cga tta acc ctg ttt gcc agc gat atg agt aaa
Asn Ala Gly Leu Val Arg Leu Thr Leu Phe Ala Ser Asp Met Ser Lys
                    335                 340                 345

1286
ggt acg gtt tct gcc gcg atg gga atg ctg caa atg ctg atc ttt acc
Gly Thr Val Ser Ala Ala Met Gly Met Leu Gln Met Leu Ile Phe Thr
                350                 355                 360

1334
gtt ggt att gaa atc agc aaa cat gcc tgg ctg aac ggg ggc aac gga
Val Gly Ile Glu Ile Ser Lys His Ala Trp Leu Asn Gly Gly Asn Gly
            365                 370                 375

1382
ctg ttt aat ctc ttc aac ctt gtc aac gga att ttg tgg ctg tcg ctg
Leu Phe Asn Leu Phe Asn Leu Val Asn Gly Ile Leu Trp Leu Ser Leu
380                 385                 390

1430
atg gtt atc ttt tta aaa gat aaa cag atg gga aat tct cac gaa ggg
Met Val Ile Phe Leu Lys Asp Lys Gln Met Gly Asn Ser His Glu Gly
395                 400                 405                 410 taaaaaaatg cctgactgct tgtgcgatc aggcattctc gaattaatgg tgatggtcgt    1490
caatctggtg ttcgataacc atcccttcac ctacgctggc aagatggcga acataaggat    1550
gcgggcggta agccggagct ggcgcaggag ccacatagac ggtttgcggc acagtcgcga    1610
cgctgaccgc ttgtggaacg ctg                                           1633

<210> SEQ ID NO 32
<211> LENGTH: 1431
<212> TYPE: DNA
<213> ORGANISM: Escherichia coli
<220> FEATURE:
<221> NAME/KEY: CDS
<222> LOCATION: (201)..(575)
<220> FEATURE:
<221> NAME/KEY: CDS
<222> LOCATION: (592)..(978)
<220> FEATURE:
<221> NAME/KEY: CDS
<222> LOCATION: (1013)..(1228)

<400> SEQUENCE: 32
cactctttag ctagccttgc atcgcattga acaaaacttg aaccgattta gcaaaacgtg     60
gcatcggtca attcattcat ttgacttata cttgcctggg caatattatc ccctgcaact    120
aattacttgc cagggcaact aatgtgaaaa gtaccagcga tctgttcaat gaattattc    180 cattgggtcg cttaatccat atg gtt aat cag aag aaa gat cgc ctg ctt aac    233
                         Met Val Asn Gln Lys Lys Asp Arg Leu Leu Asn
                           1               5                  10
```

```
gag tat ctg tct ccg ctg gat att acc gcg gca cag ttt aag gtg ctc       281
Glu Tyr Leu Ser Pro Leu Asp Ile Thr Ala Ala Gln Phe Lys Val Leu
         15                  20                  25 tgc tct atc cgc tgc gcg gcg tgt att act ccg gtt gaa ctg aaa aag       329
Cys Ser Ile Arg Cys Ala Ala Cys Ile Thr Pro Val Glu Leu Lys Lys
     30                  35                  40 gta ttg tcg gtc gac ctg gga gca ctg acc cgt atg ctg gat cgc ctg       377
Val Leu Ser Val Asp Leu Gly Ala Leu Thr Arg Met Leu Asp Arg Leu
 45                  50                  55 gtc tgt aaa ggc tgg gtg gaa agg ttg ccg aac ccg aat gac aag cgc       425
Val Cys Lys Gly Trp Val Glu Arg Leu Pro Asn Pro Asn Asp Lys Arg
 60                  65                  70                  75 ggc gta ctg gta aaa ctt acc acc ggc ggc gcg gca ata tgt gaa caa       473
Gly Val Leu Val Lys Leu Thr Thr Gly Gly Ala Ala Ile Cys Glu Gln
             80                  85                  90 tgc cat caa tta gtt ggc cag gac ctg cac caa gaa tta aca aaa aac       521
Cys His Gln Leu Val Gly Gln Asp Leu His Gln Glu Leu Thr Lys Asn
         95                  100                 105 ctg acg gcg gac gaa gtg gca aca ctt gag tat ttg ctt aag aaa gtc       569
Leu Thr Ala Asp Glu Val Ala Thr Leu Glu Tyr Leu Leu Lys Lys Val
     110                 115                 120 ctg ccg taaacaaaaa agaggt atg acg atg tcc aga cgc aat act gac gct    621
Leu Pro            Met Thr Met Ser Arg Arg Asn Thr Asp Ala
 125                           130                     135 att acc att cat agc att ttg gac tgg atc gag gac aac ctg gaa tcg       669
Ile Thr Ile His Ser Ile Leu Asp Trp Ile Glu Asp Asn Leu Glu Ser
                 140                 145                 150 cca ctg tca ctg gag aaa gtg tca gag cgt tcg ggt tac tcc aaa tgg       717
Pro Leu Ser Leu Glu Lys Val Ser Glu Arg Ser Gly Tyr Ser Lys Trp
             155                 160                 165 cac ctg caa cgg atg ttt aaa aaa gaa acc ggt cat tca tta ggc caa       765
His Leu Gln Arg Met Phe Lys Lys Glu Thr Gly His Ser Leu Gly Gln
         170                 175                 180 tac atc cgc agc cgt aag atg acg gaa atc gcg caa aag ctg aag gaa       813
Tyr Ile Arg Ser Arg Lys Met Thr Glu Ile Ala Gln Lys Leu Lys Glu
     185                 190                 195 agt aac gag ccg ata ctc tat ctg gca gaa cga tat ggc ttc gag tcg       861
Ser Asn Glu Pro Ile Leu Tyr Leu Ala Glu Arg Tyr Gly Phe Glu Ser
200                 205                 210                 215 caa caa act ctg acc cga acc ttc aaa aat tac ttt gat gtt ccg ccg       909
Gln Gln Thr Leu Thr Arg Thr Phe Lys Asn Tyr Phe Asp Val Pro Pro
                 220                 225                 230 cat aaa tac cgg atg acc aat atg cag ggc gaa tcg cgc ttt tta cat       957
His Lys Tyr Arg Met Thr Asn Met Gln Gly Glu Ser Arg Phe Leu His
             235                 240                 245 cca tta aat cat tac aac agc tagttgaaaa cgtgacaacg tcactgaggc aatc    1012
Pro Leu Asn His Tyr Asn Ser
         250 atg aaa cca ctt tca tcc gca ata gca gct gcg ctt att ctc ttt tcc     1060
Met Lys Pro Leu Ser Ser Ala Ile Ala Ala Ala Leu Ile Leu Phe Ser
255                 260                 265                 270 gcg cag ggc gtt gcg gaa caa acc acg cag cca gtt gtt act tct tgt     1108
Ala Gln Gly Val Ala Glu Gln Thr Thr Gln Pro Val Val Thr Ser Cys
                 275                 280                 285 gcc aat gtc gtg gtt gtt ccc cca tcg cag gaa cac cca ccg ttt gat     1156
Ala Asn Val Val Val Val Pro Ser Gln Glu His Pro Pro Phe Asp
             290                 295                 300 tta aat cac atg ggt act ggc agt gat aag tcg gat gcg ctc ggc gtg     1204
Leu Asn His Met Gly Thr Gly Ser Asp Lys Ser Asp Ala Leu Gly Val
         305                 310                 315
```

-continued

```
ccc tat tat aat caa cac gct atg tagtttgttc tggccccgac atctcgggc      1258
Pro Tyr Tyr Asn Gln His Ala Met
    320                 325 ttattaactt cccaccttta ccgctttacg ccaccgcaag ccaaatacat tgatatacag    1318
cccggtcata atgagcaccg cacctaaaaa ttgcagaccc gttaagcgtt catccaacaa    1378
tagtgccgca cttgccagtc ctactacggg caccagtaac gataacggtg caa           1431

<210> SEQ ID NO 33
<211> LENGTH: 4766
<212> TYPE: DNA
<213> ORGANISM: Escherichia coli
<220> FEATURE:
<221> NAME/KEY: CDS
<222> LOCATION: (201)..(1391)
<220> FEATURE:
<221> NAME/KEY: CDS
<222> LOCATION: (1417)..(4563)

<400> SEQUENCE: 33
gccacatcga ggatgtgttg gcgcgtttct tgcgcttctt gtttggtttt tcgtgccata      60
tgttcgtgaa tttacaggcg ttagatttac atacatttgt gaatgtatgt accatagcac    120
gacgataata taaacgcagc aatgggttta ttaacttttg accattgacc aatttgaaat    180
cggacactcg aggtttacat atg aac aaa aac aga ggg ttt acg cct ctg gcg   233
                       Met Asn Lys Asn Arg Gly Phe Thr Pro Leu Ala
                         1               5                  10 gtt gtt ctg atg ctc tca ggc agc tta gcc cta aca gga tgt gac gac     281
Val Val Leu Met Leu Ser Gly Ser Leu Ala Leu Thr Gly Cys Asp Asp
         15                  20                  25 aaa cag gcc caa caa ggt ggc cag cag atg ccc gcc gtt ggc gta gta     329
Lys Gln Ala Gln Gln Gly Gly Gln Gln Met Pro Ala Val Gly Val Val
     30                  35                  40 aca gtc aaa act gaa cct ctg cag atc aca acc gag ctt ccg ggt cgc     377
Thr Val Lys Thr Glu Pro Leu Gln Ile Thr Thr Glu Leu Pro Gly Arg
 45                  50                  55 acc agt gcc tac cgg atc gca gaa gtt cgt cct caa gtt agc ggg att     425
Thr Ser Ala Tyr Arg Ile Ala Glu Val Arg Pro Gln Val Ser Gly Ile
 60                  65                  70                  75 atc ctg aag cgt aat ttc aaa gaa ggt agc gac atc gaa gca ggt gtc     473
Ile Leu Lys Arg Asn Phe Lys Glu Gly Ser Asp Ile Glu Ala Gly Val
             80                  85                  90 tct ctc tat cag att gat cct gcg acc tat cag gcg aca tac gac agt     521
Ser Leu Tyr Gln Ile Asp Pro Ala Thr Tyr Gln Ala Thr Tyr Asp Ser
         95                 100                 105 gcg aaa ggt gat ctg gcg aaa gcc cag gct gca gcc aat atc gcg caa     569
Ala Lys Gly Asp Leu Ala Lys Ala Gln Ala Ala Ala Asn Ile Ala Gln
     110                 115                 120 ttg acg gtg aat cgt tat cag aaa ctg ctc ggt act cag tac atc agt     617
Leu Thr Val Asn Arg Tyr Gln Lys Leu Leu Gly Thr Gln Tyr Ile Ser
 125                 130                 135 aag caa gag tac gat cag gct ctg gct gat gcg caa cag gcg aat gct     665
Lys Gln Glu Tyr Asp Gln Ala Leu Ala Asp Ala Gln Gln Ala Asn Ala
140                 145                 150                 155 gcg gta act gcg gcg aaa gct gcc gtt gaa act gcg cgg atc aat ctg     713
Ala Val Thr Ala Ala Lys Ala Ala Val Glu Thr Ala Arg Ile Asn Leu
                 160                 165                 170 gct tac acc aaa gtc acc tct ccg att agc ggt cgc att ggt aag tcg     761
Ala Tyr Thr Lys Val Thr Ser Pro Ile Ser Gly Arg Ile Gly Lys Ser
         175                 180                 185 aac gtg acg gaa ggc gca ttg gta cag aac ggt cag gcg act gcg ctg     809
Asn Val Thr Glu Gly Ala Leu Val Gln Asn Gly Gln Ala Thr Ala Leu
```

-continued

| | | |
|---|---|---|
| Asn Val Thr Glu Gly Ala Leu Val Gln Asn Gly Gln Ala Thr Ala Leu<br>190 195 200 | | |
| gca acc gtg cag caa ctt gat ccg atc tac gtt gat gtg acc cag tcc<br>Ala Thr Val Gln Gln Leu Asp Pro Ile Tyr Val Asp Val Thr Gln Ser<br>205 210 215 | 857 | |
| agc aac gac ttc ctg cgc ctg aaa cag gaa ctg gcg aat ggc acg ctg<br>Ser Asn Asp Phe Leu Arg Leu Lys Gln Glu Leu Ala Asn Gly Thr Leu<br>220 225 230 235 | 905 | |
| aaa caa gag aac ggc aaa gcc aaa gtg tca ctg atc acc agt gac ggc<br>Lys Gln Glu Asn Gly Lys Ala Lys Val Ser Leu Ile Thr Ser Asp Gly<br>240 245 250 | 953 | |
| att aag ttc ccg cag gac ggt acg ctg gaa ttc tct gac gtt acc gtt<br>Ile Lys Phe Pro Gln Asp Gly Thr Leu Glu Phe Ser Asp Val Thr Val<br>255 260 265 | 1001 | |
| gat cag acc act ggg tct atc acc cta cgc gct atc ttc ccg aac ccg<br>Asp Gln Thr Thr Gly Ser Ile Thr Leu Arg Ala Ile Phe Pro Asn Pro<br>270 275 280 | 1049 | |
| gat cac act ctg ctg ccg ggt atg ttc gtg cgc gca cgt ctg gaa gaa<br>Asp His Thr Leu Leu Pro Gly Met Phe Val Arg Ala Arg Leu Glu Glu<br>285 290 295 | 1097 | |
| ggg ctt aat cca aac gct att tta gtc ccg caa cag ggc gta acc cgt<br>Gly Leu Asn Pro Asn Ala Ile Leu Val Pro Gln Gln Gly Val Thr Arg<br>300 305 310 315 | 1145 | |
| acg ccg cgt ggc gat gcc acc gta ctg gta gtt ggc gcg gat gac aaa<br>Thr Pro Arg Gly Asp Ala Thr Val Leu Val Val Gly Ala Asp Asp Lys<br>320 325 330 | 1193 | |
| gtg gaa acc cgt ccg atc gtt gca agc cag gct att ggc gat aag tgg<br>Val Glu Thr Arg Pro Ile Val Ala Ser Gln Ala Ile Gly Asp Lys Trp<br>335 340 345 | 1241 | |
| ctg gtg aca gaa ggt ctg aaa gca ggc gat cgc gta gta ata agt ggg<br>Leu Val Thr Glu Gly Leu Lys Ala Gly Asp Arg Val Val Ile Ser Gly<br>350 355 360 | 1289 | |
| ctg cag aaa gtg cgt cct ggt gtc cag gta aaa gca caa gaa gtt acc<br>Leu Gln Lys Val Arg Pro Gly Val Gln Val Lys Ala Gln Glu Val Thr<br>365 370 375 | 1337 | |
| gct gat aat aac cag caa gcc gca agc ggt gct cag cct gaa cag tcc<br>Ala Asp Asn Asn Gln Gln Ala Ala Ser Gly Ala Gln Pro Glu Gln Ser<br>380 385 390 395 | 1385 | |
| aag tct taacttaaac aggagccgtt aagac atg cct aat ttc ttt atc gat<br>Lys Ser Met Pro Asn Phe Phe Ile Asp<br>400 | 1437 | |
| cgc ccg att ttt gcg tgg gtg atc gcc att atc atc atg ttg gca ggg<br>Arg Pro Ile Phe Ala Trp Val Ile Ala Ile Ile Ile Met Leu Ala Gly<br>405 410 415 420 | 1485 | |
| ggg ctg gcg atc ctc aaa ctg ccg gtg gcg caa tat cct acg att gca<br>Gly Leu Ala Ile Leu Lys Leu Pro Val Ala Gln Tyr Pro Thr Ile Ala<br>425 430 435 | 1533 | |
| ccg ccg gca gta acg atc tcc gcc tcc tac ccc ggc gct gat gcg aaa<br>Pro Pro Ala Val Thr Ile Ser Ala Ser Tyr Pro Gly Ala Asp Ala Lys<br>440 445 450 | 1581 | |
| aca gtg cag gac acg gtg aca cag gtt atc gaa cag aat atg aac ggt<br>Thr Val Gln Asp Thr Val Thr Gln Val Ile Glu Gln Asn Met Asn Gly<br>455 460 465 | 1629 | |
| atc gat aac ctg atg tac atg tcc tct aac agt gac tcc acg ggt acc<br>Ile Asp Asn Leu Met Tyr Met Ser Ser Asn Ser Asp Ser Thr Gly Thr<br>470 475 480 | 1677 | |
| gtg cag atc acc ctg acc ttt gag tct ggt act gat gcg gat atc gcg<br>Val Gln Ile Thr Leu Thr Phe Glu Ser Gly Thr Asp Ala Asp Ile Ala<br>485 490 495 500 | 1725 | |
| cag gtt cag gtg cag aac aaa ctg cag ctg gcg atg ccg ttg ctg ccg | 1773 | |

-continued

| | | | | | | | | | | | | | | | | |
|---|---|---|---|---|---|---|---|---|---|---|---|---|---|---|---|---|
| Gln | Val | Gln | Val | Gln | Asn | Lys | Leu | Gln | Leu | Ala | Met | Pro | Leu | Leu | Pro | |
| | | | | 505 | | | | 510 | | | | | 515 | | | |

```
caa gaa gtt cag cag caa ggg gtg agc gtt gag aaa tca tcc agc agc      1821
Gln Glu Val Gln Gln Gln Gly Val Ser Val Glu Lys Ser Ser Ser Ser
            520                 525                 530 ttc ctg atg gtt gtc ggc gtt atc aac acc gat ggc acc atg acg cag      1869
Phe Leu Met Val Val Gly Val Ile Asn Thr Asp Gly Thr Met Thr Gln
        535                 540                 545 gag gat atc tcc gac tac gtg gcg gcg aat atg aaa gat gcc atc agc      1917
Glu Asp Ile Ser Asp Tyr Val Ala Ala Asn Met Lys Asp Ala Ile Ser
    550                 555                 560 cgt acg tcg ggc gtg ggt gat gtt cag ttg ttc ggt tca cag tac gcg      1965
Arg Thr Ser Gly Val Gly Asp Val Gln Leu Phe Gly Ser Gln Tyr Ala
565                 570                 575                 580 atg cgt atc tgg atg aac ccg aat gag ctg aac aaa ttc cag cta acg      2013
Met Arg Ile Trp Met Asn Pro Asn Glu Leu Asn Lys Phe Gln Leu Thr
            585                 590                 595 ccg gtt gat gtc att acc gcc atc aaa gcg cag aac gcc cag gtt gcg      2061
Pro Val Asp Val Ile Thr Ala Ile Lys Ala Gln Asn Ala Gln Val Ala
        600                 605                 610 gcg ggt cag ctc ggt ggt acg ccg ccg gtg aaa ggc caa cag ctt aac      2109
Ala Gly Gln Leu Gly Gly Thr Pro Pro Val Lys Gly Gln Gln Leu Asn
    615                 620                 625 gcc tct att att gct cag acg cgt ctg acc tct act gaa gag ttc ggc      2157
Ala Ser Ile Ile Ala Gln Thr Arg Leu Thr Ser Thr Glu Glu Phe Gly
630                 635                 640 aaa atc ctg ctg aaa gtg aat cag gat ggt tcc cgc gtg ctg ctg cgt      2205
Lys Ile Leu Leu Lys Val Asn Gln Asp Gly Ser Arg Val Leu Leu Arg
645                 650                 655                 660 gac gtc gcg aag att gag ctg ggt ggt gag aac tac gac atc atc gca      2253
Asp Val Ala Lys Ile Glu Leu Gly Gly Glu Asn Tyr Asp Ile Ile Ala
            665                 670                 675 gag ttt aac ggc caa ccg gct tcc ggt ctg ggg atc aag ctg gcg acc      2301
Glu Phe Asn Gly Gln Pro Ala Ser Gly Leu Gly Ile Lys Leu Ala Thr
        680                 685                 690 ggt gca aac gcg ctg gat acc gct gcg gca atc cgt gct gaa ctg gcg      2349
Gly Ala Asn Ala Leu Asp Thr Ala Ala Ala Ile Arg Ala Glu Leu Ala
    695                 700                 705 aag atg gaa ccg ttc ttc ccg tcg ggt ctg aaa att gtt tac cca tac      2397
Lys Met Glu Pro Phe Phe Pro Ser Gly Leu Lys Ile Val Tyr Pro Tyr
710                 715                 720 gac acc acg ccg ttc gtg aaa atc tct att cac gaa gtg gtt aaa acg      2445
Asp Thr Thr Pro Phe Val Lys Ile Ser Ile His Glu Val Val Lys Thr
725                 730                 735                 740 ctg gtc gaa gcg atc atc ctc gtg ttc ctg gtt atg tat ctg ttc ctg      2493
Leu Val Glu Ala Ile Ile Leu Val Phe Leu Val Met Tyr Leu Phe Leu
            745                 750                 755 cag aac ttc cgc gcg acg ttg att ccg acc att gcc gta ccg gtg gta      2541
Gln Asn Phe Arg Ala Thr Leu Ile Pro Thr Ile Ala Val Pro Val Val
        760                 765                 770 ttg ctc ggg acc ttt gcc gtc ctt gcc gcc ttt ggc ttc tcg ata aac      2589
Leu Leu Gly Thr Phe Ala Val Leu Ala Ala Phe Gly Phe Ser Ile Asn
    775                 780                 785 acg cta aca atg ttc ggg atg gtg ctc gcc atc ggc ctg ttg gtg gat      2637
Thr Leu Thr Met Phe Gly Met Val Leu Ala Ile Gly Leu Leu Val Asp
790                 795                 800 gac gcc atc gtt gtg gta gaa aac gtt gag cgt gtt atg gcg gaa gaa      2685
Asp Ala Ile Val Val Val Glu Asn Val Glu Arg Val Met Ala Glu Glu
805                 810                 815                 820 ggt ttg ccg cca aaa gaa gct acc cgt aag tcg atg ggg cag att cag      2733
Gly Leu Pro Pro Lys Glu Ala Thr Arg Lys Ser Met Gly Gln Ile Gln
```

```
                                               -continued

Gly Leu Pro Pro Lys Glu Ala Thr Arg Lys Ser Met Gly Gln Ile Gln
            825                 830                 835 ggc gct ctg gtc ggt atc gcg atg gta ctg tcg gcg gta ttc gta ccg    2781
Gly Ala Leu Val Gly Ile Ala Met Val Leu Ser Ala Val Phe Val Pro
            840                 845                 850 atg gcc ttc ttt ggc ggt tct act ggt gct atc tat cgt cag ttc tct    2829
Met Ala Phe Phe Gly Gly Ser Thr Gly Ala Ile Tyr Arg Gln Phe Ser
            855                 860                 865 att acc att gtt tca gca atg gcg ctg tcg gta ctg gtg gcg ttg atc    2877
Ile Thr Ile Val Ser Ala Met Ala Leu Ser Val Leu Val Ala Leu Ile
            870                 875                 880 ctg act cca gct ctt tgt gcc acc atg ctg aaa ccg att gcc aaa ggc    2925
Leu Thr Pro Ala Leu Cys Ala Thr Met Leu Lys Pro Ile Ala Lys Gly
885                 890                 895                 900 gat cac ggg gaa ggt aaa aaa ggc ttc ttc ggc tgg ttt aac cgc atg    2973
Asp His Gly Glu Gly Lys Lys Gly Phe Phe Gly Trp Phe Asn Arg Met
                905                 910                 915 ttc gag aag agc acg cac cac tac acc gac agc gta ggc ggt att ctg    3021
Phe Glu Lys Ser Thr His His Tyr Thr Asp Ser Val Gly Gly Ile Leu
            920                 925                 930 cgc agt acg ggg cgt tac ctg gtg ctg tat ctg atc atc gtg gtc ggc    3069
Arg Ser Thr Gly Arg Tyr Leu Val Leu Tyr Leu Ile Ile Val Val Gly
            935                 940                 945 atg gcc tat ctg ttc gtg cgt ctg cca agc tcc ttc ttg cca gat gag    3117
Met Ala Tyr Leu Phe Val Arg Leu Pro Ser Ser Phe Leu Pro Asp Glu
            950                 955                 960 gac cag ggc gtg ttt atg acc atg gtt cag ctg cca gca ggt gca acg    3165
Asp Gln Gly Val Phe Met Thr Met Val Gln Leu Pro Ala Gly Ala Thr
965                 970                 975                 980 cag gaa cgt aca cag aaa gtg ctc aat gag gta acg cat tac tat ctg    3213
Gln Glu Arg Thr Gln Lys Val Leu Asn Glu Val Thr His Tyr Tyr Leu
                985                 990                 995 acc aaa gaa aag  aac aac gtt gag tcg  gtg ttc gcc gtt aac  ggc     3258
Thr Lys Glu Lys Asn Asn Val Glu Ser Val Phe Ala Val Asn Gly
                1000                1005                1010 ttc ggc ttt gcg  gga cgt ggt cag aat  acc ggt att gcg ttc  gtt     3303
Phe Gly Phe Ala Gly Arg Gly Gln Asn Thr Gly Ile Ala Phe Val
            1015                1020                1025 tcc ttg aag gac  tgg gcc gat cgt ccg  ggc gaa gaa aac aaa  gtt     3348
Ser Leu Lys Asp Trp Ala Asp Arg Pro Gly Glu Glu Asn Lys Val
            1030                1035                1040 gaa gcg att acc  atg cgt gca aca cgc  gct ttc tcg caa atc  aaa     3393
Glu Ala Ile Thr Met Arg Ala Thr Arg Ala Phe Ser Gln Ile Lys
            1045                1050                1055 gat gcg atg gtt  ttc gcc ttt aac ctg  ccc gca atc gtg gaa  ctg     3438
Asp Ala Met Val Phe Ala Phe Asn Leu Pro Ala Ile Val Glu Leu
            1060                1065                1070 ggt act gca acc  ggc ttt gac ttt gag  ctg att gac cag gct  ggc     3483
Gly Thr Ala Thr Gly Phe Asp Phe Glu Leu Ile Asp Gln Ala Gly
            1075                1080                1085 ctt ggt cac gaa  aaa ctg act cag gcg  cgt aac cag ttg ctt  gca     3528
Leu Gly His Glu Lys Leu Thr Gln Ala Arg Asn Gln Leu Leu Ala
            1090                1095                1100 gaa gca gcg aag  cac cct gat atg ttg  acc agc gta cgt cca  aac     3573
Glu Ala Ala Lys His Pro Asp Met Leu Thr Ser Val Arg Pro Asn
            1105                1110                1115 ggt ctg gaa gat  acc ccg cag ttt aag  att gat atc gac cag  gaa     3618
Gly Leu Glu Asp Thr Pro Gln Phe Lys Ile Asp Ile Asp Gln Glu
            1120                1125                1130 aaa gcg cag gcg  ctg ggt gtt tct atc  aac gac att aac acc  act     3663
```

-continued

```
                Lys Ala Gln Ala Leu Gly Val Ser Ile Asn Asp Ile Asn Thr Thr
                                1135                1140                1145 ctg ggc gct gca tgg ggc ggc agc tat gtg aac gac ttt atc gac      3708
Leu Gly Ala Ala Trp Gly Gly Ser Tyr Val Asn Asp Phe Ile Asp
            1150                1155                1160 cgc ggt cgt gtg aag aaa gtt tat gtc atg tca gaa gcg aaa tac      3753
Arg Gly Arg Val Lys Lys Val Tyr Val Met Ser Glu Ala Lys Tyr
            1165                1170                1175 cgt atg ctg ccg gat gat atc ggc gac tgg tat gtt cgt gct gct      3798
Arg Met Leu Pro Asp Asp Ile Gly Asp Trp Tyr Val Arg Ala Ala
            1180                1185                1190 gat ggt cag atg gtg cca ttc tcg gcg ttc tcc tct tct cgt tgg      3843
Asp Gly Gln Met Val Pro Phe Ser Ala Phe Ser Ser Ser Arg Trp
            1195                1200                1205 gag tac ggt tcg ccg cgt ctg gaa cgt tac aac ggc ctg cca tcc      3888
Glu Tyr Gly Ser Pro Arg Leu Glu Arg Tyr Asn Gly Leu Pro Ser
            1210                1215                1220 atg gaa atc tta ggc cag gcg gca ccg ggt aaa agt acc ggt gaa      3933
Met Glu Ile Leu Gly Gln Ala Ala Pro Gly Lys Ser Thr Gly Glu
            1225                1230                1235 gca atg gag ctg atg gaa caa ctg gcg agc aaa ctg cct acc ggt      3978
Ala Met Glu Leu Met Glu Gln Leu Ala Ser Lys Leu Pro Thr Gly
            1240                1245                1250 gtt ggc tat gac tgg acg ggg atg tcc tat cag gaa cgt ctc tcc      4023
Val Gly Tyr Asp Trp Thr Gly Met Ser Tyr Gln Glu Arg Leu Ser
            1255                1260                1265 ggc aac cag gca cct tca ctg tac gcg att tcg ttg att gtc gtg      4068
Gly Asn Gln Ala Pro Ser Leu Tyr Ala Ile Ser Leu Ile Val Val
            1270                1275                1280 ttc ctg tgt ctg gcg gcg ctg tac gag agc tgg tcg att ccg ttc      4113
Phe Leu Cys Leu Ala Ala Leu Tyr Glu Ser Trp Ser Ile Pro Phe
            1285                1290                1295 tcc gtt atg ctg gtc gtt ccg ctg ggg gtt atc ggt gcg ttg ctg      4158
Ser Val Met Leu Val Val Pro Leu Gly Val Ile Gly Ala Leu Leu
            1300                1305                1310 gct gcc acc ttc cgt ggc ctg acc aat gac gtt tac ttc cag gta      4203
Ala Ala Thr Phe Arg Gly Leu Thr Asn Asp Val Tyr Phe Gln Val
            1315                1320                1325 ggc ctg ctc aca acc att ggg ttg tcg gcg aag aac gcg atc ctt      4248
Gly Leu Leu Thr Thr Ile Gly Leu Ser Ala Lys Asn Ala Ile Leu
            1330                1335                1340 atc gtc gaa ttc gcc aaa gac ttg atg gat aaa gaa ggt aaa ggt      4293
Ile Val Glu Phe Ala Lys Asp Leu Met Asp Lys Glu Gly Lys Gly
            1345                1350                1355 ctg att gaa gcg acg ctt gat gcg gtg cgg atg cgt tta cgt ccg      4338
Leu Ile Glu Ala Thr Leu Asp Ala Val Arg Met Arg Leu Arg Pro
            1360                1365                1370 atc ctg atg acc tcg ctg gcg ttt atc ctc ggc gtt atg ccg ctg      4383
Ile Leu Met Thr Ser Leu Ala Phe Ile Leu Gly Val Met Pro Leu
            1375                1380                1385 gtt atc agt act ggt gct ggt tcc ggc gcg cag aac gca gta ggt      4428
Val Ile Ser Thr Gly Ala Gly Ser Gly Ala Gln Asn Ala Val Gly
            1390                1395                1400 acc ggt gta atg ggc ggg atg gtg acc gca acg gta ctg gca atc      4473
Thr Gly Val Met Gly Gly Met Val Thr Ala Thr Val Leu Ala Ile
            1405                1410                1415 ttc ttc gtt ccg gta ttc ttt gtg gtg gtt cgc cgc cgc ttt agc      4518
Phe Phe Val Pro Val Phe Phe Val Val Val Arg Arg Arg Phe Ser
            1420                1425                1430 cgc aag aat gaa gat atc gag cac agc cat act gtc gat cat cat      4563
```

-continued

```
Arg Lys Asn Glu  Asp Ile Glu His  Ser His Thr Val  Asp His His
         1435              1440              1445 tgatacaacg tgtaatcact aaggccgcgt aagcggcctt ttttatgcat aacctacgaa    4623
cattaaggag taattgaacc accaactcag gatctcatac gaaaaccagt attaaccacg    4683
gataaaattc ataaaaaata ctgattgtta gttaatttat attaagtagc gctaatagat    4743
ttaataatcc ataatcattt aga                                            4766

<210> SEQ ID NO 34
<211> LENGTH: 3128
<212> TYPE: DNA
<213> ORGANISM: Escherichia coli
<220> FEATURE:
<221> NAME/KEY: CDS
<222> LOCATION: (201)..(1370)
<220> FEATURE:
<221> NAME/KEY: CDS
<222> LOCATION: (1390)..(2925)

<400> SEQUENCE: 34
aaatcacccg caaattgctc tcccgtctcg accagatgga acaagacggt gtggttctcg     60
aagcgatgag ctaacgcgtc atctcgctca aaatccaga tttataaaag aaaaaatgac    120
tggccagcat cgcaacatgc tggccttttt ggcaagcagg tcggctcagc cgatgagtta    180
agaagatcgt ggagaacaat atg agc gca aat gcg gag act caa acc ccg cag    233
                        Met Ser Ala Asn Ala Glu Thr Gln Thr Pro Gln
                          1               5                      10 caa ccg gta aag aag agc ggc aaa cgt aag cgt ctg ctc ctc ctt ctc      281
Gln Pro Val Lys Lys Ser Gly Lys Arg Lys Arg Leu Leu Leu Leu Leu
                15                  20                  25 acc ttg ctc ttt ata att att gcc gta gcg ata ggg att tat tgg ttt      329
Thr Leu Leu Phe Ile Ile Ile Ala Val Ala Ile Gly Ile Tyr Trp Phe
         30                  35                  40 ttg gta ctg cgt cac ttc gaa gaa acc gat gac gca tac gtg gca ggg      377
Leu Val Leu Arg His Phe Glu Glu Thr Asp Asp Ala Tyr Val Ala Gly
     45                  50                  55 aat caa att caa att atg tct cag gtg tct ggc agc gtg acg aaa gtc      425
Asn Gln Ile Gln Ile Met Ser Gln Val Ser Gly Ser Val Thr Lys Val
 60                  65                  70                  75 tgg gcc gat aac acc gat ttt gta aaa gaa ggc gac gtg ctg gtc act      473
Trp Ala Asp Asn Thr Asp Phe Val Lys Glu Gly Asp Val Leu Val Thr
                 80                  85                  90 ctc gac ccg aca gat gct cgc cag gcg ttt gaa aaa gcc aaa act gca      521
Leu Asp Pro Thr Asp Ala Arg Gln Ala Phe Glu Lys Ala Lys Thr Ala
             95                 100                 105 ctg gct tcc agc gtt cgc caa acc cac cag ctg atg att aac agc aag      569
Leu Ala Ser Ser Val Arg Gln Thr His Gln Leu Met Ile Asn Ser Lys
         110                 115                 120 cag ttg cag gcg aat att gag gtg cag aaa atc gcc ctc gcg aaa gca      617
Gln Leu Gln Ala Asn Ile Glu Val Gln Lys Ile Ala Leu Ala Lys Ala
     125                 130                 135 caa agc gac tac aac cgc cgt gtg ccg ctg ggc aat gcc aac ctg att      665
Gln Ser Asp Tyr Asn Arg Arg Val Pro Leu Gly Asn Ala Asn Leu Ile
140                 145                 150                 155 ggt cgc gaa gag ctg caa cac gcc cgc gac gcc gtc acc agt gcc cag      713
Gly Arg Glu Glu Leu Gln His Ala Arg Asp Ala Val Thr Ser Ala Gln
                 160                 165                 170 gcg caa ctg gac gtc gcg att caa caa tac aat gcc aat cag gcg atg      761
Ala Gln Leu Asp Val Ala Ile Gln Gln Tyr Asn Ala Asn Gln Ala Met
             175                 180                 185 att ctg ggg act aaa ctg gaa gat cag cca gcc gtg caa cag gct gcc      809
```

```
                Ile Leu Gly Thr Lys Leu Glu Asp Gln Pro Ala Val Gln Gln Ala Ala
                    190                 195                 200 acc gaa gta cgt aac gcc tgg ctg gcg ctg gag cgt act cgt att atc        857
Thr Glu Val Arg Asn Ala Trp Leu Ala Leu Glu Arg Thr Arg Ile Ile
        205                 210                 215 agt ccg atg acc ggt tat gtc tcc cgc cgc gcg gta cag cct ggg gcg        905
Ser Pro Met Thr Gly Tyr Val Ser Arg Arg Ala Val Gln Pro Gly Ala
220                 225                 230                 235 caa att agc cca acg acg ccg ctg atg gcg gtc gtt cca gcc acc aat        953
Gln Ile Ser Pro Thr Thr Pro Leu Met Ala Val Val Pro Ala Thr Asn
                240                 245                 250 atg tgg gtg gat gcc aac ttt aaa gag acg cag att gcc aat atg cgt       1001
Met Trp Val Asp Ala Asn Phe Lys Glu Thr Gln Ile Ala Asn Met Arg
            255                 260                 265 atc ggt cag ccg gtc act atc acc acg gat att tac ggc gat gat gtg       1049
Ile Gly Gln Pro Val Thr Ile Thr Thr Asp Ile Tyr Gly Asp Asp Val
        270                 275                 280 aaa tac acc ggt aaa gtg gtt ggt ctg gat atg ggc aca ggt agc gcg       1097
Lys Tyr Thr Gly Lys Val Val Gly Leu Asp Met Gly Thr Gly Ser Ala
285                 290                 295 ttc tca ctg ctt cca gcg caa aat gcg acc ggt aac tgg atc aaa gtc       1145
Phe Ser Leu Leu Pro Ala Gln Asn Ala Thr Gly Asn Trp Ile Lys Val
300                 305                 310                 315 gtt cag cgt ctg cct gtg cgt atc gaa ctg gac cag aaa cag ctg gag       1193
Val Gln Arg Leu Pro Val Arg Ile Glu Leu Asp Gln Lys Gln Leu Glu
            320                 325                 330 caa tat ccg ctg cgt atc ggt ttg tcc acg ctg gtg agc gtc aat acc       1241
Gln Tyr Pro Leu Arg Ile Gly Leu Ser Thr Leu Val Ser Val Asn Thr
        335                 340                 345 act aac cgt gac ggt cag gta ctg gca aat aaa gta cgt tcc act ccg       1289
Thr Asn Arg Asp Gly Gln Val Leu Ala Asn Lys Val Arg Ser Thr Pro
    350                 355                 360 gta gcg gta agc acc gcg cgt gaa atc agc ctg gca cct gtc aat aaa       1337
Val Ala Val Ser Thr Ala Arg Glu Ile Ser Leu Ala Pro Val Asn Lys
365                 370                 375 ctg atc gac gat atc gta aaa gct aac gct ggc taatccagag gtgcgtgtg     1389
Leu Ile Asp Asp Ile Val Lys Ala Asn Ala Gly
380                 385                 390 atg caa cag caa aaa ccg ctg gaa ggc gcg caa ctg gtc att atg acg       1437
Met Gln Gln Gln Lys Pro Leu Glu Gly Ala Gln Leu Val Ile Met Thr
            395                 400                 405 att gcg ctg tca ctg gcg aca ttc atg cag gtg ctg gac tcc acc att       1485
Ile Ala Leu Ser Leu Ala Thr Phe Met Gln Val Leu Asp Ser Thr Ile
        410                 415                 420 gct aac gtg gcg atc ccc act atc gcc ggg aat ctg ggc tca tcg ctc       1533
Ala Asn Val Ala Ile Pro Thr Ile Ala Gly Asn Leu Gly Ser Ser Leu
    425                 430                 435 agc cag gga acg tgg gta atc act tct ttc ggg gtg gcg aat gcc atc       1581
Ser Gln Gly Thr Trp Val Ile Thr Ser Phe Gly Val Ala Asn Ala Ile
440                 445                 450 tcg atc ccg ctt acc ggc tgg ctg gca aag cgc gtc ggg gaa gtg aaa       1629
Ser Ile Pro Leu Thr Gly Trp Leu Ala Lys Arg Val Gly Glu Val Lys
455                 460                 465                 470 ctg ttc ctt tgg tcc acc atc gcc ttt gct att gcg tcg tgg gcg tgt       1677
Leu Phe Leu Trp Ser Thr Ile Ala Phe Ala Ile Ala Ser Trp Ala Cys
            475                 480                 485 ggt gtc tcc agc agc ctg aat atg ctg atc ttc ttc cgc gtg att cag       1725
Gly Val Ser Ser Ser Leu Asn Met Leu Ile Phe Phe Arg Val Ile Gln
        490                 495                 500 ggg att gtc gcc ggg ccg ttg atc ccg ctt tcg caa agt cta ttg ctg       1773
```

-continued

```
         Gly Ile Val Ala Gly Pro Leu Ile Pro Leu Ser Gln Ser Leu Leu Leu
                 505                 510                 515 aat aac tac ccg cca gcc aaa cgc tcg atc gcg ctg gcg ttg tgg tcg       1821
Asn Asn Tyr Pro Pro Ala Lys Arg Ser Ile Ala Leu Ala Leu Trp Ser
520                 525                 530 atg acg gtg att gtc gcg cca att tgc ggc ccg atc ctc ggc ggt tat       1869
Met Thr Val Ile Val Ala Pro Ile Cys Gly Pro Ile Leu Gly Gly Tyr
535                 540                 545                 550 atc agc gat aat tac cac tgg ggc tgg ata ttc ttc atc aac gtg ccg       1917
Ile Ser Asp Asn Tyr His Trp Gly Trp Ile Phe Phe Ile Asn Val Pro
                555                 560                 565 att ggc gtg gcg gtg gtg ttg atg aca ctg caa act ctg cgc gga cgt       1965
Ile Gly Val Ala Val Val Leu Met Thr Leu Gln Thr Leu Arg Gly Arg
            570                 575                 580 gaa acc cgc acc gaa cgg cgg cgg att gat gcc gtg ggg ctg gca ctg       2013
Glu Thr Arg Thr Glu Arg Arg Arg Ile Asp Ala Val Gly Leu Ala Leu
                585                 590                 595 ctg gtt att ggt atc ggc agc ctg cag att atg ctc gac cgc ggt aaa       2061
Leu Val Ile Gly Ile Gly Ser Leu Gln Ile Met Leu Asp Arg Gly Lys
600                 605                 610 gag ctg gac tgg ttt tca tca cag gaa att atc atc ctt acc gtg gtg       2109
Glu Leu Asp Trp Phe Ser Ser Gln Glu Ile Ile Ile Leu Thr Val Val
615                 620                 625                 630 gcg gtg gtg gct atc tgc ttc ctg att gtc tgg gag ctg acc gac gat       2157
Ala Val Val Ala Ile Cys Phe Leu Ile Val Trp Glu Leu Thr Asp Asp
                635                 640                 645 aac ccg ata gtc gat ctg tcg ttg ttt aag tcg cgc aac ttc acc atc       2205
Asn Pro Ile Val Asp Leu Ser Leu Phe Lys Ser Arg Asn Phe Thr Ile
            650                 655                 660 ggc tgc ttg tgt atc agc ctc gcg tat atg ctc tac ttc ggc gct att       2253
Gly Cys Leu Cys Ile Ser Leu Ala Tyr Met Leu Tyr Phe Gly Ala Ile
                665                 670                 675 gtt ctg ctg ccg cag ttg ttg cag gag gtc tac ggt tac acg gcg acc       2301
Val Leu Leu Pro Gln Leu Leu Gln Glu Val Tyr Gly Tyr Thr Ala Thr
            680                 685                 690 tgg gca ggt ttg gcc tct gcg ccg gta ggg att att ccg gtg atc ctg       2349
Trp Ala Gly Leu Ala Ser Ala Pro Val Gly Ile Ile Pro Val Ile Leu
695                 700                 705                 710 tcg ccg att atc ggc cgc ttc gcg cat aaa ctg gat atg cgg cgg ctg       2397
Ser Pro Ile Ile Gly Arg Phe Ala His Lys Leu Asp Met Arg Arg Leu
                715                 720                 725 gta acc ttc agc ttt att atg tat gcc gtc tgc ttc tac tgg cgt gcc       2445
Val Thr Phe Ser Phe Ile Met Tyr Ala Val Cys Phe Tyr Trp Arg Ala
            730                 735                 740 tat acc ttt gaa cca ggt atg gat ttt ggc gcg tcg gcc tgg ccg cag       2493
Tyr Thr Phe Glu Pro Gly Met Asp Phe Gly Ala Ser Ala Trp Pro Gln
        745                 750                 755 ttt atc cag ggg ttt gcg gtg gcc tgc ttc ttt atg ccg ctg acc acc       2541
Phe Ile Gln Gly Phe Ala Val Ala Cys Phe Phe Met Pro Leu Thr Thr
760                 765                 770 att acg ctg tct ggt ttg cca ccg gaa cga ctg gcg gcg gca tcg agc       2589
Ile Thr Leu Ser Gly Leu Pro Pro Glu Arg Leu Ala Ala Ala Ser Ser
775                 780                 785                 790 ctc tct aac ttt acg cga acg ctg gcg ggg tct atc ggc acg tcg ata       2637
Leu Ser Asn Phe Thr Arg Thr Leu Ala Gly Ser Ile Gly Thr Ser Ile
                795                 800                 805 acc acg acc atg tgg acc aac cgc gag tcg atg cac cat gcg cag ttg       2685
Thr Thr Thr Met Trp Thr Asn Arg Glu Ser Met His His Ala Gln Leu
                810                 815                 820 act gag tcg gta aac ccg ttc aac ccg aat gcc cag gcg atg tac agt       2733
```

```
                    Thr Glu Ser Val Asn Pro Phe Asn Pro Asn Ala Gln Ala Met Tyr Ser
                        825                 830                 835 caa ctg gaa ggg ctt ggg atg acg caa cag cag gca tca ggc tgg att           2781
Gln Leu Glu Gly Leu Gly Met Thr Gln Gln Gln Ala Ser Gly Trp Ile
840                 845                 850 gcc cag cag atc acc aat cag ggg ctg att att tcc gcc aat gag atc           2829
Ala Gln Gln Ile Thr Asn Gln Gly Leu Ile Ile Ser Ala Asn Glu Ile
855                 860                 865                 870 ttc tgg atg tca gcc ggg ata ttc ctc gtc ctg ggg ctg gtg tgg               2877
Phe Trp Met Ser Ala Gly Ile Phe Leu Val Leu Gly Leu Val Trp
                875                 880                 885 ttt gct aaa ccg cca ttt ggc gca ggt ggc gga ggc ggt gcg cac               2925
Phe Ala Lys Pro Pro Phe Gly Ala Gly Gly Gly Gly Gly Ala His
890                 895                 900 taagtacaac taagccagtt catttgaact ggcttttttc aattaattgt gaagatagtt         2985
tactgactag atgtgcagtt cctgcaactt ctctttcggc agtgccagtt cttcgttgct         3045
gttgatgcgt acgtcacgtt ccagaatgct acgcgcaata tcctgcgctt cctgcaacga         3105
gtgcatctgg taagtgccac act                                                  3128

<210> SEQ ID NO 35
<211> LENGTH: 733
<212> TYPE: DNA
<213> ORGANISM: Escherichia coli
<220> FEATURE:
<221> NAME/KEY: CDS
<222> LOCATION: (201)..(530)

<400> SEQUENCE: 35
ttaccggttc gctaccagag aagaatggga aggaaaggtg agcacgaatc tgattttaa           60 ggagtgtcgc cagagtgccg cgatgaaacg ggtattgagg gtatataaaa gaacatcaat         120
gggaacacaa tgatgaaaca ggtgagttga gttcaaactg tagtacaatt ctctccagtt         180
tgaacaggaa agaatatgct atg aac cct tat att tat ctt ggt ggt gca ata         233
                        Met Asn Pro Tyr Ile Tyr Leu Gly Gly Ala Ile
                        1               5                   10 ctt gca gag gtc att ggt aca acc tta atg aag ttt tca gaa ggt ttt           281
Leu Ala Glu Val Ile Gly Thr Thr Leu Met Lys Phe Ser Glu Gly Phe
            15                  20                  25 aca cgg tta tgg cca tct gtt ggt aca att att tgt tat tgt gca tca           329
Thr Arg Leu Trp Pro Ser Val Gly Thr Ile Ile Cys Tyr Cys Ala Ser
        30                  35                  40 ttc tgg tta tta gct cag acg ctg gct tat att cct aca ggg att gct           377
Phe Trp Leu Leu Ala Gln Thr Leu Ala Tyr Ile Pro Thr Gly Ile Ala
    45                  50                  55 tat gct atc tgg tca gga gtc ggt att gtc ctg att agc tta ctg tca           425
Tyr Ala Ile Trp Ser Gly Val Gly Ile Val Leu Ile Ser Leu Leu Ser
60                  65                  70                  75 tgg gga ttt ttc ggc caa cgg ctg gac ctg cca gcc att ata ggc atg           473
Trp Gly Phe Phe Gly Gln Arg Leu Asp Leu Pro Ala Ile Ile Gly Met
                80                  85                  90 atg ttg att tgt gcc ggt gtg ttg att att aat tta ttg tca cga agc           521
Met Leu Ile Cys Ala Gly Val Leu Ile Ile Asn Leu Leu Ser Arg Ser
            95                  100                 105 aca cca cat taaataatt tgtttctaaa cgactaaaat atggaggctc                    570
Thr Pro His
        110 ttatatttat atgagcctcg ttttatgctt tttgttaatg tctttatttt ttatgtattc         630 ttttgtgctt tcaagattat ggcgtaagaa aattgcaata cgattattgt tgtatattca         690
```

```
                                  -continued agataatgtg accttaattg tctttttaaa taaaaaataa aca                    733

<210> SEQ ID NO 36
<211> LENGTH: 1612
<212> TYPE: DNA
<213> ORGANISM: Escherichia coli
<220> FEATURE:
<221> NAME/KEY: CDS
<222> LOCATION: (201)..(1409)

<400> SEQUENCE: 36
gaacgcgatg cagctcctgt gccgcagcgc taaaactacc attacgcgct accgcatcaa   60
caacttcgag tgaatattct gaccacatag tctgcctgca aaattttga aaccagtcat   120 caaatattac cgtttcacaa cactaatttc actccctaca ctttgcggcg gtgtttaatt   180
gagagattta gagaatatac atg caa cct ggg aaa aga ttt tta gtc tgg ctg   233
                         Met Gln Pro Gly Lys Arg Phe Leu Val Trp Leu
                          1               5                  10 gcg ggt ttg agc gta ctc ggt ttt ctg gca acc gat atg tat ctg cct    281
Ala Gly Leu Ser Val Leu Gly Phe Leu Ala Thr Asp Met Tyr Leu Pro
         15                  20                  25 gct ttc gcc gcc ata cag gcc gac ctg caa acg cct gcg tct gct gtc    329
Ala Phe Ala Ala Ile Gln Ala Asp Leu Gln Thr Pro Ala Ser Ala Val
     30                  35                  40 agt gcc agc ctt agt ctg ttc ctt gcc ggt ttt gcc gca gcc cag ctt    377
Ser Ala Ser Leu Ser Leu Phe Leu Ala Gly Phe Ala Ala Ala Gln Leu
 45                  50                  55 ctg tgg ggg ccg ctc tcc gac cgt tat ggt cgt aaa ccg gta tta tta   425
Leu Trp Gly Pro Leu Ser Asp Arg Tyr Gly Arg Lys Pro Val Leu Leu
60                  65                  70                  75 atc ggc ctg aca att ttt gcg tta ggt agt ctg ggg atg ctg tgg gta    473
Ile Gly Leu Thr Ile Phe Ala Leu Gly Ser Leu Gly Met Leu Trp Val
             80                  85                  90 gaa aac gcc gct acg ctg ctg gta ttg cgt ttt gta cag gct gtg ggt   521
Glu Asn Ala Ala Thr Leu Leu Val Leu Arg Phe Val Gln Ala Val Gly
         95                 100                 105 gtc tgc gcc gcg gcg gtt atc tgg caa gca tta gtg aca gat tat tat   569
Val Cys Ala Ala Ala Val Ile Trp Gln Ala Leu Val Thr Asp Tyr Tyr
    110                 115                 120 cct tca cag aaa gtt aac cgt att ttt gcg gcc atc atg ccg ctg gtg   617
Pro Ser Gln Lys Val Asn Arg Ile Phe Ala Ala Ile Met Pro Leu Val
125                 130                 135 ggt cta tct ccg gca ctg gct cct ctg tta gga agc tgg ctg ctg gtc   665
Gly Leu Ser Pro Ala Leu Ala Pro Leu Leu Gly Ser Trp Leu Leu Val
140                 145                 150                 155 cat ttt tcc tgg cag gcg att ttc gcc acc ctg ttt gcc att acc gtg   713
His Phe Ser Trp Gln Ala Ile Phe Ala Thr Leu Phe Ala Ile Thr Val
             160                 165                 170 gtg ctg att ctg cct att ttc tgg ctc aaa ccc acg acg aag gcc cgt   761
Val Leu Ile Leu Pro Ile Phe Trp Leu Lys Pro Thr Thr Lys Ala Arg
         175                 180                 185 aac aat agt cag gat ggt ctg acc ttt acc gac ctg cta cgt tct aaa   809
Asn Asn Ser Gln Asp Gly Leu Thr Phe Thr Asp Leu Leu Arg Ser Lys
    190                 195                 200 acc tat cgc ggc aac gtg ctg ata tac gca gcc tgt tca gcc agt ttt   857
Thr Tyr Arg Gly Asn Val Leu Ile Tyr Ala Ala Cys Ser Ala Ser Phe
205                 210                 215 ttt gca tgg ctg acc ggt tca ccg ttc atc ctt agt gaa atg ggc tac   905
Phe Ala Trp Leu Thr Gly Ser Pro Phe Ile Leu Ser Glu Met Gly Tyr
220                 225                 230                 235 agc ccg gca gtt att ggt tta agt tat gtc ccg caa act atc gcg ttt   953
```

```
Ser Pro Ala Val Ile Gly Leu Ser Tyr Val Pro Gln Thr Ile Ala Phe
                240                 245                 250 ctg att ggt ggt tat ggc tgt cgc gcc gcg ctg cag aaa tgg caa ggc    1001
Leu Ile Gly Gly Tyr Gly Cys Arg Ala Ala Leu Gln Lys Trp Gln Gly
            255                 260                 265 aag cag tta tta ccg tgg ttg ctg gtg ctg ttt gct gtc agc gtc att    1049
Lys Gln Leu Leu Pro Trp Leu Leu Val Leu Phe Ala Val Ser Val Ile
        270                 275                 280 gcg acc tgg gct gcg ggc ttc att agc cat gtg tcg ctg gtc gaa atc    1097
Ala Thr Trp Ala Ala Gly Phe Ile Ser His Val Ser Leu Val Glu Ile
    285                 290                 295 ctg atc cca ttc tgt gtg atg gcg att gcc aat ggc gcg atc tac cct    1145
Leu Ile Pro Phe Cys Val Met Ala Ile Ala Asn Gly Ala Ile Tyr Pro
300                 305                 310                 315 att gtt gtc gcc cag gcg ctg cgt ccc ttc cca cac gca act ggt cgc    1193
Ile Val Val Ala Gln Ala Leu Arg Pro Phe Pro His Ala Thr Gly Arg
                320                 325                 330 gcc gca gcg ttg cag aac act ctt caa ctg ggt ctg tgc ttc ctc gca    1241
Ala Ala Ala Leu Gln Asn Thr Leu Gln Leu Gly Leu Cys Phe Leu Ala
            335                 340                 345 agt ctg gta gtt tcc tgg ctg atc agt atc agc acg cca ttg ctc acc    1289
Ser Leu Val Val Ser Trp Leu Ile Ser Ile Ser Thr Pro Leu Leu Thr
        350                 355                 360 acc acc agc gtg atg tta tca aca gta atg ctg gtc gcg ctg ggt tac    1337
Thr Thr Ser Val Met Leu Ser Thr Val Met Leu Val Ala Leu Gly Tyr
    365                 370                 375 atg atg caa cgt tgt gaa gaa gtt ggc tgc cag aat cat ggc aat gcc    1385
Met Met Gln Arg Cys Glu Glu Val Gly Cys Gln Asn His Gly Asn Ala
380                 385                 390                 395 gaa gtc gct cat agc gaa tca cac tgatctatat cgatatactt atacttaggc   1439
Glu Val Ala His Ser Glu Ser His
                400 tgctaacaaa attttgttgt atgattgaaa ttagcggcct atactaattt cgagttgtta   1499 aagctacgat aaatattatg tttttacggg gacaggatcg ttcccgactc actatggata   1559 gtcattcgg caagggttcc tcctttccct ctgttctacg tcggattata gac            1612

<210> SEQ ID NO 37
<211> LENGTH: 1588
<212> TYPE: DNA
<213> ORGANISM: Escherichia coli
<220> FEATURE:
<221> NAME/KEY: CDS
<222> LOCATION: (201)..(1385)

<400> SEQUENCE: 37
cgacattcta ccgcctctga atttcatctt ttgtaagcaa tcaacttagc tgaatttact    60
tttctttaac agttgattcg ttagtcgccg gttacgacgg cattaatgcg caaataagtc   120
gctatacttc ggattttgc catgctattt ctttacatct ctaaaacaaa acataacgaa    180
acgcactgcc ggacagacaa atg aac tta tcc cta cga cgc tct acc agc gcc   233
                        Met Asn Leu Ser Leu Arg Arg Ser Thr Ser Ala
                        1               5                   10 ctt ctt gcc tcg tcg ttg tta tta acc atc gga cgc ggc gct acg ctg     281
Leu Leu Ala Ser Ser Leu Leu Leu Thr Ile Gly Arg Gly Ala Thr Leu
            15                  20                  25 cca ttt atg acc att tac ttg agt cgc cag tac agc ctg agt gtc gat     329
Pro Phe Met Thr Ile Tyr Leu Ser Arg Gln Tyr Ser Leu Ser Val Asp
        30                  35                  40 cta atc ggt tat gcg atg aca att gcg ctc act att ggc gtc gtt ttt     377
Leu Ile Gly Tyr Ala Met Thr Ile Ala Leu Thr Ile Gly Val Val Phe
```

```
                 45                  50                  55
agc ctc ggt ttt ggt atc ctg gcg gat aag ttc gac aag aaa cgc tat          425
Ser Leu Gly Phe Gly Ile Leu Ala Asp Lys Phe Asp Lys Lys Arg Tyr
 60                  65                  70                  75 atg tta ctg gca att acc gcc ttc gcc agc ggt ttt att gcc att act          473
Met Leu Leu Ala Ile Thr Ala Phe Ala Ser Gly Phe Ile Ala Ile Thr
                 80                  85                  90 tta gtg aat aac gtg acg ctg gtt gtg ctc ttt ttt gcc ctc att aac          521
Leu Val Asn Asn Val Thr Leu Val Val Leu Phe Phe Ala Leu Ile Asn
             95                 100                 105 tgc gcc tat tct gtt ttt gct acc gtg ctg aaa gcc tgg ttt gcc gac          569
Cys Ala Tyr Ser Val Phe Ala Thr Val Leu Lys Ala Trp Phe Ala Asp
        110                 115                 120 aat ctt tcg tcc acc agc aaa acg aaa atc ttc tca atc aac tac acc          617
Asn Leu Ser Ser Thr Ser Lys Thr Lys Ile Phe Ser Ile Asn Tyr Thr
    125                 130                 135 atg cta aac att ggc tgg acc atc ggt ccg ccg ctc ggc acg ctg ttg          665
Met Leu Asn Ile Gly Trp Thr Ile Gly Pro Pro Leu Gly Thr Leu Leu
140                 145                 150                 155 gta atg cag agc atc aat ctg ccc ttc tgg ctg gca gct atc tgt tcc          713
Val Met Gln Ser Ile Asn Leu Pro Phe Trp Leu Ala Ala Ile Cys Ser
                160                 165                 170 gcg ttt ccc atg ctt ttc att caa att tgg gta aag cgc agc gag aaa          761
Ala Phe Pro Met Leu Phe Ile Gln Ile Trp Val Lys Arg Ser Glu Lys
            175                 180                 185 atc atc gcc acg gaa aca ggc agt gtc tgg tcg ccg aaa gtt tta tta          809
Ile Ile Ala Thr Glu Thr Gly Ser Val Trp Ser Pro Lys Val Leu Leu
        190                 195                 200 caa gat aaa gca ctg ttg tgg ttt acc tgc tct ggt ttt ctg gct tct          857
Gln Asp Lys Ala Leu Leu Trp Phe Thr Cys Ser Gly Phe Leu Ala Ser
    205                 210                 215 ttt gta agc ggc gca ttt gct tca tgc att tca caa tat gtg atg gtg          905
Phe Val Ser Gly Ala Phe Ala Ser Cys Ile Ser Gln Tyr Val Met Val
220                 225                 230                 235 att gct gat ggg gat ttt gcc gaa aag gtg gtc gcg gtt gtt ctt ccg          953
Ile Ala Asp Gly Asp Phe Ala Glu Lys Val Val Ala Val Val Leu Pro
                240                 245                 250 gtg aat gct gcc atg gtg gtt acg ttg caa tat tcc gtg ggc cgc cga         1001
Val Asn Ala Ala Met Val Val Thr Leu Gln Tyr Ser Val Gly Arg Arg
            255                 260                 265 ctt aac ccg gct aac atc cgc gcg ctg atg aca gca ggc acc ctc tgt         1049
Leu Asn Pro Ala Asn Ile Arg Ala Leu Met Thr Ala Gly Thr Leu Cys
        270                 275                 280 ttc gtc atc ggt ctg gtc ggt ttt att ttt tcc ggc aac agc ctg cta         1097
Phe Val Ile Gly Leu Val Gly Phe Ile Phe Ser Gly Asn Ser Leu Leu
    285                 290                 295 ttg tgg ggt atg tca gct gcg gta ttt act gtc ggt gaa atc att tat         1145
Leu Trp Gly Met Ser Ala Ala Val Phe Thr Val Gly Glu Ile Ile Tyr
300                 305                 310                 315 gcg ccg ggc gag tat atg ttg att gac cat att gcg ccg cca gaa atg         1193
Ala Pro Gly Glu Tyr Met Leu Ile Asp His Ile Ala Pro Pro Glu Met
                320                 325                 330 aaa gcc agc tat ttt tcc gcc cag tct tta ggc tgg ctt ggt gcc gcg         1241
Lys Ala Ser Tyr Phe Ser Ala Gln Ser Leu Gly Trp Leu Gly Ala Ala
            335                 340                 345 att aac cca tta gtg agt ggc gta gtg cta acc agc ctg ccg cct tcc         1289
Ile Asn Pro Leu Val Ser Gly Val Val Leu Thr Ser Leu Pro Pro Ser
        350                 355                 360 tcg ctg ttt gtc atc tta gcg ttg gtg atc att gct gcg tgg gtg ctg         1337
Ser Leu Phe Val Ile Leu Ala Leu Val Ile Ile Ala Ala Trp Val Leu
```

```
                365                 370                 375
atg tta aaa ggg att cga gca aga ccg tgg ggg cag ccc gcg ctt tgt    1385
Met Leu Lys Gly Ile Arg Ala Arg Pro Trp Gly Gln Pro Ala Leu Cys
380                 385                 390                 395 tgatttaagt cgaacacaat aaagatttaa ttcagccttc gtttaggtta cctctgctaa   1445
tatctttctc attgagatga aaattaaggt aagcgaggaa acacaccaca ccataaacgg   1505
aggcaaataa tgctgggtaa tatgaatgtt tttatggccg tactgggaat aattttattt   1565
tctggttttc tggccgcgta ttt                                          1588

<210> SEQ ID NO 38
<211> LENGTH: 1591
<212> TYPE: DNA
<213> ORGANISM: Escherichia coli
<220> FEATURE:
<221> NAME/KEY: CDS
<222> LOCATION: (201)..(1388)

<400> SEQUENCE: 38
ccacctatac ccgcaaccgc caaaacgcca gacctccctg aacgtcatta aaccgtgatg     60
ttaccgactc tctgacgcgt gaaagaatca gcgtcagaga acggaaaac gcgatccaga    120 tcacaaatgc attgtattca catcattaac cgttttaaga tcatttcatc acttttcgc    180 aactcacccg ataatctgtt atg aca aca aac act gtt tcc cgc aaa gtg gcg   233
                       Met Thr Thr Asn Thr Val Ser Arg Lys Val Ala
                        1               5                  10 tgg cta cgg gtc gtt acg ctg gca gtc gcc gcc ttc atc ttc aac acc     281
Trp Leu Arg Val Val Thr Leu Ala Val Ala Ala Phe Ile Phe Asn Thr
         15                  20                  25 acc gaa ttt gtc cct gtt ggc ctg ctc tct gac att gcg caa agt ttt     329
Thr Glu Phe Val Pro Val Gly Leu Leu Ser Asp Ile Ala Gln Ser Phe
     30                  35                  40 cac atg caa acc gct cag gtc ggc atc atg ttg acc att tac gca tgg     377
His Met Gln Thr Ala Gln Val Gly Ile Met Leu Thr Ile Tyr Ala Trp
 45                  50                  55 gta gta gcg cta atg tca ttg cct ttt atg tta atg acc agt cag gtt     425
Val Val Ala Leu Met Ser Leu Pro Phe Met Leu Met Thr Ser Gln Val
60                  65                  70                  75 gaa cgg cgc aaa tta ctg atc tgc ctg ttt gtg gtg ttt att gcc agc     473
Glu Arg Arg Lys Leu Leu Ile Cys Leu Phe Val Val Phe Ile Ala Ser
             80                  85                  90 cac gta ctg tcg ttt ttg tcg tgg agc ttt acc gtt ctg gtg atc agt     521
His Val Leu Ser Phe Leu Ser Trp Ser Phe Thr Val Leu Val Ile Ser
         95                  100                 105 cgc att ggt gtg gct ttt gca cat gcg att ttc tgg tcg att acg gcg     569
Arg Ile Gly Val Ala Phe Ala His Ala Ile Phe Trp Ser Ile Thr Ala
     110                 115                 120 tct ctg gcg atc cgt atg gct ccg gcc ggg aag cga gca cag gca ttg     617
Ser Leu Ala Ile Arg Met Ala Pro Ala Gly Lys Arg Ala Gln Ala Leu
125                 130                 135 agt tta att gcc acc ggt aca gca ctg gcg atg gtc tta ggt tta cct     665
Ser Leu Ile Ala Thr Gly Thr Ala Leu Ala Met Val Leu Gly Leu Pro
140                 145                 150                 155 ctc ggg cgc att gtg ggc cag tat ttc ggt tgg cga atg acc ttc ttc     713
Leu Gly Arg Ile Val Gly Gln Tyr Phe Gly Trp Arg Met Thr Phe Phe
             160                 165                 170 gcg att ggt att ggg gcg ctt atc acc ctt ttg tgc ctg att aag tta     761
Ala Ile Gly Ile Gly Ala Leu Ile Thr Leu Leu Cys Leu Ile Lys Leu
     175                 180                 185 ctt ccc tta ctg ccc agt gag cat tcc ggt tca ctg aaa agc ctc ccg     809
```

```
                Leu Pro Leu Leu Pro Ser Glu His Ser Gly Ser Leu Lys Ser Leu Pro
                        190                 195                 200 cta ttg ttc cgc cgc ccg gca ttg atg agc att tat ttg tta act gtg    857
Leu Leu Phe Arg Arg Pro Ala Leu Met Ser Ile Tyr Leu Leu Thr Val
        205                 210                 215 gtg gtt gtc acc gcc cat tac acg gca tac agc tat atc gag cct ttt    905
Val Val Val Thr Ala His Tyr Thr Ala Tyr Ser Tyr Ile Glu Pro Phe
220                 225                 230                 235 gta caa aac att gcg gga ttc agc gcc aac ttt gcc acg gca tta ctg    953
Val Gln Asn Ile Ala Gly Phe Ser Ala Asn Phe Ala Thr Ala Leu Leu
                240                 245                 250 tta tta ctc ggt ggt gcg ggc att att ggc agc gtg att ttc ggt aaa   1001
Leu Leu Leu Gly Gly Ala Gly Ile Ile Gly Ser Val Ile Phe Gly Lys
                255                 260                 265 ctg ggt aat cag tat gcg tct gcg ttg gtg agt acg gcg att gcg ctg   1049
Leu Gly Asn Gln Tyr Ala Ser Ala Leu Val Ser Thr Ala Ile Ala Leu
        270                 275                 280 ttg ctg gtg tgc ctg gca ttg ctg tta cct gcg gcg aac agt gaa ata   1097
Leu Leu Val Cys Leu Ala Leu Leu Leu Pro Ala Ala Asn Ser Glu Ile
285                 290                 295 cac ctc ggg gtg ctg agt att ttc tgg ggg atc gcg atg atg atc atc   1145
His Leu Gly Val Leu Ser Ile Phe Trp Gly Ile Ala Met Met Ile Ile
300                 305                 310                 315 ggg ctt ggt atg cag gtt aaa gtg ctg gcg ctg gca cca gat gct acc   1193
Gly Leu Gly Met Gln Val Lys Val Leu Ala Leu Ala Pro Asp Ala Thr
                320                 325                 330 gac gtc gcg atg gcg cta ttc tcc ggc ata ttt aat att gga atc ggg   1241
Asp Val Ala Met Ala Leu Phe Ser Gly Ile Phe Asn Ile Gly Ile Gly
        335                 340                 345 gcg ggt gcg ttg gta ggt aat cag gtg agt ttg cac tgg tca atg tcg   1289
Ala Gly Ala Leu Val Gly Asn Gln Val Ser Leu His Trp Ser Met Ser
                350                 355                 360 atg att ggt tat gtg ggc gcg gtg cct gct ttt gcc gcg tta att tgg   1337
Met Ile Gly Tyr Val Gly Ala Val Pro Ala Phe Ala Ala Leu Ile Trp
365                 370                 375 tca atc att ata ttt cgc cgc tgg cca gtg aca ctc gaa gaa cag acg   1385
Ser Ile Ile Ile Phe Arg Arg Trp Pro Val Thr Leu Glu Glu Gln Thr
380                 385                 390                 395 caa tagttgaaag gcccattcgg gcctttttta atggtacgtt ttaatgattt         1438
Gln ccaggatgcc gttaataata aactgcacac ccatacatac cagcaggaat cccatcagac   1498
gggagatcgc ttcaatgcca cccttgccca ccagccgcat aattgcgccg gagctgcgta   1558
ggcttcccca caaataacc gccaccagga aaa                                 1591

<210> SEQ ID NO 39
<211> LENGTH: 4132
<212> TYPE: DNA
<213> ORGANISM: Escherichia coli
<220> FEATURE:
<221> NAME/KEY: CDS
<222> LOCATION: (1231)..(2391)
<220> FEATURE:
<221> NAME/KEY: CDS
<222> LOCATION: (2394)..(3929)

<400> SEQUENCE: 39
gggacttatg tactgcaatc acaagatttt ttttgctcgc taaccaacgt aattccttgt     60
tgctcagacg tagtggatca agtgtgcacg ggttgttact actgatgcca cgatattcga   120
tgtaatcttc gtctgcgaaa cttatggtcg accaagacc acaacagaga agaaaaatat    180
```

-continued

```
agggtaaaaa cttcatgtgg ttagccgatt ttgttacgtt gtgcgaatgt gtaaagatcc    240
atcagtgatt tacattctaa tttttccatc aggcgacttt tataagtgct gacagttttg    300
ttgctgatga acatttttc agcaatgtca ttattatcct tgccatcaag aatataccgc     360 atgcactaa tttcttgttt cgataaggag tcgagttttt gctggtcgga cgttaaactt     420
ccaacaaacc ggttgagaga aaggggaaa tagcagtagc catttttttgc agcttcaata    480 gccgcaatga tattgttcat gccttctttt ttactcacga aaccattagc gccagcatca    540
gcacaatgtt tcccgtaaaa atggtcattt ttagcggaga cgataataat aattccgcta   600
tattggcgct tcctcagcgt ttctaacacc tggataccgt taactccggg gatatcgaca    660
tcaatgatga cgatatcagg cttaagtgtt tccacccgct gaacggcact tccgccttca    720
gtcaactctg ctaagatttc aatatcgttt ttgatcaata aattacgaat tgctgcgata    780
gcaagaggat ggtcatcaat aattattgcg ttcatagatt attccctttg caatgaagca    840
tctcccttct ccctgtagta atacagacat aaggcgtcat ctcattttct caataaaaat    900
aagaaaatct gagcttcctt taagataatt cgacaagtat accatataaa tagtcggcat    960
aaatgaaatg tcaacaataa aatcaggat tgtaccgatg atttatagtt tcaagttggc    1020
actataagtc ttcttactaa tcctacaggc gtaagaattg tattgcaaaa gccacggttt    1080
agtcctctgt tgttttttt gcacctcatt taaattaggc ctccaacgtt cctgggataa    1140
tgtgcaacac atgcactgtg tttgatatga agaatgaatg ctcttttcat tcaattcata    1200
aatttcatct atgagaaatg agagataata gtg gaa cag att aat tca aat aaa   1254
                                   Met Glu Gln Ile Asn Ser Asn Lys
                                     1               5 aaa cat tct aac aga aga aaa tac ttt tct tta ttg gcg gta gtt tta    1302
Lys His Ser Asn Arg Arg Lys Tyr Phe Ser Leu Leu Ala Val Val Leu
     10              15                  20 ttt att gcg ttt tca ggt gcc tat gcc tat tgg tca atg gaa tta gaa    1350
Phe Ile Ala Phe Ser Gly Ala Tyr Ala Tyr Trp Ser Met Glu Leu Glu
 25              30                  35                  40 gac atg att agt aca gat gac gcc tat gtc acg ggg aat gca gat cca    1398
Asp Met Ile Ser Thr Asp Asp Ala Tyr Val Thr Gly Asn Ala Asp Pro
                 45                  50                  55 att tct gca caa gtc tca ggt agt gtc act gtc gtt aat cat aaa gat    1446
Ile Ser Ala Gln Val Ser Gly Ser Val Thr Val Val Asn His Lys Asp
         60                  65                  70 acg aac tac gtt cga caa ggt gac att tta gtt tca ctg gat aaa act    1494
Thr Asn Tyr Val Arg Gln Gly Asp Ile Leu Val Ser Leu Asp Lys Thr
             75                  80                  85 gat gcc act atc gca ctc aat aaa gct aaa aat aat ctg gca aat att    1542
Asp Ala Thr Ile Ala Leu Asn Lys Ala Lys Asn Asn Leu Ala Asn Ile
 90                  95                 100 gtt cgg caa acg aat aaa cta tac tta cag gat aaa caa tac agt gcc    1590
Val Arg Gln Thr Asn Lys Leu Tyr Leu Gln Asp Lys Gln Tyr Ser Ala
105                 110                 115                 120 gaa gtc gct tca gca cgt att cag tat caa caa tct tta gaa gat tat    1638
Glu Val Ala Ser Ala Arg Ile Gln Tyr Gln Gln Ser Leu Glu Asp Tyr
                125                 130                 135 aac cgt cga gtg ccg tta gcg aag cag ggg gtt att tca aaa gaa acg    1686
Asn Arg Arg Val Pro Leu Ala Lys Gln Gly Val Ile Ser Lys Glu Thr
            140                 145                 150 ctg gag cat acc aaa gat acg tta ata agt agc aaa gcg gca ttg aat    1734
Leu Glu His Thr Lys Asp Thr Leu Ile Ser Ser Lys Ala Ala Leu Asn
                155                 160                 165 gcc gct atc cag gct tat aaa gcg aat aaa gct tta gta atg aac aca    1782
Ala Ala Ile Gln Ala Tyr Lys Ala Asn Lys Ala Leu Val Met Asn Thr
```

```
                     170                 175                 180
cca tta aac cgt cag cca caa gtc gtt gaa gcg gcg gat gca act aaa      1830
Pro Leu Asn Arg Gln Pro Gln Val Val Glu Ala Ala Asp Ala Thr Lys
185                 190                 195                 200 gaa gcc tgg ttg gcg ctt aaa cgt acg gat att aag agt ccg gtt acc      1878
Glu Ala Trp Leu Ala Leu Lys Arg Thr Asp Ile Lys Ser Pro Val Thr
                205                 210                 215 ggc tat att gcc cag aga agt gtt cag gtc ggc gaa aca gtg agc ccc      1926
Gly Tyr Ile Ala Gln Arg Ser Val Gln Val Gly Glu Thr Val Ser Pro
                    220                 225                 230 gga caa tcg tta atg gct gtc gta ccg gca cgt caa atg tgg gtt aat      1974
Gly Gln Ser Leu Met Ala Val Val Pro Ala Arg Gln Met Trp Val Asn
                        235                 240                 245 gcc aac ttt aaa gaa aca caa ctc acg gat gta cgg att ggt caa tcg      2022
Ala Asn Phe Lys Glu Thr Gln Leu Thr Asp Val Arg Ile Gly Gln Ser
        250                 255                 260 gtc aat att atc agc gat ctt tat ggt gaa aat gtt gtg ttt cat ggt      2070
Val Asn Ile Ile Ser Asp Leu Tyr Gly Glu Asn Val Val Phe His Gly
265                 270                 275                 280 cgg gtg aca ggg atc aat atg gga acc ggc aat gcg ttc tcc tta tta      2118
Arg Val Thr Gly Ile Asn Met Gly Thr Gly Asn Ala Phe Ser Leu Leu
                    285                 290                 295 cct gca caa aat gcg aca ggg aac tgg atc aaa atc gtt cag cgt gta      2166
Pro Ala Gln Asn Ala Thr Gly Asn Trp Ile Lys Ile Val Gln Arg Val
                300                 305                 310 ccg gtt gaa gtt tct ctt gat cca aaa gaa ctc atg gaa cac ccc ttg      2214
Pro Val Glu Val Ser Leu Asp Pro Lys Glu Leu Met Glu His Pro Leu
            315                 320                 325 cgt att ggt tta tcg atg aca gca act att gat acg aag aac gaa gac      2262
Arg Ile Gly Leu Ser Met Thr Ala Thr Ile Asp Thr Lys Asn Glu Asp
330                 335                 340 att gcc gag atg cct gag ctg gct tca acc gtg acc tcc atg ccg gct      2310
Ile Ala Glu Met Pro Glu Leu Ala Ser Thr Val Thr Ser Met Pro Ala
345                 350                 355                 360 tat acc agt aag gct tta gtt atc gat acc agt ccg ata gaa aaa gaa      2358
Tyr Thr Ser Lys Ala Leu Val Ile Asp Thr Ser Pro Ile Glu Lys Glu
                    365                 370                 375 att agc aac att att tcg cat aat gga caa ctt  ta atg gca atc act      2405
Ile Ser Asn Ile Ile Ser His Asn Gly Gln Leu     Met Ala Ile Thr
                    380                 385                 390 aaa tca act ccg gca cca tta acc ggt ggg acg tta tgg tgc gtc act      2453
Lys Ser Thr Pro Ala Pro Leu Thr Gly Gly Thr Leu Trp Cys Val Thr
                395                 400                 405 att gca ttg tca tta gcg aca ttt atg caa atg ttg gat tcc act att      2501
Ile Ala Leu Ser Leu Ala Thr Phe Met Gln Met Leu Asp Ser Thr Ile
            410                 415                 420 tct aac gtc gca ata ccg aca ata tct ggc ttt ctg gga gca tca aca      2549
Ser Asn Val Ala Ile Pro Thr Ile Ser Gly Phe Leu Gly Ala Ser Thr
        425                 430                 435 gac gaa ggc acc tgg gtt atc acc tcg ttt ggt gta gca aat gcc att      2597
Asp Glu Gly Thr Trp Val Ile Thr Ser Phe Gly Val Ala Asn Ala Ile
440                 445                 450                 455 gcg atc cct gtt act ggc agg ttg gca caa aga ata ggc gaa tta aga      2645
Ala Ile Pro Val Thr Gly Arg Leu Ala Gln Arg Ile Gly Glu Leu Arg
                    460                 465                 470 tta ttt tta ctt tca gtc act ttt ttt tcg ctg tct tca tta atg tgt      2693
Leu Phe Leu Leu Ser Val Thr Phe Phe Ser Leu Ser Ser Leu Met Cys
                475                 480                 485 agc cta tcg acc aat ctt gat gtg ctg ata ttt ttt aga gtc gtt cag      2741
Ser Leu Ser Thr Asn Leu Asp Val Leu Ile Phe Phe Arg Val Val Gln
```

-continued

| | |
|---|---|
| ggg tta atg gcg ggg ccg tta att cca ctg tca cag agt tta tta tta<br>Gly Leu Met Ala Gly Pro Leu Ile Pro Leu Ser Gln Ser Leu Leu Leu<br>505                      510                       515 | 2789 |
| agg aat tat ccg cca gaa aaa aga aca ttt gct ctg gca tta tgg tca<br>Arg Asn Tyr Pro Pro Glu Lys Arg Thr Phe Ala Leu Ala Leu Trp Ser<br>520                      525                       530                535 | 2837 |
| atg acc gtg att atc gct ccg ata tgt ggg ccg ata ttg ggc ggt tat<br>Met Thr Val Ile Ile Ala Pro Ile Cys Gly Pro Ile Leu Gly Gly Tyr<br>                  540                       545                       550 | 2885 |
| att tgt gat aac ttt agc tgg ggt tgg ata ttt tta atc aat gtc cct<br>Ile Cys Asp Asn Phe Ser Trp Gly Trp Ile Phe Leu Ile Asn Val Pro<br>                555                       560                       565 | 2933 |
| atg ggg att atc gtc ctg aca tta tgc tta acc tta ctt aaa gga aga<br>Met Gly Ile Ile Val Leu Thr Leu Cys Leu Thr Leu Leu Lys Gly Arg<br>        570                       575                       580 | 2981 |
| gaa act gag act tca ccg gtc aaa atg aat cta cca gga ctg acc ctg<br>Glu Thr Glu Thr Ser Pro Val Lys Met Asn Leu Pro Gly Leu Thr Leu<br>585                      590                       595 | 3029 |
| tta gtg ctc ggt gtt ggt ggc ttg caa att atg ctt gat aaa ggg cgc<br>Leu Val Leu Gly Val Gly Gly Leu Gln Ile Met Leu Asp Lys Gly Arg<br>600                      605                       610                615 | 3077 |
| gat ctg gat tgg ttc aac tcg agt aca ata ata ata tta aca gta gta<br>Asp Leu Asp Trp Phe Asn Ser Ser Thr Ile Ile Ile Leu Thr Val Val<br>                  620                       625                       630 | 3125 |
| tca gtt att tct ctg atc tct tta gtc att tgg gag tcg acc tca gag<br>Ser Val Ile Ser Leu Ile Ser Leu Val Ile Trp Glu Ser Thr Ser Glu<br>                635                       640                       645 | 3173 |
| aac ccg att ctt gat ctc agt ttg ttt aag tcc cgt aac ttc acc att<br>Asn Pro Ile Leu Asp Leu Ser Leu Phe Lys Ser Arg Asn Phe Thr Ile<br>        650                       655                       660 | 3221 |
| ggt att gtg agt atc aca tgc gcg tat tta ttt tac tct gga gcg atc<br>Gly Ile Val Ser Ile Thr Cys Ala Tyr Leu Phe Tyr Ser Gly Ala Ile<br>665                      670                       675 | 3269 |
| gtc ctt atg ccg cag tta ctc cag gaa acg atg ggg tat aat gcg ata<br>Val Leu Met Pro Gln Leu Leu Gln Glu Thr Met Gly Tyr Asn Ala Ile<br>680                      685                       690                695 | 3317 |
| tgg gcc gga ctt gct tat gcg ccc atc ggc atc atg cca cta tta att<br>Trp Ala Gly Leu Ala Tyr Ala Pro Ile Gly Ile Met Pro Leu Leu Ile<br>                  700                       705                       710 | 3365 |
| tca cct ttg ata gga cgt tat ggc aac aaa ata gac atg cgg ttg tta<br>Ser Pro Leu Ile Gly Arg Tyr Gly Asn Lys Ile Asp Met Arg Leu Leu<br>                715                       720                       725 | 3413 |
| gtg aca ttt agt ttt ttg atg tat gcg gtt tgc tat tac tgg cgt tct<br>Val Thr Phe Ser Phe Leu Met Tyr Ala Val Cys Tyr Tyr Trp Arg Ser<br>                730                       735                       740 | 3461 |
| gtg aca ttt atg cca acg att gat ttt aca ggc atc att ttg ccg cag<br>Val Thr Phe Met Pro Thr Ile Asp Phe Thr Gly Ile Ile Leu Pro Gln<br>745                      750                       755 | 3509 |
| ttt ttt cag gga ttc gcc gtt gcc tgt ttc ttt tta ccc tta aca acg<br>Phe Phe Gln Gly Phe Ala Val Ala Cys Phe Phe Leu Pro Leu Thr Thr<br>760                      765                       770                775 | 3557 |
| att tcg ttt tca ggc ttg cca gat aat aaa ttt gcc aat gcc tcg agt<br>Ile Ser Phe Ser Gly Leu Pro Asp Asn Lys Phe Ala Asn Ala Ser Ser<br>                  780                       785                       790 | 3605 |
| atg agt aat ttt ttt cgt acc ttg tca gga tca gtt ggt acg tcg ttg<br>Met Ser Asn Phe Phe Arg Thr Leu Ser Gly Ser Val Gly Thr Ser Leu<br>                795                       800                       805 | 3653 |
| aca atg acg ctg tgg gga cga cgc gaa tcg tta cac cat agt cag ttg<br>Thr Met Thr Leu Trp Gly Arg Arg Glu Ser Leu His His Ser Gln Leu | 3701 |

```
                810                 815                 820
aca gca acc atc gat caa ttt aac ccc gtg ttt aat tca tcg tca caa    3749
Thr Ala Thr Ile Asp Gln Phe Asn Pro Val Phe Asn Ser Ser Ser Gln
        825                 830                 835 att atg gat aaa tat tat ggt tcg ctt tca gga gtt ctt aat gaa att    3797
Ile Met Asp Lys Tyr Tyr Gly Ser Leu Ser Gly Val Leu Asn Glu Ile
840                 845                 850                 855 aat aat gaa ata acc cag cag tca ctt tct att tct gca aat gag att    3845
Asn Asn Glu Ile Thr Gln Gln Ser Leu Ser Ile Ser Ala Asn Glu Ile
                860                 865                 870 ttc cgt atg gcg gct att gct ttt atc tta ctt acg gtt ttg gtt tgg    3893
Phe Arg Met Ala Ala Ile Ala Phe Ile Leu Leu Thr Val Leu Val Trp
        875                 880                 885 ttt gcg aaa ccg ccg ttt aca gcg aaa ggc gtt ggg tgatgataaa         3939
Phe Ala Lys Pro Pro Phe Thr Ala Lys Gly Val Gly
        890                 895 aggaggggt tatagcgggt aagaccgggg atcttaagtc tgcgccatcg gcagcatcgc    3999
tcacccaggg aaaggattgc gatgctgcgt tgaaacgtta ttaacggcct tttgccagat    4059
attgattcat ctcttcttcc ggcaccattc cacctcccgt cgcccacacc agatgagtgg    4119
tattacgcag ttg                                                      4132

<210> SEQ ID NO 40
<211> LENGTH: 4132
<212> TYPE: DNA
<213> ORGANISM: Escherichia coli
<220> FEATURE:
<221> NAME/KEY: CDS
<222> LOCATION: (3318)..(3929)

<400> SEQUENCE: 40
caactgcgta ataccactca tctggtgtgg gcgacgggag gtggaatggt gccggaagaa      60
gagatgaatc aatatctggc aaaaggccgt aataacgttt caacgcagc atcgcaatcc     120 tttccctggg tgagcgatgc tgccgatggc gcagacttaa gatccccggt cttacccgct    180 ataccccct cctttatca tcacccaacg cctttcgctg taaacggcgg tttcgcaaac    240
caaaccaaaa ccgtaagtaa gataaaagca atagccgcca tacggaaaat ctcatttgca    300
gaaatagaaa gtgactgctg ggttatttca ttattaattt cattaagaac tcctgaaagc    360
gaaccataat atttatccat aatttgtgac gatgaattaa acacggggtt aaattgatcg    420
atggttgctg tcaactgact atggtgtaac gattcgcgtc gtccccacag cgtcattgtc    480
aacgacgtac caactgatcc tgacaaggta cgaaaaaaat tactcatact cgaggcattg    540
gcaaatttat tatctggcaa gcctgaaaac gaaatcgttg ttaagggtaa aaagaaacag    600
gcaacggcga atccctgaaa aaactgcggc aaaatgatgc ctgtaaaatc aatcgttggc    660
ataaatgtca cagaacgcca gtaatagcaa accgcataca tcaaaaaact aaatgtcact    720
aacaaccgca tgtctatttt gttgccataa cgtcctatca aaggtgaaat taatagtggc    780
atgatgccga tgggcgcata agcaagtccg gcccatatcg cattataccc catcgttttcc    840 tggagtaact gcggcataag gacgatcgct ccagagtaaa ataaatacgc gcatgtgata    900
ctcacaatac caatggtgaa gttacgggac ttaaacaaac tgagatcaag aatcgggttc    960
tctgaggtcg actcccaaat gactaaagag atcagagaaa taactgatac tactgttaat   1020
attattattg tactcgagtt gaaccaatcc agatcgcgcc ctttatcaag cataatttgc   1080
aagccaccaa caccgagcac taacagggtc agtcctggta gattcatttt gaccggtgaa   1140
gtctcagttt ctcttccttt aagtaaggtt aagcataatg tcaggacgat aatcccccata   1200
```

```
gggacattga ttaaaaatat ccaaccccag ctaaagttat cacaaatata accgcccaat    1260
atcggcccac atatcggagc gataatcacg gtcattgacc ataatgccag agcaaatgtt    1320
cttttttctg gcggataatt ccttaataat aaactctgtg acagtggaat taacggcccc    1380
gccattaacc cctgaacgac tctaaaaaat atcagcacat caagattggt cgataggcta    1440
cacattaatg aagacagcga aaaaaaagtg actgaaagta aaataatct taattcgcct     1500 attctttgtg ccaacctgcc agtaacaggg atcgcaatgg catttgctac accaaacgag    1560
gtgataaccc aggtgccttc gtctgttgat gctcccagaa agccagatat tgtcggtatt    1620
gcgacgttag aaatagtgga atccaacatt tgcataaatg tcgctaatga caatgcaata    1680
gtgacgcacc ataacgtccc accggttaat ggtgccggag ttgatttagt gattgccatt    1740
aaagttgtcc attatgcgaa ataatgttgc taatttcttt ttctatcgga ctggtatcga    1800
taactaaagc cttactggta taagccggca tggaggtcac ggttgaagcc agctcaggca    1860
tctcggcaat gtcttcgttc ttcgtatcaa tagttgctgt catcgataaa ccaatacgca    1920
aggggtgttc catgagttct tttggatcaa gagaaacttc aaccggtaca cgctgaacga    1980
ttttgatcca gttccctgtc gcattttgtg caggtaataa ggagaacgca ttgccggttc    2040
ccatattgat ccctgtcacc cgaccatgaa acacaacatt ttcaccataa agatcgctga    2100
taatattgac cgattgacca atccgtacat ccgtgagttg tgtttcttta aagttggcat    2160
taacccacat ttgacgtgcc ggtacgacag ccattaacga ttgtccgggg ctcactgttt    2220
cgccgacctg aacacttctc tgggcaatat agccggtaac cggactctta atatccgtac    2280
gtttaagcgc caaccaggct tctttagttg catccgccgc ttcaacgact tgtggctgac    2340
ggtttaatgg tgtgttcatt actaaagctt tattcgcttt ataagcctgg atagcggcat    2400
tcaatgccgc tttgctactt attaacgtat ctttggtatg ctccagcgtt tcttttgaaa    2460
taaccccctg cttcgctaac ggcactcgac ggttataatc ttctaaagat tgttgatact    2520
gaatacgtgc tgaagcgact tcggcactgt attgtttatc ctgtaagtat agtttattcg    2580
tttgccgaac aatatttgcc agattatttt tagctttatt gagtgcgata gtggcatcag    2640
ttttatccag tgaaactaaa atgtcacctt gtcgaacgta gttcgtatct ttatgattaa    2700
cgacagtgac actacctgag acttgtgcag aaattggatc tgcattcccc gtgacatagg    2760
cgtcatctgt actaatcatg tcttctaatt ccattgacca ataggcatag gcacctgaaa    2820
acgcaataaa taaactacc gccaataaag aaaagtattt tcttctgtta gaatgttttt     2880
tatttgaatt aatctgttcc actattatct ctcatttctc atagatgaaa tttatgaatt    2940
gaatgaaaag agcattcatt cttcatatca aacacagtgc atgtgttgca cattatccca    3000
ggaacgttgg aggcctaatt taaatgaggt gcaaaaaaaa caacagagga ctaaaccgtg    3060
gcttttgcaa tacaattctt acgcctgtag gattagtaag aagacttata gtgccaactt    3120
gaaactataa atcatcggta caatccctga ttttattgtt gacatttcat ttatgccgac    3180
tatttatatg gtatacttgt cgaattatct taaaggaagc tcagattttc ttattttat    3240 tgagaaaatg agatgacgcc ttatgtctgt attactacag ggagaaggga gatgcttcat    3300
tgcaagggga ataatct atg aac gca ata att att gat gac cat cct ctt      3350
                    Met Asn Ala Ile Ile Ile Asp Asp His Pro Leu
                     1               5                  10 gct atc gca gca att cgt aat tta ttg atc aaa aac gat att gaa atc     3398
Ala Ile Ala Ala Ile Arg Asn Leu Leu Ile Lys Asn Asp Ile Glu Ile
        15                  20                  25 tta gca gag ttg act gaa ggc gga agt gcc gtt cag cgg gtg gaa aca     3446
```

```
                                                       -continued

Leu Ala Glu Leu Thr Glu Gly Gly Ser Ala Val Gln Arg Val Glu Thr
             30                  35                  40 ctt aag cct gat atc gtc atc att gat gtc gat atc ccc gga gtt aac        3494
Leu Lys Pro Asp Ile Val Ile Ile Asp Val Asp Ile Pro Gly Val Asn
 45                  50                  55 ggt atc cag gtg tta gaa acg ctg agg aag cgc caa tat agc gga att        3542
Gly Ile Gln Val Leu Glu Thr Leu Arg Lys Arg Gln Tyr Ser Gly Ile
 60                  65                  70                  75 att att atc gtc tcc gct aaa aat gac cat ttt tac ggg aaa cat tgt        3590
Ile Ile Ile Val Ser Ala Lys Asn Asp His Phe Tyr Gly Lys His Cys
                 80                  85                  90 gct gat gct ggc gct aat ggt ttc gtg agt aaa aaa gaa ggc atg aac        3638
Ala Asp Ala Gly Ala Asn Gly Phe Val Ser Lys Lys Glu Gly Met Asn
             95                 100                 105 aat atc att gcg gct att gaa gct gca aaa aat ggc tac tgc tat ttc        3686
Asn Ile Ile Ala Ala Ile Glu Ala Ala Lys Asn Gly Tyr Cys Tyr Phe
        110                 115                 120 ccc ttc tct ctc aac cgg ttt gtt gga agt tta acg tcc gac cag caa        3734
Pro Phe Ser Leu Asn Arg Phe Val Gly Ser Leu Thr Ser Asp Gln Gln
125                 130                 135 aaa ctc gac tcc tta tcg aaa caa gaa att agt gtc atg cgg tat att        3782
Lys Leu Asp Ser Leu Ser Lys Gln Glu Ile Ser Val Met Arg Tyr Ile
140                 145                 150                 155 ctt gat ggc aag gat aat aat gac att gct gaa aaa atg ttc atc agc        3830
Leu Asp Gly Lys Asp Asn Asn Asp Ile Ala Glu Lys Met Phe Ile Ser
                160                 165                 170 aac aaa act gtc agc act tat aaa agt cgc ctg atg gaa aaa tta gaa        3878
Asn Lys Thr Val Ser Thr Tyr Lys Ser Arg Leu Met Glu Lys Leu Glu
            175                 180                 185 tgt aaa tca ctg atg gat ctt tac aca ttc gca caa cgt aac aaa atc        3926
Cys Lys Ser Leu Met Asp Leu Tyr Thr Phe Ala Gln Arg Asn Lys Ile
        190                 195                 200 ggc taaccacatg aagttttac cctatatttt tcttctctgt tgtggtcttt             3979
Gly ggtcgaccat aagtttcgca gacgaagatt acatcgaata tcgtggcatc agtagtaaca     4039
accgtgtcac acttgatcca ctacgtctga gcaacaagga attacgttgg ttagcgagca     4099
aaaaaaatct tgtgattgca gtacataagt ccc                                  4132

<210> SEQ ID NO 41
<211> LENGTH: 1585
<212> TYPE: DNA
<213> ORGANISM: Escherichia coli
<220> FEATURE:
<221> NAME/KEY: CDS
<222> LOCATION: (201)..(1382)

<400> SEQUENCE: 41
atgctgacgc atcttatccg ccctaccatc tctcccggca acatttattg ccgcttttgt       60
ttacatattc tgccgctaaa caattcccca ttcctggcgt atatctggct aacattcatc      120
aatgtgatag attcctctcc cgcatttatg ggaatgcgta gtgacttatt ctaattattt      180
ttataaaagc atccgtgata atg aaa agg caa aga aac gtc aat ttg tta ttg      233
                         Met Lys Arg Gln Arg Asn Val Asn Leu Leu Leu
                           1               5                  10 atg ttg gta tta ctc gtg gcc gtc ggt cag atg gcg caa acc att tat        281
Met Leu Val Leu Leu Val Ala Val Gly Gln Met Ala Gln Thr Ile Tyr
         15                  20                  25 att cca gct att gcc gat atg gcg cgc gat ctc aac gtc cgt gaa ggg        329
Ile Pro Ala Ile Ala Asp Met Ala Arg Asp Leu Asn Val Arg Glu Gly
             30                  35                  40
```

| | | | | | | | | | | | | | | | | |
|---|---|---|---|---|---|---|---|---|---|---|---|---|---|---|---|---|
| gcg | gtg | cag | agc | gta | atg | ggc | gct | tat | ctg | ctg | act | tac | ggt | gtc | tca | 377 |
| Ala | Val | Gln | Ser | Val | Met | Gly | Ala | Tyr | Leu | Leu | Thr | Tyr | Gly | Val | Ser | |
| | 45 | | | | 50 | | | | | 55 | | | | | | |
| cag | ctg | ttt | tat | ggc | ccg | att | tcc | gac | cgc | gtg | ggc | cgc | cga | ccg | gtg | 425 |
| Gln | Leu | Phe | Tyr | Gly | Pro | Ile | Ser | Asp | Arg | Val | Gly | Arg | Arg | Pro | Val | |
| 60 | | | | | 65 | | | | | 70 | | | | | 75 | |
| atc | ctc | gtc | gga | atg | tcc | att | ttt | atg | ctg | gca | acg | ctg | gtc | gcg | gtc | 473 |
| Ile | Leu | Val | Gly | Met | Ser | Ile | Phe | Met | Leu | Ala | Thr | Leu | Val | Ala | Val | |
| | | | | | | | | 80 | | | | | 85 | | | |
| | | | | | | | | | | | | | | | | |
| acg | acc | tcc | agt | ttg | acg | gtg | ttg | att | gcc | gcc | agc | gcg | atg | cag | ggg | 521 |
| Thr | Thr | Ser | Ser | Leu | Thr | Val | Leu | Ile | Ala | Ala | Ser | Ala | Met | Gln | Gly | |
| | | | | 95 | | | | | 100 | | | | | 105 | | |
| atg | ggc | acc | ggc | gtt | ggc | ggc | gta | atg | gcg | cgt | act | tta | ccg | cga | gat | 569 |
| Met | Gly | Thr | Gly | Val | Gly | Gly | Val | Met | Ala | Arg | Thr | Leu | Pro | Arg | Asp | |
| | | | 110 | | | | | 115 | | | | | 120 | | | |
| tta | tat | gaa | cgg | aca | cag | ttg | cgc | cat | gct | aac | agc | ctg | tta | aac | atg | 617 |
| Leu | Tyr | Glu | Arg | Thr | Gln | Leu | Arg | His | Ala | Asn | Ser | Leu | Leu | Asn | Met | |
| | 125 | | | | | 130 | | | | | 135 | | | | | |
| ggg | att | ctc | gtc | agt | ccg | ttg | ctc | gca | ccg | cta | atc | ggc | ggt | ctg | ctg | 665 |
| Gly | Ile | Leu | Val | Ser | Pro | Leu | Leu | Ala | Pro | Leu | Ile | Gly | Gly | Leu | Leu | |
| 140 | | | | | 145 | | | | | 150 | | | | | 155 | |
| gat | acg | atg | tgg | aac | tgg | cgc | gcc | tgt | tat | ctc | ttt | ttg | ttg | gtt | ctt | 713 |
| Asp | Thr | Met | Trp | Asn | Trp | Arg | Ala | Cys | Tyr | Leu | Phe | Leu | Leu | Val | Leu | |
| | | | | 160 | | | | | 165 | | | | | 170 | | |
| tgt | gct | ggt | gtg | acc | ttc | agt | atg | gcc | cgc | tgg | atg | ccg | gaa | acg | cgt | 761 |
| Cys | Ala | Gly | Val | Thr | Phe | Ser | Met | Ala | Arg | Trp | Met | Pro | Glu | Thr | Arg | |
| | | | 175 | | | | | 180 | | | | | 185 | | | |
| ccg | gtc | gat | gca | ccg | cgc | acg | cgc | ctg | ctt | acc | agt | tat | aaa | acg | ctt | 809 |
| Pro | Val | Asp | Ala | Pro | Arg | Thr | Arg | Leu | Leu | Thr | Ser | Tyr | Lys | Thr | Leu | |
| | | 190 | | | | | 195 | | | | | 200 | | | | |
| ttc | ggt | aac | agc | ggt | ttt | aac | tgt | tat | ttg | ctg | atg | ctg | att | ggc | ggt | 857 |
| Phe | Gly | Asn | Ser | Gly | Phe | Asn | Cys | Tyr | Leu | Leu | Met | Leu | Ile | Gly | Gly | |
| | 205 | | | | | 210 | | | | | 215 | | | | | |
| ctg | gcc | ggg | att | gcc | gcc | ttt | gaa | gcc | tgc | tcc | ggc | gtg | ctg | atg | ggc | 905 |
| Leu | Ala | Gly | Ile | Ala | Ala | Phe | Glu | Ala | Cys | Ser | Gly | Val | Leu | Met | Gly | |
| 220 | | | | | 225 | | | | | 230 | | | | | 235 | |
| gcg | gtg | tta | ggg | ctg | agc | agt | atg | acg | gtc | agt | att | ttg | ttt | att | ctg | 953 |
| Ala | Val | Leu | Gly | Leu | Ser | Ser | Met | Thr | Val | Ser | Ile | Leu | Phe | Ile | Leu | |
| | | | 240 | | | | | 245 | | | | | 250 | | | |
| ccg | att | ccg | gca | gcg | ttt | ttt | ggc | gca | tgg | ttt | gcc | gga | cgt | ccc | aat | 1001 |
| Pro | Ile | Pro | Ala | Ala | Phe | Phe | Gly | Ala | Trp | Phe | Ala | Gly | Arg | Pro | Asn | |
| | | 255 | | | | | 260 | | | | | 265 | | | | |
| aaa | cgc | ttc | tcc | acg | tta | atg | tgg | cag | tcg | gtt | atc | tgc | tgc | ctg | ctg | 1049 |
| Lys | Arg | Phe | Ser | Thr | Leu | Met | Trp | Gln | Ser | Val | Ile | Cys | Cys | Leu | Leu | |
| | 270 | | | | | 275 | | | | | 280 | | | | | |
| gct | ggc | ttg | ctg | atg | tgg | atc | ccc | gac | tgg | ttt | ggc | gtg | atg | aat | gtc | 1097 |
| Ala | Gly | Leu | Leu | Met | Trp | Ile | Pro | Asp | Trp | Phe | Gly | Val | Met | Asn | Val | |
| 285 | | | | | 290 | | | | | 295 | | | | | | |
| tgg | acg | ctg | ctc | gtt | ccc | gcc | gcg | ctg | ttc | ttt | ttc | ggt | gcc | ggg | atg | 1145 |
| Trp | Thr | Leu | Leu | Val | Pro | Ala | Ala | Leu | Phe | Phe | Phe | Gly | Ala | Gly | Met | |
| 300 | | | | | 305 | | | | | 310 | | | | | 315 | |
| ctg | ttt | ccg | ctg | gcg | acc | agc | ggc | gcg | atg | gag | ccg | ttc | ccc | ttc | ctg | 1193 |
| Leu | Phe | Pro | Leu | Ala | Thr | Ser | Gly | Ala | Met | Glu | Pro | Phe | Pro | Phe | Leu | |
| | | | | 320 | | | | | 325 | | | | | 330 | | |
| gcg | ggc | acg | gct | ggc | gcg | ctg | gtc | ggc | ggt | ctg | caa | aac | att | ggt | tcc | 1241 |
| Ala | Gly | Thr | Ala | Gly | Ala | Leu | Val | Gly | Gly | Leu | Gln | Asn | Ile | Gly | Ser | |
| | | | 335 | | | | | 340 | | | | | 345 | | | |
| ggc | gtg | ctg | gcg | tcg | ctc | tct | gcg | atg | ttg | ccg | caa | acc | ggt | cag | ggc | 1289 |
| Gly | Val | Leu | Ala | Ser | Leu | Ser | Ala | Met | Leu | Pro | Gln | Thr | Gly | Gln | Gly | |
| | 350 | | | | | 355 | | | | | 360 | | | | | |

-continued

```
agc ctg ggg ttg ttg atg acc tta atg gga ttg ttg atc gtg ctg tgc    1337
Ser Leu Gly Leu Leu Met Thr Leu Met Gly Leu Leu Ile Val Leu Cys
365                 370                 375 tgg ctg ccg ctg gcg acg cgg atg tcg cat cag ggg cag ccc gtt        1382
Trp Leu Pro Leu Ala Thr Arg Met Ser His Gln Gly Gln Pro Val
380                 385                 390 taagcgcacg tcaccgcagc atcgtcatca gctccatggg agaacgatgc tgctttatca   1442
gatcacgcat cacccgcata tgcggtgcgg agtaagaata aaacgcctga tagcccgcac   1502
aaagcacgct gtctggcgtc tcctgccgag cgtgcgggca caggcgatgc cagtcgcacg   1562
cctggcagtc acagcgcggt tgc                                          1585

<210> SEQ ID NO 42
<211> LENGTH: 1771
<212> TYPE: DNA
<213> ORGANISM: Escherichia coli
<220> FEATURE:
<221> NAME/KEY: CDS
<222> LOCATION: (201)..(1568)

<400> SEQUENCE: 42
gatgtccgtt gattttatgg taccggactc gcatacgctg ctggctgctg tgtggtaaca    60
aaacctctct attaaaaagg tgctacggca ccttttttct tagcattaga acatatcccc   120
tctcgaaata tttactaaaa aatccgcatg tttaccccat tcgtttgccg ctttacacta   180
gtcgcgaatt taaaacagag gtg gta atg aac gat tat aaa atg acg cca ggt   233
                        Met Val Met Asn Asp Tyr Lys Met Thr Pro Gly
                         1               5                  10 gag agg cgc gcg acc tgg ggt tta ggg acc gta ttc tcg ttg cgc atg    281
Glu Arg Arg Ala Thr Trp Gly Leu Gly Thr Val Phe Ser Leu Arg Met
            15                  20                  25 ctg ggc atg ttt atg gtt ctg ccg gtt ctg acc acg tac ggc atg gct    329
Leu Gly Met Phe Met Val Leu Pro Val Leu Thr Thr Tyr Gly Met Ala
        30                  35                  40 ctg caa ggt gcc agc gaa gca tta atc ggt att gcc att ggt att tat    377
Leu Gln Gly Ala Ser Glu Ala Leu Ile Gly Ile Ala Ile Gly Ile Tyr
    45                  50                  55 ggt ctg act cag gcc gtt ttt cag att ccg ttt ggc ctg ctt tcc gac    425
Gly Leu Thr Gln Ala Val Phe Gln Ile Pro Phe Gly Leu Leu Ser Asp
60                  65                  70                  75 cgc att ggt cgc aaa cca tta att gtc ggt ggg ctg gcg gtg ttt gcc    473
Arg Ile Gly Arg Lys Pro Leu Ile Val Gly Gly Leu Ala Val Phe Ala
                80                  85                  90 gcc ggt agc gtt atc gct gcg ctt tcc gac tcc atc tgg gga att att    521
Ala Gly Ser Val Ile Ala Ala Leu Ser Asp Ser Ile Trp Gly Ile Ile
            95                 100                 105 ctg ggc cgg gcg cta caa ggc tct gga gca att gcc gcc gcc gtt atg    569
Leu Gly Arg Ala Leu Gln Gly Ser Gly Ala Ile Ala Ala Ala Val Met
       110                 115                 120 gcg ctg ctt tcc gat ctc acg cgc gaa caa aac cgc acc aaa gcg atg    617
Ala Leu Leu Ser Asp Leu Thr Arg Glu Gln Asn Arg Thr Lys Ala Met
    125                 130                 135 gcg ttt atc ggc gtg agc ttt ggc att acc ttt gcc att gcg atg gtg    665
Ala Phe Ile Gly Val Ser Phe Gly Ile Thr Phe Ala Ile Ala Met Val
140                 145                 150                 155 ctt ggc ccg atc atc act cac aaa ctt ggg ctg cac gcg ctg ttc tgg    713
Leu Gly Pro Ile Ile Thr His Lys Leu Gly Leu His Ala Leu Phe Trp
                160                 165                 170 atg atc gct att ctg gca acg acc ggc att gcg ttg acc att tgg gtt    761
Met Ile Ala Ile Leu Ala Thr Thr Gly Ile Ala Leu Thr Ile Trp Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 175 |     |     |     |     | 180 |     |     |     |     | 185 |     |     |     |      |
| gtg | ccc | aac | agt | agc | act | cac | gta | ctt | aat | cgt | gag | tcc | gga | atg | gtg | 809  |
| Val | Pro | Asn | Ser | Ser | Thr | His | Val | Leu | Asn | Arg | Glu | Ser | Gly | Met | Val |      |
|     |     | 190 |     |     |     |     | 195 |     |     |     |     | 200 |     |     |     |      |
| aaa | ggc | agt | ttc | agt | aaa | gtg | ctg | gcg | gaa | ccg | cgg | ctg | ctg | aaa | ctc | 857  |
| Lys | Gly | Ser | Phe | Ser | Lys | Val | Leu | Ala | Glu | Pro | Arg | Leu | Leu | Lys | Leu |      |
| 205 |     |     |     |     | 210 |     |     |     |     | 215 |     |     |     |     |     |      |
| aac | ttt | ggc | att | atg | tgt | ctg | cat | att | ttg | ctg | atg | tcg | acg | ttt | gtt | 905  |
| Asn | Phe | Gly | Ile | Met | Cys | Leu | His | Ile | Leu | Leu | Met | Ser | Thr | Phe | Val |      |
| 220 |     |     |     |     | 225 |     |     |     |     | 230 |     |     |     |     | 235 |      |
| gcc | ctg | ccc | gga | caa | ctg | gct | gat | gca | ggg | ttc | ccg | gcg | gct | gaa | cac | 953  |
| Ala | Leu | Pro | Gly | Gln | Leu | Ala | Asp | Ala | Gly | Phe | Pro | Ala | Ala | Glu | His |      |
|     |     |     |     | 240 |     |     |     |     | 245 |     |     |     |     | 250 |     |      |
| tgg | aag | gtc | tat | ctg | gcg | aca | atg | cta | atc | gcc | ttt | ggc | tcg | gtc | gtg | 1001 |
| Trp | Lys | Val | Tyr | Leu | Ala | Thr | Met | Leu | Ile | Ala | Phe | Gly | Ser | Val | Val |      |
|     |     |     | 255 |     |     |     |     | 260 |     |     |     |     | 265 |     |     |      |
| cct | ttc | att | atc | tac | gct | gaa | gtt | aag | cgc | aaa | atg | aag | caa | gtc | ttt | 1049 |
| Pro | Phe | Ile | Ile | Tyr | Ala | Glu | Val | Lys | Arg | Lys | Met | Lys | Gln | Val | Phe |      |
|     |     | 270 |     |     |     |     | 275 |     |     |     |     | 280 |     |     |     |      |
| gtc | ttc | tgc | gtc | ggg | ttg | atc | gtg | gtt | gcg | gaa | att | gtg | ttg | tgg | aac | 1097 |
| Val | Phe | Cys | Val | Gly | Leu | Ile | Val | Val | Ala | Glu | Ile | Val | Leu | Trp | Asn |      |
| 285 |     |     |     |     | 290 |     |     |     |     | 295 |     |     |     |     |     |      |
| gcg | caa | acg | cag | ttc | tgg | caa | ctg | gtg | gtc | ggc | gtg | cag | ctt | ttc | ttt | 1145 |
| Ala | Gln | Thr | Gln | Phe | Trp | Gln | Leu | Val | Val | Gly | Val | Gln | Leu | Phe | Phe |      |
| 300 |     |     |     |     | 305 |     |     |     |     | 310 |     |     |     |     | 315 |      |
| gtg | gcg | ttt | aat | ttg | atg | gaa | gcc | ctc | ctg | ccc | tca | ctt | atc | agt | aaa | 1193 |
| Val | Ala | Phe | Asn | Leu | Met | Glu | Ala | Leu | Leu | Pro | Ser | Leu | Ile | Ser | Lys |      |
|     |     |     | 320 |     |     |     |     | 325 |     |     |     |     | 330 |     |     |      |
| gag | tcg | cca | gca | ggt | tac | aaa | ggt | acg | gcg | atg | ggt | gtt | tac | tcc | acc | 1241 |
| Glu | Ser | Pro | Ala | Gly | Tyr | Lys | Gly | Thr | Ala | Met | Gly | Val | Tyr | Ser | Thr |      |
|     |     |     | 335 |     |     |     |     | 340 |     |     |     |     | 345 |     |     |      |
| agc | cag | ttt | ctt | ggc | gtg | gcg | att | ggc | ggt | tcg | ctg | ggc | ggc | tgg | att | 1289 |
| Ser | Gln | Phe | Leu | Gly | Val | Ala | Ile | Gly | Gly | Ser | Leu | Gly | Gly | Trp | Ile |      |
|     |     | 350 |     |     |     |     | 355 |     |     |     |     | 360 |     |     |     |      |
| aac | ggc | atg | ttt | gac | ggt | cag | ggg | gta | ttt | ctc | gct | ggc | gca | atg | ctg | 1337 |
| Asn | Gly | Met | Phe | Asp | Gly | Gln | Gly | Val | Phe | Leu | Ala | Gly | Ala | Met | Leu |      |
| 365 |     |     |     |     | 370 |     |     |     |     | 375 |     |     |     |     |     |      |
| gcc | gca | gtg | tgg | ctg | aca | gtc | gcc | agt | acc | atg | aaa | gaa | ccg | ccg | tat | 1385 |
| Ala | Ala | Val | Trp | Leu | Thr | Val | Ala | Ser | Thr | Met | Lys | Glu | Pro | Pro | Tyr |      |
| 380 |     |     |     |     | 385 |     |     |     |     | 390 |     |     |     |     | 395 |      |
| gtc | agc | agt | ttg | cgc | att | gaa | atc | ccg | gcg | aac | att | gcc | gca | aac | gag | 1433 |
| Val | Ser | Ser | Leu | Arg | Ile | Glu | Ile | Pro | Ala | Asn | Ile | Ala | Ala | Asn | Glu |      |
|     |     |     | 400 |     |     |     |     | 405 |     |     |     |     | 410 |     |     |      |
| gcg | tta | aaa | gtg | cgt | ttg | cta | gaa | act | gaa | ggc | atc | aaa | gaa | gtg | ttg | 1481 |
| Ala | Leu | Lys | Val | Arg | Leu | Leu | Glu | Thr | Glu | Gly | Ile | Lys | Glu | Val | Leu |      |
|     |     | 415 |     |     |     |     | 420 |     |     |     |     | 425 |     |     |     |      |
| att | gca | gaa | gaa | gaa | cat | tca | gct | tat | gtg | aaa | atc | gac | agc | aaa | gtg | 1529 |
| Ile | Ala | Glu | Glu | Glu | His | Ser | Ala | Tyr | Val | Lys | Ile | Asp | Ser | Lys | Val |      |
|     | 430 |     |     |     |     | 435 |     |     |     |     | 440 |     |     |     |     |      |
| acg | aat | cgc | ttt | gag | ata | gaa | cag | gca | att | cgt | cag | gca | taaaaaacgc |  |  | 1578 |
| Thr | Asn | Arg | Phe | Glu | Ile | Glu | Gln | Ala | Ile | Arg | Gln | Ala |     |     |     |      |
|     | 445 |     |     |     |     | 450 |     |     |     |     | 455 |     |     |     |     |      |

| | |
|---|---|
| ggcgaattgc tgctgcgct acgcttatca ggcctacaaa gtttctgaat acaaaccctt | 1638 |
| tgtaggccga atcaggcgtt catgccgcat ctgacatgaa caaaacgcac atagtcgcga | 1698 |
| ttaatcgcgg aagttttga actggaacgg ctgaccgaga tcgccaccac gtaccatcgc | 1758 |
| catgacagcc tgc | 1771 |

<210> SEQ ID NO 43

-continued

```
<211> LENGTH: 1816
<212> TYPE: DNA
<213> ORGANISM: Escherichia coli
<220> FEATURE:
<221> NAME/KEY: CDS
<222> LOCATION: (201)..(1613)

<400> SEQUENCE: 43
cggcgctgtt tggtgcgctg ccgctggtat tgtcgggcgg cgacggctcg gagctgcggc      60 aaccccctggg gatcaccatt gtcggcggac tggtaatgag ccagctcctt acgctgtata    120
ccacgccggt ggtgtatctc ttttttcgacc gtctgcggct gcgttttttcg cgtaaaccta   180 aacaaacggt aaccgagtaa atg aca gat ctt ccc gac agc acc cgt tgg caa    233
                        Met Thr Asp Leu Pro Asp Ser Thr Arg Trp Gln
                          1               5                  10 ttg tgg att gtg gct ttc ggc ttc ttt atg cag tcg ctg gac acc acc      281
Leu Trp Ile Val Ala Phe Gly Phe Phe Met Gln Ser Leu Asp Thr Thr
         15                  20                  25 atc gta aac acc gcc ctt ccc tca atg gcg caa agc ctc ggg gaa agt      329
Ile Val Asn Thr Ala Leu Pro Ser Met Ala Gln Ser Leu Gly Glu Ser
     30                  35                  40 ccg ttg cat atg cac atg gtc att gtc tct tat gtg ctg acc gtg gcg      377
Pro Leu His Met His Met Val Ile Val Ser Tyr Val Leu Thr Val Ala
 45                  50                  55 gtg atg ctg ccc gcc agc ggc tgg ctg gcg gac aaa gtc ggc gtg cgc      425
Val Met Leu Pro Ala Ser Gly Trp Leu Ala Asp Lys Val Gly Val Arg
 60                  65                  70                  75 aat att ttc ttt acc gcc atc gtg ctg ttt act ctc ggt tca ctg ttt      473
Asn Ile Phe Phe Thr Ala Ile Val Leu Phe Thr Leu Gly Ser Leu Phe
             80                  85                  90 tgc gcg ctt tcc ggc acg ctg aac gaa ctg ttg ctg gca cgc gcg tta      521
Cys Ala Leu Ser Gly Thr Leu Asn Glu Leu Leu Leu Ala Arg Ala Leu
         95                 100                 105 cag ggc gtt ggc ggc gcg atg atg gtg ccg gtc ggc aga ttg acg gtg      569
Gln Gly Val Gly Gly Ala Met Met Val Pro Val Gly Arg Leu Thr Val
     110                 115                 120 atg aaa atc gta ccg cgc gag caa tat atg gcg gcg atg acc ttt gtc      617
Met Lys Ile Val Pro Arg Glu Gln Tyr Met Ala Ala Met Thr Phe Val
 125                 130                 135 acg tta ccc ggt cag gtc ggt ccg ctc ctc ggt ccg gcg ctc ggc ggt      665
Thr Leu Pro Gly Gln Val Gly Pro Leu Leu Gly Pro Ala Leu Gly Gly
140                 145                 150                 155 ctg ctg gtg gag tac gca tcg tgg cac tgg atc ttt ttg atc aac att      713
Leu Leu Val Glu Tyr Ala Ser Trp His Trp Ile Phe Leu Ile Asn Ile
             160                 165                 170 ccg gtg ggg att atc ggt gcg atc gcc aca ttg ctg tta atg ccg aac      761
Pro Val Gly Ile Ile Gly Ala Ile Ala Thr Leu Leu Leu Met Pro Asn
         175                 180                 185 tac acc atg cag acg cgg cgc ttt gat ctc tcc gga ttt tta ttg ctg      809
Tyr Thr Met Gln Thr Arg Arg Phe Asp Leu Ser Gly Phe Leu Leu Leu
     190                 195                 200 gcg gtt ggc atg gcg gta tta acc ctg gcg ctg gac ggc agt aaa ggt      857
Ala Val Gly Met Ala Val Leu Thr Leu Ala Leu Asp Gly Ser Lys Gly
 205                 210                 215 aca ggt tta tcg ccg ctg acg att gca ggc ctg gtc gca gtt ggc gtg      905
Thr Gly Leu Ser Pro Leu Thr Ile Ala Gly Leu Val Ala Val Gly Val
220                 225                 230                 235 gtg gca ctg gtg ctt tat ctg ctg cac gcc aga aat aac aac cgt gcc      953
Val Ala Leu Val Leu Tyr Leu Leu His Ala Arg Asn Asn Asn Arg Ala
             240                 245                 250 ctg ttc agt ctg aaa ctg ttc cgt act cgt acc ttt tcg ctg ggc ctg     1001
Leu Phe Ser Leu Lys Leu Phe Arg Thr Arg Thr Phe Ser Leu Gly Leu
```

-continued

```
                Leu Phe Ser Leu Lys Leu Phe Arg Thr Arg Thr Phe Ser Leu Gly Leu
                                255                 260                 265 gcg ggg agc ttt gcc gga cgt att ggc agt ggc atg ttg ccc ttt atg            1049
Ala Gly Ser Phe Ala Gly Arg Ile Gly Ser Gly Met Leu Pro Phe Met
            270                 275                 280 aca ccg gtt ttc ctg caa att ggc ctc ggt ttc tcg ccg ttt cat gcc            1097
Thr Pro Val Phe Leu Gln Ile Gly Leu Gly Phe Ser Pro Phe His Ala
    285                 290                 295 gga ctg atg atg atc ccg atg gtg ctt ggc agc atg gga atg aag cga            1145
Gly Leu Met Met Ile Pro Met Val Leu Gly Ser Met Gly Met Lys Arg
300                 305                 310                 315 att gtg gta cag gtg gtg aat cgc ttt ggt tat cgt cgg gta ctg gta            1193
Ile Val Val Gln Val Val Asn Arg Phe Gly Tyr Arg Arg Val Leu Val
                320                 325                 330 gcg acc acg ctg ggt ctg tcg ctg gtc acc ctg ttt atg act acc                1241
Ala Thr Thr Leu Gly Leu Ser Leu Val Thr Leu Leu Phe Met Thr Thr
            335                 340                 345 gcc ctg ctg ggc tgg tac tac gtt ttg ccg ttc gtc ctg ttt tta caa            1289
Ala Leu Leu Gly Trp Tyr Tyr Val Leu Pro Phe Val Leu Phe Leu Gln
    350                 355                 360 ggg atg gtc aac tcg acg cgt ttc tcc tcc atg aac acc ctg acg ctg            1337
Gly Met Val Asn Ser Thr Arg Phe Ser Ser Met Asn Thr Leu Thr Leu
365                 370                 375 aaa gat ctc ccg gac aat ctg gcg agc agc ggc aac agc ctg ctg tcg            1385
Lys Asp Leu Pro Asp Asn Leu Ala Ser Ser Gly Asn Ser Leu Leu Ser
380                 385                 390                 395 atg att atg caa ttg tcg atg agt atc ggc gtc act atc gcc ggg ctg            1433
Met Ile Met Gln Leu Ser Met Ser Ile Gly Val Thr Ile Ala Gly Leu
                400                 405                 410 ttg ctg gga ctt ttt ggt tca cag cat gtc agc gtc gac agc ggc acc            1481
Leu Leu Gly Leu Phe Gly Ser Gln His Val Ser Val Asp Ser Gly Thr
            415                 420                 425 aca caa acc gtc ttt atg tac acc tgg ctt agc atg gcg ttg atc atc            1529
Thr Gln Thr Val Phe Met Tyr Thr Trp Leu Ser Met Ala Leu Ile Ile
    430                 435                 440 gcc ctt ccg gcg ttc atc ttt gcc aga gtg ccg aac gat acg cat caa            1577
Ala Leu Pro Ala Phe Ile Phe Ala Arg Val Pro Asn Asp Thr His Gln
445                 450                 455 aat gta gct att tcg cgg cga aaa agg agc gcg caa tgaagttctg                 1623
Asn Val Ala Ile Ser Arg Arg Lys Arg Ser Ala Gln
460                 465                 470 gcgacccggt attaccggca aactgtttct ggcgattttc gccacctgca ttgtcttgct          1683
gatcagtatg cactgggcgg tgcgtatcag ttttgagcgt ggctttattg attacatcaa          1743
gcatggtaat gaacagcgat tacaactgtt aagtgatgcg cttggcgagc agtatgcgca          1803
gcatggcaac tgg                                                             1816

<210> SEQ ID NO 44
<211> LENGTH: 1576
<212> TYPE: DNA
<213> ORGANISM: Escherichia coli
<220> FEATURE:
<221> NAME/KEY: CDS
<222> LOCATION: (201)..(1373)

<400> SEQUENCE: 44
ctctttggta taaccgtgat tttgtgctgg ttcggcaacg tctttaacgt gttacctaaa           60
tttggctaaa tccttcaaga agccagccat tcgctggctt cttgcctctc aggaaatcac         120
ttatgtccaa atggcaactc gcctgatcct ccttcaccac gtatgctttg cgtcacctta         180
```

```
ctatcaggac gctttagccc atg tcc cgc ttt ttg att tgt agt ttt gcc ctg      233
                     Met Ser Arg Phe Leu Ile Cys Ser Phe Ala Leu
                      1               5                      10 gtt tta ctt tat ccc gcc ggg att gat atg tac ctc gtt ggt tta ccg         281
Val Leu Leu Tyr Pro Ala Gly Ile Asp Met Tyr Leu Val Gly Leu Pro
            15                  20                  25 cgc atc gcc gcc gat ctc aat gcc agc gaa gcg cag ttg cat att gcg         329
Arg Ile Ala Ala Asp Leu Asn Ala Ser Glu Ala Gln Leu His Ile Ala
        30                  35                  40 ttc tcc gta tat ctg gcg ggg atg gca gct gcg atg tta ttt gcc ggt         377
Phe Ser Val Tyr Leu Ala Gly Met Ala Ala Ala Met Leu Phe Ala Gly
    45                  50                  55 aaa gtg gcc gat cgt tca ggg aga aag ccg gtc gcc ata ccc ggc gcg         425
Lys Val Ala Asp Arg Ser Gly Arg Lys Pro Val Ala Ile Pro Gly Ala
60                  65                  70                  75 gcg cta ttt att att gcc tcg gtg ttc tgt tca ctg gct gaa acc agc         473
Ala Leu Phe Ile Ile Ala Ser Val Phe Cys Ser Leu Ala Glu Thr Ser
                80                  85                  90 acg tta ttt ctt gca ggc cga ttt cta cag ggg ttg ggc gca ggc tgt         521
Thr Leu Phe Leu Ala Gly Arg Phe Leu Gln Gly Leu Gly Ala Gly Cys
            95                  100                 105 tgt tac gta gtg gcg ttc gct att ttg cgc gac acg ctg gat gat cga         569
Cys Tyr Val Val Ala Phe Ala Ile Leu Arg Asp Thr Leu Asp Asp Arg
        110                 115                 120 cgt cgg gct aaa gtg ctg tca tta ctc aac ggt att acc tgc atc att         617
Arg Arg Ala Lys Val Leu Ser Leu Leu Asn Gly Ile Thr Cys Ile Ile
    125                 130                 135 ccg gtg tta gcg cca gtg ctc gga cat ctg att atg ctt aaa ttc ccg         665
Pro Val Leu Ala Pro Val Leu Gly His Leu Ile Met Leu Lys Phe Pro
140                 145                 150                 155 tgg cag agt ctg ttc tgg gcg atg gca atg atg ggc atc gcg gta ctg         713
Trp Gln Ser Leu Phe Trp Ala Met Ala Met Met Gly Ile Ala Val Leu
                160                 165                 170 atg ttg tct ttg ttt att tta aaa gaa acg cgc cca gcg gcc ccc gca         761
Met Leu Ser Leu Phe Ile Leu Lys Glu Thr Arg Pro Ala Ala Pro Ala
            175                 180                 185 gct tcg gat aaa cca cga gaa aat agc gag tcg ctg ctt aac cgt ttt         809
Ala Ser Asp Lys Pro Arg Glu Asn Ser Glu Ser Leu Leu Asn Arg Phe
        190                 195                 200 ttc ctc agc cgt gtt gtt atc acc acc ctc agc gtt tcg gtg atc ctc         857
Phe Leu Ser Arg Val Val Ile Thr Thr Leu Ser Val Ser Val Ile Leu
    205                 210                 215 act ttc gtc aac acg tca ccg gta ttg ctg atg gaa atc atg ggg ttt         905
Thr Phe Val Asn Thr Ser Pro Val Leu Leu Met Glu Ile Met Gly Phe
220                 225                 230                 235 gag cgc ggt gaa tac gcc acc att atg gcg ctg acc gct ggc gtc agc         953
Glu Arg Gly Glu Tyr Ala Thr Ile Met Ala Leu Thr Ala Gly Val Ser
                240                 245                 250 atg acc gtt tca ttc tcc acg cca ttt gcg ctg gga att ttt aag cca        1001
Met Thr Val Ser Phe Ser Thr Pro Phe Ala Leu Gly Ile Phe Lys Pro
            255                 260                 265 cgt acg ttg atg atc acc tcg cag gtg tta ttc ctg gcg gcg ggg atc        1049
Arg Thr Leu Met Ile Thr Ser Gln Val Leu Phe Leu Ala Ala Gly Ile
        270                 275                 280 act ctt gcc gtt tca cct tcc cat gcg gtt tct ctg ttt ggt atc acg        1097
Thr Leu Ala Val Ser Pro Ser His Ala Val Ser Leu Phe Gly Ile Thr
    285                 290                 295 ctg att tgc gcc ggt ttc tcg gta ggt ttt ggt gtg gcg atg agt cag        1145
Leu Ile Cys Ala Gly Phe Ser Val Gly Phe Gly Val Ala Met Ser Gln
300                 305                 310                 315
```

```
gcg tta ggg ccg ttt tca tta cgc gcg ggc gta gcc agc tcg acc tta         1193
Ala Leu Gly Pro Phe Ser Leu Arg Ala Gly Val Ala Ser Ser Thr Leu
            320                 325                 330 ggt att gcg cag gtt tgc ggt tcg tca ctg tgg att tgg ctg gca gcg         1241
Gly Ile Ala Gln Val Cys Gly Ser Ser Leu Trp Ile Trp Leu Ala Ala
            335                 340                 345 gtg gtt ggt atc ggc gca tgg aat atg ctg atc ggg att ctg att gcc         1289
Val Val Gly Ile Gly Ala Trp Asn Met Leu Ile Gly Ile Leu Ile Ala
            350                 355                 360 tgt agc ata gtg agc ctg ttg ctg att atg ttc gtc gcg cct gga cgc         1337
Cys Ser Ile Val Ser Leu Leu Leu Ile Met Phe Val Ala Pro Gly Arg
            365                 370                 375 ccc gtt gcc gct cat gaa gaa atc cat cac cac gct tgatctcaat             1383
Pro Val Ala Ala His Glu Glu Ile His His His Ala
380                 385                 390 ctgctgcttt gtctgcaact gctgatgcag gagcgcagcg taaccaaagc ggcgaagcgg       1443
ataaacgtga caccttcggc ggtgagtaag tcgctggcaa agttaagagc gtggtttgac       1503
gacccgctct ttgtgaactc accgctgggt ctgtcgccca caccgctgat ggtcagcatg       1563
gagcaaaatc tgg                                                          1576

<210> SEQ ID NO 45
<211> LENGTH: 1828
<212> TYPE: DNA
<213> ORGANISM: Escherichia coli
<220> FEATURE:
<221> NAME/KEY: CDS
<222> LOCATION: (201)..(1625)

<400> SEQUENCE: 45
tttgacctca ttcgcctcgc tattccattc ggtttatcac acttacttca cgtcaattac         60
cagcgacaca gtgataaagc tggatctgca tcaggcgatt gtcgatgcga ttatccaaag        120
cgatggcgac gcggcattta aagcttgtca ggcgctgcta cgctcacctg ataagtgata        180
acccgataac aggacattga atg agc gat aaa aag aag cgc agt atg gcg ggt        233
                        Met Ser Asp Lys Lys Lys Arg Ser Met Ala Gly
                        1               5                   10 ttg ccg tgg atc gcg gcg atg gcc ttc ttc atg cag gca ctt gat gcc         281
Leu Pro Trp Ile Ala Ala Met Ala Phe Phe Met Gln Ala Leu Asp Ala
            15                  20                  25 act att ctt aat acc gcc tta ccc gca atc gct cat agc ctt aat cgt         329
Thr Ile Leu Asn Thr Ala Leu Pro Ala Ile Ala His Ser Leu Asn Arg
        30                  35                  40 tct cct ctc gcg atg caa tca gcc atc atc agt tat acg ctg acg gtg         377
Ser Pro Leu Ala Met Gln Ser Ala Ile Ile Ser Tyr Thr Leu Thr Val
        45                  50                  55 gcg atg ctt att ccg gta agc gga tgg cta gcc gat cgc ttc ggt acg         425
Ala Met Leu Ile Pro Val Ser Gly Trp Leu Ala Asp Arg Phe Gly Thr
60                  65                  70                  75 cgt cgc att ttt acc ctt gcc gtg agt ctg ttc aca ttg ggt tct ctg         473
Arg Arg Ile Phe Thr Leu Ala Val Ser Leu Phe Thr Leu Gly Ser Leu
            80                  85                  90 gcc tgc gca ctt tct aat tcg cta cca cag ctg gtt gtc ttc cgg gtt         521
Ala Cys Ala Leu Ser Asn Ser Leu Pro Gln Leu Val Val Phe Arg Val
        95                  100                 105 att cag ggg ata ggc ggc gca atg atg atg cct gtt gct cgg ctg gcc         569
Ile Gln Gly Ile Gly Gly Ala Met Met Met Pro Val Ala Arg Leu Ala
        110                 115                 120 tta ctg cgc gct tat cct cgt aat gaa ctt ctt cca gta ttg aat ttt         617
Leu Leu Arg Ala Tyr Pro Arg Asn Glu Leu Leu Pro Val Leu Asn Phe
        125                 130                 135
```

| | | |
|---|---|---|
| gtc gcc atg ccg ggt ctg gtg ggg cca att tta ggc ccc gtt ctt ggc<br>Val Ala Met Pro Gly Leu Val Gly Pro Ile Leu Gly Pro Val Leu Gly<br>140                         145                       150                   155 | 665 |
| ggc gtg ctg gtc acc tgg gca acc tgg cac tgg ata ttt tta atc aat<br>Gly Val Leu Val Thr Trp Ala Thr Trp His Trp Ile Phe Leu Ile Asn<br>                  160                       165                     170 | 713 |
| atc ccc ata ggt att gcg ggc ctt ctt tac gcg cgc aaa cat atg ccc<br>Ile Pro Ile Gly Ile Ala Gly Leu Leu Tyr Ala Arg Lys His Met Pro<br>             175                       180                     185 | 761 |
| aat ttc acc acc gca cga cgc aga ttc gat atc act ggc ttt ttg ctg<br>Asn Phe Thr Thr Ala Arg Arg Arg Phe Asp Ile Thr Gly Phe Leu Leu<br>                  190                       195                     200 | 809 |
| ttt ggc ctc agc ctt gtt ctc ttc tca agc gga ata gag cta ttc ggg<br>Phe Gly Leu Ser Leu Val Leu Phe Ser Ser Gly Ile Glu Leu Phe Gly<br>205                         210                       215 | 857 |
| gaa aag att gtc gcc agc tgg att gcc ttg acg gta att gtc acc agc<br>Glu Lys Ile Val Ala Ser Trp Ile Ala Leu Thr Val Ile Val Thr Ser<br>220                         225                       230                   235 | 905 |
| atc ggg tta ctg ctt ctc tat att ctc cat gca cga cgc acg cca aac<br>Ile Gly Leu Leu Leu Leu Tyr Ile Leu His Ala Arg Arg Thr Pro Asn<br>                  240                       245                     250 | 953 |
| cca tta att tca tta gat tta ttt aaa acc cgc act ttc tcg atc ggt<br>Pro Leu Ile Ser Leu Asp Leu Phe Lys Thr Arg Thr Phe Ser Ile Gly<br>                  255                       260                     265 | 1001 |
| atc gta ggc aat att gca acc cgt ctg ggg acc ggc tgt gta ccg ttc<br>Ile Val Gly Asn Ile Ala Thr Arg Leu Gly Thr Gly Cys Val Pro Phe<br>             270                       275                     280 | 1049 |
| ctt atg cca ttg atg tta cag gta gga ttt ggt tat cag gcg ttt att<br>Leu Met Pro Leu Met Leu Gln Val Gly Phe Gly Tyr Gln Ala Phe Ile<br>285                         290                       295 | 1097 |
| gct ggc tgt atg atg gca ccg aca gcg tta ggt tcc att att gca aaa<br>Ala Gly Cys Met Met Ala Pro Thr Ala Leu Gly Ser Ile Ile Ala Lys<br>300                         305                       310                   315 | 1145 |
| tcg atg gtt acc caa gtc tta cgt cgt ctg ggc tat cgc cat acg tta<br>Ser Met Val Thr Gln Val Leu Arg Arg Leu Gly Tyr Arg His Thr Leu<br>                  320                       325                     330 | 1193 |
| gtg ggg atc acg gtg att att ggg cta atg atc gct cag ttc tct ttg<br>Val Gly Ile Thr Val Ile Ile Gly Leu Met Ile Ala Gln Phe Ser Leu<br>             335                       340                     345 | 1241 |
| caa tca cca gca atg gct ata tgg atg ctg atc ttg ccg ttg ttt ata<br>Gln Ser Pro Ala Met Ala Ile Trp Met Leu Ile Leu Pro Leu Phe Ile<br>             350                       355                     360 | 1289 |
| tta ggg atg gct atg tcg acg cag ttt acc gcg atg aat acc atc aca<br>Leu Gly Met Ala Met Ser Thr Gln Phe Thr Ala Met Asn Thr Ile Thr<br>365                         370                       375 | 1337 |
| ctt gcc gat ctg acc gat gac aat gcc agc agc ggt aac agt gtt ctg<br>Leu Ala Asp Leu Thr Asp Asp Asn Ala Ser Ser Gly Asn Ser Val Leu<br>380                         385                       390                   395 | 1385 |
| gcg gtc acg cag caa ctg tcg att agt tta ggc gtt gct gta agt gcg<br>Ala Val Thr Gln Gln Leu Ser Ile Ser Leu Gly Val Ala Val Ser Ala<br>                  400                       405                     410 | 1433 |
| gcc gtc ctt cgc gtt tat gaa gga atg gaa ggc aca acg act gtc gaa<br>Ala Val Leu Arg Val Tyr Glu Gly Met Glu Gly Thr Thr Thr Val Glu<br>             415                       420                     425 | 1481 |
| caa ttc cac tat acg ttt atc aca atg ggc att att act gtt gct tca<br>Gln Phe His Tyr Thr Phe Ile Thr Met Gly Ile Ile Thr Val Ala Ser<br>             430                       435                     440 | 1529 |
| gca gca atg ttc atg ctt ctg aaa aca acc gat ggt aat aat ttg atc<br>Ala Ala Met Phe Met Leu Leu Lys Thr Thr Asp Gly Asn Asn Leu Ile<br>445                         450                       455 | 1577 |

-continued

```
aaa aga cag cgt aaa tct aag ccg aac cgc gtt cca tca gaa tcg gag    1625
Lys Arg Gln Arg Lys Ser Lys Pro Asn Arg Val Pro Ser Glu Ser Glu
460                 465                 470                 475 taagttgtaa tcgttgttgc tgaagggtcg gctgggttat ccgatggatg agtacatcaa    1685
tcgccagctc ccccagttca tctttcggtt ggtggatagt ggttaatggt ggcgtcataa    1745
agcttgccag ttcgatatcg tcatagccaa tcaccgcgat atcctgcgga acctgtaact    1805
ctgcctgata taacgcctgg taa                                           1828

<210> SEQ ID NO 46
<211> LENGTH: 1633
<212> TYPE: DNA
<213> ORGANISM: Escherichia coli
<220> FEATURE:
<221> NAME/KEY: CDS
<222> LOCATION: (201)..(1430)

<400> SEQUENCE: 46
gactatttgt aatcgttata cattctgacc cgaagtcaga agtatttct ctgtctgtgt      60 gttcacaggc agtgtggttg attacatgaa attcagtaca tttgcagtct cgttgccctt    120
ctcacctgcc tttcgtcatt accgacggta ttgaatttcg ttttccccgt tggggttctc    180
cggacaagga gttgtttgtt atg cca cgt ttt ttt acc cgc cat gcc gcc acg    233
                       Met Pro Arg Phe Phe Thr Arg His Ala Ala Thr
                        1               5                  10 ctg ttt ttc ccg atg gcg ttg att ttg tat gac ttt gct gcg tat ctg      281
Leu Phe Phe Pro Met Ala Leu Ile Leu Tyr Asp Phe Ala Ala Tyr Leu
             15                  20                  25 tcg acg gat ctg atc cag cct ggg atc att aat gtg gta cgt gat ttt      329
Ser Thr Asp Leu Ile Gln Pro Gly Ile Ile Asn Val Val Arg Asp Phe
 30                  35                  40 aat gcc gat gtc agt ctg gcc cct gct gcc gtc agt ctc tat ctt gct      377
Asn Ala Asp Val Ser Leu Ala Pro Ala Ala Val Ser Leu Tyr Leu Ala
 45                  50                  55 ggc ggt atg gcg tta cag tgg ctg ctg ggg ccg ctt tcc gac aga att      425
Gly Gly Met Ala Leu Gln Trp Leu Leu Gly Pro Leu Ser Asp Arg Ile
 60                  65                  70                  75 ggc cgc agg ccg gtg ctg att acc ggg gcg cta att ttt acc ctt gcc      473
Gly Arg Arg Pro Val Leu Ile Thr Gly Ala Leu Ile Phe Thr Leu Ala
             80                  85                  90 tgc gcc gcg aca atg ttc aca acg tct atg aca cag ttt ctt atc gcg      521
Cys Ala Ala Thr Met Phe Thr Thr Ser Met Thr Gln Phe Leu Ile Ala
             95                 100                 105 cgt gca att cag ggc acc agt atc tgt ttt att gcc acc gtt ggt tat      569
Arg Ala Ile Gln Gly Thr Ser Ile Cys Phe Ile Ala Thr Val Gly Tyr
            110                 115                 120 gtc acg gtg cag gag gcg ttc gga cag aca aaa ggg atc aag ttg atg      617
Val Thr Val Gln Glu Ala Phe Gly Gln Thr Lys Gly Ile Lys Leu Met
125                 130                 135 gcg att atc acc tcc atc gta ctg att gcg ccg att atc ggc ccg ctt      665
Ala Ile Ile Thr Ser Ile Val Leu Ile Ala Pro Ile Ile Gly Pro Leu
140                 145                 150                 155 tcc ggc gca gct ctg atg cac ttt atg cac tgg aaa gtc ctt ttt gcc      713
Ser Gly Ala Ala Leu Met His Phe Met His Trp Lys Val Leu Phe Ala
            160                 165                 170 atc att gcg gtt atg ggt ttt atc tca ttt gtt ggc tta ctg ttg gcg      761
Ile Ile Ala Val Met Gly Phe Ile Ser Phe Val Gly Leu Leu Leu Ala
            175                 180                 185 atg cca gag acg gtg aag cgc ggc gcg gtt ccg ttt agc gcc aaa agc      809
Met Pro Glu Thr Val Lys Arg Gly Ala Val Pro Phe Ser Ala Lys Ser
```

|  |  |  |  |  |  |  |  |  |  |  |  |  |  |  |  |
|---|---|---|---|---|---|---|---|---|---|---|---|---|---|---|---|
| gtc | ttg | cgc | gat | ttt | cgt | aat | gtc | ttt | tgc | aat | cgg | ctg | ttc | ctc | ttt |
| Val | Leu | Arg | Asp | Phe | Arg | Asn | Val | Phe | Cys | Asn | Arg | Leu | Phe | Leu | Phe |
|  | 205 |  |  |  | 210 |  |  |  | 215 |  |  |  |  |  |  |

857 ggc gca gca acc atc tct tta agc tat atc ccg atg atg agc tgg gtg  905
Gly Ala Ala Thr Ile Ser Leu Ser Tyr Ile Pro Met Met Ser Trp Val
220          225              230              235 gct gtc tcg ccg gtg atc ctt atc gat gca ggc agc tta aca act tcg  953
Ala Val Ser Pro Val Ile Leu Ile Asp Ala Gly Ser Leu Thr Thr Ser
             240              245              250 cag ttc gcc tgg aca cag gtt ccg gtg ttc ggc gcg gtg att gtt gcg  1001
Gln Phe Ala Trp Thr Gln Val Pro Val Phe Gly Ala Val Ile Val Ala
        255              260              265 aat gcc atc gtg gcg cgt ttt gtt aaa gat ccg acc gaa ccg cgg ttt  1049
Asn Ala Ile Val Ala Arg Phe Val Lys Asp Pro Thr Glu Pro Arg Phe
   270              275              280 atc tgg cgt gcc gta ccc att caa ctg gtc ggc ctc tcg ctg ttg att  1097
Ile Trp Arg Ala Val Pro Ile Gln Leu Val Gly Leu Ser Leu Leu Ile
285              290              295 gtc ggc aat ctg ctg tcg ccg cac gtc tgg ctg tgg tcg gtg ctg ggc  1145
Val Gly Asn Leu Leu Ser Pro His Val Trp Leu Trp Ser Val Leu Gly
300              305              310              315 acc agt ctg tat gct ttc ggg att ggt ttg att ttc ccg acc tta ttc  1193
Thr Ser Leu Tyr Ala Phe Gly Ile Gly Leu Ile Phe Pro Thr Leu Phe
             320              325              330 cgc ttt acg ctg ttt tcc aat aag tta ccg aaa ggg acc gtc tcc gca  1241
Arg Phe Thr Leu Phe Ser Asn Lys Leu Pro Lys Gly Thr Val Ser Ala
        335              340              345 tcg cta aat atg gtg atc ctg atg gtg atg tcg gtc tcg gtc gaa atc  1289
Ser Leu Asn Met Val Ile Leu Met Val Met Ser Val Ser Val Glu Ile
   350              355              360 ggc cgc tgg cta tgg ttt aac ggc ggt cgc ttg ccg ttt cat ctg tta  1337
Gly Arg Trp Leu Trp Phe Asn Gly Gly Arg Leu Pro Phe His Leu Leu
365              370              375 gcc gtt gtg gcg ggc gtt atc gtc gtt ttc acc ctg gcg gga ttg ctc  1385
Ala Val Val Ala Gly Val Ile Val Val Phe Thr Leu Ala Gly Leu Leu
380              385              390              395 aat cgc gtg cgc cag cat cag gca gcc gag cta gtg gag gag cag      1430
Asn Arg Val Arg Gln His Gln Ala Ala Glu Leu Val Glu Glu Gln
             400              405              410 tgattttgc gcgatccggc cgtcaggctc tattcttaac gttatgaata aactcatcga  1490
actcagacgc gccaaaaggt tggcgctctc tttactgctt atcgccgctg ctacctttgt  1550
cgttacgctg tttttgccgc ccaattttg ggtgagcggc gtgaaggcga ttgctgaagc  1610
ggcgatggtc ggcgcgctgg cgg                                          1633

<210> SEQ ID NO 47
<211> LENGTH: 518
<212> TYPE: PRT
<213> ORGANISM: Escherichia coli

<400> SEQUENCE: 47

Met Ile Pro Asp Val Ser Gln Ala Leu Ala Trp Leu Glu Lys His Pro
1               5                   10                  15

Gln Ala Leu Lys Gly Ile Gln Arg Gly Leu Glu Arg Glu Thr Leu Arg
            20                  25                  30

Val Asn Ala Asp Gly Thr Leu Ala Thr Thr Gly His Pro Glu Ala Leu
        35                  40                  45

Gly Ser Ala Leu Thr His Lys Trp Ile Thr Thr Asp Phe Ala Glu Ala

-continued

```
                50                      55                      60
Leu Leu Glu Phe Ile Thr Pro Val Asp Gly Asp Ile Glu His Met Leu
 65                      70                      75                      80

Thr Phe Met Arg Asp Leu His Arg Tyr Thr Ala Arg Asn Met Gly Asp
                         85                      90                      95

Glu Arg Met Trp Pro Leu Ser Met Pro Cys Tyr Ile Ala Glu Gly Gln
                        100                     105                     110

Asp Ile Glu Leu Ala Gln Tyr Gly Thr Ser Asn Thr Gly Arg Phe Lys
                115                     120                     125

Thr Leu Tyr Arg Glu Gly Leu Lys Asn Arg Tyr Gly Ala Leu Met Gln
130                     135                     140

Thr Ile Ser Gly Val His Tyr Asn Phe Ser Leu Pro Met Ala Phe Trp
145                     150                     155                     160

Gln Ala Lys Cys Gly Asp Ile Ser Gly Ala Asp Ala Lys Glu Lys Ile
                        165                     170                     175

Ser Ala Gly Tyr Phe Arg Val Ile Arg Asn Tyr Tyr Arg Phe Gly Trp
                180                     185                     190

Val Ile Pro Tyr Leu Phe Gly Ala Ser Pro Ala Ile Cys Ser Ser Phe
            195                     200                     205

Leu Gln Gly Lys Pro Thr Ser Leu Pro Phe Glu Lys Thr Glu Cys Gly
210                     215                     220

Met Tyr Tyr Leu Pro Tyr Ala Thr Ser Leu Arg Leu Ser Asp Leu Gly
225                     230                     235                     240

Tyr Thr Asn Lys Ser Gln Ser Asn Leu Gly Ile Thr Phe Asn Asp Leu
                        245                     250                     255

Tyr Glu Tyr Val Ala Gly Leu Lys Gln Ala Ile Lys Thr Pro Ser Glu
                260                     265                     270

Glu Tyr Ala Lys Ile Gly Ile Glu Lys Asp Gly Lys Arg Leu Gln Ile
            275                     280                     285

Asn Ser Asn Val Leu Gln Ile Glu Asn Glu Leu Tyr Ala Pro Ile Arg
290                     295                     300

Pro Lys Arg Val Thr Arg Ser Gly Glu Ser Pro Ser Asp Ala Leu Leu
305                     310                     315                     320

Arg Gly Gly Ile Glu Tyr Ile Glu Val Arg Ser Leu Asp Ile Asn Pro
                        325                     330                     335

Phe Ser Pro Ile Gly Val Asp Glu Gln Val Arg Phe Leu Asp Leu
                340                     345                     350

Phe Met Val Trp Cys Ala Leu Ala Asp Ala Pro Glu Met Ser Ser Ser
            355                     360                     365

Glu Leu Ala Cys Thr Arg Val Asn Trp Asn Arg Val Ile Leu Glu Gly
370                     375                     380

Arg Lys Pro Gly Leu Thr Leu Gly Ile Gly Cys Glu Thr Ala Gln Phe
385                     390                     395                     400

Pro Leu Pro Gln Val Gly Lys Asp Leu Phe Arg Asp Leu Lys Arg Val
                        405                     410                     415

Ala Gln Thr Leu Asp Ser Ile Asn Gly Gly Glu Ala Tyr Gln Lys Val
                420                     425                     430

Cys Asp Glu Leu Val Ala Cys Phe Asp Asn Pro Asp Leu Thr Phe Ser
            435                     440                     445

Ala Arg Ile Leu Arg Ser Met Ile Asp Thr Gly Ile Gly Gly Thr Gly
            450                     455                     460

Lys Ala Phe Ala Glu Ala Tyr Arg Asn Leu Leu Arg Glu Glu Pro Leu
465                     470                     475                     480
```

-continued

Glu Ile Leu Arg Glu Glu Asp Phe Val Ala Glu Arg Glu Ala Ser Glu
            485                 490                 495

Arg Arg Gln Gln Glu Met Glu Ala Ala Asp Thr Glu Pro Phe Ala Val
        500                 505                 510

Trp Leu Glu Lys His Ala
        515

<210> SEQ ID NO 48
<211> LENGTH: 316
<212> TYPE: PRT
<213> ORGANISM: Escherichia coli

<400> SEQUENCE: 48

Met Ile Lys Leu Gly Ile Val Met Asp Pro Ile Ala Asn Ile Asn Ile
1               5                   10                  15

Lys Lys Asp Ser Ser Phe Ala Met Leu Leu Glu Ala Gln Arg Arg Gly
            20                  25                  30

Tyr Glu Leu His Tyr Met Glu Met Gly Asp Leu Tyr Leu Ile Asn Gly
        35                  40                  45

Glu Ala Arg Ala His Thr Arg Thr Leu Asn Val Lys Gln Asn Tyr Glu
    50                  55                  60

Glu Trp Phe Ser Phe Val Gly Glu Gln Asp Leu Pro Leu Ala Asp Leu
65                  70                  75                  80

Asp Val Ile Leu Met Arg Lys Asp Pro Pro Phe Asp Thr Glu Phe Ile
                85                  90                  95

Tyr Ala Thr Tyr Ile Leu Glu Arg Ala Glu Gly Lys Gly Thr Leu Ile
            100                 105                 110

Val Asn Lys Pro Gln Ser Leu Arg Asp Cys Asn Glu Lys Leu Phe Thr
        115                 120                 125

Ala Trp Phe Ser Asp Leu Thr Pro Glu Thr Leu Val Thr Arg Asn Lys
    130                 135                 140

Ala Gln Leu Lys Ala Phe Trp Glu Lys His Ser Asp Ile Ile Leu Lys
145                 150                 155                 160

Pro Leu Asp Gly Met Gly Gly Ala Ser Ile Phe Arg Val Lys Glu Gly
                165                 170                 175

Asp Pro Asn Leu Gly Val Ile Ala Glu Thr Leu Thr Glu His Gly Thr
            180                 185                 190

Arg Tyr Cys Met Ala Gln Asn Tyr Leu Pro Ala Ile Lys Asp Gly Asp
        195                 200                 205

Lys Arg Val Leu Val Val Asp Gly Glu Pro Val Pro Tyr Cys Leu Ala
    210                 215                 220

Arg Ile Pro Gln Gly Gly Glu Thr Arg Gly Asn Leu Ala Ala Gly Gly
225                 230                 235                 240

Arg Gly Glu Pro Arg Pro Leu Thr Glu Ser Asp Trp Lys Ile Ala Arg
                245                 250                 255

Gln Ile Gly Pro Thr Leu Lys Glu Lys Gly Leu Ile Phe Val Gly Leu
            260                 265                 270

Asp Ile Ile Gly Asp Arg Leu Thr Glu Ile Asn Val Thr Ser Pro Thr
        275                 280                 285

Cys Ile Arg Glu Ile Glu Ala Glu Phe Pro Val Ser Ile Thr Gly Met
    290                 295                 300

Leu Met Asp Ala Ile Glu Ala Arg Leu Gln Gln Gln
305                 310                 315

<210> SEQ ID NO 49
<211> LENGTH: 1754

-continued

```
<212> TYPE: DNA
<213> ORGANISM: Escherichia coli
<220> FEATURE:
<221> NAME/KEY: CDS
<222> LOCATION: (201)..(1754)

<400> SEQUENCE: 49
tgtgtctgtt agcgggatgg atgcgcatct cgtggggacc ggtaatcttt tttttgtgcc        60
ttggtaaagc gttacgctat gttgcagttg cagcagcgac cgttcagggc atgatgtggt      120
ggcactaatt gtaggcctgc acatatggtc accattacag ttatgctaat taaaacgatt      180
ttgacaggcg ggaggtcaat  ttg atc ccg gac gta tca cag gcg ctg gcc        230
                      Met Ile Pro Asp Val Ser Gln Ala Leu Ala
                       1               5                  10 tgg ctg gaa aaa cat cct cag gcg tta aag ggg ata cag cgt ggg ctg        278
Trp Leu Glu Lys His Pro Gln Ala Leu Lys Gly Ile Gln Arg Gly Leu
                15                  20                  25 gag cgc gaa act ttg cgt gtt aat gct gat ggc aca ctg gca aca aca        326
Glu Arg Glu Thr Leu Arg Val Asn Ala Asp Gly Thr Leu Ala Thr Thr
         30                  35                  40 ggt cat cct gaa gca tta ggt tcc gca ctg acg cac aaa tgg att act        374
Gly His Pro Glu Ala Leu Gly Ser Ala Leu Thr His Lys Trp Ile Thr
     45                  50                  55 acc gat ttt gcg gaa gca ttg ctg gaa ttc att aca cca gtg gat ggt        422
Thr Asp Phe Ala Glu Ala Leu Leu Glu Phe Ile Thr Pro Val Asp Gly
 60                  65                  70 gat att gaa cat atg ctg acc ttt atg cgc gat ctg cat cgt tat acg        470
Asp Ile Glu His Met Leu Thr Phe Met Arg Asp Leu His Arg Tyr Thr
 75                  80                  85                  90 gcg cgc aat atg ggc gat gag cgg atg tgg ccg tta agt atg cca tgc        518
Ala Arg Asn Met Gly Asp Glu Arg Met Trp Pro Leu Ser Met Pro Cys
                 95                 100                 105 tac atc gca gaa ggt cag gac atc gaa ctg gca cag tac ggc act tct        566
Tyr Ile Ala Glu Gly Gln Asp Ile Glu Leu Ala Gln Tyr Gly Thr Ser
            110                 115                 120 aac acc gga cgc ttt aaa acg ctg tat cgt gaa ggg ctg aaa aat cgc        614
Asn Thr Gly Arg Phe Lys Thr Leu Tyr Arg Glu Gly Leu Lys Asn Arg
        125                 130                 135 tac ggc gcg ctg atg caa acc att tcc ggc gtg cac tac aat ttc tct        662
Tyr Gly Ala Leu Met Gln Thr Ile Ser Gly Val His Tyr Asn Phe Ser
    140                 145                 150 ttg cca atg gca ttc tgg caa gcg aag tgc ggt gat atc tcg ggc gct        710
Leu Pro Met Ala Phe Trp Gln Ala Lys Cys Gly Asp Ile Ser Gly Ala
155                 160                 165                 170 gat gcc aaa gag aaa att tct gcg ggc tat ttc cgc gtt atc cgc aat        758
Asp Ala Lys Glu Lys Ile Ser Ala Gly Tyr Phe Arg Val Ile Arg Asn
                175                 180                 185 tac tat cgt ttc ggt tgg gtc att cct tat ctg ttt ggt gca tct ccg        806
Tyr Tyr Arg Phe Gly Trp Val Ile Pro Tyr Leu Phe Gly Ala Ser Pro
            190                 195                 200 gcg att tgt tct tct ttc ctg caa gga aaa cca acg tcg ctg ccg ttt        854
Ala Ile Cys Ser Ser Phe Leu Gln Gly Lys Pro Thr Ser Leu Pro Phe
        205                 210                 215 gag aaa acc gag tgc ggt atg tat tac ctg ccg tat gcg acc tct ctt        902
Glu Lys Thr Glu Cys Gly Met Tyr Tyr Leu Pro Tyr Ala Thr Ser Leu
    220                 225                 230 cgt ttg agc gat ctc ggc tat acc aat aaa tcg caa agc aat ctt ggt        950
Arg Leu Ser Asp Leu Gly Tyr Thr Asn Lys Ser Gln Ser Asn Leu Gly
235                 240                 245                 250 att acc ttc aac gat ctt tac gag tac gta gcg ggc ctt aaa cag gca        998
Ile Thr Phe Asn Asp Leu Tyr Glu Tyr Val Ala Gly Leu Lys Gln Ala
```

|  |  |  |  |  |  |  |  |  |  |  |  |  |
|---|---|---|---|---|---|---|---|---|---|---|---|---|
|  |  | 255 |  |  |  | 260 |  |  |  | 265 |  |  |
| atc | aaa | acg | cca | tcg | gaa | gag | tac | gcg | aag | att | ggt | att | gag | aaa | gac | 1046 |
| Ile | Lys | Thr | Pro | Ser | Glu | Glu | Tyr | Ala | Lys | Ile | Gly | Ile | Glu | Lys | Asp |  |
|  |  | 270 |  |  |  | 275 |  |  |  | 280 |  |  |

```
atc aaa acg cca tcg gaa gag tac gcg aag att ggt att gag aaa gac    1046
Ile Lys Thr Pro Ser Glu Glu Tyr Ala Lys Ile Gly Ile Glu Lys Asp
        270                 275                 280 ggt aag agg ctg caa atc aac agc aac gtg ttg cag att gaa aac gaa    1094
Gly Lys Arg Leu Gln Ile Asn Ser Asn Val Leu Gln Ile Glu Asn Glu
            285                 290                 295 ctg tac gcg ccg att cgt cca aaa cgc gtt acc cgc agc ggc gag tcg    1142
Leu Tyr Ala Pro Ile Arg Pro Lys Arg Val Thr Arg Ser Gly Glu Ser
300                 305                 310 cct tct gat gcg ctg tta cgt ggc ggc att gaa tat att gaa gtg cgt    1190
Pro Ser Asp Ala Leu Leu Arg Gly Gly Ile Glu Tyr Ile Glu Val Arg
315                 320                 325                 330 tcg ctg gac atc aac ccg ttc tcg ccg att ggt gta gat gaa cag cag    1238
Ser Leu Asp Ile Asn Pro Phe Ser Pro Ile Gly Val Asp Glu Gln Gln
                335                 340                 345 gtg cga ttc ctc gac ctg ttt atg gtc tgg tgt gcg ctg gct gat gca    1286
Val Arg Phe Leu Asp Leu Phe Met Val Trp Cys Ala Leu Ala Asp Ala
            350                 355                 360 ccg gaa atg agc agt agc gaa ctt gcc tgt aca cgc gtt aac tgg aac    1334
Pro Glu Met Ser Ser Ser Glu Leu Ala Cys Thr Arg Val Asn Trp Asn
                365                 370                 375 cgg gtg atc ctc gaa ggt cgc aaa ccg ggt ctg acg ctg ggt atc ggc    1382
Arg Val Ile Leu Glu Gly Arg Lys Pro Gly Leu Thr Leu Gly Ile Gly
380                 385                 390 tgc gaa acc gca cag ttc ccg tta ccg cag gtg ggt aaa gat ctg ttc    1430
Cys Glu Thr Ala Gln Phe Pro Leu Pro Gln Val Gly Lys Asp Leu Phe
395                 400                 405                 410 cgc gat ctg aaa cgc gtc gcg caa acg ctg gat agt att aac ggc ggc    1478
Arg Asp Leu Lys Arg Val Ala Gln Thr Leu Asp Ser Ile Asn Gly Gly
                415                 420                 425 gaa gcg tat cag aaa gtg tgt gat gaa ctg gtt gcc tgc ttc gat aat    1526
Glu Ala Tyr Gln Lys Val Cys Asp Glu Leu Val Ala Cys Phe Asp Asn
            430                 435                 440 ccc gat ctg act ttc tct gcc cgt atc tta agg tct atg att gat act    1574
Pro Asp Leu Thr Phe Ser Ala Arg Ile Leu Arg Ser Met Ile Asp Thr
                445                 450                 455 ggt att ggc gga aca ggc aaa gca ttt gca gaa gcc tac cgt aat ctg    1622
Gly Ile Gly Gly Thr Gly Lys Ala Phe Ala Glu Ala Tyr Arg Asn Leu
460                 465                 470 ctg cgt gaa gag ccg ctg gaa att ctg cgc gaa gag gat ttt gta gcc    1670
Leu Arg Glu Glu Pro Leu Glu Ile Leu Arg Glu Glu Asp Phe Val Ala
475                 480                 485                 490 gag cgc gag gcg tct gaa cgc cgt cag cag gaa atg gaa gcc gct gat    1718
Glu Arg Glu Ala Ser Glu Arg Arg Gln Gln Glu Met Glu Ala Ala Asp
                495                 500                 505 acc gaa ccg ttt gcg gtg tgg ctg gaa aaa cac gcc                    1754
Thr Glu Pro Phe Ala Val Trp Leu Glu Lys His Ala
            510                 515

<210> SEQ ID NO 50
<211> LENGTH: 1148
<212> TYPE: DNA
<213> ORGANISM: Escherichia coli
<220> FEATURE:
<221> NAME/KEY: CDS
<222> LOCATION: (201)..(1148)

<400> SEQUENCE: 50
tgccgttacc ggttgaacgc gtccgcctgc tgattggccc ggaaggcggt ttatcggcag    60
atgaaattgc catgactgcc cgctatcaat ttactgatat cctgttggga cctcgcgttt   120
```

-continued

```
tgcgtacaga gacaactgcg ctcaccgcca ttaccgcgct acaagtacga tttggcgatt      180
tgggctaacg gagaagaata atg atc aag ctc ggc atc gtg atg gac ccc        230
                     Met Ile Lys Leu Gly Ile Val Met Asp Pro
                      1               5                  10 atc gca aac atc aac atc aag aaa gat tcc agt ttt gct atg ttg ctg      278
Ile Ala Asn Ile Asn Ile Lys Lys Asp Ser Ser Phe Ala Met Leu Leu
                 15                  20                  25 gaa gca cag cgt cgt ggt tac gaa ctt cac tat atg gag atg ggc gat      326
Glu Ala Gln Arg Arg Gly Tyr Glu Leu His Tyr Met Glu Met Gly Asp
             30                  35                  40 ctg tat ctg atc aat ggt gaa gcc cgc gcc cat acc cgc acg ctg aac      374
Leu Tyr Leu Ile Asn Gly Glu Ala Arg Ala His Thr Arg Thr Leu Asn
         45                  50                  55 gtg aag cag aac tac gaa gag tgg ttt tcg ttc gtc ggt gaa cag gat      422
Val Lys Gln Asn Tyr Glu Glu Trp Phe Ser Phe Val Gly Glu Gln Asp
     60                  65                  70 ctg ccg ctg gcc gat ctc gat gtg atc ctg atg cgt aaa gac ccg ccg      470
Leu Pro Leu Ala Asp Leu Asp Val Ile Leu Met Arg Lys Asp Pro Pro
 75                  80                  85                  90 ttt gat acc gag ttt atc tac gcg acc tat att ctg gaa cgt gcc gaa      518
Phe Asp Thr Glu Phe Ile Tyr Ala Thr Tyr Ile Leu Glu Arg Ala Glu
                 95                 100                 105 gag aaa ggg acg ctg atc gtt aac aag ccg cag agc ctg cgc gac tgt      566
Glu Lys Gly Thr Leu Ile Val Asn Lys Pro Gln Ser Leu Arg Asp Cys
            110                 115                 120 aac gag aaa ctg ttt acc gcc tgg ttc tct gac tta acg cca gaa acg      614
Asn Glu Lys Leu Phe Thr Ala Trp Phe Ser Asp Leu Thr Pro Glu Thr
        125                 130                 135 ctg gtt acg cgc aat aaa gcg cag cta aaa gcg ttc tgg gag aaa cac      662
Leu Val Thr Arg Asn Lys Ala Gln Leu Lys Ala Phe Trp Glu Lys His
    140                 145                 150 agc gac atc att ctt aag ccg ctg gac ggt atg ggc ggc gcg tcg att      710
Ser Asp Ile Ile Leu Lys Pro Leu Asp Gly Met Gly Gly Ala Ser Ile
155                 160                 165                 170 ttc cgc gtg aaa gaa ggc gat cca aac ctc ggc gtg att gcc gaa acc      758
Phe Arg Val Lys Glu Gly Asp Pro Asn Leu Gly Val Ile Ala Glu Thr
                175                 180                 185 ctg act gag cat ggc act cgc tac tgc atg gcg caa aat tac ctg cca      806
Leu Thr Glu His Gly Thr Arg Tyr Cys Met Ala Gln Asn Tyr Leu Pro
            190                 195                 200 gcc att aaa gat ggc gac aaa cgc gtg ctg gtg gtg gat ggc gag ccg      854
Ala Ile Lys Asp Gly Asp Lys Arg Val Leu Val Val Asp Gly Glu Pro
        205                 210                 215 gta ccg tac tgc ctg gcg cgt att ccg cag ggg ggc gaa acc cgt ggc      902
Val Pro Tyr Cys Leu Ala Arg Ile Pro Gln Gly Gly Glu Thr Arg Gly
    220                 225                 230 aat ctg gct gcc ggt ggt cgc ggt gaa cct cgt ccg ctg acg gaa agt      950
Asn Leu Ala Ala Gly Gly Arg Gly Glu Pro Arg Pro Leu Thr Glu Ser
235                 240                 245                 250 gac tgg aaa atc gcc cgt cag atc ggg ccg acg ctg aaa gaa aaa ggg      998
Asp Trp Lys Ile Ala Arg Gln Ile Gly Pro Thr Leu Lys Glu Lys Gly
                255                 260                 265 ctg att ttt gtt ggt ctg gat atc atc ggc gac cgt ctg act gaa att     1046
Leu Ile Phe Val Gly Leu Asp Ile Ile Gly Asp Arg Leu Thr Glu Ile
            270                 275                 280 aac gtc acc agc cca acc tgt att cgt gag att gaa gca gag ttt ccg     1094
Asn Val Thr Ser Pro Thr Cys Ile Arg Glu Ile Glu Ala Glu Phe Pro
        285                 290                 295 gtg tcg atc acc gga atg tta atg gat gcc atc gaa gca cgt tta cag     1142
```

```
Val Ser Ile Thr Gly Met Leu Met Asp Ala Ile Glu Ala Arg Leu Gln
        300                 305                 310 cag cag                                                              1148
Gln Gln
315
```

<210> SEQ ID NO 51
<211> LENGTH: 580
<212> TYPE: PRT
<213> ORGANISM: Escherichia coli

<400> SEQUENCE: 51

```
Met Ile Lys Pro Thr Phe Leu Arg Arg Val Ala Ile Ala Ala Leu Leu
  1               5                  10                  15

Ser Gly Ser Cys Phe Ser Ala Ala Ala Pro Pro Ala Pro Pro Val
             20                  25                  30

Ser Tyr Gly Val Glu Glu Asp Val Phe His Pro Val Arg Ala Lys Gln
             35                  40                  45

Gly Met Val Ala Ser Val Asp Ala Thr Ala Thr Gln Val Gly Val Asp
         50                  55                  60

Ile Leu Lys Glu Gly Gly Asn Ala Val Asp Ala Ala Val Ala Val Gly
 65                  70                  75                  80

Tyr Ala Leu Ala Val Thr His Pro Gln Ala Gly Asn Leu Gly Gly Gly
                 85                  90                  95

Gly Phe Met Leu Ile Arg Ser Lys Asn Gly Asn Thr Thr Ala Ile Asp
            100                 105                 110

Phe Arg Glu Met Ala Pro Ala Lys Ala Thr Arg Asp Met Phe Leu Asp
            115                 120                 125

Asp Gln Gly Asn Pro Asp Ser Lys Lys Ser Leu Thr Ser His Leu Ala
        130                 135                 140

Ser Gly Thr Pro Gly Thr Val Ala Gly Phe Ser Leu Ala Leu Asp Lys
145                 150                 155                 160

Tyr Gly Thr Met Pro Leu Asn Lys Val Val Gln Pro Ala Phe Lys Leu
                165                 170                 175

Ala Arg Asp Gly Phe Ile Val Asn Asp Ala Leu Ala Asp Asp Leu Lys
            180                 185                 190

Thr Tyr Gly Ser Glu Val Leu Pro Asn His Glu Asn Ser Lys Ala Ile
        195                 200                 205

Phe Trp Lys Glu Gly Glu Pro Leu Lys Lys Gly Asp Thr Leu Val Gln
    210                 215                 220

Ala Asn Leu Ala Lys Ser Leu Glu Met Ile Ala Glu Asn Gly Pro Asp
225                 230                 235                 240

Glu Phe Tyr Lys Gly Thr Ile Ala Glu Gln Ile Ala Gln Glu Met Gln
                245                 250                 255

Lys Asn Gly Gly Leu Ile Thr Lys Glu Asp Leu Ala Ala Tyr Lys Ala
            260                 265                 270

Val Glu Arg Thr Pro Ile Ser Gly Asp Tyr Arg Gly Tyr Gln Val Tyr
        275                 280                 285

Ser Met Pro Pro Pro Ser Ser Gly Gly Ile His Ile Val Gln Ile Leu
    290                 295                 300

Asn Ile Leu Glu Asn Phe Asp Met Lys Lys Tyr Gly Phe Gly Ser Ala
305                 310                 315                 320

Asp Ala Met Gln Ile Met Ala Glu Ala Glu Lys Tyr Ala Tyr Ala Asp
                325                 330                 335

Arg Ser Glu Tyr Leu Gly Asp Pro Asp Phe Val Lys Val Pro Trp Gln
            340                 345                 350
```

```
Ala Leu Thr Asn Lys Ala Tyr Ala Lys Ser Ile Ala Asp Gln Ile Asp
        355                 360                 365

Ile Asn Lys Ala Lys Pro Ser Ser Glu Ile Arg Pro Gly Lys Leu Ala
    370                 375                 380

Pro Tyr Glu Ser Asn Gln Thr Thr His Tyr Val Val Asp Lys Asp
385                 390                 395                 400

Gly Asn Ala Val Ala Val Thr Tyr Thr Leu Asn Thr Thr Phe Gly Thr
                405                 410                 415

Gly Ile Val Ala Gly Glu Ser Gly Ile Leu Asn Asn Gln Met Asp
            420                 425                 430

Asp Phe Ser Ala Lys Pro Gly Val Pro Asn Val Tyr Gly Leu Val Gly
        435                 440                 445

Gly Asp Ala Asn Ala Val Gly Pro Asn Lys Arg Pro Leu Ser Ser Met
    450                 455                 460

Ser Pro Thr Ile Val Val Lys Asp Gly Lys Thr Trp Leu Val Thr Gly
465                 470                 475                 480

Ser Pro Gly Gly Ser Arg Ile Ile Thr Thr Val Leu Gln Met Val Val
                485                 490                 495

Asn Ser Ile Asp Tyr Gly Leu Asn Val Ala Glu Ala Thr Asn Ala Pro
            500                 505                 510

Arg Phe His His Gln Trp Leu Pro Asp Glu Leu Arg Val Glu Lys Gly
        515                 520                 525

Phe Ser Pro Asp Thr Leu Lys Leu Leu Glu Ala Lys Gly Gln Lys Val
    530                 535                 540

Ala Leu Lys Glu Ala Met Gly Ser Thr Gln Ser Ile Met Val Gly Pro
545                 550                 555                 560

Asp Gly Glu Leu Tyr Gly Ala Ser Asp Pro Arg Ser Val Asp Asp Leu
                565                 570                 575

Thr Ala Gly Tyr
            580

<210> SEQ ID NO 52
<211> LENGTH: 1940
<212> TYPE: DNA
<213> ORGANISM: Escherichia coli
<220> FEATURE:
<221> NAME/KEY: CDS
<222> LOCATION: (201)..(1940)

<400> SEQUENCE: 52
gttagggttg ttcagagtat taatgggctg tgcaaagccg acaaacggca ggagtgccgt     60
aagaatcaga agtcgtttca tcgcgtatcc tcctctgaag atatccttta agtttactcg    120
cttcccgaca aaacgatgat taattcagag ttatatacca ggcttagctg gggttgcccc    180
ttaatctctg gagaataacg atg ata aaa ccg acg ttt tta cgc cgg gtg       230
                        Met Ile Lys Pro Thr Phe Leu Arg Arg Val
                          1               5                  10 gcc att gct gct ctg ctc tca gga agt tgt ttt agc gcc gcc gcc gcg     278
Ala Ile Ala Ala Leu Leu Ser Gly Ser Cys Phe Ser Ala Ala Ala Ala
             15                  20                  25 cct cct gcg ccg ccc gtc tcg tat ggt gtg gag gaa gat gtc ttc cac     326
Pro Pro Ala Pro Pro Val Ser Tyr Gly Val Glu Glu Asp Val Phe His
        30                  35                  40 ccg gta cgc gcg aaa cag gga atg gta gcg tct gtg gac gcc act gcc     374
Pro Val Arg Ala Lys Gln Gly Met Val Ala Ser Val Asp Ala Thr Ala
    45                  50                  55 act cag gtg ggg gtg gat att ctc aag gag ggc ggg aat gcc gtt gat     422
Thr Gln Val Gly Val Asp Ile Leu Lys Glu Gly Gly Asn Ala Val Asp
```

```
                    Thr Gln Val Gly Val Asp Ile Leu Lys Glu Gly Gly Asn Ala Val Asp
                         60                  65                  70 gcc gcc gtg gcg gtg ggc tac gcg ctg gcg gta acg cat ccg cag gca        470
Ala Ala Val Ala Val Gly Tyr Ala Leu Ala Val Thr His Pro Gln Ala
 75                  80                  85                  90 ggg aat ctg ggc ggt ggt ggt ttt atg tta atc cgc tcg aaa aat ggc        518
Gly Asn Leu Gly Gly Gly Gly Phe Met Leu Ile Arg Ser Lys Asn Gly
                 95                 100                 105 aat acc acg gct atc gat ttc cgc gaa atg gca ccc gcc aaa gcg acc        566
Asn Thr Thr Ala Ile Asp Phe Arg Glu Met Ala Pro Ala Lys Ala Thr
            110                 115                 120 cgc gat atg ttc ctc gat gat cag ggc aac ccg gac agc aaa aaa tca        614
Arg Asp Met Phe Leu Asp Asp Gln Gly Asn Pro Asp Ser Lys Lys Ser
        125                 130                 135 ctc act tcg cat ctg gct tcc ggc aca ccg ggt acg gta gca ggt ttc        662
Leu Thr Ser His Leu Ala Ser Gly Thr Pro Gly Thr Val Ala Gly Phe
    140                 145                 150 tcg ctg gcg ctg gat aaa tac ggc acc atg ccg ctg aac aaa gtc gtg        710
Ser Leu Ala Leu Asp Lys Tyr Gly Thr Met Pro Leu Asn Lys Val Val
155                 160                 165                 170 cag ccc gcg ttt aaa ctg gca cgc gat ggt ttt atc gtt aac gac gcg        758
Gln Pro Ala Phe Lys Leu Ala Arg Asp Gly Phe Ile Val Asn Asp Ala
                175                 180                 185 ctg gct gac gat ctc aaa acc tac ggt agc gaa gtg ttg ccg aat cac        806
Leu Ala Asp Asp Leu Lys Thr Tyr Gly Ser Glu Val Leu Pro Asn His
            190                 195                 200 gaa aac agt aaa gct atc ttc tgg aaa gag ggc gag ccg ctg aaa aag        854
Glu Asn Ser Lys Ala Ile Phe Trp Lys Glu Gly Glu Pro Leu Lys Lys
        205                 210                 215 ggc gac acg ctg gtg cag gcg aac ctg gca aag agc ctg gag atg att        902
Gly Asp Thr Leu Val Gln Ala Asn Leu Ala Lys Ser Leu Glu Met Ile
    220                 225                 230 gct gaa aac ggc ccg gac gaa ttc tat aaa ggc acg att gcg gaa cag        950
Ala Glu Asn Gly Pro Asp Glu Phe Tyr Lys Gly Thr Ile Ala Glu Gln
235                 240                 245                 250 atc gcc cag gag atg cag aaa aac ggt ggc ttg atc act aaa gaa gat        998
Ile Ala Gln Glu Met Gln Lys Asn Gly Gly Leu Ile Thr Lys Glu Asp
                255                 260                 265 tta gca gcc tat aaa gcg gtc gaa cgc act ccg ata agc ggc gat tat       1046
Leu Ala Ala Tyr Lys Ala Val Glu Arg Thr Pro Ile Ser Gly Asp Tyr
            270                 275                 280 cgc ggg tat cag gtt tac tcc atg cca ccg cca tcc tcc ggc ggg atc       1094
Arg Gly Tyr Gln Val Tyr Ser Met Pro Pro Pro Ser Ser Gly Gly Ile
        285                 290                 295 cat atc gta caa atc ctc aat att ctg gaa aac ttc gat atg aag aaa       1142
His Ile Val Gln Ile Leu Asn Ile Leu Glu Asn Phe Asp Met Lys Lys
    300                 305                 310 tac ggc ttt ggc agc gcc gat gcg atg caa atc atg gca gaa gcg gag       1190
Tyr Gly Phe Gly Ser Ala Asp Ala Met Gln Ile Met Ala Glu Ala Glu
315                 320                 325                 330 aaa tac gcc tac gcc gac cgc tcg gaa tat ctt ggc gac ccg gat ttt       1238
Lys Tyr Ala Tyr Ala Asp Arg Ser Glu Tyr Leu Gly Asp Pro Asp Phe
                335                 340                 345 gtc aaa gta ccg tgg cag gcg ctg acc aat aaa gcc tat gcc aaa tct       1286
Val Lys Val Pro Trp Gln Ala Leu Thr Asn Lys Ala Tyr Ala Lys Ser
            350                 355                 360 att gcc gat caa att gat atc aat aaa gcg aag cca tcc agc gaa att       1334
Ile Ala Asp Gln Ile Asp Ile Asn Lys Ala Lys Pro Ser Ser Glu Ile
        365                 370                 375 cgc ccc ggc aag ctt gcg cct tat gag agt aat caa act acc cat tac       1382
```

```
                                                                        -continued Arg Pro Gly Lys Leu Ala Pro Tyr Glu Ser Asn Gln Thr Thr His Tyr
    380             385                 390 tca gtg gtg gat aaa gat ggt aac gcg gtg gcg gtg acc tat acg ctg      1430
Ser Val Val Asp Lys Asp Gly Asn Ala Val Ala Val Thr Tyr Thr Leu
395                 400                 405                 410 aac acc acc ttc ggt acg ggc att gtc gcg ggc gag agc ggt att ctg      1478
Asn Thr Thr Phe Gly Thr Gly Ile Val Ala Gly Glu Ser Gly Ile Leu
                415                 420                 425 ctt aat aac cag atg gat gat ttc tcc gcc aaa ccg ggc gta ccg aac      1526
Leu Asn Asn Gln Met Asp Asp Phe Ser Ala Lys Pro Gly Val Pro Asn
        430                 435                 440 gtt tac ggg ctg gtg ggc ggt gat gcc aac gcc gtc ggg ccg aac aaa      1574
Val Tyr Gly Leu Val Gly Gly Asp Ala Asn Ala Val Gly Pro Asn Lys
            445                 450                 455 cgc ccg ctg tcg tcg atg tcg ccg acc att gtg gtg aaa gac ggt aaa      1622
Arg Pro Leu Ser Ser Met Ser Pro Thr Ile Val Val Lys Asp Gly Lys
        460                 465                 470 acc tgg ctg gtt acc ggt agc cca ggc ggt agc cgg atc atc act aca      1670
Thr Trp Leu Val Thr Gly Ser Pro Gly Gly Ser Arg Ile Ile Thr Thr
475                 480                 485                 490 gtg ctg caa atg gtg gtg aat agc atc gat tat ggc ttg aac gtc gcc      1718
Val Leu Gln Met Val Val Asn Ser Ile Asp Tyr Gly Leu Asn Val Ala
                495                 500                 505 gaa gcg acc aat gcg ccg cgt ttc cac cat cag tgg ttg ccg gac gag      1766
Glu Ala Thr Asn Ala Pro Arg Phe His His Gln Trp Leu Pro Asp Glu
        510                 515                 520 ctg cgt gtc gaa aaa ggg ttt agc ccg gat acg ctc aag ctg ctg gaa      1814
Leu Arg Val Glu Lys Gly Phe Ser Pro Asp Thr Leu Lys Leu Leu Glu
            525                 530                 535 gca aaa ggt cag aaa gtg gcg ctg aaa gag gcg atg ggc agt aca caa      1862
Ala Lys Gly Gln Lys Val Ala Leu Lys Glu Ala Met Gly Ser Thr Gln
        540                 545                 550 agc att atg gtt ggg ccg gac ggt gag ttg tac ggc gca tcc gac ccg      1910
Ser Ile Met Val Gly Pro Asp Gly Glu Leu Tyr Gly Ala Ser Asp Pro
555                 560                 565                 570 cgc tcg gtg gat gat tta acg gcg ggg tac                              1940
Arg Ser Val Asp Asp Leu Thr Ala Gly Tyr
                575                 580

<210> SEQ ID NO 53
<211> LENGTH: 321
<212> TYPE: PRT
<213> ORGANISM: Escherichia coli

<400> SEQUENCE: 53

Met Gly Lys Ala Val Ile Ala Ile His Gly Gly Ala Gly Ala Ile Ser
1               5                   10                  15

Arg Ala Gln Met Ser Leu Gln Gln Glu Leu Arg Tyr Ile Glu Ala Leu
                20                  25                  30

Ser Ala Ile Val Glu Thr Gly Gln Lys Met Leu Glu Ala Gly Glu Ser
            35                  40                  45

Ala Leu Asp Val Val Thr Glu Ala Val Arg Leu Leu Glu Glu Cys Pro
        50                  55                  60

Leu Phe Asn Ala Gly Ile Gly Ala Val Phe Thr Arg Asp Glu Thr His
65                  70                  75                  80

Glu Leu Asp Ala Cys Val Met Asp Gly Asn Thr Leu Lys Ala Gly Ala
                85                  90                  95

Val Ala Gly Val Ser His Leu Arg Asn Pro Val Leu Ala Ala Arg Leu
            100                 105                 110
```

-continued

Val Met Glu Gln Ser Pro His Val Met Met Ile Gly Glu Gly Ala Glu
            115                 120                 125

Asn Phe Ala Phe Ala Arg Gly Met Glu Arg Val Ser Pro Glu Ile Phe
130                 135                 140

Ser Thr Ser Leu Arg Tyr Glu Gln Leu Ala Ala Arg Lys Glu Gly
145                 150                 155                 160

Ala Thr Val Leu Asp His Ser Gly Ala Pro Leu Asp Glu Lys Gln Lys
                165                 170                 175

Met Gly Thr Val Gly Ala Val Ala Leu Asp Leu Asp Gly Asn Leu Ala
            180                 185                 190

Ala Ala Thr Ser Thr Gly Gly Met Thr Asn Lys Leu Pro Gly Arg Val
        195                 200                 205

Gly Asp Ser Pro Leu Val Gly Ala Gly Cys Tyr Ala Asn Asn Ala Ser
210                 215                 220

Val Ala Val Ser Cys Thr Gly Thr Gly Glu Val Phe Ile Arg Ala Leu
225                 230                 235                 240

Ala Ala Tyr Asp Ile Ala Ala Leu Met Asp Tyr Gly Gly Leu Ser Leu
                245                 250                 255

Ala Glu Ala Cys Glu Arg Val Val Met Glu Lys Leu Pro Ala Leu Gly
            260                 265                 270

Gly Ser Gly Gly Leu Ile Ala Ile Asp His Glu Gly Asn Val Ala Leu
        275                 280                 285

Pro Phe Asn Thr Glu Gly Met Tyr Arg Ala Trp Gly Tyr Ala Gly Asp
290                 295                 300

Thr Pro Thr Thr Gly Ile Tyr Arg Glu Lys Gly Asp Thr Val Ala Thr
305                 310                 315                 320

Gln

<210> SEQ ID NO 54
<211> LENGTH: 629
<212> TYPE: PRT
<213> ORGANISM: Escherichia coli

<400> SEQUENCE: 54

Met Lys Lys Gly Thr Pro Leu Pro His Ser Asp Glu Leu Asp Ala Gly
1               5                   10                  15

Asn Val Leu Ala Val Glu Asn Leu Asn Ile Ala Phe Met Gln Asp Gln
            20                  25                  30

Gln Lys Ile Ala Ala Val Arg Asn Leu Ser Phe Ser Leu Gln Arg Gly
        35                  40                  45

Glu Thr Leu Ala Ile Val Gly Glu Ser Gly Ser Gly Lys Ser Val Thr
    50                  55                  60

Ala Leu Ala Leu Met Arg Leu Leu Glu Gln Ala Gly Gly Leu Val Gln
65                  70                  75                  80

Cys Asp Lys Met Leu Leu Gln Arg Arg Ser Arg Glu Val Ile Glu Leu
                85                  90                  95

Ser Glu Gln Asn Ala Ala Gln Met Arg His Val Arg Gly Ala Asp Met
            100                 105                 110

Ala Met Ile Phe Gln Glu Pro Met Thr Ser Leu Asn Pro Val Phe Thr
        115                 120                 125

Val Gly Glu Gln Ile Ala Glu Ser Ile Arg Leu His Gln Asn Ala Ser
    130                 135                 140

Arg Glu Glu Ala Met Val Glu Ala Lys Arg Met Leu Asp Gln Val Arg
145                 150                 155                 160

Ile Pro Glu Ala Gln Thr Ile Leu Ser Arg Tyr Pro His Gln Leu Ser

-continued

```
            165                 170                 175
Gly Gly Met Arg Gln Arg Val Met Ile Ala Met Ala Leu Ser Cys Arg
            180                 185                 190

Pro Ala Val Leu Ile Ala Asp Glu Pro Thr Thr Ala Leu Asp Val Thr
            195                 200                 205

Ile Gln Ala Gln Ile Leu Gln Leu Ile Lys Val Leu Gln Lys Glu Met
            210                 215                 220

Ser Met Gly Val Ile Phe Ile Thr His Asp Met Gly Val Val Ala Glu
225                 230                 235                 240

Ile Ala Asp Arg Val Leu Val Met Tyr Gln Gly Glu Ala Val Glu Thr
                245                 250                 255

Gly Thr Val Glu Gln Ile Phe His Ala Pro Gln His Pro Tyr Thr Arg
            260                 265                 270

Ala Leu Leu Ala Ala Val Pro Gln Leu Gly Ala Met Lys Gly Leu Asp
            275                 280                 285

Tyr Pro Arg Arg Phe Pro Leu Ile Ser Leu Glu His Pro Ala Lys Gln
            290                 295                 300

Ala Pro Pro Ile Glu Gln Lys Thr Val Asp Gly Glu Pro Val Leu
305                 310                 315                 320

Arg Val Arg Asn Leu Val Thr Arg Phe Pro Leu Arg Ser Gly Leu Leu
                325                 330                 335

Asn Arg Val Thr Arg Glu Val His Ala Val Glu Lys Val Ser Phe Asp
            340                 345                 350

Leu Trp Pro Gly Glu Thr Leu Ser Leu Val Gly Glu Ser Gly Ser Gly
            355                 360                 365

Lys Ser Thr Thr Gly Arg Ala Leu Leu Arg Leu Val Glu Ser Gln Gly
            370                 375                 380

Gly Glu Ile Ile Phe Asn Gly Gln Arg Ile Asp Thr Leu Ser Pro Gly
385                 390                 395                 400

Lys Leu Gln Ala Leu Arg Arg Asp Ile Gln Phe Ile Phe Gln Asp Pro
                405                 410                 415

Tyr Ala Ser Leu Asp Pro Arg Gln Thr Ile Gly Asp Ser Ile Ile Glu
            420                 425                 430

Pro Leu Arg Val His Gly Leu Leu Pro Gly Lys Asp Ala Ala Ala Arg
            435                 440                 445

Val Ala Trp Leu Leu Glu Arg Val Gly Leu Leu Pro Glu His Ala Trp
            450                 455                 460

Arg Tyr Pro His Glu Phe Ser Gly Gly Gln Arg Gln Arg Ile Cys Ile
465                 470                 475                 480

Ala Arg Ala Leu Ala Leu Asn Pro Lys Val Ile Ile Ala Asp Glu Ala
                485                 490                 495

Val Ser Ala Leu Asp Val Ser Ile Arg Gly Gln Ile Ile Asn Leu Leu
            500                 505                 510

Leu Asp Leu Gln Arg Asp Phe Gly Ile Ala Tyr Leu Phe Ile Ser His
            515                 520                 525

Asp Met Ala Val Val Glu Arg Ile Ser His Arg Val Ala Val Met Tyr
            530                 535                 540

Leu Gly Gln Ile Val Glu Ile Gly Pro Arg Arg Ala Val Phe Glu Asn
545                 550                 555                 560

Pro Gln His Pro Tyr Thr Arg Lys Leu Leu Ala Ala Val Pro Val Ala
                565                 570                 575

Glu Pro Ser Arg Gln Arg Pro Gln Arg Val Leu Leu Ser Asp Asp Leu
            580                 585                 590
```

```
Pro Ser Asn Ile His Leu Arg Gly Glu Glu Val Ala Ala Val Ser Leu
        595                 600                 605
Gln Cys Val Gly Pro Gly His Tyr Val Ala Gln Pro Gln Ser Glu Tyr
610                 615                 620
Ala Phe Met Arg Arg
625

<210> SEQ ID NO 55
<211> LENGTH: 512
<212> TYPE: PRT
<213> ORGANISM: Escherichia coli

<400> SEQUENCE: 55

Met Ala Arg Ala Val His Arg Ser Gly Leu Val Ala Leu Gly Ile Ala
1               5                   10                  15
Thr Ala Leu Met Ala Ser Cys Ala Phe Ala Ala Lys Asp Val Val Val
            20                  25                  30
Ala Val Gly Ser Asn Phe Thr Thr Leu Asp Pro Tyr Asp Ala Asn Asp
        35                  40                  45
Thr Leu Ser Gln Ala Val Ala Lys Ser Phe Tyr Gln Gly Leu Phe Gly
    50                  55                  60
Leu Asp Lys Glu Met Lys Leu Lys Asn Val Leu Ala Glu Ser Tyr Thr
65                  70                  75                  80
Val Ser Asp Asp Gly Ile Thr Tyr Thr Val Lys Leu Arg Glu Gly Ile
                85                  90                  95
Lys Phe Gln Asp Gly Thr Asp Phe Asn Ala Ala Val Lys Ala Asn
            100                 105                 110
Leu Asp Arg Ala Ser Asp Pro Ala Asn His Leu Lys Arg Tyr Asn Leu
        115                 120                 125
Tyr Lys Asn Ile Ala Lys Thr Glu Ala Ile Asp Pro Thr Thr Val Lys
    130                 135                 140
Ile Thr Leu Lys Gln Pro Phe Ser Ala Phe Ile Asn Ile Leu Ala His
145                 150                 155                 160
Pro Ala Thr Ala Met Ile Ser Pro Ala Ala Leu Glu Lys Tyr Gly Lys
                165                 170                 175
Glu Ile Gly Phe Tyr Pro Val Gly Thr Gly Pro Tyr Glu Leu Asp Thr
            180                 185                 190
Trp Asn Gln Thr Asp Phe Val Lys Val Lys Phe Ala Gly Tyr Trp
        195                 200                 205
Gln Pro Gly Leu Pro Lys Leu Asp Ser Ile Thr Trp Arg Pro Val Ala
    210                 215                 220
Asp Asn Asn Thr Arg Ala Ala Met Leu Gln Thr Gly Glu Ala Gln Phe
225                 230                 235                 240
Ala Phe Pro Ile Pro Tyr Glu Gln Ala Thr Leu Leu Glu Lys Asn Lys
                245                 250                 255
Asn Ile Glu Leu Met Ala Ser Pro Ser Ile Met Gln Arg Tyr Ile Ser
            260                 265                 270
Met Asn Val Thr Gln Lys Pro Phe Asp Asn Pro Lys Val Arg Glu Ala
        275                 280                 285
Leu Asn Tyr Ala Ile Asn Arg Pro Ala Leu Val Lys Val Ala Phe Ala
    290                 295                 300
Gly Tyr Ala Thr Pro Ala Thr Gly Val Val Pro Ser Ile Ala Tyr
305                 310                 315                 320
Ala Gln Ser Tyr Lys Pro Trp Pro Tyr Asp Pro Val Lys Ala Arg Glu
                325                 330                 335
```

Leu Leu Lys Glu Ala Gly Tyr Pro Asn Gly Phe Ser Thr Thr Leu Trp
            340                 345                 350

Ser Ser His Asn His Ser Thr Ala Gln Lys Val Leu Gln Phe Thr Gln
        355                 360                 365

Gln Gln Leu Ala Gln Val Gly Ile Lys Ala Gln Val Thr Ala Met Asp
370                 375                 380

Ala Gly Gln Arg Ala Ala Glu Val Glu Gly Lys Gly Gln Lys Glu Ser
385                 390                 395                 400

Gly Val Arg Met Phe Tyr Thr Gly Trp Ser Ala Ser Thr Gly Glu Ala
                405                 410                 415

Asp Trp Ala Leu Ser Pro Leu Phe Ala Ser Gln Asn Trp Pro Pro Thr
                420                 425                 430

Leu Phe Asn Thr Ala Phe Tyr Ser Asn Lys Gln Val Asp Asp Phe Leu
            435                 440                 445

Ala Gln Ala Leu Lys Thr Asn Asp Pro Ala Glu Lys Thr Arg Leu Tyr
        450                 455                 460

Lys Ala Ala Gln Asp Ile Ile Trp Gln Glu Ser Pro Trp Ile Pro Leu
465                 470                 475                 480

Val Val Glu Lys Leu Val Ser Ala His Ser Lys Asn Leu Thr Gly Phe
                485                 490                 495

Trp Ile Met Pro Asp Thr Gly Phe Ser Phe Glu Asp Ala Asp Leu Gln
                500                 505                 510

<210> SEQ ID NO 56
<211> LENGTH: 306
<212> TYPE: PRT
<213> ORGANISM: Escherichia coli

<400> SEQUENCE: 56

Met Leu Asn Tyr Val Ile Lys Arg Leu Leu Gly Leu Ile Pro Thr Leu
1               5                   10                  15

Phe Ile Val Ser Val Leu Val Phe Leu Phe Val His Met Leu Pro Gly
                20                  25                  30

Asp Pro Ala Arg Leu Ile Ala Gly Pro Glu Ala Asp Ala Gln Val Ile
            35                  40                  45

Glu Leu Val Arg Gln Gln Leu Gly Leu Asp Gln Pro Leu Tyr His Gln
        50                  55                  60

Phe Trp His Tyr Ile Ser Asn Ala Val Gln Gly Asp Phe Gly Leu Ser
65                  70                  75                  80

Met Val Ser Arg Arg Pro Val Ala Asp Glu Ile Ala Ser Arg Phe Met
                85                  90                  95

Pro Thr Leu Trp Leu Thr Ile Thr Ser Met Val Trp Ala Val Ile Phe
                100                 105                 110

Gly Met Ala Ala Gly Ile Ile Ala Ala Val Trp Arg Asn Arg Trp Pro
            115                 120                 125

Asp Arg Leu Ser Met Thr Ile Ala Val Ser Gly Ile Ser Phe Pro Ala
        130                 135                 140

Phe Ala Leu Gly Met Leu Leu Ile Gln Val Phe Ser Val Glu Leu Gly
145                 150                 155                 160

Trp Leu Pro Thr Val Gly Ala Asp Ser Trp Gln His Tyr Ile Leu Pro
                165                 170                 175

Ser Leu Thr Leu Gly Ala Ala Val Ala Ala Val Met Ala Arg Phe Thr
            180                 185                 190

Arg Ala Ser Phe Val Asp Val Leu Ser Glu Asp Tyr Met Arg Thr Ala
        195                 200                 205

```
Arg Ala Lys Gly Val Ser Glu Thr Trp Val Leu Lys His Gly Leu
    210                 215                 220

Arg Asn Ala Met Ile Pro Val Val Thr Met Met Gly Leu Gln Phe Gly
225                 230                 235                 240

Phe Leu Leu Gly Gly Ser Ile Val Val Glu Lys Val Phe Asn Trp Pro
                245                 250                 255

Gly Leu Gly Arg Leu Leu Val Asp Ser Val Glu Met Arg Asp Tyr Pro
            260                 265                 270

Val Ile Gln Ala Glu Ile Leu Leu Phe Ser Leu Glu Phe Ile Leu Ile
        275                 280                 285

Asn Leu Val Val Asp Val Leu Tyr Ala Ala Ile Asn Pro Ala Ile Arg
    290                 295                 300

Tyr Lys
305

<210> SEQ ID NO 57
<211> LENGTH: 303
<212> TYPE: PRT
<213> ORGANISM: Escherichia coli

<400> SEQUENCE: 57

Met Arg Leu Phe Asn Trp Arg Arg Gln Ala Val Leu Asn Ala Met Pro
1               5                   10                  15

Leu Val Lys Pro Asp Gln Val Arg Thr Pro Trp His Glu Phe Trp Arg
                20                  25                  30

Arg Phe Arg Arg Gln His Met Ala Met Thr Ala Ala Leu Phe Val Ile
            35                  40                  45

Leu Leu Ile Val Val Ala Ile Phe Ala Arg Trp Ile Ala Pro Tyr Asp
    50                  55                  60

Ala Glu Asn Tyr Phe Asp Tyr Asp Asn Leu Asn Asn Gly Pro Ser Leu
65              70                  75                  80

Gln His Trp Phe Gly Val Asp Ser Leu Gly Arg Asp Ile Phe Ser Arg
                85                  90                  95

Val Leu Val Gly Ala Gln Ile Ser Leu Ala Ala Gly Val Phe Ala Val
            100                 105                 110

Phe Ile Gly Ala Ala Ile Gly Thr Leu Leu Gly Leu Leu Ala Gly Tyr
    115                 120                 125

Tyr Glu Gly Trp Trp Asp Arg Leu Ile Met Arg Ile Cys Asp Val Leu
130                 135                 140

Phe Ala Phe Pro Gly Ile Leu Leu Ala Ile Ala Val Val Ala Val Leu
145                 150                 155                 160

Gly Ser Gly Ile Ala Asn Val Ile Ile Ala Val Ala Ile Phe Ser Ile
                165                 170                 175

Pro Ala Phe Ala Arg Leu Val Arg Gly Asn Thr Leu Val Leu Lys Gln
            180                 185                 190

Gln Thr Phe Ile Glu Ser Ala Arg Ser Ile Gly Ala Ser Asp Met Thr
    195                 200                 205

Val Leu Leu Arg His Ile Leu Pro Gly Thr Val Ser Ser Ile Val Val
210                 215                 220

Phe Phe Thr Met Arg Ile Gly Thr Ser Ile Ile Ser Ala Ala Ser Leu
225                 230                 235                 240

Ser Phe Leu Gly Leu Gly Ala Gln Pro Pro Thr Pro Glu Trp Gly Ala
                245                 250                 255

Met Leu Asn Glu Ala Arg Ala Asp Met Val Ile Ala Pro His Val Ala
            260                 265                 270
```

```
Val Phe Pro Ala Leu Ala Ile Phe Leu Thr Val Leu Ala Phe Asn Leu
        275                 280                 285

Leu Gly Asp Gly Leu Arg Asp Ala Leu Asp Pro Lys Ile Lys Gly
        290                 295                 300
```

<210> SEQ ID NO 58
<211> LENGTH: 6431
<212> TYPE: DNA
<213> ORGANISM: Escherichia coli
<220> FEATURE:
<221> NAME/KEY: gene
<222> LOCATION: (1)..(6431)

<400> SEQUENCE: 58

| | | | | | |
|---|---|---|---|---|---|
| aacactcctg | cggaggcaaa | atcgaatttg | cctattatgt | cagaaaaacg | ccacagactg | 60 |
| tatgccacct | cgggcgtagc | gctgggtcct | gcctttacat | gccatatcca | tctttctata | 120 |
| ttcaaaaatt | gaatgagtaa | ttcataaaaa | ttctgatatt | tatagcaaaa | gtggcgaacc | 180 |
| acccttaatg | gacgaatact | atgggcaaag | cagtcattgc | aattcatggt | ggcgcaggtg | 240 |
| caattagccg | cgcgcagatg | agtctgcaac | aggaattacg | ctacatcgag | gcgttgtctg | 300 |
| ccattgttga | aaccgggcag | aaaatgctgg | aagcgggcga | agtgcgctg | atgtggtga | 360 |
| cggaagcggt | gcgtctgctg | gaagagtgtc | cactgtttaa | cgccggaatt | ggcgctgtct | 420 |
| ttacgcgtga | tgaaacccat | gaactggacg | cctgtgtgat | ggatggtaac | ccctgaaag | 480 |
| ccggtgcggt | ggcgggcgtt | agtcatctgc | gtaatccggt | tcttgccgcc | ggctggtga | 540 |
| tggagcaaag | cccgcatgtg | atgatgattg | gcgaaggggc | agaaaatttt | gcgtttgctc | 600 |
| gtggcatgga | gcgcgtctcg | ccggagattt | tctccacgtc | tttgcgttat | gaacaactac | 660 |
| tggcagcgcg | caaggaaggg | gcaaccgtcc | tcgaccatag | cggtgcgcca | ctggatgaaa | 720 |
| aacagaaaat | gggcaccgtg | ggggccgtgg | cgttggattt | agacggcaat | tggcggcag | 780 |
| ccacgtccac | aggcggaatg | accaataaat | tacccggacg | agttggcgat | agtcccttag | 840 |
| tgggtgccgg | atgctacgcc | aataacgcca | gtgtggcggt | ttcttgtacc | ggcacgggcg | 900 |
| aagtcttcat | ccgcgcgctg | gcggcatatg | acatcgccgc | gttaatggat | tacgcggat | 960 |
| taagtctcgc | ggaagcctgc | gagcgggtag | taatggaaaa | actccctgcg | cttggcggta | 1020 |
| gcggtggctt | aatcgctatc | gaccatgaag | ggaatgtcgc | gctaccgttt | aacaccgaag | 1080 |
| gaatgtatcg | cgcctggggc | tacgcaggcg | atacgccaac | caccggtatc | taccgtgaaa | 1140 |
| aaggggacac | cgttgccaca | cagtgatgaa | cttgatgccg | gtaatgtgct | ggcggttgaa | 1200 |
| aatctgaata | ttgcctttat | gcaggaccag | cagaaaatag | ctgcggtccg | caatctctct | 1260 |
| tttagtctgc | aacgcggtga | gacgctggca | attgttggcg | aatccggctc | cggtaagtca | 1320 |
| gtgactgcgt | tggcattgat | gcgcctgttg | gaacaggcgg | gcggtttagt | acagtgcgat | 1380 |
| aaaatgctgt | tgcagcggcg | cagtcgcgaa | gtgattgaac | ttagcgagca | gaacgctgca | 1440 |
| caaatgcgcc | atgttcgcgg | tcggatatg | gcgatgatat | tcaggagcc | gatgacatcg | 1500 |
| ctgaacccgg | tatttactgt | gggtgaacag | attgccgaat | caattcgtct | gcatcagaac | 1560 |
| gccagtcgtg | aagaagcgat | ggtcgaggcg | aagcggatgc | tggatcaggt | acgcattcct | 1620 |
| gaggcacaaa | ccattctttc | acgttatccg | catcaactct | ctggcgggat | gcgccagcga | 1680 |
| gtgatgattg | cgatggcgct | gtcatgccgc | ccggcggtgc | tgattgccga | tgagccaacc | 1740 |
| accgcgctgg | atgtcactat | tcaggcgcag | atcctgcaat | taatcaaagt | attgcaaaaa | 1800 |
| gagatgtcga | tggcgttat | ctttatcact | cacgatatgg | gcgtggtggc | agagattgcc | 1860 |
| gatcgggtac | tggtgatgta | tcagggcgag | gcggtggaaa | cgggtaccgt | cgaacagatt | 1920 |

| | |
|---|---|
| tttcatgcac cgcaacatcc ttacacccgt gcgctgttag ctgctgttcc gcaacttggt | 1980 |
| gcgatgaaag ggttagatta tccccgacgt ttcccgttga tatcgcttga acatccagcg | 2040 |
| aaacaggccc cccccatcga gcagaaaacg gtggtggatg gcgaacctgt tttacgagtg | 2100 |
| cgtaatcttg tcacccgttt ccctttgcgc agcggtttgt tgaatcgcgt aacgcgggaa | 2160 |
| gtgcatgccg ttgagaaagt cagttttgat ctctggcctg gcgaaacgct atcgctggtg | 2220 |
| ggcgagtctg gcagcggtaa atccactacc gggcgggcgt tgctgcgcct ggtcgaatcg | 2280 |
| cagggcggcg aaattatctt taacggtcag cgaatcgata ccttgtcacc cggcaaactt | 2340 |
| caggcattac gccgggatat tcagtttatt tttcaggacc cttacgcttc gctggaccca | 2400 |
| cgtcagacca tcggtgattc gattatcgaa ccgctgcgtg tacacggttt attgccaggt | 2460 |
| aaagacgcgg ctgcacgcgt tgcgtggttg ctggagcgcg tgggcctgtt acctgaacat | 2520 |
| gcctggcgtt acccgcatga gttttccggc ggtcagcgcc agcgcatctg cattgctcgc | 2580 |
| gcgttggcat tgaatccaaa agtgatcatt gccgacgaag ccgtttcggc gctggatgtt | 2640 |
| tctattcgcg ggcagattat caacttgttg ctcgatctcc agcgtgattt cggcattgcg | 2700 |
| tatctgttta tctcccacga tatggcgtg gtagagcgga ttagtcatcg tgtggcggtg | 2760 |
| atgtatctcg ggcaaattgt tgaaattggt ccacggcgcg cggtcttcga aacccgcag | 2820 |
| catccttata cgcgtaaatt actggcggca gttccggtcg ctgaaccgtc ccgacaacga | 2880 |
| ccgcagcgtg tactgctgtc ggacgatctt cccagcaata ttcatctgcg tggcgaagag | 2940 |
| gtggcagccg tctcgttgca atgcgtcggg ccggggcatt acgtcgcaca accacaatca | 3000 |
| gaatacgcat tcatgcgtag ataacattca ggcggagaat aaaatggcaa gagctgtaca | 3060 |
| ccgtagtggg ttagtggcgc tgggcattgc gacagcgttg atggcatctt gtgcattcgc | 3120 |
| tgccaaagat gtggtggtgg cggtaggatc gaatttcacc acgctcgatc cgtatgacgc | 3180 |
| aaatgacacg ttatctcagg ccgtagcgaa atcgttttac caggggctgt tcggtctgga | 3240 |
| taaagagatg aaactgaaaa acgtgctggc ggagagttat accgtttccg atgacggcat | 3300 |
| tacttacacc gtgaaattgc gggaaggcat taaattccag gatggcaccg atttcaacgc | 3360 |
| cgcggcggtg aaagcgaatc tggaccgggc cagcgatccg gcgaatcatc ttaaacgcta | 3420 |
| taacctgtat aagaatattg ctaaaacgga agcgatcgat ccgacaacgg taaagattac | 3480 |
| cctcaaacag ccgttctcag cgtttattaa tattcttgcc catccggcga ccgcgatgat | 3540 |
| ttcaccggca gcgctggaaa atatggcaa ggagattggt ttttatccgg tgggaaccgg | 3600 |
| accgtatgaa ctggatacct ggaatcagac cgattttgtg aaggtgaaaa aattcgcggg | 3660 |
| ttactggcag ccaggattgc ccaaactgga cagcataacc tggcgtccgg tggcggataa | 3720 |
| caacacccgc gcggcaatgc tgcaaaccgg tgaagcgcag tttgctttcc ccattcctta | 3780 |
| cgagcaggcc acactgctgg agaaaaacaa aaatatcgag ttgatggcca gtccgtcaat | 3840 |
| tatgcagcgt tatatcagta tgaacgtgac gcaaaagccg ttcgataacc cgaaggtccg | 3900 |
| tgaggcgctg aattacgcca ttaaccgtcc ggcgctggtg aaagttgcct ttgcgggcta | 3960 |
| tgcaacgcca gctactggtg tggtaccgcc aagtatcgcc tacgcgcaaa gttataaacc | 4020 |
| gtggccttac gatccagtga aagcgcgcga attactgaaa gaggcgggat atcccaacgg | 4080 |
| tttcagtacc acgctgtggt cgtcacataa ccacagcacc gcgcagaaag tgctgcaatt | 4140 |
| tacccagcag cagttagcgc aggtcgggat taaagcccag gtgactgcga tggatgccgg | 4200 |
| acagcgggcg gcagaagttg aaggtaaagg gcaaaaagag agcggcgtgc ggatgttcta | 4260 |
| cactggctgg tcggcttcaa ccggcgaagc ggactgggca ctatcgccgc tgtttgcctc | 4320 |

-continued

```
gcagaactgg ccaccgacgc tgtttaatac cgcgttttac agcaataaac aggtggatga    4380
cttcctggct caggcactga aaactaatga tccggcggaa aagacccgct tatataaggc    4440
ggcgcaggat atcatctggc aagaatcgcc gtggatcccg ctggtggtag aaaaactggt    4500
gtcggcacac agtaaaaacc tgaccggttt ttggatcatg ccagacaccg gcttcagctt    4560
tgaagacgcg gatttgcaat aagcaacgca gggagtggaa tgcttaatta cgttatcaaa    4620
cgcttactgg ggttgattcc gacgctgttt atcgtctcgg tgctggtgtt tttatttgtc    4680
catatgctgc ccggcgatcc ggcgcgattg attgccgggc ccgaagctga tgcgcaggtt    4740
atagaactgg tgcgtcagca gctggggttg gatcagccgc tgtatcacca gttctggcac    4800
tatatcagca atgctgtgca gggggatttt ggcctgtcga tggtgtcgcg tcgtccggtt    4860
gccgatgaga ttgccagccg ctttatgcca acgctgtggc tgaccataac cagtatggtc    4920
tgggcggtta tatttggtat ggcggcggga attatcgccg ccgtctggcg taaccgttgg    4980
ccggatcgat tgagtatgac cattgcggtg tcggggatct cgtttccggc atttgctctg    5040
gggatgcttt taattcaggt attctccgtt gaactgggct ggctgcctac cgtgggagca    5100
gacagttggc agcactacat tttaccctcc ctgacgctcg gcgcggcagt ggccgccgtg    5160
atggcgcgct tacccgcgc gtcgtttgtc gatgttttaa gcgaagatta tatgcgtacc    5220
gcgagggcga aaggggtgag cgaaacctgg gttgtcctca aacacgggct acgtaacgcg    5280
atgatcccgg tagtgaccat gatgggctta cagtttggct ttttgctcgg tggttccatc    5340
gttgtggaga aagttttcaa ctggccggga cttggacgct tactcgttga ctccgtagaa    5400
atgcgtgatt acccggtgat tcaggcggaa attctgcttt tctcgctgga atttattctt    5460
atcaacttag tggtggatgt gctttacgcc gccattaacc cggctatcag gtacaagtaa    5520
ggatgcgact attaactggc gacgtcagg cggtgttaaa cgccatgcca ctggtcaaac    5580
ctgaccaggt acgtacaccg tggcatgaat tctggcgacg atttcgccgt cagcatatgg    5640
cgatgaccgc cgcattattc gttattttat tgattgtggt ggccatttt gcacgctgga    5700 tcgctcccta tgacgccgaa aattattttg attatgacaa tctgaataac ggaccttctt    5760
tgcagcactg gtttggcgtc gattcactgg ggcgtgacat tttcagccgt gtcctggttg    5820
gtgcgcaaat ctcgctggcg gcgggcgtgt ttgccgtgtt tatcggtgcg gcgatcggga    5880
cgttgctggg cttgctcgct ggatattatg aaggctggtg ggatcggctg atcatgcgca    5940
tttgcgatgt gctgttttgcc ttcccgggta ttttactggc gatcgctgtt gttgcggtgt    6000
tgggaagcgg cattgctaac gtgattattg cagtcgccat ttttccatc cccgcgtttg    6060 cccgcctggt gcgcggcaac acgctggtgt tgaaacagca aacctttatt gagtcagcac    6120
gcagtattgg tgccagcgat atgaccgttt tgttgcgtca tatcctgcct gggaccgtct    6180
cttctatcgt ggtgttttc accatgcgca ttggtacctc gattatctct gccgccagcc    6240
tctcatttct cggcctcggt gcgcagccgc cgacaccaga gtgggagca atgctcaatg    6300 aggctcgagc ggatatggtt atcgcgccgc atgtcgctgt ttttccggcc ctggctattt    6360
ttctgaccgt actggcgttc aatttgttgg gcgatggttt acgcgatgcg ctggatccga    6420
aaattaaagg a                                                         6431
```

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence: Synthetic

DNA

<400> SEQUENCE: 59
tttatcgata aggaggtcaa tatgatcccg gacgtatcac aggcg					45

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 60
tatggatcct caggcgtgtt tttccagcca					30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 61
ttaagatctc ggagaagaat aatgatcaag					30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 62
taaggatcct tactgctgct gtaaacgtgc					30

<210> SEQ ID NO 63
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 63
ataaagcttt tcggccggta caggctgcat ggcagc					36

<210> SEQ ID NO 64
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 64
ataggatcct tacaaaccct gcttgaactg gtaataacg					39

<210> SEQ ID NO 65
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

```
<400> SEQUENCE: 65
tttaagcttt gactttcagg agcccgttg                                    29

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 66
tttgagctca tatatcgggg gaatgatag                                    29

<210> SEQ ID NO 67
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 67
ataatcgata agcggaacaa cacgatgagt gag                               33

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 68
tgtggatcct taatgacggc gctgcca                                      27

<210> SEQ ID NO 69
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 69
ataatcgatc agcggattgc tatgtcaccc tgt                               33

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 70
ataggatcct cagttcgata cctgggg                                      27

<210> SEQ ID NO 71
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 71
```
atagaattcc cacggtaatc aaatctttag caa                                         33

<210> SEQ ID NO 72
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 72
atagtcgact taccttcgt gagaatttcc cat                                          33

<210> SEQ ID NO 73
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 73
atagaattct gacgattacg ttcggcactg ttc                                         33

<210> SEQ ID NO 74
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 74
ataggatccc tacatagcgt gttgattata ataggg                                      36

<210> SEQ ID NO 75
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 75
atagtcgact ggatcgccag ggaattttgc ctg                                         33

<210> SEQ ID NO 76
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 76
atagcatgct caatgatgat cgacagtatg gct                                         33

<210> SEQ ID NO 77
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 77
atagaattcg cgacgcgtat tgccgatgaa ctg                                         33

<210> SEQ ID NO 78
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 78
ataggatcct tagtgcgcac cgcctccgcc gcc                                33

<210> SEQ ID NO 79
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 79
atagaattct cgaatgtgat tacaatcggt ggc                                33

<210> SEQ ID NO 80
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 80
ataggatcct taatgtggtg tgcttcgtga caa                                33

<210> SEQ ID NO 81
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 81
atagaattcg ctaactgacc gcgccagccg ttc                                33

<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 82
aatggatcct cagtgtgatt cgctatgagc gac                                33

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

```
<400> SEQUENCE: 83
atagaattct taacagttga ttcgttagtc                                      30

<210> SEQ ID NO 84
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 84
ataggatcct caacaaagcg cgggctgccc                                      30

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 85
atagaattcg aaacggaaaa cgcgatccag                                      30

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 86
ataggatccc tattgcgtct gttcttcgag                                      30

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 87
atagaattct aatcttcgtc tgcgaaactt atg                                  33

<210> SEQ ID NO 88
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 88
ataggatcct tatcatcacc caacgccttt cgc                                  33

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 89
```

```
tttgaattcg gtgataatga aaaggcaaag                                30
```

<210> SEQ ID NO 90
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 90

```
tttctgcagt taaacgggct gcccctgat                                 29
```

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 91

```
tttgaattcg gtggtaatga acgattataa                                30
```

<210> SEQ ID NO 92
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 92

```
tttctgcagt tatgcctgac gaattgcct                                 29
```

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 93

```
tttgaattcg atgacagatc ttcccgacag                                30
```

<210> SEQ ID NO 94
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 94

```
tttctgcagt cattgcgcgc tcctttttc                                 29
```

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 95

```
tttgaattcg atgtcccgct ttttgatttg                                30
```

```
<210> SEQ ID NO 96
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 96
tttctgcagt caagcgtggt gatggattt                                        29

<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 97
tttgaattcg atgagcgata aaaagaagcg                                       30

<210> SEQ ID NO 98
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 98
tttctgcagt tactccgatt ctgatggaa                                        29

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 99
tttgaattcg atgccacgtt tttttacccg                                       30

<210> SEQ ID NO 100
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 100
tttctgcagt cactgctcct ccactagct                                        29

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 101
tagggttgtt cagagtatta a                                                21

<210> SEQ ID NO 102
```

```
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 102
gaagcagctc cagcctacac agtggcagtg gcgtccacag acgctaccat tccctg      56

<210> SEQ ID NO 103
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 103
ctaaggagga tattcatatg acagtgctgc aaatggtggt gaatagcatc gattat      56

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 104
gacaaaatag ccctcttccc a                                             21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 105
cactcctgcg gaggcaaaat c                                             21

<210> SEQ ID NO 106
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 106
gaagcagctc cagcctacac cagacgcacc gcttccgtca ccacatccag cgcact      56

<210> SEQ ID NO 107
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 107
ctaaggagga tattcatatg cactacattt taccctccct gacgctcggc gcggca      56

<210> SEQ ID NO 108
<211> LENGTH: 21
<212> TYPE: DNA
```

-continued

```
<213> ORGANISM: Artificial Sequence
<220> FEATURE:
<223> OTHER INFORMATION: Description of Artificial Sequence: Synthetic
      DNA

<400> SEQUENCE: 108
ccgcctgacg tcgccagtta a                                              21
```

US 8,647,839 B2

METHOD FOR PRODUCTION OF GLUTATHIONE OR GAMMA-GLUTAMYLCYSTEINE

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 313,680 bytes ASCII (Text) file named "705523ReplacementSequenceListing.txt," created Mar. 31, 2010.

TECHNICAL FIELD

The present invention relates to methods of producing glutathione or γ-glutamylcysteine.

BACKGROUND ART

Glutathione (γ-L-glutamyl-L-cysteinyl-glycine), a substance that occurs widely in organisms, is known to act as a coenzyme, and to exhibit detoxicating action in the liver. Therefore, glutathione is widely used as a product, starting material or intermediate for pharmaceuticals, health foods, cosmetics and the like.

γ-glutamylcysteine (γ-L-glutamyl-L-cysteine), an intermediate for the biosynthesis of glutathione as stated above, is a thiol compound expected to have a flavor-improving effect similar to that of cysteine, and to serve as a therapeutic drug for lifestyle-related diseases and Alzheimer's disease.

Glutathione is known to be biosynthesized in *Escherichia coli* by conversion of L-glutamic acid and L-cysteine to γ-glutamylcysteine by γ-glutamylcysteine synthetase (GSHI), followed by the addition of glycine to the γ-glutamylcysteine by glutathione synthetase (GSHII); the gshA gene, which encodes GSHI, and the gshB gene, which encodes GSHII, have been isolated from *E. coli* (Non-patent Documents 1 and 2).

As methods for production of glutathione, enzymatic methods and fermentative methods are known. As enzymatic methods, methods are known wherein *E. coli* cells are used as an enzyme source in the presence of L-glutamic acid, L-cysteine, glycine and a surfactant (Patent Documents 1 and 2). As fermentative methods, methods are known wherein wild strains or mutant strains of *Saccharomyces cerevisiae* and *Candida utilis*, and recombinant strains of *E. coli, S. cerevisiae* and *Lactococcus lactis* transformed with the gshA gene and the gshB gene, are used (Non-patent Documents 3 and 4); in all the fermentative methods, glutathione is reportedly intracellularly accumulated.

Meanwhile, it is reported that the wild strain of *E. coli* extracellularly accumulates glutathione temporarily in the late logarithmic growth phase, although the amount is small (Non-patent Document 5).

It is known that a mutant strain of *E. coli* with a reduced or lost activity of γ-glutamyl transpeptidase exhibits an increased amount of glutathione accumulated in the medium, compared with the wild strain (Non-patent Documents 6 and 7), and it is also known that strains lacking the γ-glutamyl transpeptidase gene (ggt gene) and the yliAB gene, which encodes the glutathione uptake protein, exhibit further increased amounts of glutathione accumulated, compared with the strain lacking the ggt gene only (Non-patent Document 8).

It is also known that the protein encoded by the ybiK gene regulates glutathione uptake into cells (Non-patent Document 9), and that the ybiK gene has formed an operon with the yliABCD gene (Non-patent Document 8).

Although it is known that the protein encoded by the *E. coli* cydDC gene has an activity to deliver intracellular glutathione to periplasm (Non-patent Document 10), it is not known that the amount of glutathione accumulated in the medium increases when the protein's activity is enhanced.

The *E. coli* yceE gene, marA gene, marB gene, acrA gene, acrB gene, emrA gene, emrB gene, emrE gene, ydhC gene, ydeA gene, emrK gene, emrY gene, emrD gene, yajR gene, yegB gene, yidY gene, yieO gene and yjiO gene are estimated to be drug transporting genes, and the activity has been confirmed in some of these genes (Non-patent Document 19).

The ygeD gene is known as the lysophospholipid transporting gene (Non-patent Document 11). The bcr gene is known as the bicyclomycin resistance gene (Non-patent Document 12). The cmr gene is known as the chloramphenicol resistance gene (Non-patent Document 13). The marR gene is known as a multidrug resistance gene (Non-patent Document 14). The evgA gene is known as a drug efflux gene (Non-patent Document 15). The function of the ydeE gene is unknown.

As stated above, no genes are known to encode a protein having an activity to transport intracellular glutathione to the outside of cells.

As methods for production of γ-glutamylcysteine, methods of production using a mutant yeast strain in which the glutathione synthetase gene destroyed or weakened have been reported (Non-patent Documents 16 to 18); however, in all these fermentation methods, γ-glutamylcysteine is reportedly accumulated in cells.

patent document 1: JP-A-60-27396
patent document 2: JP-A-60-27397
non-patent document 1: Appl. Environ. Microbiol., 44, 1444 (1982)
non-patent document 2: Agric. Biol. Chem., 47, 1381 (1983)
non-patent document 3: Appl. Microbiol. Biotechnol., 66, 233 (2004)
non-patent document 4: Appl. Microbiol. Biotechnol., 24, 375 (1986)
non-patent document 5: J. Bacteriol., 168, 109 (1986)
non-patent document 6: Appl. Environ. Microbiol., 47, 653 (1984)
non-patent document 7: J. Bacteriol., 169, 3926 (1987)
non-patent document 8: J. Bacteriol., 187, 5861 (2005)
non-patent document 9: FEMS Microbiol. Letters, 209, 81 (2002)
non-patent document 10: J. Biol. Chem., 280, 32254 (2005)
non-patent document 11: J. Biol. Chem., 280, 12028 (2005)
non-patent document 12: Gene, 127, 117 (1993)
non-patent document 13: J. Bacteriol., 178, 3188 (1996)
non-patent document 14: J. Bacteriol., 175, 1484 (1993)
non-patent document 15: Microbiology, 149, 2819 (2003)
non-patent document 16: Agr. Biol. Chem., 54, 3145 (1990)
non-patent document 17: Molecular Biology of the Cell, 8, 1699 (1997)
non-patent document 18: Biochinica et Biophysica Acta, 1395, 315 (1998)
non-patent document 19: J. Bacteriol., 183, 5803 (2001)

DISCLOSURE OF THE INVENTION

Problems to Be Solved by the Invention

The present invention is directed to providing a process for efficiently producing glutathione or γ-glutamylcysteine.

Means for Solving the Problems

The present invention relates to (1) to (16) below.

(1) A process for producing glutathione or γ-glutamylcysteine, comprising culturing in a medium a microorganism with a higher activity of a protein having an activity to transport intracellular glutathione to the outside of cells (hereinafter referred to as glutathione transporting activity), described in any of [1] to [3] below, and a higher activity of a protein involved in glutathione or γ-glutamylcysteine biosynthesis, compared with that of the parent strain, forming and accumulating glutathione or γ-glutamylcysteine in the medium, and recovering the glutathione or γ-glutamylcysteine from the culture:

[1] a protein having the amino acid sequence shown by any of SEQ ID NOs: 1 to 26,

[2] a protein consisting of an amino acid sequence wherein one or more amino acids have been deleted, substituted or added in the amino acid sequence shown by any of SEQ ID NOs: 1 to 26, and having glutathione transporting activity,

[3] a protein having an amino acid sequence having 80% or more homology to the amino acid sequence shown by any of SEQ ID NOs: 1 to 26, and having glutathione transporting activity.

(2) The process according to (1) above, wherein the microorganism is a microorganism obtained by transforming a parent strain with a DNA described in any of [1] to [3] below:

[1] a DNA that encodes a protein described in any of (1) [1] to [3] above,

[2] a DNA having the base sequence of a coding region in the base sequence shown by any of SEQ ID NOs: 27 to 46,

[3] a DNA that hybridizes with a DNA consisting of a base sequence complementary to the base sequence of a coding region in the base sequence shown by any of SEQ ID NOs: 27 to 46 under stringent conditions, and that encodes a protein having glutathione transporting activity.

(3) The process according to (1) or (2) above, wherein the protein involved in glutathione or γ-glutamylcysteine biosynthesis is γ-glutamylcysteine synthetase (GSHI) or glutathione synthetase (GSHII).

(4) The process according to (3) above, wherein the GSHI or GSHII is a protein described in any of [1] to [3] below:

[1] a protein having the amino acid sequence shown by SEQ ID NO: 47 or 48,

[2] a protein consisting of an amino acid sequence wherein one or more amino acids have been deleted, substituted or added in the amino acid sequence shown by SEQ ID NO: 47 or 48, and having γ-glutamylcysteine synthetase activity or glutathione synthetase activity,

[3] a protein having an amino acid sequence having 80% or more homology to the amino acid sequence shown by SEQ ID NO: 47 or 48, and having γ-glutamylcysteine synthetase activity or glutathione synthetase activity.

(5) The process according to any one of (1) to (3) above, wherein the microorganism is a microorganism obtained by transformation with a DNA that encodes GSHI or GSHII.

(6) The process according to (5) above, wherein the DNA that encodes GSHI or GSHII is a DNA described in any of [1] to [4] below:

[1] a DNA that encodes a protein described in any of (4) [1] to [3] above,

[2] a DNA having the base sequence shown by SEQ ID NO: 49 or 50,

[3] a DNA having the base sequence of a coding region in the base sequence shown by SEQ ID NO: 49 or 50,

[4] a DNA that hybridizes with a DNA consisting of a base sequence complementary to the base sequence of a coding region in the base sequence shown by SEQ ID NO: 49 or 50 under stringent conditions, and that encodes a protein having γ-glutamylcysteine synthetase activity or glutathione synthetase activity.

(7) The process according to any one of (1) to (6) above, wherein the microorganism is a microorganism with a reduced or lost activity of a protein having glutathione or γ-glutamylcysteine degrading activity, compared with that of the parent strain.

(8) The process according to (7) above, wherein the protein having glutathione or γ-glutamylcysteine degrading activity is γ-glutamyl transpeptidase.

(9) The process according to (8) above, wherein the γ-glutamyl transpeptidase is a protein described in [1] or [2] below:

[1] a protein having the amino acid sequence shown by SEQ ID NO: 51,

[2] a protein having an amino acid sequence having 80% or more homology to the amino acid sequence shown by SEQ ID NO: 51, and having γ-glutamyl transpeptidase activity.

(10) The process according to (7) above, wherein the microorganism with a reduced or lost activity of a protein having glutathione or γ-glutamylcysteine degrading activity, compared with that of the parent strain, is a microorganism having a chromosomal DNA lacking a gene that encodes γ-glutamyl transpeptidase.

(11) The process according to (10) above, wherein the gene that encodes γ-glutamyl transpeptidase is a DNA described in any of [1] to [4] below:

[1] a DNA that encodes a protein described in (9) [1] or [2] above,

[2] a DNA having the base sequence shown by SEQ ID NO: 52,

[3] a DNA having the base sequence of a coding region in the base sequence shown by SEQ ID NO: 52,

[4] a DNA that hybridizes with a DNA consisting of a base sequence complementary to the base sequence of a coding region in the base sequence shown by SEQ ID NO: 52 under stringent conditions, and that encodes a protein having γ-glutamyl transpeptidase activity.

(12) The process according to any one of (1) to (11) above, wherein the microorganism is a microorganism with a reduced or lost activity of a protein having an activity involved in glutathione or γ-glutamylcysteine uptake (hereinafter referred to as glutathione uptake activity), compared with that of the parent strain.

(13) The process according to (12) above, wherein the protein having glutathione uptake activity is a protein described in [1] or [2] below:

[1] a protein having the amino acid sequence shown by any of SEQ ID NOs: 53 to 57,

[2] a protein having an amino acid sequence having 80% or more homology to the amino acid sequence shown by any of SEQ ID NOs: 53 to 57, and having glutathione uptake activity.

(14) The process according to (12) above, wherein the microorganism is a microorganism having a chromosomal DNA lacking a gene that encodes a protein having glutathione uptake activity.
(15) The process according to (14) above, wherein the gene that encodes a protein having glutathione uptake activity is a DNA described in any of [1] to [4] below:
[1] a DNA that encodes a protein described in (13) [1] or [2] above,
[2] a DNA having the base sequence shown by SEQ ID NO: 58,
[3] a DNA having the base sequence of any coding region in the base sequence shown by SEQ ID NO: 58,
[4] a DNA that hybridizes with a DNA consisting of a base sequence complementary to the base sequence of any coding region in the base sequence shown by SEQ ID NO: 58 under stringent conditions, and that encodes a protein having glutathione uptake activity.
(16) The process according to any one of (1) to (15) above, wherein the microorganism is a microorganism belonging to the genus *Escherichia*.

Effect of the Invention

According to the present invention, glutathione or γ-glutamylcysteine can be produced efficiently and inexpensively.

BEST MODE FOR CARRYING OUT THE INVENTION

1. Microorganisms used in processes for production of the present Invention
(1) Microorganism with a higher activity of a protein having an activity to transport intracellular glutathione to the outside of cells, compared with that of the parent strain A microorganism with a higher activity of a protein having an activity to transport intracellular glutathione to the outside of cells (hereinafter referred to as glutathione transporting activity), compared with that of the parent strain, is (a) a microorganism obtained by modifying a gene that encodes a protein having glutathione transporting activity, present on the chromosomal DNA of the parent strain, the microorganism being i) a microorganism with an increased specific activity of the protein compared with that of the parent strain, or ii) a microorganism with an increased production of the protein having glutathione transporting activity compared with that of the parent strain, or (b) a microorganism obtained by transforming the parent strain with a DNA that encodes a protein having glutathione transporting activity. As mentioned herein, a parent strain, whether a wild strain or a mutant strain, is an original strain to be modified or transformed. As the parent strain, when the microorganism is *Escherichia coli*, for example, wild strains or mutant strains of *E. coli* K-12 strain, B strain, and B/r strain can be mentioned; as the mutant strains, *E. coli* XL1-Blue, *E. coli* XL2-Blue, *E. coli* DH1, *E. coli* MC1000, *E. coli* ATCC 12435, *E. coli* W1485, *E. coli* JM109, *E. coli* HB101, *E. coli* No. 49, *E. coli* W3110, *E. coli* NY49, *E. coli* MP347, *E. coli* NM522, *E. coli* BL21, *E. coli* ME8415 and the like can be mentioned.

As proteins having glutathione transporting activity,
[1] a protein having the amino acid sequence shown by any of SEQ ID NOs: 1 to 26,
[2] a protein consisting of the amino acid sequence wherein one or more amino acids have been deleted, substituted or added in the amino acid sequence shown by any of SEQ ID NOs: 1 to 26, and having glutathione transporting activity,
[3] a protein having 80% or more homology to the amino acid sequence shown by any of SEQ ID NOs: 1 to 26, and having glutathione transporting activity,
and the like can be mentioned.

The above protein consisting of an amino acid sequence wherein one or more amino acid residues are deleted, substituted or added and having glutathione transporting activity can be obtained, for example, by introducing a site-directed mutation into DNA encoding a protein consisting of the amino acid sequence of any of SEQ ID NOs: 1 to 26 by site-directed mutagenesis described in Molecular Cloning, A Laboratory Manual, Third Edition, Cold Spring Harbor Laboratory Press (1989) (hereinafter referred to as Molecular Cloning, Third Edition); Current Protocols in Molecular Biology, John Wiley & Sons (1987-1997) (hereinafter referred to as Current Protocols in Molecular Biology); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc.

The number of amino acid residues which are deleted, substituted or added is not specifically limited, but is within the range where deletion, substitution or addition is possible by known methods such as the above-mentioned site-directed mutagenesis. The number is 1 to dozens, preferably 1 to 20, more preferably 1 to 10, further preferably 1 to 5.

The expression "one or more amino acid residues are deleted, substituted or added in the amino acid sequence of SEQ ID NO: 1 or 2" means that the amino acid sequence may contain deletion, substitution or addition of a single or plural amino acid residues at an arbitrary position therein.

Deletion or addition of amino acid residues may be contained, for example, in the N-terminal or C-terminal one to 10 amino acid residue of the amino acid sequence of any of SEQ ID NOs: 1 to 26.

Deletion, substitution and addition may be simultaneously contained in one sequence, and amino acids to be substituted or added may be either natural or not. Examples of the natural amino acids are L-alanine, L-asparagine, L-aspartic acid, L-arginine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine and L-cysteine.

The following are examples of the amino acids capable of mutual substitution. The amino acids in the same group can be mutually substituted.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine In addition, examples of the protein having glutathione transporting activity include a protein consisting an amino acid sequence having 80% or more, preferably 90% or more, more preferably 95% or more, more preferably 97% or more, particularly preferably 98% or more, most preferably 99% or more homology to the amino acid sequence shown by any of SEQ ID NOs: 1 to 26, and a protein having glutathione transporting activity.

The homology among amino acid sequences and base sequences can be determined by using algorithm BLAST by Karlin and Altschul [Pro. Natl. Acad. Sci. USA, 90, 5873 (1993)] and FASTA [Methods Enzymol., 183, 63 (1990)]. On the basis of the algorithm BLAST, programs such as BLASTN and BLASTX have been developed [J. Mol. Biol., 215, 403 (1990)]. When a base sequence is analyzed by BLASTN on the basis of BLAST, the parameters, for instance, are as follows: score=100 and wordlength=12. When an amino acid sequence is analyzed by BLASTX on the basis of BLAST, the parameters, for instance, are as follows: score=50 and wordlength=3. When BLAST and Gapped BLAST programs are used, default parameters of each program are used. The specific techniques for these analyses are well known.

The identity of a protein consisting of an amino acid sequence wherein one or more amino acids have been deleted, substituted or added in the amino acid sequence shown by any of SEQ ID NOs: 1 to 26, as a protein having glutathione transporting activity can be confirmed by, for example, a method wherein a transformant that expresses a protein whose activity is to be confirmed is prepared using a DNA recombination technique, and labeled glutathione and inside-out membrane vesicles that can be prepared from the transformant [J. Biol. Chem., 277, 49841 (2002)] are used [J. Biol. Chem., 280, 32254 (2005)].

Examples of the microorganism of the above-mentioned (a) i), having an improved specific activity of the protein having a glutathione transporting activity as compared to that of the parental strain, include a microorganism containing a mutant protein improved in the activity as compared to that of the protein having a glutathione transporting activity of the parental strain, since the protein has the amino acid sequence, wherein not less than one amino acid, preferably 1-10 amino acids, more preferably 1-5 amino acids, still more preferably 1-3 amino acids, are substituted in the amino acid sequence of the protein of the parental strain.

Examples of the microorganism improved in the production amount of the protein having a glutathione transporting activity as compared to that of the parental strain in the above-mentioned (a) ii) include a microorganism showing an improved production amount of the protein as compared to that of the protein having a glutathione transporting activity of the parental strain, since it has a promoter region wherein not less than one base, preferably 1 to 10 bases, more preferably 1 to 5 bases, still more preferably 1 to 3 bases, are substituted in the base sequence of the transcription regulatory region or promoter region of the gene encoding the protein, which is present on the chromosomal DNA of the parental strain.

Examples of the microorganism obtained by transforming the parental strain of the above-mentioned (b) with a DNA encoding the protein having a glutathione transporting activity include a microorganism obtained by transforming the parental strain with

[4] a DNA encoding a protein of any of the above-mentioned [1] to [3],

[5] a DNA having a base sequence of the coding region in the base sequence shown by any of SEQ ID NOs: 27 to 46, or

[6] a DNA hybridizing with a DNA having a base sequence complementary to a base sequence of a coding region in the base sequence shown by any of SEQ ID NOs: 27 to 46 under stringent conditions, and encoding the protein having a glutathione transporting activity.

Examples of the microorganism include i) a microorganism having an exogenous DNA encoding a protein having a glutathione transporting activity on the chromosomal DNA thereof and ii) a microorganism having an exogenous DNA encoding a protein having a glutathione transporting activity outside the chromosome thereof. In other words, the microorganism of i) means that the parental strain does not have a DNA encoding a protein having a glutathione transporting activity and one or more newly-introduced DNAs are present on the chromosomal DNA, or the parental strain intrinsically has a DNA encoding a protein having a glutathione transporting activity, and two or more DNAs encoding a protein having a glutathione transporting activity, which includes the newly-introduced DNA, are present on the chromosomal DNA. The microorganism of ii) is a microorganism having a DNA encoding a protein having a glutathione transporting activity on the plasmid DNA.

"To hybridize" in the above refers to a step of hybridization of a DNA with a DNA having a specific base sequence or a part of the DNA. Therefore, the DNA having a specific base sequence or a part of the DNA can be used as a probe for Northern or Southern blot analysis or can be used as an oligonucleotide primer for PCR analysis. DNAs used as a probe include DNAs comprising at least 100 or more bases, preferably 200 or more bases, more preferably 500 or more bases, and DNAs used as a primer include DNAs comprising at least 10 or more bases, preferably 15 or more bases.

The methods of hybridization experiments of a DNA are well known and, for example, those of ordinary skill in the art can determine the hybridization conditions according to the description of the specification of the present application. The hybridization conditions can be employed according to many standard textbooks, including the description in Molecular Cloning Second Edition, Third Edition (2001), Methods for General and Molecular Bacteriolgy, ASM Press (1994) and Immunology methods manual, Academic press (Molecular).

Hybridization under the above stringent conditions is carried out, for example, as follows. A DNA-immobilized filter and a probe DNA are incubated in a solution comprising 50% formamide, 5×SSC (750 mmol/l sodium chloride and 75 mmol/l sodium citrate), 50 mmol/l sodium phosphate (pH 7.6), 5×Denhardt's solution, 10% dextran sulfate and 20 µg/l denatured salmon sperm DNA at 42° C. overnight, and after the incubation, for example, the filter is preferably washed in 0.2×SSC solution at about 65° C. Less stringent conditions can also be employed. Modification of the stringent conditions can be made by adjusting the concentration of formamide (the conditions become less stringent as the concentration of formamide is lowered) and by changing the salt concentrations and the temperature conditions. Hybridization under less stringent conditions is carried out, for example, by incubating a filter with DNA immobilized thereon and a probe DNA in a solution comprising 6×SSCE (20×SSCE: 3 mol/l sodium chloride, 0.2 mol/l sodium dihydrogenphosphate and 0.02 mol/l EDTA, pH 7.4), 0.5% SDS, 30% formamide and 100 µg/l denatured salmon sperm DNA at 37° C. overnight, and washing the filter with 1×SSC solution containing 0.1% SDS at 50° C. Hybridization under still less stringent conditions is carried out by hybridization under the above less stringent conditions using a solution having a high salt concentration (for example, 5×SSC), and washing the filter.

Various conditions described above can also be established by adding a blocking reagent which is used to reduce the background of hybridization or changing the reagent. The addition of the above blocking reagent may be accompanied by changes of conditions for hybridization to make the conditions suitable for the purpose.

The above-described DNA capable of hybridization under stringent conditions includes DNA having at least 90% or more homology, preferably 95% or more homology, more preferably 97% or more homology, further preferably 98% or more homology, particularly preferably 99% or more homology to the DNA having base sequence of a coding region of the base sequence of any of SEQ ID NOs: 27 to 46 as calculated by use of programs such as BLAST and FASTA described above based on the above parameters.

(2) Microorganisms with a higher activity of a protein involved in glutathione or γ-glutamylcysteine biosynthesis than that of the parent strain A microorganism with a higher activity of a protein involved in glutathione or γ-glutamylcysteine biosynthesis than that of the parent strain is (a) a microorganism obtained by modifying a gene that encodes a protein involved in glutathione or γ-glutamylcysteine biosynthesis, present on the chromosomal DNA of the parent strain, the microorganism being i) a microorganism with an increased specific activity of the protein compared with that of the parent strain, or ii) a microorganism with an increased production of a protein involved in glutathione or γ-glutamylcysteine biosynthesis compared with that of the parent strain, or (b) a microorganism obtained by transforming the parent strain with a DNA that encodes a protein involved in glutathione or γ-glutamylcysteine biosynthesis.

The parent strain is as defined in (1) above, and can be exemplified by the same strains.

A protein involved in glutathione biosynthesis is a protein involved in a reaction in which glutathione is formed from L-glutamic acid, L-cysteine and glycine; as the protein, γ-glutamylcysteine synthetase and glutathione synthetase can be mentioned. A protein involved in γ-glutamylcysteine biosynthesis is a protein involved in a reaction in which γ-glutamylcysteine is formed from L-glutamic acid and L-cysteine; as the protein, γ-glutamylcysteine synthetase can be mentioned.

A microorganism with a higher activity of a protein involved in glutathione or γ-glutamylcysteine biosynthesis than that of the parent strain may be a microorganism with a higher activity of either γ-glutamylcysteine synthetase or glutathione synthetase, or higher activities of both γ-glutamylcysteine synthetase and glutathione synthetase, than either or both activities of the parent strain.

Any protein involved in glutathione or γ-glutamylcysteine biosynthesis and any DNA that encodes the protein can be used in the present invention, as far as they are a protein having γ-glutamylcysteine synthetase activity or glutathione synthetase activity and a DNA that encodes the protein.

As proteins involved in glutathione or γ-glutamylcysteine biosynthesis,

[7] a protein having the amino acid sequence shown by SEQ ID NO: 47 or 48,
[8] a protein consisting of an amino acid sequence wherein one or more amino acids have been deleted, substituted or added in the amino acid sequence shown by SEQ ID NO: 47 or 48, and having γ-glutamylcysteine synthetase activity or glutathione synthetase activity, and
[9] a protein having 80% or more homology to the amino acid sequence shown by SEQ ID NO: 47 or 48, and having γ-glutamylcysteine synthetase activity or glutathione synthetase activity,
can be mentioned.

As mentioned above, a protein consisting of an amino acid sequence wherein one or more amino acids have been deleted, substituted or added, and having γ-glutamylcysteine synthetase activity or glutathione synthetase activity, may be a protein obtained in the same manner as (1) above, and having an amino acid sequence having a similar number of amino acid residues deleted, substituted or added.

The position, kind and the like of an amino acid residue which may be deleted, substituted or added are as described in (1) above.

As a protein involved in glutathione or γ-glutamylcysteine biosynthesis, a protein consisting of an amino acid sequence having a homology of 80% or more, preferably 90% or more, more preferably 95% or more, still more preferably 97% or more, particularly preferably 98% or more, and most preferably 99% or more, to the amino acid sequence shown by SEQ ID NO:47 or 48, and having γ-glutamylcysteine synthetase activity or glutathione synthetase activity, can be mentioned.

The homology among amino acid sequences and base sequences is as defined in (1) above.

As an example means for confirming that a protein consisting of an amino acid sequence wherein one or more amino acids have been deleted, substituted or added in the amino acid sequence shown by SEQ ID NO: 47 or 48 is a protein having glutathione synthetase activity or γ-glutamylcysteine synthetase activity, a method can be mentioned wherein a transformant that expresses a protein whose activity is to be confirmed is prepared using a DNA recombination technique, and the protein is produced using the transformant, after which the protein and γ-glutamylcysteine and glycine, or L-glutamic acid and L-cysteine, are allowed to be present in an aqueous medium, and whether or not glutathione or γ-glutamylcysteine is produced and accumulated in the aqueous medium is determined by HPLC and the like.

As the microorganism (a)i) above with an increased specific activity of a protein involved in glutathione or γ-glutamylcysteine biosynthesis, compared with that of the parent strain, a microorganism having a mutated protein with the activity increased compared with the parent strain's protein involved in glutathione or γ-glutamylcysteine biosynthesis, because the microorganism has a protein having an amino acid sequence wherein one amino acid or more, preferably 1 to 10 amino acids, more preferably 1 to 5 amino acids, and still more preferably 1 to 3 amino acids, have been substituted in the amino acid sequence of the protein present in the parent strain, can be mentioned.

As the microorganism (a)ii) above with an increased production of a protein involved in glutathione or γ-glutamylcysteine biosynthesis, compared with that of the parent strain, a microorganism with the production of the protein increased compared with the production of the parent strain's protein involved in glutathione biosynthesis, because the microorganism has a promoter region wherein one base or more, preferably 1 to 10 bases, more preferably 1 to 5 bases, and still more preferably 1 to 3 bases, have been substituted in the base sequence of the transcription regulatory region or promoter region of a DNA that encodes the protein on the chromosomal DNA of the parent strain, can be mentioned.

As a transformant obtained by transformation with a DNA that encodes a protein involved in glutathione or γ-glutamylcysteine biosynthesis, a microorganism obtained by transformation using:

[10] a DNA that encodes a protein described in any of [7] to [9] above,
[11] a DNA having the base sequence shown by SEQ ID NO: 49 or 50,
[12] a DNA having the base sequence of a coding region in a base sequence shown by SEQ ID NO: 49 or 50, or
[13] a DNA that hybridizes with a DNA consisting of a base sequence complementary to the base sequence of a coding region in the base sequence shown by SEQ ID NO: 49 or 50 under stringent conditions, and that encodes a protein having γ-glutamylcysteine synthetase activity or glutathione synthetase activity, can be mentioned.

As the microorganism, i) a microorganism having an exogenous DNA that encodes a protein involved in glutathione or γ-glutamylcysteine biosynthesis on the chromosomal DNA thereof, and ii) a microorganism having a DNA encoding an exogenous protein having a glutathione transporting activity outside of the chromosome can be mentioned. Specifically, the microorganism i) is a microorganism having one or two or more of such newly transferred DNAs, on the chromosomal DNA, provided that the parent strain does not have any DNA that encodes a protein involved in glutathione or γ-glutamylcysteine biosynthesis, or a microorganism having two or more DNAs that encode a protein involved in glutathione biosynthesis, including such a newly transferred DNA, on the chromosomal DNA, provided that the parent strain intrinsically has a DNA that encodes a protein involved in glutathione or γ-glutamylcysteine biosynthesis. The microorganism ii) is a microorganism having a DNA that encodes a protein involved in glutathione or γ-glutamylcysteine biosynthesis on the plasmid DNA.

As mentioned above, "hybridize" is as defined in (1) above.

As examples of the above-described DNA capable of hybridizing under stringent conditions, a DNA having a homology of at least 90% or more, preferably 95% or more, more preferably 97% or more, still more preferably 98% or more, and particularly preferably 99% or more, to the base sequence shown by SEQ ID NO: 49 or 50, as calculated by use of programs such as BLAST and FASTA described above based on the above parameters.

(3) Microorganism with a reduced or lost glutathione or γ-glutamylcysteine degrading activity compared with that of the parent strain As microorganisms with a reduced or lost glutathione or γ-glutamylcysteine degrading activity compared with that of the parent strain, used in the present invention, a microorganism obtained by introducing a base deletion, substitution or addition into the base sequence of a gene that encodes a protein involved in glutathione or γ-glutamylcysteine degradation on chromosomal DNA, the microorganism being (a) a microorganism with the glutathione or γ-glutamylcysteine degrading activity reduced to 80% or less, preferably 50% or less, more preferably 30% or less, still more preferably 20% or less, particularly preferably 10% or less, and most preferably 0%, compared with that of the parent strain before introduction of the base substitution or the like, and (b) a microorganism with the amount of transcription of the gene or the production of a protein involved in glutathione or γ-glutamylcysteine degradation reduced to 80% or less, preferably 50% or less, more preferably 30% or less, still more preferably 20% or less, particularly preferably 10% or less, and most preferably 0%, compared with that of the parent strain before introduction of the base substitution or the like, can be mentioned. More preferably, a microorganism lacking a part or all of a gene that encodes a protein involved in glutathione or γ-glutamylcysteine degradation, still more preferably a microorganism lacking the entire coding region in the gene, can be mentioned.

The protein involved in glutathione or γ-glutamylcysteine degradation may be a protein involved in any step of glutathione or γ-glutamylcysteine degradation; preferably, γ-glutamyl transpeptidase, γ-glutamyl-γ-aminobutyric acid hydrolase [YcjL protein: J. Bacteriol., 280, 4602 (2005)] and the like can be mentioned.

As the γ-glutamyl transpeptidase,

[14] a protein having the amino acid sequence shown by SEQ ID NO: 51, and

[15] a protein having a homology of 80% or more, preferably 90% or more, more preferably 95% or more, still more preferably 97% or more, particularly preferably 98% or more, and most preferably 99% or more, to the amino acid sequence shown by SEQ ID NO: 51, and having γ-glutamyl transpeptidase activity, and the like can be mentioned.

The homology among amino acid sequences and base sequences is as defined in (1) above.

As genes that encode γ-glutamyl transpeptidase, the following DNAs:

[16] a DNA that encodes a protein according to [14] or [15] above,

[17] a DNA having the base sequence shown by SEQ ID NO: 52,

[18] a DNA having the base sequence of a coding region in the base sequence shown by SEQ ID NO: 52,

[19] a DNA that hybridizes with a DNA consisting of a base sequence complementary to the base sequence of a coding region in the base sequence shown by SEQ ID NO: 52 under stringent conditions, and that encodes a protein having γ-glutamyl transpeptidase activity, and the like can be mentioned.

As mentioned herein, a gene refers to a DNA that may comprise, in addition to a protein coding region, a transcription regulatory region, a promoter region and the like.

As the transcription regulatory region, a DNA consisting of 100 bases, preferably 50 bases, upstream of the 5' end of a coding region on the chromosomal DNA, can be mentioned; as the promoter region, regions corresponding to −10 and −35 regions can be mentioned.

Regarding the introduction of a base deletion, substitution or addition into a gene that encodes a protein having glutathione or γ-glutamylcysteine degrading activity is not subject to limitations as to the kind and number of bases, as far as the base deletion, substitution or addition reduces or loses the protein's activity compared with that of the parent strain; as a base deletion, a deletion of preferably 10 bases or more, more preferably 20 bases or more, and still more preferably the entire region, for the promoter and transcription regulatory regions, can be mentioned; for the coding region, a deletion of preferably 10 bases or more, more preferably 20 bases or more, still more preferably 100 bases or more, particularly preferably 200 bases or more, and most preferably the entire coding region, can be mentioned.

As a base substitution, a substitution wherein a base within the 150th position from the 5' end of the coding region, preferably a base within the 100th position, more preferably a base within the 50th position, particularly preferably a base within the 30th position, and most preferably a base within the 20th position, is substituted to introduce a nonsense codon, can be mentioned.

As a base addition, an addition of a DNA fragment of 50 bases or more, preferably 100 bases or more, more preferably 200 bases or more, still more preferably 500 bases or more, and particularly preferably 1 kb or more, immediately after a base within the 150th position from the 5' end of the coding region, preferably a base within the 100th position, more preferably a base within the 50th position, particularly preferably a base within the 30th position, and most preferably a base within the 20th position, can be mentioned; particularly preferably, an insertion of the chloramphenicol resistance gene, the kanamycin resistance gene or the like can be mentioned.

Being a microorganism with a reduced or lost glutathione or γ-glutamylcysteine degrading activity compared with that of the parent strain can be confirmed by measuring the degree of reduction of glutathione degrading activity compared with that of the parent strain by a publicly known method.

As mentioned above, "hybridize" is as defined in (1) above.

As examples of the above-described DNA capable of hybridizing under stringent conditions, a DNA having a homology of at least 90% or more, preferably 95% or more, more preferably 97% or more, still more preferably 98% or more, and particularly preferably 99% or more, to the base sequence shown by SEQ ID NO: 9, as calculated on the basis of the above-described parameters and the like using the above-described BLAST, FASTA and the like, can be mentioned.

(4) Microorganisms with a reduced or lost activity of protein involved in glutathione or γ-glutamylcysteine uptake, compared with that of the parent strain As a microorganism with a reduced or lost activity of a protein having activity involved in glutathione or γ-glutamylcysteine uptake (hereinafter abbreviated to glutathione uptake activity), compared with that of the parent strain, a microorganism obtained by introducing a base deletion, substitution or addition into the base sequence of any gene that encodes a protein having glutathione uptake activity on the chromosomal DNA, the microorganism being (a) a microorganism with the glutathione or γ-glutamylcysteine uptake activity reduced to 80% or less, preferably 50% or less, more preferably 30% or less, still more preferably 20% or less, particularly preferably 10% or less, and most preferably 0%, compared with that of the parent strain before introduction of the base substitution or the like, and (b) a microorganism with the amount of the transcription of any gene that encodes a protein having glutathione uptake activity or the production of a protein having glutathione uptake activity reduced to 80% or less, preferably 50% or less, more preferably 30% or less, still more preferably 20% or less, particularly preferably 10% or less, and most preferably 0%, compared with that of the parent strain before introduction of the base substitution or the like, can be mentioned. More preferably, a microorganism lacking a portion or all of the gene that encodes a protein having glutathione uptake activity, still more preferably a microorganism lacking the entire gene that encodes a protein having glutathione uptake activity, can be mentioned.

As proteins having glutathione uptake activity,

[20] a protein having the amino acid sequence shown by any of SEQ ID NOs: 53 to 57, and

[21] a protein having a homology of 80% or more, preferably 90% or more, more preferably 95% or more, still more preferably 97% or more, particularly preferably 98% or more, and most preferably 99% or more, to the amino acid sequence shown by any of SEQ ID NOs: 53 to 57, and having glutathione uptake activity, and the like can be mentioned.

The homology among amino acid sequences and base sequences is as defined in (1) above.

As genes that encode a protein having glutathione uptake activity, the following DNAs:

[22] a DNA that encodes the protein according to [20] or [21] above,

[23] a DNA having the base sequence shown by SEQ ID NO: 58,

[24] a DNA having the base sequence of any coding region in the base sequence shown by SEQ ID NO: 58, and

[25] a DNA that hybridizes with a DNA consisting of a base sequence complementary to the base sequence of any coding region in the base sequence shown by SEQ ID NO: 58 under stringent conditions, and that encodes glutathione uptake protein, and the like can be mentioned.

The above-described genes, transcription regulatory regions, and promoters are as defined in (3) above.

Introduction of a base deletion, substitution or addition into a gene that encodes a protein having glutathione uptake activity is not subject to limitations as to the kind and number of bases, as far as the base deletion, substitution or addition reduces or loses the protein's activity compared with that of the parent strain; introduction of the same base deletion, substitution or addition as (3) above can be mentioned.

Being a microorganism with a reduced or lost glutathione or γ-glutamylcysteine uptake activity compared with that of the parent strain can be confirmed by measuring the degree of reduction of glutathione or γ-glutamylcysteine uptake activity compared with that of parent strain by an uptake activity assay using labeled glutathione [J. Bacteriol., 186, 343 (2004)].

As mentioned above, "hybridize" is as defined in (1) above.

As examples of the above-described DNA capable of hybridizing under stringent conditions, a DNA having a homology of at least 90% or more, preferably 95% or more, more preferably 97% or more, still more preferably 98% or more, and particularly preferably 99% or more, to the base sequence of any coding region in the base sequence shown by SEQ ID NO: 58, as calculated by use of programs such as BLAST and FASTA described above based on the above parameters.

Although any microorganism with a higher activity of a protein having glutathione transporting activity and a higher activity of a protein involved in glutathione biosynthesis, compared with that of the parent strain, can be used in the present invention, the microorganism is preferably procaryote, more preferably bacterium, more preferably microorganism belonging to the genus *Escherichia*, most preferably *E. coli*.

2. Preparation of a microorganism used in the present invention (1) Preparation of a microorganism wherein a protein having glutathione transporting activity shows higher activity than that of parental strain Of the microorganisms wherein a protein having glutathione transporting activity shows higher activity than that of the parental strain, a microorganism wherein specific activity of the proteins having glutathione transporting activity is higher than that of the parental strain can be obtained by subjecting a DNA encoding a protein having a glutathione transporting activity to in vitro mutation treatment with a mutagen, or error-prone PCR and the like to introduce mutation into the DNA, substituting a DNA encoding a protein having a glutathione transporting activity before introduction of mutation, which is present on the chromosomal DNA of the parental strain, with the mutant DNA by a known method [Proc. Natl. Acad. Sci. USA., 97, 6640 (2000)] to give a modified strain expressing the mutant DNA, and comparing the glutathione transporting activity of the parental strain and the modified strain according to the above-mentioned methods using inside-out vesicles.

In addition, of the microorganisms wherein a protein having glutathione transporting activity shows higher activity than that of the parental strain, a microorganism wherein the production amount of the protein is higher than that of the parental strain can be confirmed by a method including subjecting a DNA having a transcription regulatory region and a promoter region of the gene encoding a protein having a glutathione transporting activity of the parental strain, for example, the base sequence of 200 bp, preferably 100 bp, upstream of the initiation codon of the protein to in vitro mutation treatment, or error-prone PCR and the like to introduce mutation into the DNA, substituting the transcription regulatory region and promoter region of the gene encoding a protein having a glutathione transporting activity before introduction of mutation, which is present on the chromosomal DNA of the parental strain, with the mutant DNA by a known method [Proc. Natl. Acad. Sci. USA., 97, 6640 (2000)] to give a modified strain having a mutant transcription regulatory region or a promoter region, and comparing the transcription amounts of genes encoding the protein having a glutathione transporting activity of the parental strain and the modified strain by RT-PCR, Northern hybridization and the like, or comparing the production amounts of the protein having a glutathione transporting activity of the parental strain and the modified strain by SDS-PAGE and the like.

In addition, a microorganism wherein the production level of the protein having a glutathione transporting activity is promoted as compared to the parental strain can also be obtained by substituting the promoter region of a gene encoding the protein having a glutathione transporting activity of the parental strain with a known strong promoter sequence.

Examples of such promoter include promoters derived from *Escherichia coli*, phage and the like, which are functional in *E. coli*, such as trp promoter ($P_{trp}$), lac promoter ($P_{lac}$ promoter, $P_R$ promoter, $P_{SE}$ promoter and the like, SPO1 promoter, SPO2 promoter, penP promoter and the like. In addition, artificially constructed promoters such as a promoter having two $P_{trp}$ connected in tandem, tac promoter, lacT7 promoter, let I promoter and the like can also be mentioned.

The method of preparing DNA encoding a protein having a glutathione transporting activity, and a method of preparing a microorganism obtained by transforming the parental strain with the DNA are explained in detail in the following.

(a) Preparation transporting activity of a DNA encoding protein having glutathione A DNA encoding a protein having a glutathione transporting activity can be obtained, for example, by Southern hybridization of chromosomal DNA library of a microorganism such as *E. coli* and the like, using a probe DNA that can be designed based on the base sequence of DNA encoding a protein having glutathione transporting activity of abovementioned 1 (1), or PCR [PCR Protocols, Academic Press (1990)] using a primer DNA that can be designed based on the base sequence and the chromosomal DNA of a microorganism, preferably *E. coli*, as a template.

In addition, it is possible to search various gene sequence databases for a sequence having 80% or more, preferably 90% or more, more preferably 95% or more, still more preferably 97% or more, particularly preferably 98% or more, most preferably 99% or more homology with the base sequence of a DNA encoding a protein having glutathione transporting activity of above-mentioned 1 (1), and, based on the base sequence obtained by the search, obtain a DNA encoding a protein having a glutathione transporting activity according to the above-mentioned methods from chromosomal DNA, cDNA library and the like of the microorganism having the base sequence.

The base sequence of the DNA can be determined by incorporating the obtained DNA directly or after cleaving with a suitable restriction enzyme and the like into a vector according to a conventional method, and introducing the obtained recombinant DNA into a host cell, and analyzing the sequence by a base sequence analysis method which is generally used, for example, dideoxy method [Proc. Natl. Acad. Sci., USA, 74, 5463 (1977)], or using a base sequence analysis apparatus such as 3700 DNA analyzer (manufactured by Applied Biosystems) and the like.

As the above-mentioned vector, pBluescriptII KS(+) (manufactured by Stratagene), pDIRECT [Nucleic Acids Res., 18, 6069 (1990)], pCR-Script Amp SK(+) (manufactured by Stratagene), pT7Blue (manufactured by Novagen), pCR II (manufactured by Invitrogen) and pCR-TRAP (manufactured by GenHunter Corporation) and the like can be mentioned.

As the host cell, microorganism belonging to the genus *Escherichia* and the like can be mentioned. Examples of the microorganism belonging to the genus *Escherichia* include *E. coli* XL1-Blue, *E. coli* XL2-Blue, *E. coli* DH1, *E. coli* MC1000, *E. coli* ATCC 12435, *E. coli* W1485, *E. coli* JM109, *E. coli* HB101, *E. coli* No. 49, *E. coli* W3110, *E. coli* NY49, *E. coli* MP347, *E. coli* NM522, *E. coli* BL21, *E. coli* ME8415 and the like.

For introduction of recombinant DNA, any method can be used as long as it introduces DNA into the above-mentioned host cell. For example, a method using calcium ion [Proc. Natl. Acad. Sci., USA, 69, 2110 (1972)], protoplast method (JP-A-63-248394), electroporation method [Nucleic Acids Res., 16, 6127 (1988)] and the like can be mentioned.

As a result of determination of the base sequence, when the obtained DNA is a partial DNA, full-length DNA can be obtained by subjecting chromosomal DNA library to a Southern hybridization method using the partial DNA as a probe and the like.

Furthermore, the object DNA can be prepared based on the determined DNA base sequence by chemical synthesis using a 8905 type DNA synthesizer manufactured by Perceptive Biosystems and the like.

Examples of the DNA obtained as mentioned above include a DNA encoding a protein having the amino acid sequence shown by any of SEQ ID NOs: 1 to 26 and a DNA having the base sequence shown by any of SEQ ID NOs: 27 to 46.

(b) Preparation of a microorganism transformed with plasmid vector expressing protein having glutathione transporting activity Based on the DNA encoding a protein having a glutathione transporting activity, which is obtained by the method of the above-mentioned (a), a DNA fragment having a suitable length and containing a part encoding the protein having a glutathione transporting activity is prepared as necessary. In addition, a transformant showing an improved productivity can be obtained by substituting the base in the base sequence of the part encoding the protein having a glutathione transporting activity, such that a codon optimal for expression in the host cell can be obtained.

Recombinant DNA is prepared by inserting the DNA fragment into the downstream of a promoter of a suitable expression vector.

By introducing the recombinant DNA into a host cell suitable for the expression vector, a transformant wherein the activity of a protein having a glutathione transporting activity is improved as compared to that of the host cell, namely, the parental strain, can be obtained.

As the host cell, microorganism, preferably procaryote, more preferably bacterium, more preferably microorganism belonging to the genus *Escherichia*, most preferably *E. coli* can be used.

The expression vectors that can be employed are those capable of autonomous replication or integration into the chromosome in the above host cells and containing a promoter at a position appropriate for the transcription of the DNA encoding protein having a glutathione transporting activity.

When a procaryote is used as the host cell, it is preferred that the recombinant DNA comprising the DNA which is capable of autonomous replication in the procaryote and which comprises a promoter, a ribosome binding sequence, the DNA encoding protein having a glutathione transporting activity and a transcription termination sequence. The recombinant DNA may further comprise a gene regulating the promoter.

Examples of the expression vectors are pColdI (manufactured by Takara Bio Inc.), pCDF-1b, pRSF-1b (both manufactured by Novagen, Inc.), pMAL-c2x (manufactured by New England Biolabs), pGEX-4T-1 (manufactured by GE Healthcare Bioscience), pTrcHis (manufactured by Invitrogen), pSE280 (manufactured by Invitrogen), pGEMEX-1 (manufactured by Promega Corp.), pQE-30 (manufactured by Qiagen, Inc.), pET-3 (manufactured by Novagen, Inc.), pKYP10 (JP-A-58-110600), pKYP200[Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pBluescriptII SK(+), pBluescript II KS(−) (manufactured by Stratagene), pTrS30 [prepared from *Escherichia coli* JM109/pTrS30 (FERN BP-5407)], pTrS32 [prepared from *Escherichia coli* JM109/pTrS32 (FERN BP-5408)], pPAC31 (WO 98/12343), pUC19 [Gene, 33, 103 (1985)], pSTV28 (manufactured by Takara Bio Inc.), pUC118 (manufactured by Takara Bio Inc.), pPA1 (JP-A-63-233798) and the like.

As the promoter, any promoter capable of functioning in host cells such as *E. coli* can be used. For example, promoters derived from *E. coli*, phage and the like, such as trp promoter ($P_{trp}$), lac promoter ($P_{lac}$), $P_L$ promoter, $P_R$ promoter and $P_{SE}$ promoter, SPO1 promoter, SPO2 promoter and penP promoter can be used. Artificially designed and modified promoters such as a promoter in which two $P_{trp}$s are combined in tandem, tac promoter, lacT7 promoter and let I promoter, etc. can also be used.

Also promoters such as xylA promoter for the expression in microorganisms belonging to the genus *Bacillus* [Appl. Microbiol. Biotechnol., 35, 594-599 (1991)] and P54-6 promoter for the expression in microorganisms belonging to the genus *Corynebacterium* [Appl. Microbiol. Biotechnol., 53, 674-679 (2000)] can be used.

It is preferred to use a plasmid in which the distance between the Shine-Dalgarno sequence (ribosome binding sequence) and the initiation codon is adjusted to an appropriate length (e.g., 6 to 18 bases).

In a recombinant DNA wherein a DNA encoding a protein having a glutathione transporting activity is ligated to an expression vector, a transcription terminator sequence is not always necessary. However, it is preferable to arrange the transcription terminator sequence immediately beneath the structural gene.

Examples of such recombinant DNA include pCYD1, pBcr2, pYgeD2, pYceE2, pCmr, pMarRAB, pAcrAB, pEmrAB, pEmrE, pYdhC, pYdeE, pYdeA, pEmrKY, pEmrD, pYajR, pYegB, pYidY, pYieO, and pYjiO below.

Examples of the host of recombinant DNA include microorganism belonging to the genera *Escherichia*, *Bacillus*, *Brevibacterium*, *Corynebacterium* and the like. For example, *E. coli* XL1-Blue, *E. coli* XL2-Blue, *E. coli* DH1, *E. coli* MC1000, *E. coli* ATCC 12435, *E. coli* W1485, *E. coli* JM109, *E. coli* HB101, *E. coli* No. 49, *E. coli* W3110, *E. coli* NY49, *E. coli* MP347, *E. coli* NM522, *E. coli* BL21, *E. coli* ME8415, *Bacillus subtilis* ATCC33712, *Batillus megaterium*, *Brevibacterium ammoniagenes*, *Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium glutamicum* ATCC14297, *Corynebacterium acetoacidophilum* ATCC13870 and the like can be mentioned. Examples of preferable host include *E. coli*.

(c) Preparation of a microorganism wherein DNA encoding protein having glutathione transporting activity is incorporated into chromosomal DNA By incorporating a DNA encoding a protein having a glutathione transporting activity obtained by the method of the above-mentioned (a) into any position of chromosomal DNA, a microorganism wherein the activity of the protein having a glutathione transporting activity is higher than that of the parental strain can also be acquired.

As the method for incorporating a DNA encoding a protein having a glutathione transporting activity into any position of chromosomal DNA of a microorganism, a method utilizing homologous recombination can be mentioned. When *E. coli* is used as a host, namely, a parental strain, the method described in Proc. Natl. Acad. Sci. USA., 97, 6640 (2000) can be mentioned.

(2) Preparation of a microorganism wherein the activity of protein relating biosynthesis of glutathione or γ-glutamylcysteine is higher than that of parental strain Of the microorganisms wherein the activity of a protein involved in biosynthesis of glutathione or γ-glutamylcysteine is higher than that of the parental strain, a microorganism showing specific activity of the protein higher than that of the parental strain, and a microorganism wherein the production amount of the protein is improved as compared to the parental strain can be obtained as in the above-mentioned (1) by substituting a mutant enzyme gene obtained by subjecting a DNA encoding a protein relating biosynthesis of glutathione or γ-glutamylcysteine to in vitro mutation treatment, error-prone PCR and the like with the gene of the parental strain.

By respectively culturing the obtained microorganism having a mutant enzyme gene and the parental strain in a liquid culture medium, and measuring and comparing the amount of glutathione or γ-glutamylcysteine contained in the culture by a known method, the higher activity of the protein relating biosynthesis of glutathione or γ-glutamylcysteine than that of the parental strain can be confirmed.

A method of obtaining DNA encoding the protein involved in biosynthesis of glutathione or γ-glutamylcysteine and a method of preparing the microorganism obtained by transforming the parental strain with the DNA are explained in the following.

(a) Preparation of DNAs that encode a protein involved in glutathione or γ-glutamylcysteine biosynthesis A DNA that encodes γ-glutamylcysteine synthetase, which is a protein involved in glutathione and γ-glutamylcysteine biosynthesis, and a DNA that encodes glutathione synthetase, which is a protein involved in glutathione biosynthesis, can be obtained in the same manner as 2(1)(a) above according to the base sequence of a DNA that encodes a protein involved in glutathione or γ-glutamylcysteinesin biosynthesis, described in 1(2) above.

As DNAs that can be obtained by the above-described method, a DNA having the base sequence shown by SEQ ID NO: 49, and encoding γ-glutamylcysteine synthetase having the amino acid sequence shown by SEQ ID NO: 47, and a DNA having the base sequence shown by SEQ ID NO: 50, and encoding glutathione synthetase having the amino acid sequence shown by SEQ ID NO: 48, can be mentioned.

(b) Preparation of microorganisms transformed with a plasmid vector that expresses a protein involved in glutathione or γ-glutamylcysteine biosynthesis A plasmid vector that expresses γ-glutamylcysteine synthetase or glutathione synthetase can be obtained in the same manner as 2(1)(b) above using a DNA obtained in 2(2)(a) above, the DNA being a DNA that encodes γ-glutamylcysteine synthetase or a DNA that encodes glutathione synthetase.

As examples of a plasmid vector that expresses a protein involved in γ-glutamylcysteine or glutathione biosynthesis, and that can be obtained by the above-described method, pGH1, which expresses γ-glutamylcysteine synthetase, and pGH3, which expresses the two enzymes γ-glutamylcysteine synthetase and glutathione synthetase, which are described below, can be mentioned.

(c) Preparation of a microorganism wherein a DNA that encodes a protein involved in glutathione or γ-glutamylcysteine biosynthesis is integrated into the chromosomal DNA By integrating a DNA that encodes a protein involved in glutathione or γ-glutamylcysteine biosynthesis, obtained by the method 2(2)(a) above, into an arbitrary position on the chromosomal DNA, a microorganism with a higher activity of the protein involved in glutathione or γ-glutamylcysteine biosynthesis, compared with that of the parent strain, can also be obtained.

The DNA that encodes a protein involved in glutathione biosynthesis, to be integrated into the chromosomal DNA, may be two DNAs, i.e., a DNA that encodes γ-glutamylcysteine synthetase and a DNA that encodes glutathione synthetase, or may be either one DNA.

Integration of the DNA into an arbitrary position on the chromosomal DNA of the microorganism can be performed in the same manner as 2(1)(c) above.

A publicly known DNA that encodes a mutated γ-glutamylcysteine synthetase with increased specific activity [Appl. Envir. Microbiol., 44, 1444 (1982), J. Gen. Microbiol., 128, 1047 (1982)] or a mutated glutathione synthetase [J. Biol. Chem., 263, 11646 (1988), Biochemistry, 31, 2259 (1992)] can also be used in a process for production of the present invention.

(d) Preparation of a microorganism with enhanced substrate supply

By enhancing the capability of a microorganism with a high activity of a protein involved in glutathione or γ-glutamylcysteine biosynthesis of producing an amino acid selected from L-glutamic acid, L-cysteine and glycine, the microorganism's capability of glutathione or γ-glutamylcysteine biosynthesis can be further enhanced.

As methods for enhancing a microorganism's capability of producing an amino acid selected from L-glutamic acid, L-cysteine and glycine,
i) a method wherein at least one of the mechanisms for controlling the biosynthesis of any one of the above-described amino acids is moderated or released,
ii) a method wherein the expression of at least one of the enzymes involved in the biosynthesis of any one of the above-described amino acids is enhanced,
iii) a method wherein the copy number of at least one of the enzyme genes involved in the biosynthesis of any one of the above-described amino acids is increased,
iv) a method wherein at least one of the metabolic pathways branching biosynthetic pathway of any one of the above-described amino acids to a metabolite other than the amino acids is weakened or blocked,
v) a method wherein a strain with a higher degree of resistance to an analogue of any of the above-described amino acids, compared with the parent strain, is selected, and the like can be mentioned; the above-described publicly known methods can be used alone or in combination.

Specific procedures of the method i) above are described in Agric. Biol. Chem., 43, 105-111 (1979), J. Bacteriol., 110, 761-763 (1972), Appl. Microbiol. Biotechnol., 39, 318-323 (1993) and elsewhere. Specific procedures of the method ii) above are described in Agric. Biol. Chem., 43, 105-111 (1979), J. Bacteriol., 110, 761-763 (1972) and elsewhere. Specific procedures of the method iii) above are described in Appl. Microbiol. Biotechnol., 39, 318-323 (1993), Agric. Biol. Chem., 39, 371-377 (1987) and elsewhere. Specific procedures of the method iv) above are described in Appl. Environ. Microbiol., 38, 181-190 (1979), Agric. Biol. Chem., 42, 1773-1778 (1978) and elsewhere. Specific procedures of the method v) above are described in Agric. Biol. Chem., 36, 1675-1684 (1972), Agric. Biol. Chem., 41, 109-116 (1977), Agric. Biol. Chem., 37, 2013-2023 (1973), Agric. Biol. Chem., 51, 2089-2094 (1987) and elsewhere. A microorganism having the capability of producing one of the above-described amino acids can be prepared with reference to the documents shown above and the like.

Furthermore, methods of preparing a microorganism having an ability to produce amino acids by any of the above-mentioned (i)-(v) or a combination thereof are described in Biotechnology 2nd ed., Vol. 6, Products of Primary Metabolism (VCH Verlagsgesellschaft mbH, Weinheim, 1996) section 14a, 14b, and Advances in Biochemical Engineering/Biotechnology, 79, 1-35 (2003), and Amino Acid Fermentation, Japan Scientific Societies Press, Hiroshi Aida et al. (1986). A microorganism having an ability to produce the above-mentioned amino acids can be prepared by reference to the above-mentioned publications and the like.

As examples of specific methods of preparing a microorganism having the capability of producing L-glutamic acid, a method wherein E. coli with a reduced or lost activity of α-ketoglutaric acid dehydrogenase (SucA protein) is prepared [Mol. Gen. Genet., 105, 182 (1969)], and a method wherein E. coli having the expression of the malate synthase (AceB protein), isocitrate lyase (AceA protein), and isocitrate dehydrogenase kinase/phosphatase (AceK protein) operon becoming constitutive is prepared [J. Bacteriol. 96, 2185 (1968)] can be mentioned (JP-A-HEI-5-244970).

As examples of specific methods of preparing a microorganism having the capability of producing L-cysteine, a method can be mentioned wherein by replacing a codon corresponding to the 256th methionine of the enzyme with a codon that encodes isoleucine in a gene that encodes E. coli serine acetyltransferase, E. coli that expresses a mutated serine acetyltransferase with a reduced feedback inhibition by L-cysteine compared with the wild-type enzyme is prepared [J. Gen., 133, 515 (1987)].

As an example of a specific method of preparing a microorganism having the capability of producing glycine, a method can be mentioned wherein E. coli with a reduced or lost activity of glycine degrading enzyme activity compared with the parent strain is prepared [Mol. Gen. Genet., 192, 15 (1983)].

(3) Preparation of microorganisms with a reduced or lost glutathione or γ-glutamylcysteine degrading activity compared with the parent strain Although how to prepare a microorganism with a reduced or lost γ-glutamyl transpeptidase activity compared with the parent strain is described below, a microorganism with a reduced or lost activity of another protein involved in glutathione or γ-glutamylcysteine degradation, compared with the parent strain, can also be prepared in the same manner.

(a) Preparation of a Gene that Encodes γ-Glutamyl Transpeptidase

A gene that encodes γ-glutamyl transpeptidase can be prepared in the same manner as 2(1)(a) above, for example, according to the base sequence of the gene 1(3) above that encodes γ-glutamyl transpeptidase.

As a gene that can be obtained by the above-described method, a gene having the base sequence shown by SEQ ID NO: 52, and encoding γ-glutamyl transpeptidase having the amino acid sequence shown by SEQ ID NO: 51, can be mentioned.

(b) Preparation of a microorganism with a reduced or lost activity of γ-glutamyl transpeptidase A microorganism with a reduced or lost activity of γ-glutamyl transpeptidase compared with the parent strain can be obtained by a method wherein a microorganism is mutagenized by UV exposure, mutagen and the like, after which a strain with a reduced or lost γ-glutamyl transpeptidase activity compared with the parent strain is selected, or a method wherein a base deletion, substitution or addition is introduced into the base sequence of a gene that encodes γ-glutamyl transpeptidase on the chromosomal DNA of a microorganism, and the like.

The positions for introducing a base deletion, substitution or addition into the base sequence of a gene that encodes γ-glutamyl transpeptidase are as described in 1(3) above.

As a method of introducing a base deletion, substitution or addition into a gene on the chromosomal DNA of a microorganism, a method utilizing homologous recombination can be mentioned. As a general method utilizing homologous recombination, a method can be mentioned wherein a mutant gene introducing a base deletion, substitution or addition is prepared using a gene that encodes γ-glutamyl transpeptidase that can be acquired in 2(3)(a) above, and ligated to a plasmid DNA having a drug resistance gene incapable of autonomous-replicating in the host cell into which the base deletion or the like is to be introduced, and the plasmid for homologous recombination thus obtained is used; as a method utilizing homologous recombination, which is often used for *E. coli*, a method can be mentioned wherein a base deletion, substitution or addition is introduced by means of a lambda phage homologous recombination system [Proc. Natl. Acad. Sci. USA, 97, 6641-6645 (2000)].

Being a microorganism with a reduced or lost glutathione or γ-glutamylcysteine degrading activity compared with the parent strain can be confirmed by measuring the degree of reduction of glutathione or γ-glutamylcysteine degrading activity compared with the parent strain by a publicly known method.

(4) Preparation of a microorganism with a reduced or lost glutathione or γ-glutamylcysteine uptake activity compared with the parent strain (a) Preparation of a gene that encodes a protein having glutathione or γ-glutamylcysteine uptake activity A gene that encodes a protein having glutathione or γ-glutamylcysteine uptake activity can be obtained in the same manner as 2(1)(a) above, for example, according to the base sequence of the gene 1(4) above, which encodes a protein having glutathione or γ-glutamylcysteine uptake activity.

As genes that can be obtained by the above-described method, a DNA having the base sequence shown by SEQ ID NO: 58, and encoding a protein involved in glutathione or γ-glutamylcysteine uptake, and having one of the amino acid sequences shown by SEQ ID NOs: 53 to 57, and a DNA comprising a coding region in the base sequence can be mentioned.

(b) Preparation of a microorganism with a reduced or lost glutathione or γ-glutamylcysteine uptake activity compared with the parent strain A microorganism with a reduced or lost glutathione or γ-glutamylcysteine uptake activity compared with the parent strain can be acquired in the same manner as 2(3)(b) above by a method wherein a microorganism is mutagenized by UV exposure, mutagen and the like, after which a strain with a reduced or lost glutathione or γ-glutamylcysteine uptake activity is selected, or a method wherein a base deletion, substitution or addition is introduced into the base sequence of a gene that encodes a protein having glutathione uptake activity on the chromosomal DNA of a microorganism, and the like.

As a method for introducing a base deletion, substitution or addition into a gene on the chromosomal DNA of a microorganism, the method 2(3)(b) above can be mentioned.

Being a microorganism with a reduced or lost glutathione or γ-glutamylcysteine uptake activity can be confirmed by measuring the degree of reduction of glutathione or γ-glutamylcysteine uptake activity compared with the parent strain by an uptake activity assay using labeled glutathione or γ-glutamylcysteine [J. Bacteriol., 186, 343 (2004)].

3. Processes of the present invention for producing glutathione or γ-glutamylcysteine As processes of the present invention for producing glutathione or γ-glutamylcysteine, processes of producing glutathione or γ-glutamylcysteine comprising culturing in a medium a microorganism with a higher activity of a protein having glutathione transporting activity, compared with the parent strain, and with a higher activity of a protein involved in glutathione or γ-glutamylcysteine biosynthesis, compared with the parent strain, forming and accumulating glutathione in the medium, and recovering glutathione or γ-glutamylcysteine from the culture, can be mentioned.

The medium used in a process for production of the present invention may be a synthetic medium or a natural medium, as far as it contains nutrients required for the growth of the microorganism used in the present invention, and for glutathione biosynthesis, such as a carbon source, a nitrogen source, an organic salt, a vitamin and the like.

An amino acid selected from among L-glutamic acid, L-cysteine and glycine may be added to the medium as required. The amount added to the medium is 0.1 to 100 g/l, preferably 1 to 50 g/l, and more preferably 5 to 20 g/l, based on each amino acid.

As the carbon source, which may be any carbon source that can be utilized by the microorganism used, saccharides such as glucose and fructose, alcohols such as ethanol and glycerol, organic acids such as acetic acid, and the like can be mentioned.

As the nitrogen source, ammonia, ammonium salts such as ammonium sulfate, nitrogen compounds such as amines, natural nitrogen sources such as peptone and soybean hydrolyzates, and the like can be mentioned.

As the inorganic salt, potassium phosphate, magnesium sulfate, sodium chloride, ferrous sulfate, potassium carbonate and the like can be mentioned.

As the vitamin, biotin, thiamin and the like can be mentioned. Furthermore, as required, substances a microorganism of the present invention require for the growth thereof (for example, in the case of a microorganism with amino acid auxotrophy, the amino acids required) can be added.

The culturing is performed preferably under aerobic conditions such as shaking culture and spinner culture. Culturing temperature is 20 to 50° C., preferably 20 to 42° C., and more preferably 28 to 38° C. The pH during the cultivation is 5 to 9, preferably 6 to 7.5. Culturing time is 5 hours to 5 days, preferably 16 hours to 3 days.

The glutathione accumulated in the culture can be recovered by an ordinary method of purification. For example, after completion of the culturing, the glutathione can be recovered by ion exchange, concentration, or crystal fractionation after removing cells and solid matter from the culture by centrifugation and the like.

The present invention is hereinafter described specifically by means of the following examples, to which, however, the present invention is not limited.

EXAMPLE 1

Construction of Plasmids that Express γ-Glutamylcysteine Synthetase or Glutathione Synthetase Using the model 8905 DNA synthesizer manufactured by Perceptive Biosystems, DNAs having the base sequences shown by SEQ ID NOs: 59 and 60 were synthesized on the basis of the gene that encodes *E. coli* γ-glutamylcysteine synthetase, and that has the base sequence shown by SEQ ID NO: 49 (gshA gene), and DNAs having the base sequences shown by SEQ ID NOs: 61 and 62 were synthesized on the basis of the base sequence of the gene that encodes the *E. coli* glutathione synthetase, and that has the base sequence shown by SEQ ID NO: 50 (gshB gene).

PCR was performed with the chromosomal DNA of the *E. coli* W3110 strain as the template, using DNAs consisting of the base sequences shown by SEQ ID NOs: 59 and 60, and SEQ ID NOs: 61 and 62, as primer sets, respectively. The PCR was performed by preparing 40 μL of a reaction mixture comprising 0.1 μg of the chromosomal DNA, 0.5 μmol/L of each primer, 2.5 units of Pfu DNA polymerase, 4 μL of x×10 buffer solution for Pfu DNA polymerase, and 200 μmol/L of each dNTP, and repeating the step of heat treatment at 94° C. for 1 minute, at 55° C. for 2 minutes, and at 72° C. for 2 minutes in 30 cycles.

In the PCR using SEQ ID NOs: 59 and 60, an about 1.6 kb fragment corresponding to a gshA gene fragment (hereinafter referred to as gshA gene amplified fragment) was obtained; in the reaction using SEQ ID NOs: 61 and 62, an about 1.0 kb fragment corresponding to a gshB gene fragment (hereinafter referred to as gshB gene amplified fragment) was obtained.

The gshA gene amplified fragment obtained above was cleaved with ClaI and BamHI, and the gshB gene amplified fragment was cleaved with BglII and BamHI, after which each amplified fragment was purified using GENECLEAN II Kit.

Likewise, the expression vector pTrS30 comprising the trp promoter was cleaved with ClaI and BamHI, after which a 4.5 kb DNA fragment was purified.

The gshA gene amplified fragment and 4.5 kb DNA fragment obtained above were joined using a ligation kit.

The *E. coli* NM522 strain was transformed using the joined DNA obtained, and a transformant was selected with ampicillin resistance as an index.

The plasmid was extracted from the transformant by a publicly known method, obtainment of an expression vector having the gshA gene joined downstream of the trp promoter was confirmed, and the plasmid was named pGH1.

After pGH1 was cleaved with BamHI, an about 6.1 kb DNA fragment was purified as described above. The DNA fragment was treated with alkaline phosphatase (*E. coli* C75, manufactured by Takara Bio Inc.) at 60° C. for 30 minutes to achieve dephosphorylation.

The gshB gene amplified fragment and alkaline phosphatase-treated 6.1 kb DNA fragment obtained above were joined using a ligation kit.

The *E. coli* NM522 strain was transformed using the ligated DNA obtained, and a transformant was selected with ampicillin resistance as an index.

The plasmid was extracted from the transformant by a publicly known method, obtainment of a plasmid having the gshB gene inserted downstream of the gshA gene in the same direction was confirmed, and the plasmid was named pGH3.

EXAMPLE 2

Construction of Plasmids that Express a Gene that Encodes a Protein Having Glutathione Transporting Activity (1) Construction of a plasmid that expresses the cydDC gene In the same manner as Example 1 above, using a DNA synthesizer, on the basis of the *E. coli* cydD gene and cydC gene having the base sequence shown by SEQ ID NO: 27 (hereinafter referred to as the cydD-cydC gene), DNAs having the base sequences shown by SEQ ID NOs: 63 and 64, respectively, were synthesized.

PCR was performed with the chromosomal DNA of the *E. coli* W3110 strain as the template, using the DNAs having the base sequences shown by SEQ ID NOs: 63 and 64 as a primer set. The PCR was performed by preparing 40 μL of a reaction mixture comprising 0.1 μg of the chromosomal DNA, 0.5 μmol/L of each primer, 2.5 units of Pfu DNA polymerase, 4 μL of ×10 buffer solution for Pfu DNA polymerase, and 200 μmol/L of each dNTP, and repeating the step of heat treatment at 94° C. for 1 minute, at 55° C. for 2 minutes, and at 72° C. for 4 minutes in 30 cycles.

In the PCR, an about 3.7 kb fragment corresponding to the cydD-cydC gene fragment (hereinafter referred to as the cydD-cydC gene amplified fragment) was obtained.

The cydD-cydC gene amplified fragment obtained was cleaved with HindIII and BamHI, after which the resulting fragment was purified using GENECLEAN II Kit.

The plasmid vector pSTV29 having a replication origin of pACYC184 and the chloramphenicol resistance gene (manufactured by Takara Bio Inc.) was cleaved with HindIII and BamHI, after which a 3.0 kb DNA fragment was purified as described above.

The 3.7 kb cydD-cydC gene amplified fragment and 3.0 kb DNA fragment obtained above were ligated using a ligation kit.

The *Escherichia coli* NM522 strain was transformed using the ligated DNA obtained, a transformant was selected with chloramphenicol resistance as an index.

The plasmid was extracted from the transformant by a publicly known method, acquirement of a cydD-cydC gene expression vector was confirmed, and the plasmid was named pCYD1.

(2) Construction of plasmids that express the bcr Gene, ygeD gene, or yceE gene

In the same manner as Example 1 above, using a DNA synthesizer, DNAs having the base sequences shown by SEQ ID NOs: 65 and 66, based on the *E. coli* bcr gene, which has the base sequence shown by SEQ ID NO: 28, DNAs having the base sequences shown by SEQ ID NOs: 67 and 68, based on the *E. coli* ygeD gene, which has the base sequence shown by SEQ ID NO: 29, and DNAs having the base sequences shown by SEQ ID NOs: 69 and 70, based on the *E. coli* yceE gene, which has the base sequence shown by SEQ ID NO: 30, were synthesized, respectively.

PCR was performed with the chromosomal DNA of the *E. coli* W3110 strain as the template, using DNAs consisting of the base sequences shown by SEQ ID NOs: 65 and 66 above, for amplifying the bcr gene fragment, by SEQ ID NOs: 67 and 68, for amplifying the ygeD gene fragment, and by SEQ ID NOs: 69 and 70, for amplifying the yceE gene fragment, as primer sets, respectively.

The PCR was performed under the same conditions as (2) above, except that the primer DNAs used are different, respectively.

In the PCR, about 1.2 kb fragments corresponding to the respective gene fragments (hereinafter referred to as the bcr gene amplified fragment, ygeD gene amplified fragment, and yceE gene amplified fragment, respectively) were obtained.

The bcr gene amplified fragment obtained was cleaved with HindIII and SacI, and the ygeD gene amplified fragment and yceE gene amplified fragment were cleaved with ClaI and BamHI, after which each fragment was purified using GENECLEAN II Kit.

The expression vector pTrS30 comprising the trp promoter was cleaved with HindIII and SacI or with ClaI and BamHI, after which each 4.5 kb DNA fragment was purified as described above.

The bcr gene amplified fragment and the HindIII and SacI cleavage fragment of pTrS30 obtained above were joined using a ligation kit. The ygeD gene amplified fragment and the yceE gene amplified fragment were ligated with the ClaI and BamHI cleavage fragment of pTrS30 obtained above, respectively, using a ligation kit.

The *E. coli* NM522 strain was transformed using each ligated DNA obtained, and transformants were selected with ampicillin resistance as an index.

The plasmids were extracted from the transformants by a publicly known method, acquirement of expression vectors comprising the bcr gene, ygeD gene or yceE gene downstream of the trp promoter (hereinafter denoted as Ptrp) was confirmed, and these were named pBcr1, pYgeD1 and pYceE1, respectively.

Next, pBcr1 was cleaved with EcoRI and SacI, and pYgeD1 and pYceE1 were cleaved with EcoRI and BamHI, after which about 1.6 kb DNA fragments having each gene arranged downstream of Ptrp (referred to as the Ptrp-bcr gene, Ptrp-ygeD gene and Ptrp-yceE gene, respectively) were purified using GENECLEAN Kit.

The plasmid vector pSTV28 having a replication origin of pACYC184, and comprising the chloramphenicol resistance gene (manufactured by Takara Bio Inc.) was cleaved with EcoRI and SacI, or with EcoRI and BamHI, after which a 3.0 kb DNA fragment was purified as described above.

The about 1.6 kb DNA fragment comprising the Ptrp-bcr gene, obtained above, and the EcoRI and SacI cleavage fragment of pSTV28, and the 1.6 kb DNA fragment comprising the Ptrp-ygeD gene or Ptrp-yceE gene and the EcoRI and BamHI cleavage fragment of pSTV28, were joined, respectively, using a ligation kit.

The *E. coli* NM522 strain was transformed using the ligated DNAs obtained, after which transformants were selected with chloramphenicol resistance as an index.

The plasmids were extracted from the transformants by a publicly known method, acquirement of bcr, ygeD, and yceE gene expression vectors was confirmed, and the plasmids were named pBcr2, pYgeD2, and pYceE2, respectively.

(3) Construction of plasmids that express the cmr gene, marR-marA-marB gene, acrA-acrB gene, emrA-emrB gene, emrE gene, ydhC gene, ydeE gene, ydeA gene, evgA-emrK-emrY gene, emrD gene, yajR gene, yegB gene, yidY gene, yieO gene, or yjiO gene In the same manner as (1) above, using a DNA synthesizer, on the basis of the base sequences of the cmr gene, the marR, marA and marB genes (hereinafter referred to as the marR-marA-marB gene), the acrA and acrB genes (hereinafter referred to as the acrA-acrB gene), the emrA and emrB genes (hereinafter referred to as the emrA-emrB gene), the emrE gene, ydhC gene, ydeE gene, ydeA gene, the evgA, emrK and emrY genes (hereinafter referred to as the evgA-emrK-emrY gene), emrD gene, yajR gene, yegB gene, yidY gene, yieO gene, and yjiO gene, primer DNAs for amplifying the genes were synthesized. The base sequences of the primer DNAs used to amplify the respective genes are shown in Table 1.

TABLE 1

| Name and base sequence of amplified gene | Primer DNA base sequences |
| --- | --- |
| cmr gene, SEQ ID NO: 31 | SEQ ID NO: 71, 72 |
| marR-marA-marB gene, SEQ ID NO: 32 | SEQ ID NO: 73, 74 |
| acrA-acrB gene, SEQ ID NO: 33 | SEQ ID NO: 75, 76 |
| emrA-emrB gene, SEQ ID NO: 34 | SEQ ID NO: 77, 78 |
| emrE gene, SEQ ID NO: 35 | SEQ ID NO: 79, 80 |
| ydhC gene, SEQ ID NO: 36 | SEQ ID NO: 81, 82 |
| ydeE gene, SEQ ID NO: 37 | SEQ ID NO: 83, 84 |
| ydeA gene, SEQ ID NO: 38 | SEQ ID NO: 85, 86 |
| evgA-emrK-emrY gene, SEQ ID NO: 39 | SEQ ID NO: 87, 88 |
| emrD gene, SEQ ID NO: 41 | SEQ ID NO: 89, 90 |
| yajR gene, SEQ ID NO: 42 | SEQ ID NO: 91, 92 |
| yegB gene, SEQ ID NO: 43 | SEQ ID NO: 93, 94 |
| yidY gene, SEQ ID NO: 44 | SEQ ID NO: 95, 96 |
| yieO gene, SEQ ID NO: 45 | SEQ ID NO: 97, 98 |
| yjiO gene, SEQ ID NO: 46 | SEQ ID NO: 99, 100 |

PCR was performed with the chromosomal DNA of the *E. coli* W3110 strain as the template, using each two kinds of DNAs consisting of base sequences shown by the sequence identification numbers in Table 1 above as a primer set, respectively.

The PCR was performed under the same conditions as (2) above, except that the primer DNAs used are different.

In the PCR, an about 1.3 kb DNA fragment as the cmr gene (hereinafter referred to as the cmr gene amplified fragment), an about 1.0 kb DNA fragment as the marR-marA-marB gene (hereinafter referred to as the marR-marA-marB gene amplified fragment), an about 4.4 kb DNA fragment as the acrA-acrB gene (hereinafter referred to as the acrA-acrB gene amplified fragment), an about 2.8 kb DNA fragment as the emrA-emrB gene (hereinafter referred to as the emrA-emrB gene amplified fragment), an about 0.4 kb DNA fragment as the emrE gene (the emrE gene amplified fragment), an about 1.3 kb DNA fragment as the ydhC gene (hereinafter referred to as ydhC gene amplified fragment), an about 1.2 kb DNA fragment as the ydeE gene (hereinafter referred to as ydeE gene amplified fragment), an about 1.2 kb DNA fragment as the ydeA gene (hereinafter referred to as ydeA gene amplified fragment), an about 3.4 kb DNA fragment as the evgA-emrK-emrY gene (hereinafter referred to as evgA-emrK-emrY gene amplified fragment), an about 1.2 kb DNA fragment as the emrD gene (hereinafter referred to as emrD gene amplified fragment), an about 1.4 kb DNA fragment as the yajR gene (hereinafter referred to as yajR gene amplified fragment), an about 1.5 kb DNA fragment as the yegB gene (hereinafter referred to as yegB gene amplified fragment), an about 1.2 kb DNA fragment as the yidY gene (hereinafter referred to as yidY gene amplified fragment), an about 1.5 kb DNA fragment as the yieO gene (hereinafter referred to as yieO gene amplified fragment), and an about 1.3 kb DNA fragment as the yjiO gene (hereinafter referred to as the yjiO gene amplified fragment) were obtained.

The cmr gene amplified fragment obtained above was cleaved with EcoRI and SalI, the acrA-acrB gene amplified fragment was cleaved with SphI and SalI, the marR-marA-marB, emrA-emrB, emrE, ydhC, ydeE, ydeA, and evgA-emrK-emrY gene amplified fragments were cleaved with EcoRI and BamHI, and the emrD, yajR, yegB, yidY, yieO, and yjiO gene amplified fragments were cleaved with EcoRI and PstI, after which each amplified fragment was purified using GENECLEAN II Kit.

Next, the plasmid vector pSTV28 was cleaved with EcoRI and SalI, with SphI and SalI, and with EcoRI and BamHI, then each DNA fragment of about 3.0 kb was purified.

The cmr gene amplified fragment and the EcoRI and SalI cleavage fragment of pSTV28; the acrA-acrB gene amplified fragment and the SphI and SalI cleavage fragment of pSTV28; each of the marR-marA-marB gene amplified fragment, emrA-emrB gene amplified fragment, emrE gene amplified fragment, ydhC gene amplified fragment, ydeE gene amplified fragment, ydeA gene amplified fragment, and evgA-emrK-emrY gene amplified fragment, and the EcoRI and BamHI cleavage fragment of pSTV28; and each of the emrD gene amplified fragment, yajR gene amplified fragment, yegB gene amplified fragment, yidY gene amplified fragment, yieO gene amplified fragment, and yjiO gene amplified fragment, and the EcoRI and PstI digested fragment of pSTV28, were ligated, respectively, using a ligation kit.

The *E. coli* NM522 strain was transformed using each ligated DNA obtained, and transformants were selected with chloramphenicol resistance as an index.

The plasmids were extracted from the transformants by a publicly known method, obtainment of the respective gene expression vectors was confirmed, and the plasmid DNAs were named pCmr, pMarRAB, pAcrAB, pEmrAB, pEmrE, pYdhC, pYdeE, pYdeA, pEmrKY, pEmrD, pYajR, pYegB, pYidY, pYieO, and pYjiO, respectively.

EXAMPLE 3

Production of Glutathione or γ-Glutamylcysteine Using a Microorganism with an Enhanced Activity of a Protein Having Glutathione Transporting Activity, Compared with the Parent Strain, and with a Higher Activity of a Protein Involved in Glutathione or γ-Glutamylcysteine Biosynthesis, Compared with the Parent Strain The *E. coli* JM101 strain was transformed using the plasmids pGH1, pGH3 and pCYD1 constructed in Example 1 and Example 2(1), and transformants were selected with ampicillin and chloramphenicol resistance indexes.

Each transformed strain obtained was inoculated to a test tube containing 8 ml of an LB medium comprising 50 μg/ml ampicillin and 25 μg/ml chloramphenicol, and cultured at 28° C. for 17 hours. The culture obtained was added at 1% to a test tube containing 8 ml of a medium comprising 100 μg/ml ampicillin, 50 μg/ml chloramphenicol and amino acids (dipotassium hydrogen phosphate 16 g/L, potassium dihydrogen phosphate 14 g/L, ammonium sulfate 4 g/L, citric acid (anhydrous) 5 g/L, casamino acid (manufactured by Difco) 4 g/L, sodium thiosulfate pentahydrate 2 g/L, glucose 20 g/l, vitamin $B_1$ 10 mg/L, magnesium sulfate heptahydrate 2 g/L, iron sulfate heptahydrate 50 mg/L, manganese sulfate heptahydrate 10 mg/L, adjusted to pH 7.2 using 10 mol/L sodium hydroxide solution; the glucose and magnesium sulfate heptahydrate were added after being separately autoclaved), and cultured at 28° C. for 24 hours.

The obtained culture was centrifuged, and the product in the supernatant thereof was analyzed by HPLC.

The analysis by HPLC was performed using Nucleosil 100-5C18 4.6 mm×150 mm (250 mm) (GL Science) as a separation column, and a 0.4% (w/v) heptanesulfonic acid and 20% (v/v) acetonitrile solution (adjusted to pH 2.0 with phosphoric acid) as an eluent, at a flow rate of 1.0 ml/min, a temperature of 40° C., and a detection wavelength of 210 nm. The analytical results are shown in Table 2. In the table, GLT represents glutathione, and GC represents γ-glutamylcysteine.

TABLE 2

| Strain | Expression-enhanced genes | GLT (mg/l) | GC (mg/l) |
|---|---|---|---|
| JM101/pTrS30, pSTV29 | None | 0 | 0 |
| JM101/pTrS30, pCYD1 | cydD, cydC | 0 | 0 |
| JM101/pGH1, pSTV29 | gshA | 102 | 238 |
| JM101/pGH1, pCYD1 | gshA, cydD, cydC | 147 | 52 |
| JM101/pGH3, pSTV29 | gshA, gshB | 200 | 33 |
| JM101/pGH3, pCYD1 | gshA, gshB, cydD, cydC | 262 | 0 |

As stated above, by enhancing the activity of a protein involved in glutathione biosynthesis, even after the logarithmic growth phase, glutathione could be accumulated in the medium. Furthermore, by enhancing the expression of the cydD and cydC genes, the amount of glutathione accumulated in the medium increased further; it was found that the proteins encoded by the cydD and cydC genes have glutathione transporting activity.

EXAMPLE 4

Production of Glutathione Using Microorganisms with a Higher Activity of a Protein Having Glutathione Transporting Activity, and a Higher Activity of a Protein Involved in Glutathione Biosynthesis, Compared with the Parent Strain The *E. coli* JM101 strain was transformed using a plasmid selected from among the plasmids pGH1 and pGH3 constructed in Example 1, and the plasmids pBcr2, pYgeD2, pYceE2, pCmr, pMarRAB, pAcrAB, pEmrAB, pEmrE, pYdhC, pYdeE, pYdeA, pEmrKY, pEmrD, pYajR, pYegB, pYidY, pYieO and pYjiO constructed in Example 2(2) and (3), and pSTV28, and transformants were selected with ampicillin and chloramphenicol resistance as indexes.

The transformed strains obtained were cultured in the same manner as Example 3, and the glutathione concentrations in the medium was measured. The results are shown in Table 3. In the table, GLT represents glutathione.

TABLE 3

| Name of strain | Expression-enhanced genes | GLT (mg/l) |
|---|---|---|
| JM101/pGH3, pSTV28 | gshA, gshB | 160 |
| JM101/pGH3, pBcr2 | gshA, gshB, bcr | 838 |
| JM101/pGH3, pYgeD2 | gshA, gshB, ygeD | 432 |
| JM101/pGH3, pYceE2 | gshA, gshB, yceE | 442 |
| JM101/pGH3, pCmr | gshA, gshB, cmr | 540 |
| JM101/pGH3, pMarRAB | gshA, gshB, marR, marA, marB | 453 |
| JM101/pGH3, pAcrAB | gshA, gshB, acrA, acrB | 253 |
| JM101/pGH3, pEmrAB | gshA, gshB, emrA, emrB | 340 |
| JM101/pGH3, pEmrE | gshA, gshB, emrE | 784 |
| JM101/pGH3, pYdhC | gshA, gshB, ydhC | 577 |
| JM101/pGH3, pYdeE | gshA, gshB, ydeE | 769 |
| JM101/pGH3, pYdeA | gshA, gshB, ydeA | 600 |
| JM101/pGH3, pEmrKY | gshA, gshB, evgA, emrK, emrY | 593 |
| JM101/pGH3, pEmrD | gshA, gshB, emrD | 563 |

TABLE 3-continued

| Name of strain | Expression-enhanced genes | GLT (mg/l) |
|---|---|---|
| JM101/pGH3, pYajR | gshA, gshB, yajR | 562 |
| JM101/pGH3, pYegB | gshA, gshB, yegB | 492 |
| JM101/pGH3, pYidY | gshA, gshB, yidY | 503 |
| JM101/pGH3, pYieO | gshA, gshB, yieO | 453 |
| JM101/pGH3, pYjiO | gshA, gshB, yjiO | 286 |

As stated above, by enhancing the expression of the bcr gene, ygeD gene, yceE gene, cmr gene, marR-marA-marB gene, acrA-acrB gene, emrA-emrB gene, emrE gene, ydhC gene, ydeE gene, ydeA gene, evgA-emrK-emrY gene, emrD gene, yajR gene, yegB gene, yidY gene, yieO gene or yjiO gene in strains with a high activity of a protein involved in glutathione biosynthesis, the amount of glutathione accumulated in the medium was further increased; it was found that the proteins encoded by the genes, like the cydD and cydC gene products, have glutathione transporting activity.

EXAMPLE 5

Preparation of a Microorganism Lacking the γ-Glutamyl Transpeptidase Gene

A strain lacking a particular gene on the *E. coli* chromosomal DNA was prepared by a method utilizing a lambda phage homologous recombination system [Proc. Natl. Acad. Sci. USA, 97, 6641-6645 (2000)].

The plasmids pKD46, pKD3 and pCP20 described below were used after being extracted by a publicly known method from *Escherichia coli* strains harboring the plasmids, obtained from the *Escherichia coli* Genetic Stock Center (Yale University, US).

(1) Cloning of a DNA fragment for deleting the ggt gene

To delete the γ-glutamyl transpeptidase gene (ggt gene) having the base sequence shown by SEQ ID NO: 52, present on the chromosomal DNA of the *E. coli* K12 strain, DNAs having base sequences homologous to base sequences consisting of 400 to 500 by located upstream and downstream of the ggt gene on the chromosomal DNA of the *Escherichia coli* K12 strain, and having a base sequence recognized by yeast-derived Flp recombinase, were synthesized using the above-described DNA synthesizer.

Specifically, as primer sets for amplifying DNA fragments for deleting the ggt gene, DNAs consisting of the base sequences shown by SEQ ID NOs: 101 and 102, and 103 and 104, respectively, were synthesized. Next, PCR was performed using these synthetic DNAs as primer sets, with the chromosomal DNA of the *E. coli* W3110 strain as the template. The PCR was performed by repeating the step of heat treatment at 94° C. for 1 minute, at 55° C. for 2 minutes, and at 72° C. for 1 minute in 30 cycles using 40 μL of a reaction liquid comprising 0.1 μg of the chromosomal DNA, 0.5 μmol/L of each primer, 2.5 units of Pfu DNA polymerase, 4 μL of ×10 buffer solution for Pfu DNA polymerase, and 200 μmol/L of each deoxyNTP.

The PCR yielded the desired fragments for deleting the ggt gene, homologous to upstream and downstream regions (referred to as upstream DNA fragment and downstream DNA fragment, respectively) were obtained.

Next, a DNA fragment having the chloramphenicol resistance gene portion of pKD3 inserted into the center thereof, and having three DNA fragments joined therein (DNA fragment for deleting the ggt gene) was obtained by a crossover PCR [J. Bacteriol., 179, 6228-6237 (1997)] with the above-described upstream DNA fragment and downstream DNA fragment, and HindIII-digested pKD3 as the templates, using DNAs consisting of the base sequences shown by SEQ ID NOs: 101 and 104.

(2) Preparation of *E. coli* lacking the γ-glutamyl transpeptidase gene

The *Escherichia coli* JM101 strain was transformed with pKD46, after which a transformant was selected with ampicillin resistance as an index, and the transformant was named *E. coli* JM101/pKD46.

The DNA fragment for deleting the ggt gene obtained as described above was transferred by electric pulsation to the *E. coli* JM101/pKD46 obtained by culturing in the presence of 10 mmol/L L-arabinose and 50 μg/ml ampicillin, and a transformant integrating the DNA fragment inserted by homologous recombination into the chromosomal DNA of *E. coli* JM101/pKD46 (*E. coli* JM101/pKD46 ggt::cat) was selected with chloramphenicol resistance as an index.

*E. coli* JM101/pKD46 ggt::cat was inoculated to an LB agar medium comprising 25 mg/L chloramphenicol, and cultured at 42° C. for 14 hours, after which single colonies were separated. Each colony obtained was replicated to an LB agar medium comprising 25 mg/L chloramphenicol and an LB agar medium comprising 100 mg/l ampicillin, and cultured at 37° C., and a strain deprived of pKD46 (*E. coli* JM101 ggt::cat) was selected with chloramphenicol resistance and ampicillin sensitivity as indexes.

Next, the *E. coli* JM101 ggt::cat obtained above was transformed using pCP20, and a transformant was selected with ampicillin resistance as an index, whereby a pKD46-deficient strain retaining pCP20 (*E. coli* JM101/pCP20 ggt::cat) was acquired.

The *E. coli* JM101/pCP20 ggt::cat acquired above was inoculated to a drug-free LB agar medium, and cultured at 42° C. for 14 hours, after which single colonies were separated. Each colony obtained was replicated to a drug-free LB agar medium, an LB agar medium comprising 25 mg/L chloramphenicol, and an LB agar medium comprising 100 mg/L ampicillin, and cultured at 30° C., and several strains exhibiting chloramphenicol sensitivity and ampicillin susceptibility were selected.

Chromosomal DNA was prepared from each strain selected above, and PCR was performed using DNAs designed on the basis of the base sequences of DNAs located outside the ggt gene on the chromosomal DNA as a primer set, with the chromosomal DNA as the template. The PCR was performed by repeating the step of heat treatment at 94° C. for 1 minute, at 55° C. for 2 minutes, and at 72° C. for 3 minutes in 30 cycles using 40 μL of a reaction liquid comprising 0.1 g of the chromosomal DNA, 0.5 μmol/L of each primer, 2.5 units of Pfu DNA polymerase, 4 μL of ×10 buffer solution for Pfu DNA polymerase, and 200 μmol/L of each deoxyNTP.

The strain that gave rise of a short amplified fragment not comprising the ggt gene in the above-described PCR was taken as a ggt gene-deficient strain, and named the *E. coli* JGT2 strain.

EXAMPLE 6

Preparation of Microorganisms Lacking a Gene that Encodes a Protein Having Glutathione Uptake Activity (1) Cloning of DNA fragment for gene deletion To delete the gene that encodes a protein having the base sequence shown by SEQ ID NO: 58, and having glutathione uptake activity, present on the chromosomal DNA of the *E. coli* K12 strain (ybiK-yliA-yliB-yliC gene), base sequences homologous to base sequences consisting of 400 to 500 by located upstream and downstream of the ybiK-yliA-yliByliC gene on the chromosomal DNA of the *E. coli* K12 strain were synthesized using the above-described DNA synthesizer.

Specifically, since the ybiK, yliA, yliB, and yliC genes were present in the form of an operon, DNAs consisting of the base sequences shown by SEQ ID NOs: 105 and 106 for amplifying an upstream region of the ybiK gene, as a primer set for deleting the gene that encodes the protein having glutathione uptake activity, and DNAs consisting of the base sequences shown by SEQ ID NOs: 107 and 108, as a primer set for amplifying the downstream region of the yliC gene, were synthesized, respectively.

Next, using these synthetic DNAs as primer sets, fragments homologous to the upstream and downstream regions for deleting the ybiK-yliA-yliB-yliC gene (referred to as upstream DNA fragment and downstream DNA fragment, respectively) were acquired in the same manner as Example 5(1), after which a DNA fragment having the chloramphenicol resistance gene portion of pKD3 inserted into the center thereof, and having three DNA fragments joined therein (DNA fragment for deleting the ybiK-yliA-yliB-yliC gene) was obtained by a crossover PCR method with the upstream DNA fragment, the downstream DNA fragment, and HindIII-cleaved pKD3 as the templates, using DNAs consisting of the base sequences shown by SEQ ID NOs: 105 and 108 as a primer set.

(2) Preparation of microorganism lacking a gene that encodes a protein having glutathione uptake activity Each of *E. coli* JM101 and the *E. coli* JGT2 strain obtained in Example 5(2) was transformed with pKD46, after which transformants were selected with ampicillin resistance as an index, and the transformants were named *E. coli* JM101/pKD46 and *E. coli* JGT2/pKD46, respectively.

Next, the DNA fragment for deleting the ybiK-yliA-yliB-yliC gene obtained in (1) above was transferred to *E. coli* JM101/pKD46 and *E. coli* JGT2/pKD46 by electric pulsation, whereby transformants integrating the DNA fragment for deleting the ybiK-yliA-yliB-yliC gene inserted into the chromosomal DNAs of *E. coli* JM101/pKD46 and *E. coli* JGT2/pKD46 by homologous recombination (*E. coli* JM101/pKD46 ybiK-yliC::cat and *E. coli* JGT2/pKD46 ybiK-yliC::cat) were obtained.

Next, by following the same procedures as Example 5(2), strains deprived of pKD46, and lacking the chloramphenicol resistance gene from the chromosomal DNA, were obtained, and these were named *E. coli* JBK19 and *E. coli* JGTBK1, respectively. Table 4 shows the names of the lacked genes in the respective gene-deficient strains.

TABLE 4

| Name of strain | Lacked genes |
|---|---|
| JM101 | None |
| JGT2 | ggt |
| JBK19 | ybiK-yliA-yliB-yliC |
| JGTBK1 | ggt, ybiK-yliA-yliB-yliC |

EXAMPLE 7

Evaluation of Glutathione and γ-Glutamylcysteine Productivity Using *Escherichia coli* that has Lost Glutathione Degrading Activity and Glutathione Uptake Activity The strains lacking a gene that encodes a protein having γ-glutamyl transpeptidase or glutathione uptake activity, obtained in Examples 5 and 6, were transformed using the plasmids pGH1, pGH3 and pCYD1 constructed in Example 1 and 2(1), and transformed strains were selected with ampicillin and chloramphenicol resistance as indexes.

The transformed strains obtained were cultured in the same manner as Example 3, and glutathione and γ-glutamylcysteine concentrations in the medium were measured. The results are shown in Table 5.

TABLE 5

| Name of strain | Lacked genes | Expression-enhanced genes | GLT (mg/l) | GC (mg/l) |
|---|---|---|---|---|
| JGT2 | ggt | None | 0 | 0 |
| JGT2/pCYD1 | ggt | cydD, cydC | 0 | 0 |
| JGT2/pGH1 | ggt | gshA | 45 | 51 |
| JGT2/pGH1, pCYD1 | ggt | gshA, cydD, cydC | 82 | 199 |
| JGT2/pGH3 | ggt | gshA, gshB | 108 | 0 |
| JGT2/pGH3, pCYD1 | ggt | gshA, gshB, cydD, cydC | 177 | 0 |
| JBK19 | ybiK-yliA-yliB-yliC | None | 0 | 0 |
| JBK19/pCYD1 | ybiK-yliA-yliB-yliC | cydD, cydC | 0 | 0 |
| JBK19/pGH1 | ybiK-yliA-yliB-yliC | gshA | 70 | 84 |
| JBK19/pGH1, pCYD1 | ybiK-yliA-yliB-yliC | gshA, cydD, cydC | 72 | 153 |
| JBK19/pGH3 | ybiK-yliA-yliB-yliC | gshA, gshB | 334 | 0 |
| JBK19/pGH3, pCYD1 | ybiK-yliA-yliB-yliC | gshA, gshB, cydD, cydC | 337 | 0 |
| JGTBK1 | ggt, ybiK-yliA-yliB-yliC | None | 0 | 0 |
| JGTBK1/pCYD1 | ggt, ybiK-yliA-yliB-yliC | cydD, cydC | 0 | 0 |
| JGTBK1/pGH1 | ggt, ybiK-yliA-yliB-yliC | gshA | 100 | 262 |
| JGTBK1/pGH1, pCYD1 | ggt, ybiK-yliA-yliB-yliC | gshA, cydD, cydC | 240 | 176 |
| JGTBK1/pGH3 | ggt, ybiK-yliA-yliB-yliC | gshA, gshB | 694 | 0 |
| JGTBK1/pGH3, pCYD1 | ggt, ybiK-yliA-yliB-yliC | gshA, gshB, cydD, cydC | 756 | 0 |

As stated above, it was found that by further losing the glutathione degrading activity and/or glutathione uptake protein activity in a microorganism with an enhanced activity of a protein involved in glutathione or γ-glutamylcysteine biosynthesis, and an enhanced activity of a protein having glutathione transporting activity, the amounts of glutathione and γ-glutamylcysteine accumulated in the medium are further increased.

Industrial Applicability

According to the present invention, glutathione or γ-glutamylcysteine can be produced efficiently and inexpensively.

Sequence Listing Free Text

SEQ ID NO: 59-explanation of artificial sequence: synthetic DNA

SEQ ID NO: 60-explanation of artificial sequence: synthetic DNA

SEQ ID NO: 61-explanation of artificial sequence: synthetic DNA
SEQ ID NO: 62-explanation of artificial sequence: synthetic DNA
SEQ ID NO: 63-explanation of artificial sequence: synthetic DNA
SEQ ID NO: 64-explanation of artificial sequence: synthetic DNA
SEQ ID NO: 65-explanation of artificial sequence: synthetic DNA
SEQ ID NO: 66-explanation of artificial sequence: synthetic DNA
SEQ ID NO: 67-explanation of artificial sequence: synthetic DNA
SEQ ID NO: 68-explanation of artificial sequence: synthetic DNA
SEQ ID NO: 69-explanation of artificial sequence: synthetic DNA
SEQ ID NO: 70-explanation of artificial sequence: synthetic DNA
SEQ ID NO: 71-explanation of artificial sequence: synthetic DNA
SEQ ID NO: 72-explanation of artificial sequence: synthetic DNA
SEQ ID NO: 73-explanation of artificial sequence: synthetic DNA
SEQ ID NO: 74-explanation of artificial sequence: synthetic DNA
SEQ ID NO: 75-explanation of artificial sequence: synthetic DNA
SEQ ID NO: 76-explanation of artificial sequence: synthetic DNA
SEQ ID NO: 77-explanation of artificial sequence: synthetic DNA
SEQ ID NO: 78-explanation of artificial sequence: synthetic DNA
SEQ ID NO: 79-explanation of artificial sequence: synthetic DNA
SEQ ID NO: 80-explanation of artificial sequence: synthetic DNA
SEQ ID NO: 81-explanation of artificial sequence: synthetic DNA
SEQ ID NO: 82-explanation of artificial sequence: synthetic DNA
SEQ ID NO: 83-explanation of artificial sequence: synthetic DNA
SEQ ID NO: 84-explanation of artificial sequence: synthetic DNA
SEQ ID NO: 85-explanation of artificial sequence: synthetic DNA
SEQ ID NO: 86-explanation of artificial sequence: synthetic DNA
SEQ ID NO: 87-explanation of artificial sequence: synthetic DNA
SEQ ID NO: 88-explanation of artificial sequence: synthetic DNA
SEQ ID NO: 89-explanation of artificial sequence: synthetic DNA
SEQ ID NO: 90-explanation of artificial sequence: synthetic DNA
SEQ ID NO: 91-explanation of artificial sequence: synthetic DNA
SEQ ID NO: 92-explanation of artificial sequence: synthetic DNA
SEQ ID NO: 93-explanation of artificial sequence: synthetic DNA
SEQ ID NO: 94-explanation of artificial sequence: synthetic DNA
SEQ ID NO: 95-explanation of artificial sequence: synthetic DNA
SEQ ID NO: 96-explanation of artificial sequence: synthetic DNA
SEQ ID NO: 97-explanation of artificial sequence: synthetic DNA
SEQ ID NO: 98-explanation of artificial sequence: synthetic DNA
SEQ ID NO: 99-explanation of artificial sequence: synthetic DNA
SEQ ID NO: 100-explanation of artificial sequence: synthetic DNA
SEQ ID NO: 101-explanation of artificial sequence: synthetic DNA
SEQ ID NO: 102-explanation of artificial sequence: synthetic DNA
SEQ ID NO: 103-explanation of artificial sequence: synthetic DNA
SEQ ID NO: 104-explanation of artificial sequence: synthetic DNA
SEQ ID NO: 105-explanation of artificial sequence: synthetic DNA
SEQ ID NO: 106-explanation of artificial sequence: synthetic DNA
SEQ ID NO: 107-explanation of artificial sequence: synthetic DNA
SEQ ID NO: 108-explanation of artificial sequence: synthetic DNA

The invention claimed is:

1. A process for producing glutathione or γ-glutamylcysteine, comprising
    (a) culturing in a medium a modified bacterial cell having a glutathione transporting activity and a glutathione or γ-glutamylcysteine biosynthesis activity that are higher than the same activities in a parental bacterial cell,
    (b) forming and accumulating glutathione or γ-glutamylcysteine in the medium, and
    (c) recovering the glutathione or γ-glutamylcysteine from the culture,
    wherein the glutathione transporting activity is provided by transforming the parental bacterial cell with
    (1) a DNA that encodes a protein having the amino acid sequence of SEQ ID NO: 3 or a homologous protein having an amino acid sequence having 95% or more homology to the amino acid sequence of SEQ ID NO: 3 and having glutathione transporting activity,
    (2) a DNA having a coding region comprising the nucleic acid sequence of SEQ ID NO: 28,
    (3) a DNA that hybridizes with a DNA consisting of a nucleic acid sequence complementary to the coding region comprising the nucleic acid sequence of SEQ ID NO: 28 under stringent conditions, and that encodes a homologous protein having glutathione transporting activity, wherein the stringent conditions comprise (a) hybridization in a solution comprising 50% formamide, 5×SSC solution (750 mmol/L sodium chloride and 75 mmol/L sodium citrate), 50 mmol/L sodium phosphate (pH 7.6), 5×Denhardt's solution, 10% dextran sulfate, and 20 μg/L denatured salmon sperm DNA at 42° C. overnight, and (b) washing in 0.2×SSC solution at about 65° C., and
    wherein the glutathione or γ-glutamylcysteine biosynthesis activity is provided by transforming the parental bacterial cell with a DNA that encodes γ-glutamylcysteine synthetase (GSHI) or glutathione synthetase (GSHII).

2. The process according to claim 1, wherein the modified bacterial cell has a base deletion, substitution, or addition in the sequence of a gene that encodes a protein involved in glutathione or γ-glutamylcysteine degradation on chromosomal DNA resulting in a reduced or lost activity of a protein having a glutathione or γ-glutamylcysteine degrading activity, compared with the same activity of the protein having a glutathione or γ-glutamylcysteine degrading activity in the parental bacterial cell.

3. The process according to claim 2, wherein the protein having glutathione or γ-glutamylcysteine degrading activity is γ-glutamyl transpeptidase.

4. The process according to claim 2, wherein the modified bacterial cell has a chromosomal DNA lacking a gene that encodes γ-glutamyl transpeptidase.

5. The process according to claim 1, wherein the modified bacterial cell has a base deletion, substitution, or addition in the sequence of a gene that encodes a protein having glutathione uptake activity on chromosomal DNA resulting in a reduced or lost activity of a protein having a glutathione uptake activity compared with the same activity of the protein having a glutathione uptake activity in the parental bacterial cell.

6. The process according to claim 5, wherein the modified bacterial cell has a chromosomal DNA lacking a portion or all of the gene that encodes a protein having the glutathione uptake activity.

7. The process according to claim 1, wherein the bacterial cell belongs to the genus *Escherichia*.

* * * * *